US010288617B2

(12) United States Patent
Grifantini et al.

(10) Patent No.: US 10,288,617 B2
(45) Date of Patent: May 14, 2019

(54) OVARY TUMOR MARKERS AND METHODS OF USE THEREOF

(75) Inventors: Renata Grifantini, Siena (IT); Piero Pileri, Siena (IT); Susanna Campagnoli, Siena (IT); Alberto Grandi, Siena (IT); Matteo Parri, Siena (IT); Andrea Pierleoni, Siena (IT); Renzo Nogarotto, Siena (IT)

(73) Assignee: Externautics Spa, Siena (IT)

( * ) Notice: Subject to any disclaimer, the term of this patent is extended or adjusted under 35 U.S.C. 154(b) by 202 days.

(21) Appl. No.: 13/503,417

(22) PCT Filed: Oct. 26, 2010

(86) PCT No.: PCT/EP2010/066154

§ 371 (c)(1), (2), (4) Date: Sep. 10, 2012

(87) PCT Pub. No.: WO2011/051280

PCT Pub. Date: May 5, 2011

(65) Prior Publication Data

US 2013/0004955 A1 Jan. 3, 2013

(30) Foreign Application Priority Data

Oct. 26, 2009 (EP) .................................... 09174062

(51) Int. Cl.

*G01N 33/574* (2006.01)
*C07K 16/30* (2006.01)
*C12N 15/113* (2010.01)

(52) U.S. Cl.

CPC ... *G01N 33/57449* (2013.01); *C07K 16/3069* (2013.01); *C12N 15/113* (2013.01); *C12N 2310/14* (2013.01); *G01N 2500/02* (2013.01)

(58) Field of Classification Search

None
See application file for complete search history.

(56) References Cited

U.S. PATENT DOCUMENTS

2002/0064818 A1* 5/2002 Ni et al. ........................ 435/69.1
2002/0137044 A1 9/2002 Tang et al.
2003/0064439 A1 4/2003 Bandaru et al.
2003/0100497 A1* 5/2003 Baker .................... A61K 38/17 435/69.1
2003/0186866 A1* 10/2003 Baker .................... A61K 38/17 514/13.3
2005/0260639 A1 11/2005 Nakamura et al.
2006/0035244 A1 2/2006 Riggins et al.
2006/0204503 A1* 9/2006 Fitchett ............ G01N 33/57423 424/155.1
2006/0275794 A1 12/2006 Carrino et al.
2007/0072178 A1 3/2007 Haferlach et al.
2007/0200637 A1 8/2007 Isogai et al.
2007/0237770 A1 10/2007 Lai et al.
2007/0298445 A1* 12/2007 Boyd et al. .................. 435/7.23
2008/0166340 A1* 7/2008 Tureci ................ C07K 14/4748 424/133.1
2008/0280779 A1 11/2008 Shaughnessy, Jr. et al.
2012/0322074 A1 12/2012 Grifantini et al.
2012/0322075 A1 12/2012 Grifantini et al.
2013/0017546 A1 1/2013 Grifantini et al.
2013/0022983 A1 1/2013 Grifantini et al.
2013/0137106 A1 5/2013 Grifantini et al.

FOREIGN PATENT DOCUMENTS

EP 1440981 7/2004
EP 1696029 8/2006
EP 2494361 1/2016
WO WO 1999/15653 4/1999
WO WO 1999/32639 7/1999
WO WO 2000/53758 9/2000
WO WO 2000/053758 9/2000
WO WO 2002/24888 3/2002
WO WO 2002/074961 9/2002
WO WO 2002/086443 10/2002
WO WO 2004/058288 7/2004
WO WO 2004/087874 10/2004
WO WO 2004/094623 * 11/2004 ............ A61K 31/17
WO WO 2005/030250 4/2005
WO WO 2007/109376 9/2007
WO WO 2008/004719 1/2008
WO WO 2008/021290 2/2008
WO WO 2008/065544 6/2008
WO WO 2009/087978 7/2009
WO WO 2010/024677 3/2010

OTHER PUBLICATIONS

Anderson, L., and Seilhamer, J. (1997); A comparison of selected mRNA and protein abundances in human liver; Electrophoresis 18, pp. 533-537.

Bjartell,A., et al.; (2006) Immunohistochemical detection of cysteine-rich secretory protein 3 in tissue and in serum from men with cancer or benign enlargement of the prostate gland; *Prostate*; vol. 66; pp. 591-603.

Bjartell,A.S., et al.; (2007), Association of cysteine-rich secretory protein 3 and beta-microseminoprotein with outcome after radical prostatectomy; *Clin. Cancer Res*; vol. 13; pp. 4130-4138.

Bouïs D, et al.; (2007) Effects of the CDT6/ANGX gene on tumour growth in immune competent mice, In Vivo, 2003 17:157-61; Bouïs DR, Dam WA, Meijer C, Mulder NH, Hospers GA. Effect of CDT6 on factors of angiogenic balance in tumour cell lines; Anticancer Res.; vol. 27; pp. 2325-2329.

Bromberg, K.D., et al.; (2007) Increased expression of the E3 ubiquitin ligase RNF5 is associated with decreased survival in breast cancer ; Cancer Res.; vol. 67, 8172-8179.

(Continued)

*Primary Examiner* — Nelson B Moseley, III
(74) *Attorney, Agent, or Firm* — Fish & Richardson P.C.

(57) ABSTRACT

Newly identified proteins as markers for the detection of ovary tumors, or as therapeutic targets for treatment thereof; affinity ligands capable of selectively interacting with the newly identified markers, methods for tumor diagnosis and therapy using the same.

11 Claims, 38 Drawing Sheets

Specification includes a Sequence Listing.

(56) References Cited

OTHER PUBLICATIONS

Chauhan, et al.; Aberrant Expression of MUC4 in Ovarian Carcinoma: Diagnostic Significance Alone and in Combination with MUC1 and MUC16 (CA125); Modern Pathology: An Official Journal of the United States and Canadian Academy of Pathology; Oct. 2006; vol. 19, No. 10; pp. 1386-1394.
Chen, G., Gharib, et al.; (2003); Protein profiles associated with survival in lung adenocarcinoma. Proc. Natl. Acad. Sci. U. S. A.; vol. 100, pp. 13537-13542.
Database accession No. ADQ66904; sequence 4065; http://www.ebi.ac.uk/Tools/dbfetch/; retrieved on Dec. 3, 2013, 3 pages.
Database accession No. CQ843230; sequence 1877; http://www.ebi.ac.uk/Tools/dbfetch/; retrieved on Dec. 3, 2013, 2 pages.
Didier, C., et al.; (2003); RNF5, a RING finger protein that regulates cell motility by targeting paxillin ubiquitination and altered localization; Mol. Cell. Biol.; vol. 23; pp. 5331-5345.
Garcia-Rudaz,C., et al.; (2007); Fxna, a novel gene differentially expressed in the rat ovary at the time of folliculogenesis, is required for normal ovarian histogenesi; Development vol. 134, pp. 945-957.
Ginestier, C. et al.; (2002); Distinct and complementary information provided by use of tissue and DNA microarrays in the study of breast tumor markers; Am. J. Pathol.; vol. 161, pp. 1223-1233.
Gygi, S.P., et al. (1999); Correlation between Protein and mRNA Abundance in Yeast; Molecular and Cellular Biology; vol. 19, No. 3, pp. 1720-1730.
Huang X, et al.; (2006) Genes Chromosomes Cancer, 45:1058-69. Comprehensive genome and transcriptome analysis of the 11q13 amplicon in human oral cancer and synteny to the 7F5 amplicon in murine oral carcinoma; Genes Chromosomes Cancer, vol. 45; pp. 1058-1069.
International Preliminary Report on Patentability; PCT/EP2010/066154; A. Wittmann-Regis; dated May 1, 2012; 8 pp.
International Search Report and Written Opinion; PCT/EP2010/066154; dated Apr. 11, 2011;M. Langer and T. Vogt; 16 pp.
Kagara, et al., Zinc and Its Transporter ZIP10 are Involved in Invasive Behavior of Breast Cancer Cells; Cancer Science; vol. 98, No. 5; May 2007; pp. 692-697.
Kasper G, et al.; (2005) Expression levels of the putative zinc transporter LIV-1 are associated with a better outcome of breast cancer patients; Int J Cancer.; vol. 117; pp. 961-973.
Kratzschmar J, et al.; (1996) The human cysteine-rich secretory protein (CRISP) family. Primary structure and tissue distribution of CRISP-1, CRISP-2 and CRISP-3; Eur. J. Biochem.,vol. 236; pp. 827-836.
Nguyen ST, et al.; (2007) Identification of a predictive gene expression signature of cervical lymph node metastasis in oral squamous cell carcinoma; Cancer Sci; vol. 98; pp. 740-746.
Nicholas B, et al.; (2006) Shotgun proteomic analysis of human-induced sputum; (2006) Proteomics; vol. 6: pp. 4390-4401.
Nishizuka, et al.; (2003); Proteomic profiling of the NCI-60 cancer cell lines using new high-density reverse-phase lysate microarrays; Proc. Natl. Acad. Sci. U.S.A.; vol. 100, pp. 14229-14234.
Peek R, et al.; (2002) The angiopoietin-like factor cornea-derived transcript 6 is a putative morphogen for human cornea; J. Biol. Chem.; vol. 277; pp. 686-693.
Sladek R, et al.; (2007); A genome-wide association study identifies novel risk loci for type 2 diabetes; Nature; vol. 445; pp. 881-885.
Tyers, M., et al.; (2003); From genomics to proteomics; Nature; vol. 422; pp. 193-197.
Wan,B., et al.; (2008) hOLFML1, a novel secreted glycoprotein, enhances the proliferation of human cancer cell lines in vitro; FEBS Lett.; vol. 582; pp. 3185-3192.
Yin, Beatrice et al.; Ovarian Cancer Antigen CA125 is Encoded by the MUC16 Mucin Gene; *International Journal of Cancer*; Apr. 10, 2002; vol. 98, No. 5; pp. 737-740.
Adachi J, et al.; The human urinary proteome contains more than 1500 proteins including a large proportion of membranes proteins; (2006) Genome Biol. ; 7:R80.
Adams G.P. et al.; (2005); Monoclonal antibody therapy cancer. Nat Biotechnol. 23: 1 147-1 157.
Albrecht et al.; Zinc Transporter MRNA Expression in the RWPE-1 Human Prostate Epithelial Cell Line; Biometals; vol. 21, No. 4; Aug. 2008; pp. 405-416.
Aslanidis C, et al.; (1990); Ligation-independent cloning of PCR products (LIC-PCR). Nucleic Acids Res. 18:6069-74.
Ausch C, et al.: (2009) Caspase-cleaved cytokeratin 18 fragment (M30) as marker of postoperative residual tumor load in colon cancer patients, Eur. J. Surg. Oncol., vol. 35, No. 11, 1164-1168.
Ghaemmaghami et al.; "Global analysis of protein expression in yeast"; Nature, 425: 737-741, 2003.
Huang J, et al.; (2010); Genetic and epigenetic silencing of SCARA5 may contribute to human hepatocellular carcinoma by activating FAK signaling. J Clin Invest. 120:223-41.
International Preliminary Report on Patentability and Written Opinion; PCT/EP2010/066144; dated May 1, 2012; 8 pp.
International Preliminary Report on Patentability and Written Opinion; PCT/EP2010/066147; dated May 1, 2012; 10 pp.
International Preliminary Report on Patentability and Written Opinion; PCT/EP2011/056825; dated Nov. 6, 2012; 8 pp.
International Preliminary Report on Patentability; PCT/EP2010/066146; Y. Cussac; dated May 1, 2012; 10 pp.
International Report on Patentability for International Application No. PCT/EP2010/066134, dated May 1, 2012, 10 pages.
International Search Report and Written Opinion for International Application No. PCT/EP2010/066134, dated May 16, 2011, 17 pages.
International Search Report and Written Opinion; PCT/EP2010/066144; dated Mar. 4, 2011; 15 pp.
International Search Report and Written Opinion; PCT/EP2010/066146; dated Mar. 18, 2011; M. Langer; 17 pp.
International Search Report and Written Opinion; PCT/EP2010/066147; dated Mar. 21, 2011; 17 pages.
International Search Report; PCT/EP2011/056825; A. Weijland; dated Aug. 18, 2011.; 5 pp.
Jiang; "Lipids and Lipoproteins: Identification and Characterization of Murine SCARA5, a Novel Class A Scavenger Receptor That Is Expressed by Populations of Epithelial Cells"; J. Biol. Chem. 2006, 281:11834-11845.
Kallioniemi OP, et al.; (2001) Tissue microarray technology for high-throughput molecular profiling of cancer. Hum Mol Genet. 10:657-62.
Kononen J, et al.; (1998); Tissue microarrays for high-throughput molecular profiling of tumor specimens. Nat Med. 4:844-7.
Nguyen et al., "Identification of a predictive gene expression signature of cervical lymph node metastasis in oral squamous cell carcinoma," Cancer Sci, May 2007, 98(5):741-746.
Parri et al.; "Angiopoietin-like 7, a novel pro-angiogenetic factor over-expressed in cancer"; Angiogenesis; Jun. 6, 2014; 16 pp.
Smith et al., "Genome-wide Association Study of Bipolar Disorder in European American and African American Individuals," Mol Psychiatry, Aug. 2009, 14(8):755-763.
Studier FW. (2005); Protein production by auto-induction in high density shaking cultures. Protein Expr Purif. 41 :207-34.
Yang, et al.; (2005), Polyethylene Glycol-Mediated Cell Fusion, Springer Protocols, 325 :59-66, DOI—10.1385/1-59745-005-7:59).
[No Author Listed] ATCC Product Sheet for the MCF7 cell line, American Type Culture Collection, 3 pages.
[No Author Listed] "KLRG2," The Human Protein Atlas, http://www.proteinatlas.org/ENSG0000018883-KLRG2/cancer, 2 pages.
[No Author Listed] "Tumor Markers," National Cancer Institute, (Nov. 2015), 9 pages.
Database accession No. ABX13629; http://www.ebi.ac.uk/Tools/dbfetch/; retrieved on Mar. 20, 2018, 6 pages.
Database accession No. ADZ14621; sequence 137; http://www.ebi.ac.uk/Tools/dbfetch/; retrieved on Mar. 20, 2018, 4 pages.
Database accession No. ADZ14622; sequence 138; http://www.ebi.ac.uk/Tools/dbfetch/; retrieved on Mar. 20, 2018, 5 pages.
Henry et al., "Cancer Biomarkers," Mol. Oncol., 6(2):140-6 (Apr. 2012).
Kampf et al., "Antibody-Based Tissue Profiling As a Tool for Clinical Proteomics," Clin. Proteomics, 1:285-300 (2004).
Kohler & Milstein, "Continuous cultures of fused cells secreting antibody of predefined specificity," Nature, 265:495 (1975).

(56) References Cited

OTHER PUBLICATIONS

Opposition filed in European Patent Application No. 10778593.3, dated Mar. 8, 2017, 10 pages.
Patentee's Response to Opposition in European Patent Application No. 10778593.3, dated Jul. 28, 2017, 29 pages.
Preliminary Opinion of the Opposition Division in European Patent Application No. 10778593.3, dated Oct. 27, 2017, 11 pages.
Tan et al., "PPM1D is a potential therapeutic target in ovarian clear cell carcinomas," Clinical Cancer Research, 15(7):2269-2280 (2009).

* cited by examiner

Ovary cancer

Ovarian cancer

Ovary cancer

Ovary cancer

Ovary cancer

Ovary, cancer

Ovary, cancer

Ovary, cancer

Ovary, cancer

Ovary, cancer

Ovary, cancer

Ovary, cancer

KDa
19
14

KDa

Figure 37

Ovary, cancer

OVARY TUMOR MARKERS AND METHODS OF USE THEREOF

The present invention relates to newly identified proteins as markers for the detection of ovary tumors, or as targets for their treatment. Also provided are affinity ligands capable of selectively interacting with the newly identified markers, as well as methods for tumor diagnosis and therapy using such ligands.

BACKGROUND OF THE INVENTION

Tumor Markers (or Biomarkers)

Tumor markers are substances that can be produced by tumor cells or by other cells of the body in response to cancer. In particular, a protein biomarker is either a single protein or a panel of different proteins that could be used to unambiguously distinguish a disease state. Ideally, a biomarker would have both a high specificity and sensitivity, being represented in a significant percentage of the cases of given disease and not in healthy state.

Biomarkers can be identified in different biological samples, like tissue biopsies or preferably biological fluids (saliva, urine, blood-derivatives and other body fluids), whose collection does not necessitate invasive treatments. Tumor marker levels may be categorized in three major classes on the basis of their clinical use. Diagnostic markers can be used in the detection and diagnosis of cancer. Prognostics markers are indicative of specific outcomes of the disease and can be used to define predictive models that allow the clinicians to predict the likely prognosis of the disease at time of diagnosis. Moreover, prognosis markers are helpful to monitor the patient response to a drug therapy and facilitate a more personalized patient management. A decrease or return to a normal level may indicate that the cancer is responding to therapy, whereas an increase may indicate that the cancer is not responding. After treatment has ended, tumor marker levels may be used to check for recurrence of the tumor. Finally, therapeutic markers can be used to develop tumor-specific drugs or affinity ligand (i.e. antibodies) for a prophylactic intervention.

Currently, although an abnormal tumor marker level may suggest cancer, this alone is usually not enough to accurately diagnose cancer and their measurement in body fluids is frequently combined with other tests, such as a biopsy and radioscopic examination. Frequently, tumor marker levels are not altered in all of people with a certain cancer disease, especially if the cancer is at early stage. Some tumor marker levels can also be altered in patients with noncancerous conditions. Most biomarkers commonly used in clinical practice do not reach a sufficiently high level of specificity and sensitivity to unambiguously distinguish a tumor from a normal state.

To date the number of markers that are expressed abnormally is limited to certain types/subtypes of cancer, some of which are also found in other diseases. (www.cancer.gov/cancertopics/factsheet).

For example, prostate-specific antigen (PSA) levels are often used to screen men for prostate cancer, but this is controversial since elevated PSA levels can be caused by both prostate cancer or benign conditions, and most men with elevated PSA levels turn out not to have prostate cancer.

Another tumor marker, Cancer Antigen 125, (CA 125), is sometimes used to screen women who have an increased risk for ovarian cancer. Scientists are studying whether measurement of CA 125, along with other tests and exams, is useful to find ovarian cancer before symptoms develop. So far, CA 125 measurement is not sensitive or specific enough to be used to screen all women for ovarian cancer. Mostly, CA 125 is used to monitor response to treatment and check for recurrence in women with ovarian cancer. Finally, human epidermal growth factor receptor (HER2) is a marker protein overproduced in about 20% of breast cancers, whose expression is typically associated with more aggressive and recurrent tumors of this class.

Routine Screening Test for Tumor Diagnosis

Screening tests are a way of detecting cancer early, before there are any symptoms. For a screening test to be helpful, it should have high sensitivity and specificity. Sensitivity refers to the test's ability to identify people who have the disease. Specificity refers to the test's ability to identify people who do not have the disease. Different molecular biology approaches such as analysis of DNA sequencing, small nucleotide polymorphisms, in situ hybridization and whole transcriptional profile analysis have done remarkable progresses to discriminate a tumor state from a normal state and are accelerating the knowledge process in the tumor field. However so far different reasons are delaying their use in the common clinical practice, including the higher analysis complexity and their expense. Other diagnosis tools whose application is increasing in clinics include in situ hybridization and gene sequencing.

Currently, Immuno-HistoChemistry (IHC), a technique that allows the detection of proteins expressed in tissues and cells using specific antibodies, is the most commonly used method for the clinical diagnosis of tumor samples. This technique enables the analysis of cell morphology and the classification of tissue samples on the basis of their immunoreactivity. However, at present, IHC can be used in clinical practice to detect cancerous cells of tumor types for which protein markers and specific antibodies are available. In this context, the identification of a large panel of markers for the most frequent cancer classes would have a great impact in the clinical diagnosis of the disease.

Anti-Cancer Therapies

In the last decades, an overwhelming number of studies remarkably contributed to the comprehension of the molecular mechanisms leading to cancer. However, this scientific progress in the molecular oncology field has not been paralleled by a comparable progress in cancer diagnosis and therapy. Surgery and/or radiotherapy are the still the main modality of local treatment of cancer in the majority of patients. However, these treatments are effective only at initial phases of the disease and in particular for solid tumors of epithelial origin, as is the case of colon, lung, breast, prostate and others, while they are not effective for distant recurrence of the disease. In some tumor classes, chemotherapy treatments have been developed, which generally relies on drugs, hormones and antibodies, targeting specific biological processes used by cancers to grow and spread. However, so far many cancer therapies had limited efficacy due to severity of side effects and overall toxicity. Indeed, a major effort in cancer therapy is the development of treatments able to target specifically tumor cells causing limited damages to surrounding normal cells thereby decreasing adverse side effects. Recent developments in cancer therapy in this direction are encouraging, indicating that in some cases a cancer specific therapy is feasible. In particular, the development and commercialization of humanized monoclonal antibodies that recognize specifically tumor-associated markers and promote the elimination of cancer is one of the most promising solution that appears to be an extremely favorable market opportunity for pharmaceutical companies. However, at present the number of therapeutic antibodies available on the market or under clinical studies is very limited and restricted to specific cancer classes. So far licensed monoclonal antibodies currently used in clinics for the therapy of specific tumor classes, show only a partial efficacy and are frequently associated with chemotherapies to increase their therapeutic effect. Administration of Trastuzumab (Herceptin), a commercial monoclonal antibody targeting HER2, a protein overproduced in about 20% of breast cancers, in conjunction with Taxol adjuvant chemotherapy induces tumor remission in about 42% of the cases. Bevacizumab (Avastin) and Cetuximab (Erbitux) are two monoclonal antibodies recently licensed for use in humans, targeting the endothelial and epithelial growth factors respectively that, combined with adjuvant chemotherapy, proved to be effective against different tumor diseases. Bevacizumab proved to be effective in prolonging the life of patients with metastatic colorectal, breast and lung cancers. Cetuximab demonstrated efficacy in patients with tumor types refractory to standard chemotherapeutic treatments (Adams G. P. and Weiner L. M. (2005) Monoclonal antibody therapy cancer. *Nat. Biotechnol.* 23:1147-57).

In summary, available screening tests for tumor diagnosis are uncomfortable or invasive and this sometimes limits their applications. Moreover tumor markers available today have a limited utility in clinics due to either their incapability to detect all tumor subtypes of the defined cancers types and/or to distinguish unambiguously tumor vs. normal tissues. Similarly, licensed monoclonal antibodies combined with standard chemotherapies are not effective against the majority of cases. Therefore, there is a great demand for new tools to advance the diagnosis and treatment of cancer.

Experimental Approaches Commonly Used to Identify Tumor Markers

Most popular approaches used to discover new tumor markers are based on genome-wide transcription profile or total protein content analyses of tumor. These studies usually lead to the identification of groups of mRNAs and proteins, which are differentially expressed in tumors. Validation experiments then follow to eventually single out, among the hundreds of RNAs/proteins identified, the very few that have the potential to become useful markers. Although often successful, these approaches have several limitations and often, do not provide firm indications on the association of protein markers with tumor. A first limitation is that, since frequently mRNA levels not always correlate with corresponding protein abundance (approx. 50% correlation), studies based on transcription profile do not provide solid information regarding the expression of protein markers in tumor (1, 2, 3, 4).

A second limitation is that neither transcription profiles nor analysis of total protein content discriminate post-translation modifications, which often occur during oncogenesis. These modifications, including phosphorylations, acetylations, and glycosylations, or protein cleavages influence significantly protein stability, localization, interactions, and functions (5).

As a consequence, large scale studies generally result in long lists of differentially expressed genes that would require complex experimental paths in order to validate the potential markers. However, large scale genomic/proteomic studies reporting novel tumor markers frequently lack of confirmation data on the reported potential novel markers and thus do not provide solid demonstration on the association of the described protein markers with tumor.

The approach that we used to identify the protein markers included in the present invention is based on an innovative immuno-proteomic technology. In essence, a library of recombinant human proteins has been produced from *E. coli* and is being used to generate polyclonal antibodies against each of the recombinant proteins.

The screening of the antibodies library on Tissue microarrays (TMAs) carrying clinical samples from different patients affected by the tumor under investigation lead to the identification of specific tumor marker proteins. Therefore, by screening TMAs with the antibody library, the tumor markers are visualized by immuno-histochemistry, the classical technology applied in all clinical pathology laboratories. Since TMAs also include healthy tissues, the specificity of the antibodies for the tumors can be immediately appreciated and information on the relative level of expression and cellular localization of the markers can be obtained. In our approach the markers are subjected to a validation process consisting in a molecular and cellular characterization.

Altogether, the detection the marker proteins disclosed in the present invention selectively in tumor samples and the subsequent validation experiments lead to an unambiguous confirmation of the marker identity and confirm its association with defined tumor classes. Moreover this process provides an indication of the possible use of the proteins as tools for diagnostic or therapeutic intervention. For instance, markers showing a surface cellular localization could be both diagnostic and therapeutic markers against which both chemical and antibody therapies can be developed. Differently, markers showing a cytoplasmic expression could be more likely considered for the development of tumor diagnostic tests and chemotherapy/small molecules treatments.

SUMMARY OF THE INVENTION

The present invention provides new means for the detection and treatment of tumors, in particular ovary tumor, based on the identification of protein markers specific for these tumor type, namely:

i) Killer cell lectin-like receptor subfamily G member 2 (C-type lectin domain family 15 member B) (KLRG2);
ii) Solute carrier family 39 (zinc transporter), member 10 (SLC39A10);
iii) G protein-coupled receptor 107 (GPR107);
iv) DPY-19-like 3 (DPY19L3);
v) Uncharacterized protein FLJ42986 (FLJ42986);
vi) Collagen, type XX, alpha 1 (COL20A1);
vii) Glycosyltransferase 25 domain containing 2 (GLT25D2);
viii) Synaptotagmin-like 3 (SYTL3);
ix) DENN/MADD domain containing 1B (DENND1B);
x) Putative uncharacterized protein (FLJ3710);
xi) Chromosome 6 open reading frame 98 (C6orf98);
xii) Family with sequence similarity 69, member B (Fam69B);
xiii) EMI domain-containing protein 1 Precursor (EMID1);
xiv) Endoplasmic reticulum metallopeptidase 1 (ERMP1);
xv) Vitelline membrane outer layer protein 1 homolog Precursor (VMO1)

The invention also provides a method for the diagnosis of these cancer types, comprising a step of detecting the above-identified markers in a biological sample, e.g. in a tissue sample of a subject suspected of having or at risk of developing malignancies or susceptible to cancer recurrences.

In addition, the tumor markers identify novel targets for affinity ligands, which can be used for therapeutic applications. Also provided are affinity ligands, particularly antibodies, capable of selectively interacting with the newly identified protein markers.

DETAILED DISCLOSURE OF THE INVENTION

The present invention is based on the surprising finding of antibodies that are able to specifically stain tumor tissues from patients, while negative or very poor staining is observed in normal tissues from the same patients. These antibodies have been found to specifically bind to proteins for which no previous association with tumor has been reported. Hence, in a first aspect, the invention provides an ovarian tumor marker, which is selected from the group consisting of:

i) KLRG2, SEQ ID NO:85, SEQ ID NO:86 or a different isoform having sequence identity of at least 80%, preferably at least 90%, more preferably at least 95% to SEQ ID NO:85, SEQ ID NO:86 or a nucleic acid molecule containing a sequence coding for a KLRG2 protein, said encoding sequence being preferably selected from SEQ ID NO: 87 and SEQ ID NO:88;

ii) SLC39A10 in one of its variant isoforms SEQ ID NO:1, SEQ ID NO:2 or a different isoform having sequence identity of at least 80%, preferably at least 90%, more preferably at least 95% to SEQ ID NO:1 or SEQ ID NO:2; or a nucleic acid molecule containing a sequence coding for a SLC39A10 protein, said encoding sequence being preferably selected from SEQ ID NO: 3 and SEQ ID NO: 4;

iii) GPR107, in one of its variant isoforms SEQ ID NO:5, SEQ ID NO:6, SEQ ID NO:7, or a different isoform having sequence identity of at least 80%, preferably at least 90%, more preferably at least 95% to any of SEQ ID NO:5, SEQ ID NO:6, SEQ ID NO:7, or a nucleic acid molecule containing a sequence coding for a GPR107 protein, said encoding sequence being preferably selected from SEQ ID NO:8, SEQ ID NO:9 and SEQ ID NO:10;

iv) DPY19L3, in one of its variant isoforms SEQ ID NO:11, SEQ ID NO:12, SEQ ID NO:13, SEQ ID NO:14, or a different isoform having sequence identity of at least 80%, preferably at least 90%, more preferably at least 95% to SEQ ID NO:11, SEQ ID NO:12, SEQ ID NO:13 or SEQ ID NO:14, or a nucleic acid molecule containing a sequence coding for a DPY19L3 protein, said encoding sequence being preferably selected from SEQ ID NO:15, SEQ ID NO:16, SEQ ID NO:17 and SEQ ID NO:18;

v) FLJ42986, SEQ ID NO:19 or a different isoform having sequence identity of at least 80%, preferably at least 90%, more preferably at least 95% to SEQ ID NO:19, or a nucleic acid molecule containing a sequence coding for a FLJ42986 protein, said encoding sequence being preferably SEQ ID NO:20;

vi) COL20A1, in one of its variant isoforms SEQ ID NO:21, SEQ ID NO:22, SEQ ID NO:23, or a different isoform having sequence identity of at least 80%, preferably at least 90%, more preferably at least 95% to any of SEQ ID NO:21, SEQ ID NO:22, SEQ ID NO:23, or a nucleic acid molecule containing a sequence coding for a COL20A1 protein, said encoding sequence being preferably selected from SEQ ID NO:24, SEQ ID NO:25 and SEQ ID NO:26;

vii) GLT25D2, in one of its variant isoforms SEQ ID NO:27, SEQ ID NO:28, SEQ ID NO:29, SEQ ID NO:30, or a different isoform having sequence identity of at least 80%, preferably at least 90%, more preferably at least 95% to any of SEQ ID NO:27, SEQ ID NO:28, SEQ ID NO:29, SEQ ID NO:30, or a nucleic acid molecule containing a sequence coding for a GLT25D2 protein, said encoding sequence being preferably selected from SEQ ID NO:31, SEQ ID NO:32, SEQ ID NO:33 and SEQ ID NO:34;

viii) SYTL3, in one of its variant isoforms SEQ ID NO:35, SEQ ID NO:36, SEQ ID NO:37, or a different isoform having sequence identity of at least 80%, preferably at least 90%, more preferably at least 95% to any of SEQ ID NO:35, SEQ ID NO:36, SEQ ID NO:37, or a nucleic acid molecule containing a sequence coding for a SYTL3 protein, said encoding sequence being preferably selected from SEQ ID NO:38, SEQ ID NO:39 and SEQ ID NO:40;

ix) DENND1B; in one of its variant isoforms SEQ ID NO:41, SEQ ID NO:42, SEQ ID NO:43, SEQ ID NO:44, or a different isoform having sequence identity of at least 80%, preferably at least 90%, more preferably at least 95% to any of SEQ ID NO:41, SEQ ID NO:42, SEQ ID NO:43, SEQ ID NO:44, or a nucleic acid molecule containing a sequence coding for a DENND1B protein, said encoding sequence being preferably selected from SEQ ID NO:45, SEQ ID NO:46, SEQ ID NO:47 and SEQ ID NO:48;

x) FLJ3710, SEQ ID NO:49 or a different isoform having sequence identity of at least 80%, preferably at least 90%, more preferably at least 95% to SEQ ID NO:49, or a nucleic acid molecule containing a sequence coding for a FLJ3710 protein, said encoding sequence being preferably SEQ ID NO:50;

xi) Chromosome 6 orf 98 (C6orf98) SEQ ID NO:51 or a different isoform having sequence identity of at least 80%, preferably at least 90%, more preferably at least 95% to SEQ ID NO:51, or a nucleic acid molecule containing a sequence coding for a C6orf98 protein, said encoding sequence being preferably SEQ ID NO:52;

xii) Family with sequence similarity 69, member B (Fam69B) SEQ ID NO:53, SEQ ID NO:54 or a different isoform having sequence identity of at least 80%, preferably at least 90%, more preferably at least 95% to SEQ ID NO:53 or SEQ ID NO:54, or a nucleic acid molecule containing a sequence coding for a Fam69B protein, said encoding sequence being preferably selected from SEQ ID NO:55 and SEQ ID NO:56;

xiii) EMI domain-containing protein 1 Precursor (EMID1) in one of its variant isoforms SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, or a different isoform having sequence identity of at least 80%, preferably at least 90%, more preferably at least 95% to SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:690R SEQ ID NO:70, or a nucleic acid molecule containing a sequence coding for a EMID protein, said encoding sequence being preferably selected from SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83 and SEQ ID NO:84;

xiv) ERMP1, SEQ ID NO:89, SEQ ID NO:90 and SEQ ID NO:91, or a different isoform having sequence identity of at least 80%, preferably at least 90%, more preferably at least 95% to SEQ ID NO:89, SEQ ID NO:90 or SEQ ID NO:91, or a nucleic acid molecule containing a sequence coding for a ERMP1 protein, said encoding sequence being preferably selected from SEQ ID NO:92, SEQ ID NO:93 and SEQ ID NO:94;

xv) VMO1, SEQ ID NO:95, SEQ ID NO:96, SEQ ID NO:97, SEQ ID NO: 98 or a different isoform having sequence identity of at least 80%, preferably at least 90%, more preferably at least 95% to SEQ ID NO:95, SEQ ID NO:96, SEQ ID NO:97, SEQ ID NO: 98 or a nucleic acid molecule containing a sequence coding for a VMO1 protein, said encoding sequence being preferably selected from SEQ ID NO:99, SEQ ID NO:100 SEQ ID NO:101 and SEQ ID NO: 102.

As used herein, "Percent (%) amino acid sequence identity" with respect to the marker protein sequences identified herein indicates the percentage of amino acid residues in a full-length protein variant or isoform according to the invention, or in a portion thereof, that are identical with the amino acid residues in the specific marker sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Identity between nucleotide sequences is preferably determined by the Smith-Waterman homology search algorithm as implemented in the MPSRCH program (Oxford Molecular), using an affine gap search with parameters gap open penalty=12 and gap extension penalty=1.

SLC39A10 mRNA has been shown to be moderately upregulated in breast cancer tissues as compared to normal samples (approximately 1.5 fold). In the same study, loss of SLC39A10 transcription in breast cell lines has been reported to reduce cell migratory activity (6). However, published studies on the expression of SLC39A10 in breast tumor cells are limited to the analysis of SLC39A10 transcript whilst, to the best of our knowledge, no data have been reported documenting the presence of SLC39A10 protein in these tumor cells.

SLC39A10 is also mentioned in a patent application reporting long lists of differentially transcribed genes in tumor cells by using genome-scale transcription profile analysis (e.g. in Publication Number: US20070237770A1). Again, no data are given documenting the expression of SLC39A10 in tumor at protein level. The lack of correlation between mRNA and protein expression, besides being a general fact, has been specifically demonstrated for LIV-1, another member of the zinc transporter family, suggesting that a similar phenomenon could be extended to other proteins of this class (7). Finally, no evidence exists on the association of SLC39A10 protein with other tumors, such as ovary tumor classes.

In the present invention we disclose SLC39A10 as a protein without previous known association with ovarian tumor classes and preferably used as a marker ovary tumors and in general for cancers of these types. As described below, an antibody generated towards the SLC39A10 protein shows a selective immunoreactivity in histological preparation of ovary cancer tissues which indicates the presence of SLC39A10 in these cancer samples and makes SLC39A10 protein and its antibody highly interesting tools for specifically distinguishing these cancer types from a normal state.

Moreover, this antibody also detected its target protein on the surface of ovary tumor cell lines and in cells transfected with a SLC39A10 encoding construct, indicating that the protein is exposed to the external environment and easily accessible to affinity ligands such as antibodies.

G protein-coupled receptor 107 (GPR107, synonyms: Protein GPR107 Precursor, Lung seven transmembrane receptor 1, Gene ID: ENSG00000148358; Transcript IDs: ENST00000347136, ENST00000372410, ENST00000372406; Protein IDs: ENSP00000336988, ENSP00000361487, ENSP00000361483) is a partially characterized protein. GPR107 has been mentioned in patent applications on pancreatic tumor (e.g. US20050260639A1) and in different patent application based on whole genome transcription profile analysis of cancer, but no supporting data are provided on the expression of GPR107 protein in tumor samples. Based on the above, in the present invention we disclose GPR107 as a protein without previous known association with the tumor class under investigation and preferably used as a marker for ovary tumor, and in general for cancers of this type. As described below, an antibody generated towards GPR107 protein shows a selective immunoreactivity in histological preparation of ovary cancer tissues, which indicates the presence of this protein in these cancer samples.

The protein was detected on the surface of tumor cell lines by anti-GPR107 antibodies, indicating that it is accessible to the binding of specific antibodies.

Protein dpy-19 homolog 3 (DPY19L3; synonym: Dpy-19-like protein 3; Gene ID: ENSG00000178904; Transcript IDs: ENST00000319326, ENST00000392250, ENST00000342179, ENST00000392248; Protein IDs: ENSP00000315672, ENSP00000376081. ENSP00000344937, ENSP00000376079) Dpy19L3 transcript has been reported as differentially expressed in multiple myeloma (Publication Number: US20080280779A1). However not data are available at level of protein expression. In the present invention we disclose Dpy19L3 protein as associated with tumor and preferably used as a marker for ovary tumor, and in general for these cancer types. As described below, an antibody generated towards DPY19L3 protein shows a selective immunoreactivity in histological preparation of ovary cancer tissues, which indicates the presence of this protein in these cancer samples.

Moreover the protein is detected on a panel of ovary tumor cell lines reinforcing the evidence. Finally the protein was detected on the surface of tumor cell lines by the specific antibody, suggesting that it can be exploited as target for affinity ligands with therapeutic activity.

Uncharacterized protein FLJ42986 (FLJ42986, Gene ID: ENSG00000196460; Transcript ID: ENST00000376826; Protein ID: ENSP00000366022) is a hypothetical protein without previous known association with ovarian tumor classes and is preferably used as a marker for ovary tumor and in general for these cancer types. As described below, an antibody generated towards FLJ42986 protein shows a selective immunoreactivity in histological preparation of ovary cancer tissues, which indicates the presence of this protein in these cancer samples.

Collagen, type XX, alpha 1 (COL20A1); Synonyms: Collagen alpha-1(XX) chain Precursor; Gene ID: ENSG00000101203; Protein IDs: ENSP00000323077; ENSP00000346302; ENSP00000351767; Transcript IDs: ENST00000326996; ENST00000354338; ENST00000358894) belongs to the family of collagenous domain, Fibronectin type III domain, heparin binding domain, von Willebrand type A domain proteins. COL20A1 is a protein without previous known association with tumor and is preferably used as a marker for ovary tumor and in general for these cancer types. As described below, an antibody generated towards COL20A1 protein shows a selective immunoreactivity in histological preparation of ovary tissues, which indicates the presence of this protein in these cancer samples.

Glycosyltransferase 25 domain containing 2 (GLT25D2; synonyms: Glycosyltransferase 25 family member 2 Precursor) Gene ID: ENSG00000198756; Transcript IDs: ENST00000367522, ENST00000361927, ENST00000367520, ENST00000367521; Protein IDs: ENSP00000356492, ENSP00000354960, ENSP00000356490, ENSP00000356491), is a protein without previous known association with ovarian tumor and is preferably used as a marker for ovary tumor and in general for these cancer types. As described below, an antibody generated towards GLT25D2 protein shows a selective immunoreactivity in histological preparation of ovarian cancer, which indicates the presence of this protein in these cancer samples.

Synaptotagmin-like 3 (SYTL3; synonyms: SLP3, SLP3-B, Synaptotagmin-like protein 3, Exophilin-6; Gene ID: ENSG00000164674; Transcript ID: ENST00000360448, ENST00000297239, ENST00000367081; Protein ID: ENSP00000353631, ENSP00000297239, ENSP00000356048) belongs the family of proteins containing C2 domain, calcium-dependent phospholipid binding, neurexin binding, phospholipid binding, protein binding, rab3A effector domain, Slp homology domain. SYTL3 is a protein without previous known association with ovarian tumor and is preferably used as a marker for ovary tumor and in general for these cancer types. As described below, an antibody generated towards SYTL3 protein shows a selective immunoreactivity in histological preparation of ovary cancer tissues, which indicates the presence of this protein in these cancer samples.

DENN/MADD domain containing 1B (DENND1B; synonyms: DENN domain-containing protein 1B, Protein FAM31B, C1 orf218; Gene ID: ENSG00000162701. Transcript IDs: ENST00000294738, ENST00000367396, ENST00000400967, ENST00000235453; Protein IDs: ENSP00000294738, ENSP00000356366, ENSP00000383751, ENSP00000235453) is a poorly characterized protein without previous known association with ovarian tumors and is preferably used as a marker for ovary tumor and in general for these cancer types. As described below, an antibody generated towards DENND1B protein shows a selective immunoreactivity in histological preparation of ovary cancer tissues, which indicates the presence of this protein in these cancer samples.

Putative uncharacterized protein FLJ37107 (FLJ37107; synonyms: LOC284581; Gene ID: ENSG00000177990, Transcript ID: gi|58218993|ref|NM_001010882.1, Protein ID: gi|58218994|ref|NP_001010882.1| hypothetical protein LOC284581 [*Homo sapiens*], gi|74729692|sp|Q8N9I1.1|YA028_HUMAN) is an uncharacterized protein without previous known association with tumor and is preferably used as a marker for ovary tumor and in general for these cancer types. As described below, an antibody generated towards FLJ3710 protein shows a selective immunoreactivity in histological preparation of ovary cancer tissues, which indicates the presence of this protein in these cancer samples.

Chromosome 6 open reading frame 98 (C6orf98; synonym: dJ45H2.2; Gene ID: EG:387079, da ENSG00000222029 has 1 transcript: ENST00000409023, associated peptide: ENSP00000386324 and 1 exon: ENSE00001576965) is an uncharacterized protein. Analysis of human genome databases (E.g. Ensembl) erroneously assigns C6orf98 as SYNE1. Although SYNE nucleic acid sequences overlap with C6ORF98 transcript, the encoded proteins show no match. In fact C6orf98 maps on an SYNE1 untranslated region (intron) and its product derives from a different reading frame than those annotated for SYNE1 isoforms in public databases. C6orf98 is a protein without C6orf98 is a protein without previous known association with tumor and is preferably used as a marker for ovary tumor and in general for these cancer types. As described below, an antibody generated towards C6orf98 protein shows a selective immunoreactivity in histological preparation of ovary cancer tissues, which indicates the presence of this protein in these cancer samples.

Family with sequence similarity 69, member B (Fam69B; synonym: C9orf136; Gene ID: ENSG00000165716; Transcript IDs: ENST00000371692, ENST00000371691; Protein IDs: ENSP00000360757, ENSP00000360756) is a hypothetical protein without previous known association with tumor. This protein has been recently associated with Type 2 diabetes mellitus disease (8) and included in patent application on diabetes (Patent publication number: WO2008065544A2). In the present invention we disclose FAM69B as associated with tumor and preferably used as a marker for ovarian tumor and in general for these cancer types. As described below, an antibody generated towards Fam69B protein shows a selective immunoreactivity in histological preparation of ovary cancer tissues, which indicates the presence of this protein in these cancer samples.

EMI domain-containing protein 1 Precursor (EMID1; synonyms: Emilin and multimerin domain-containing protein 1, Protein Emu1; Gene ID: >OTTHUMG00000030824

| Transcript IDs: | Protein IDs: |
|---|---|
| OTTHUMT00000075712 | OTTHUMP00000028901, |
| ENST00000429226 | ENSP00000403816, |
| ENST00000430127 | ENSP00000399760, |
| ENST00000435427 | ENSP00000402621, |
| ENST00000404820 | ENSP00000384452, |
| ENST00000334018 | ENSP00000335481, |
| ENST00000429415 | ENSP00000409801, |
| ENST00000448676 | ENSP00000413034, |
| ENST00000404755 | ENSP00000385414, |
| ENST00000435194 | ENSP00000417004, |
| ENST00000426629 | ENSP00000403484, |
| ENST00000457925 | ENSP00000405422, |
| ENST00000433143 | ENSP00000408339, |
| ENST00000455501 | ENSP00000413947), |

is a poorly characterized protein. EMID1 gene is mentioned in a patent application on follicular thyroid carcinoma (Publication number US2006035244 (A1). However, no data are available on the presence of this protein in the tumor class under investigation. Therefore, we disclose EMID1 as a protein without previous known association with ovary tumors and preferably used as a marker for ovary tumor and in general for these cancer types. As described below, an antibody generated towards EMID1 protein shows a selective immunoreactivity in histological preparation of ovary cancer tissues, which indicates the presence of this protein in these cancer samples. In particular this antibody stains also tumor secretion products indicating that EMID1 protein is specifically released by tumor cells.

Killer cell lectin-like receptor subfamily G member 2 (C-type lectin domain family 15 member B) (KLRG2, synonyms: CLEC15B, FLJ44186; GENE ID: ENSG00000188883; Transcript IDs: ENST00000340940, ENST00000393039; Protein IDs: ENSP00000339356, ENSP00000376759) is a poorly characterized protein. A KLRG2 sequence is included in a patent application on the use of an agent with tumor-inhibiting action of a panel of targets associated with different tumors, whose expression is mainly shown at RNA level (Publication number WO2005030250). However no data are provided documenting the presence of KLRG2 protein in the tumors. Moreover, no experimental evidence is given on the specificity of the proposed anti-tumor agent for KLRG2. Based on these considerations, in the present invention we disclose KLRG2 as a protein without previous known association with tumor class under investigation and preferably used as a marker for ovary tumor, and in general for cancers of this type. As described below, an antibody generated towards KLRG2 protein shows a selective immunoreactivity in histological preparation of ovary cancer tissues, which indicates the presence of this protein in this cancer type. In particular, the immunohistochemistry staining accumulates in the plasma membrane of tumor cells. Moreover, localization analysis of tumor cell lines showed that the protein is exposed on the cell surface and accessible to the binding of specific antibodies. Finally, silencing of KLRG2 significantly reduced the invasiveness and proliferation properties of tumor cells lines. Overall, KLRG2 is a likely target for the development of anti-cancer therapies being accessible to the action of affinity ligands and being involved in cellular processes relevant for tumor development.

Endoplasmic reticulum metallopeptidase 1 (ERMP1, synonyms: FLJ23309, FXNA, KIAA1815; GENE ID: ENSG00000099219; Transcript IDs: ENST00000214893, ENST00000339450, ENST00000381506; Protein IDs: ENSP00000214893, ENSP00000340427, ENSP00000370917) is a transmembrane metallopeptidase, so far described as localized to the endoplasmic reticulum. ERMP1 transcript has been found differentially expressed in the rat ovary at the time of folliculogenesis. A lower level of ERMP1 transcript in the rat ovary resulted in substantial loss of primordial, primary and secondary follicles, and structural disorganization of the ovary, suggesting that is required for normal ovarian histogenesis (9). ERMP1 has been also included in a patent application (Publication Number: US 2003064439) on novel nucleic acid sequences encoding melanoma associated antigen molecules. However in these publications, no solid data documented the relation of ERMP1 protein with tumor. Based on available information, ERMP1 protein has never been previously associated with tumor. In the present invention, differently with published scientific data, we disclose ERMP1 as a protein associated with tumor, preferably used as a marker for ovarian tumor, and in general for cancers of this type. As described below, an antibody generated towards ERMP1 protein shows a selective immunoreactivity in histological preparation of ovary cancer tissues, which indicates the presence of this protein in this cancer type. In particular our immunohistochemistry analysis of ovarian tissues indicates that the protein shows plasma membrane localization. Moreover, localization analysis of ovary tumor cell lines showed that the protein is exposed on the cell surface and accessible to the binding of specific antibodies. Finally, silencing of ERMP1 significantly reduced the invasiveness and proliferation properties of tumor cells lines. Based on the above evidences, ERMP1 is a likely target for the development of anti-cancer therapies being exposed to the action of affinity ligand and being involved in cellular processes relevant for tumor development.

Vitelline membrane outer layer protein 1 homolog Precursor (VMO1, synonyms: ERGA6350, PRO21055; GeneID: ENSG00000182853; Transcript ID: ENST00000328739, ENST00000354194, ENST00000416307, ENST00000441199; Protein IDs: ENSP00000328397, ENSP00000346133, ENSP00000390450, ENSP00000408166) is a marginally characterized protein. Evidences on the expression of VMO1 human protein are essentially based on studies in which the protein was detected in sputum from smoking human female and urine (10, 11).

In the present invention we disclose VMO1 as a protein without previous known association with tumor classes under investigation and preferably used as a marker for ovarian tumor, and in general for cancers of this type. As described below, an antibody generated towards VMO1 protein shows a selective immunoreactivity in histological preparation of ovarian cancer tissues, which indicates the presence of this protein in this cancer type. Immunoreactivity accumulates at the plasma membrane of tumor cells, providing a first indication that this protein is accessible to the action of affinity ligands (such as antibodies) with anti-cancer activities.

A further aspect of this invention is a method of screening a tissue sample for malignancy, which comprises determining the presence in said sample of at least one of the above-mentioned tumor markers. This method includes detecting either the marker protein, e.g. by means of labeled monoclonal or polyclonal antibodies that specifically bind to the target protein, or the respective mRNA, e.g. by means of polymerase chain reaction techniques such as RT-PCR. The methods for detecting proteins in a tissue sample are known to one skilled in the art and include immunoradiometric, immunoenzymatic or immunohistochemical techniques, such as radioimmunoassays, immunofluorescent assays or enzyme-linked immunoassays. Other known protein analysis techniques, such as polyacrylamide gel electrophoresis (PAGE), Western blot or Dot blot are suitable as well. Preferably, the detection of the protein marker is carried out with the immune-histochemistry technology, particularly by means of High Through-Put methods that allow the analyses of the antibody immune-reactivity simultaneously on different tissue samples immobilized on a microscope slide. Briefly, each Tissue Micro Array (TMA) slide includes tissue samples suspected of malignancy taken from different patients, and an equal number of normal tissue samples from the same patients as controls. The direct comparison of samples by qualitative or quantitative measurement, e.g. by enzimatic or colorimetric reactions, allows the identification of tumors.

In one embodiment, the invention provides a method of screening a sample of ovary tissue for malignancy, which comprises determining the presence in said sample of the SLC39A10, GPR107, DPY19L3, FLJ42986, COL20A1, GLT25D2, SYTL3, DENND1B, FLJ3710, C6orf98, FAM69B, EMID1, KLRG2, ERMP1, VMO1 protein tumor marker, variants or isoforms thereof as described above.

A further aspect of the invention is a method in vitro for determining the presence of an ovary tumor in a subject, which comprises the steps of:

(1) providing a sample of the tissue suspected of containing tumor cells;

(2) determining the presence of a tumor marker as above defined, or a combination thereof in said tissue sample by detecting the expression of the marker protein or the presence of the respective mRNA transcript;

wherein the detection of one or more tumor markers in the tissue sample is indicative of the presence of tumor in said subject.

The methods and techniques for carrying out the assay are known to one skilled in the art and are preferably based on immunoreactions for detecting proteins and on PCR methods for the detection of mRNAs. The same methods for detecting proteins or mRNAs from a tissue sample as disclosed above can be applied.

A further aspect of this invention is the use of the tumor markers herein provided as targets for the identification of candidate antitumor agents. Accordingly, the invention provides a method for screening a test compound which comprises contacting the cells expressing a tumor-associated protein selected from: Solute carrier family 39 (zinc transporter), member 10 (SLC39A10); G protein-coupled receptor 107 (GPR107); DPY19-like 3 (DPY19L3); Uncharacterized protein FLJ42986 (FLJ42986); Collagen, type XX, alpha 1 (COL20A1); Glycosyltransferase 25 domain containing 2 (GLT25D2); Synaptotagmin-like 3 (SYTL3); DENN/MADD domain containing 1B (DENND1B); Putative uncharacterized protein (FLJ3710); Chromosome 6 open reading frame 98 (C6orf98); Family with sequence similarity 69, member B (Fam69B); EMI domain-containing protein 1 Precursor (EMID1); Killer cell lectin-like receptor subfamily G member 2 (KLRG2); Endoplasmic reticulum metallopeptidase 1 (ERMP1); Vitelline membrane outer layer protein 1 homolog precursor (VMO1);

with the test compound, and determining the binding of said compound to said tumor-associated protein. In addition, the ability of the test compound to modulate the activity of each target molecule can be assayed.

A further aspect of the invention is an antibody or a fragment thereof, which is able to specifically recognize and bind to one of the tumor-associated proteins described above. The term "antibody" as used herein refers to all types of immunoglobulins, including IgG, IgM, IgA, IgD and IgE. Such antibodies may include polyclonal, monoclonal, chimeric, single chain, antibodies or fragments such as Fab or scFv. The antibodies may be of various origin, including human, mouse, rat, rabbit and horse, or chimeric antibodies. The production of antibodies is well known in the art. For the production of antibodies in experimental animals, various hosts including goats, rabbits, rats, mice, and others, may be immunized by injection with polypeptides of the present invention or any fragment or oligopeptide or derivative thereof which has immunogenic properties or forms a suitable epitope. Monoclonal antibodies may be produced following the procedures described in Kohler and Milstein, Nature 265:495 (1975) or other techniques known in the art.

The antibodies to the tumor markers of the invention can be used to detect the presence of the marker in histologic preparations or to distinguish tumor cells from normal cells. To that purpose, the antibodies may be labeled with radioactive, fluorescent or enzyme labels.

In addition, the antibodies can be used for treating proliferative diseases by modulating, e.g. inhibiting or abolishing the activity of a target protein according to the invention. Therefore, in a further aspect the invention provides the use of antibodies to a tumor-associated protein selected from: Solute carrier family 39 (zinc transporter), member 10 (SLC39A10); G protein-coupled receptor 107 (GPR107); DPY19-like 3 (DPY19L3); Uncharacterized protein FLJ42986 (FLJ42986); Collagen type XX, alpha 1 (COL20A1); glycosyltransferase 25 domain containing 2 (GLT25D2); Synaptotagmin-like 3 (SYTL3); DENN/MADD domain containing 1B (DENND1B); Putative uncharacterized protein (FLJ3710); Chromosome 6 open reading frame 98 (C6orf98); Family with sequence similarity 69, member B (Fam69B); EMI domain-containing protein 1 Precursor (EMID1); Killer cell lectin-like receptor subfamily G member 2 (KLRG2); Endoplasmic reticulum metallopeptidase 1 (ERMP1); Vitelline membrane outer layer protein 1 homolog Precursor (VMO1);

for the preparation of a therapeutic agent for the treatment of proliferative diseases. For use in therapy, the antibodies can be formulated with suitable carriers and excipients, optionally with the addition of adjuvants to enhance their effects.

A further aspect of the invention relates to a diagnostic kit containing suitable means for detection, in particular the polypeptides or polynucleotides, antibodies or fragments or derivatives thereof described above, reagents, buffers, solutions and materials needed for setting up and carrying out the immunoassays, nucleic acid hybridization or PCR assays described above. Parts of the kit of the invention can be packaged individually in vials or bottles or in combination in containers or multicontainer units.

Left panel: Comassie staining of purified His-tag SLC39A10 fusion protein separated by SDS-PAGE; Right panel: WB on the recombinant SLC39A10 protein stained with anti-SLC39A10 antibody. Arrow marks the protein band of the expected size. The low molecular weight bands correspond to partially degraded forms of SLC39A10 protein. Molecular weight markers are reported on the left.

Figure 2:
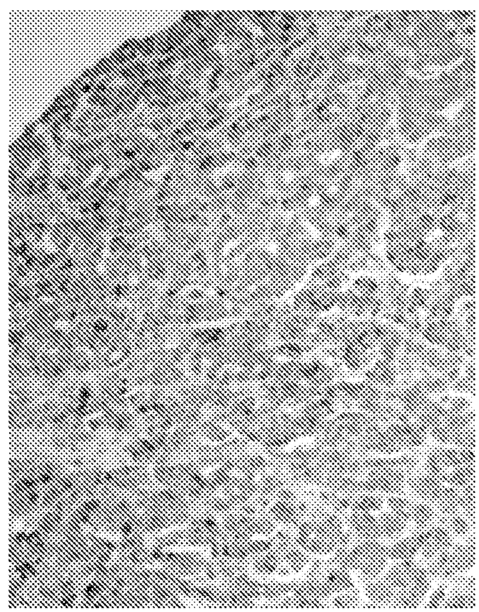

FIG. 2. Staining of ovary tumor TMA with anti-SLC39A10 antibodies

In the case of the ovarian sample, both tumor and normal cells are represented on the same image. The antibody stains specifically tumor cells (in dark gray); negative or poor staining is visible in normal cells.

Figure 3:
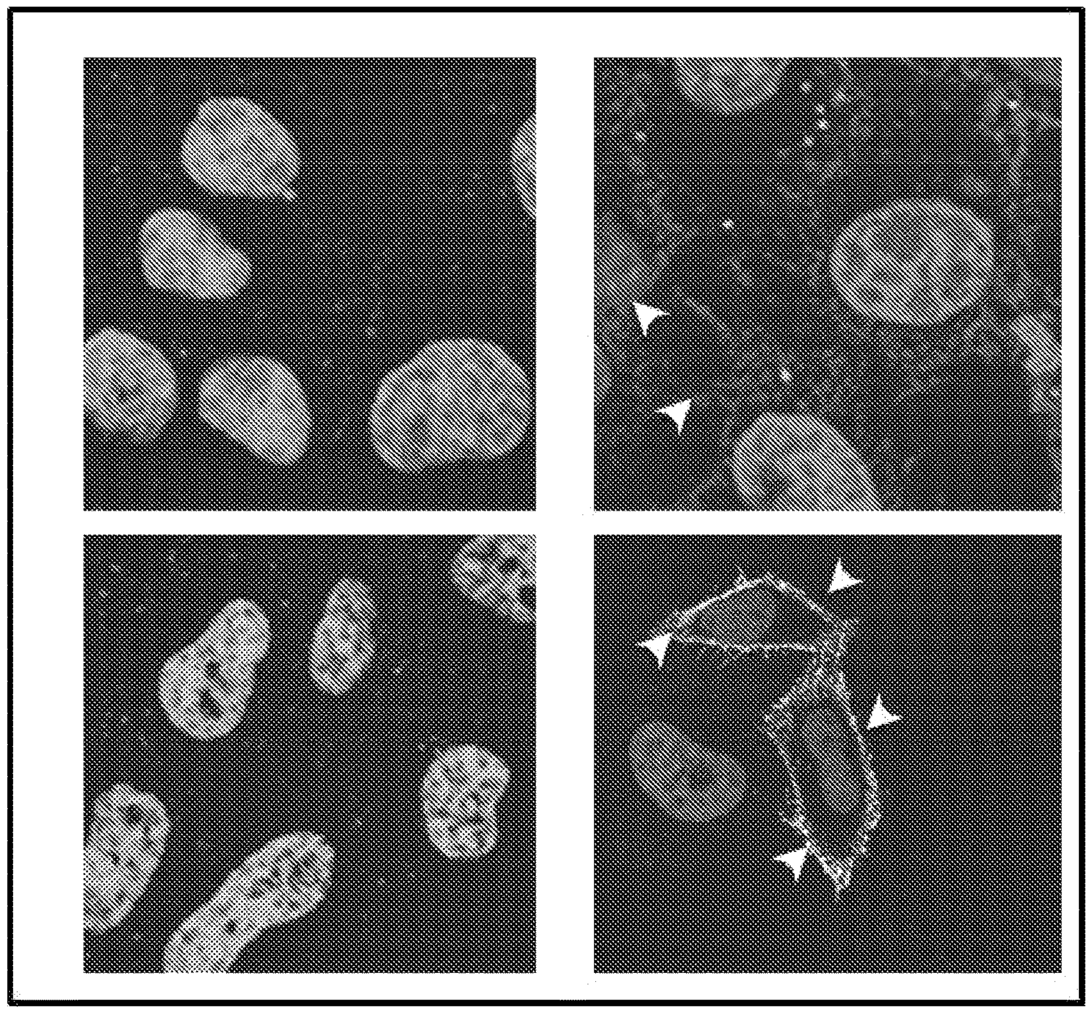

FIG. 3. Confocal microscopy analysis of expression and localization of SLC39A10 in transfected cells HeLa cells transfected with the empty pcDNA3 vector (upper panels) or with the plasmid construct encoding the SLC39A10 gene (lower panels) stained with secondary antibodies (left panels) and with anti-SLC39A10 antibodies (right panels). Arrowheads mark surface specific localization.

Figure 4:
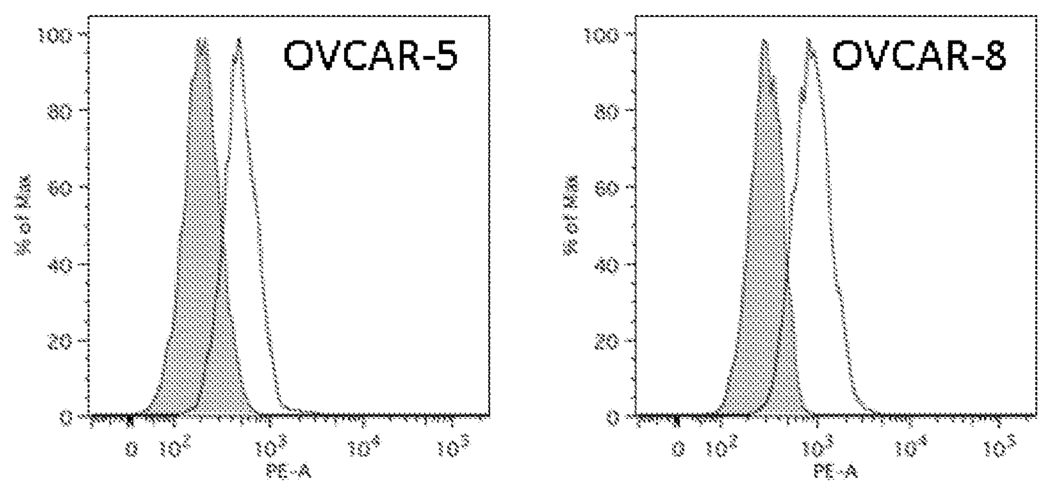

FIG. 4. Expression and localization of SLC39A10 in ovary tumor cell lines

Flow cytometry analysis of SLC39A10 cell-surface localization in OVCAR-5 (left panel) and OVCAR-8 (right panel) tumor cells stained with a negative control antibody (filled curve or with anti-SLC39A10 antibody (empty curve). X axis, Fluorescence scale; Y axis, Cells (expressed as % relatively to major peaks).

Figure 5:
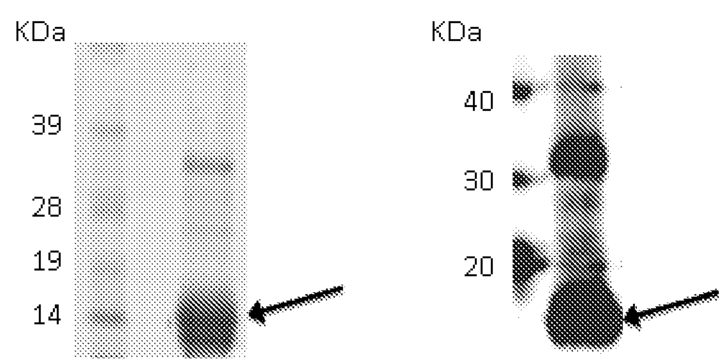

FIG. 5. Analysis of purified GPR107 recombinant protein

Left panel: Comassie staining of purified His-tag GPR107 fusion protein separated by SDS-PAGE; Right panel: WB on the recombinant GPR107 protein stained with anti-GPR107 antibody. Arrow marks the protein band of the expected size. The high molecular weight band is consistent with a protein dimer of GPR107. Molecular weight markers are reported on the left.

Figure 6:
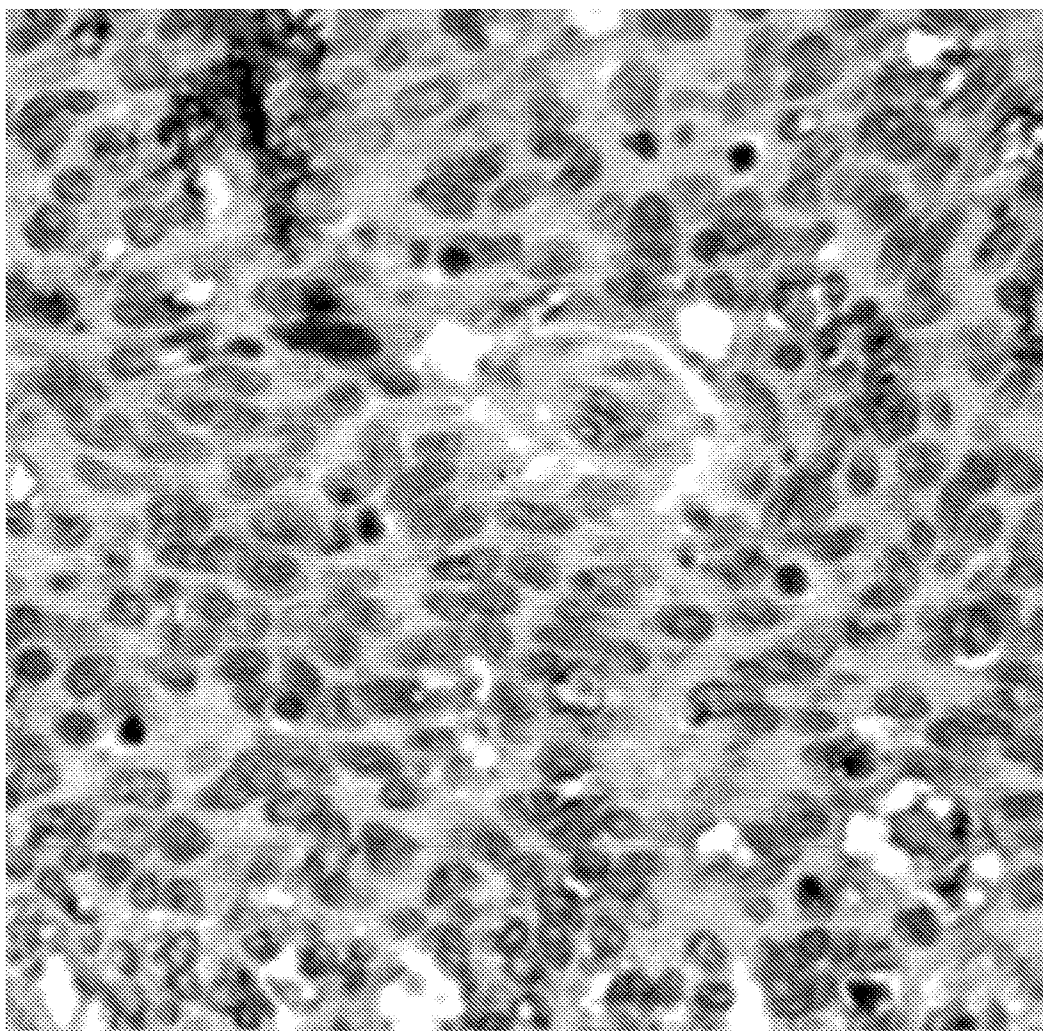

FIG. 6. Staining of ovary tumor TMA with anti-GPR107 antibodies

In the case of the ovarian sample, both tumor and normal cells are represented on the same image. The antibody stains specifically tumor cells (in dark gray); negative or poor staining is visible in normal cells.

Figure 7:
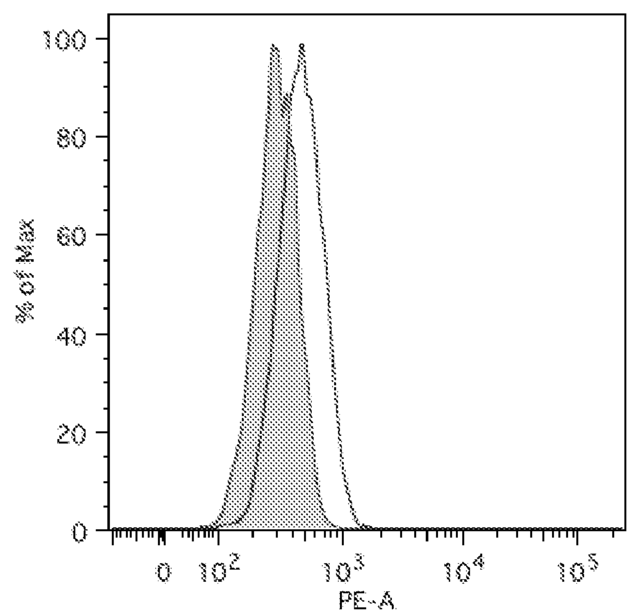

FIG. 7. Expression and localization of GPR107 in ovary tumor cells

Flow cytometry analysis of GPR107 cell surface localization in OVCAR-8 cells stained with a control antibody (filled curve or with anti-GPR107 antibody (empty curve). X axis, Fluorescence scale; Y axis, Cells (expressed as percentage, relatively to major peaks).

Figure 8:
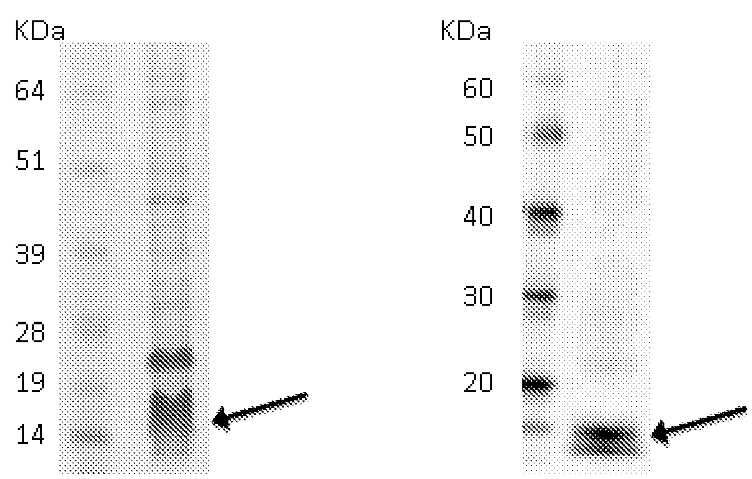

FIG. 8. Analysis of purified DPY19L3 recombinant protein

Left panel: Comassie staining of purified His-tag DPY19L3 fusion protein separated by SDS-PAGE; Right panel: WB on the recombinant DPY19L3 protein stained with anti-DPY19L3 antibody. Arrow marks the protein band of the expected size. Molecular weight markers are reported on the left.

Figure 9:
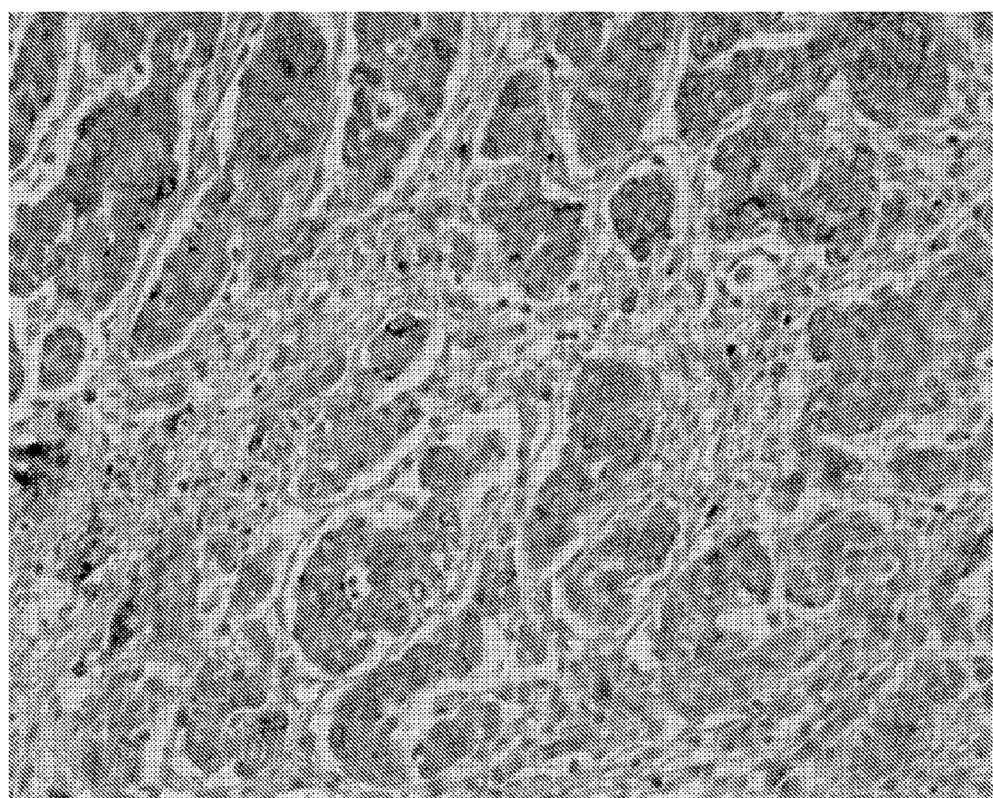

FIG. 9. Staining of ovary tumor TMA with anti-DPY19L3 antibodies

In the case of the ovarian sample, both tumor and normal cells are represented on the same image. The antibody stains specifically tumor cells (in dark gray); negative or poor staining is visible in normal cells.

Figure 10:
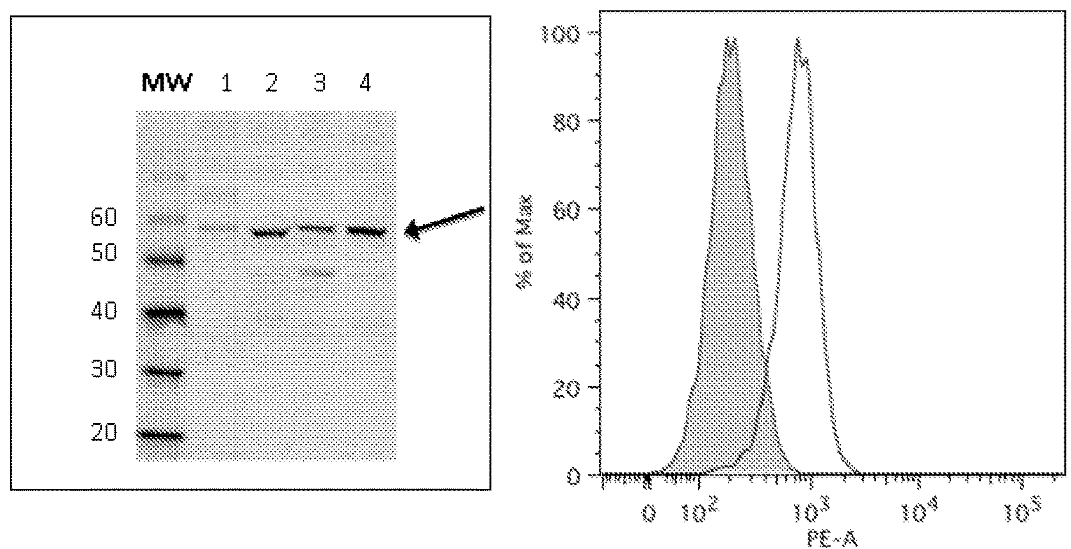

FIG. 10. Expression and localization of DPY19L3 in ovary tumor cell lines

Left panel: Western blot analysis of DPY19L3 expression in total protein extracts separated by SDS-PAGE from the ovary-derived tumor cells OVCAR-3 (lane 1), OVCAR-4 (lane 2), OVCAR-5 (lane 3), OVCAR-8 (lane 4). Arrow marks the protein band of the expected size. Molecular weight markers are reported on the left.

Right panel: Flow cytometry analysis of DPY19L3 cell surface localization in OVCAR-5 cells stained with a negative control antibody (filled curve or with anti-DPY19L3 antibody (empty curve). X axis, Fluorescence scale; Y axis, Cells (expressed as percentage, relatively to major peaks).

Figure 11:
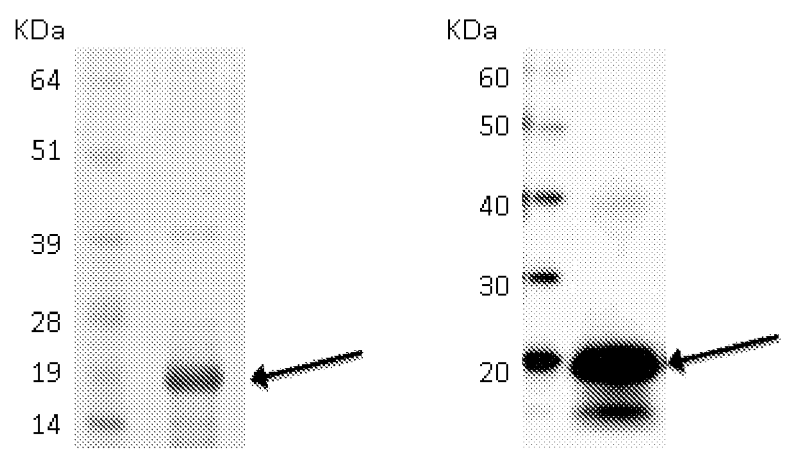

FIG. 11. Analysis of purified FLJ42986 recombinant protein

Left panel: Comassie staining of purified His-tag FLJ42986 fusion protein separated by SDS-PAGE; Right panel: WB on the recombinant FLJ42986 protein stained with anti-FLJ42986 antibody. Arrow marks the protein band of the expected size. Molecular weight markers are reported on the left.

Figure 12:
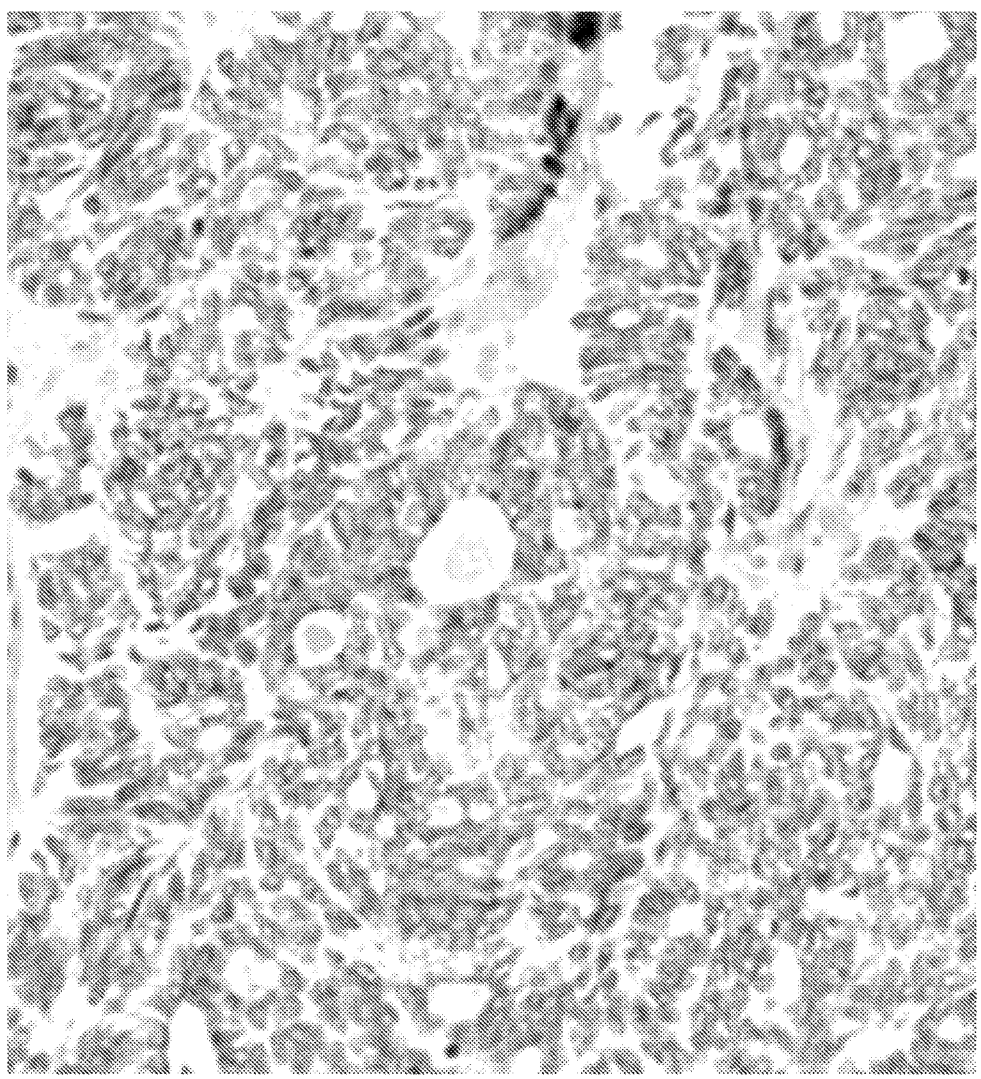

FIG. 12. Staining of ovary tumor TMA with anti-FLJ42986 antibodies

In the case of the ovarian sample, both tumor and normal cells are represented on the same image. The antibody stains specifically tumor cells (in dark gray); negative or poor staining is visible in normal cells.

Figure 13:
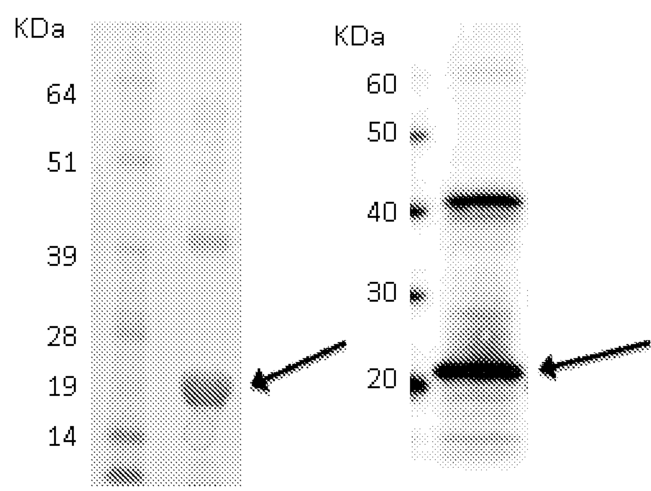

FIG. 13. Analysis of purified COL20A1 recombinant protein

Left panel: Comassie staining of purified His-tag COL20A1 fusion protein separated by SDS-PAGE; Right panel: WB on the recombinant COL20A1 protein stained with anti-COL20A1 antibody. Arrow marks the protein band of the expected size. The high molecular weight band is consistent with the formation of protein dimer. Molecular weight markers are reported on the left.

Figure 14:
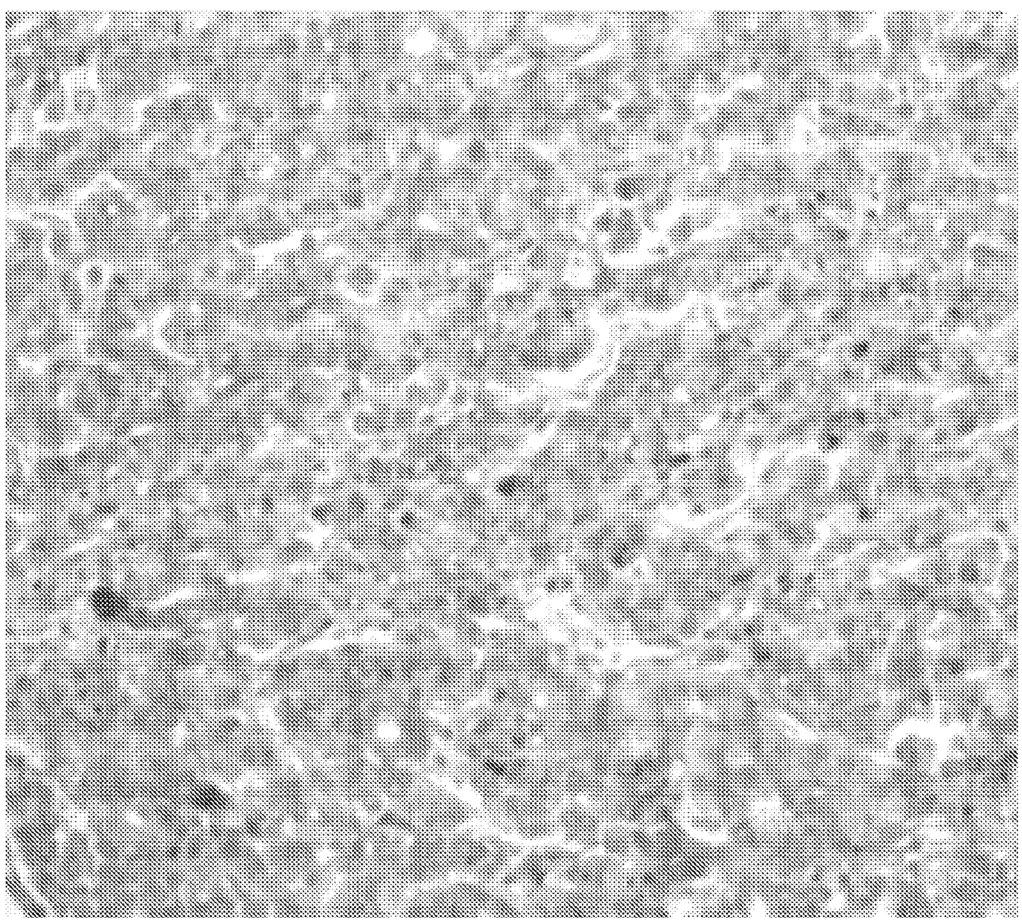

FIG. 14. Staining of ovary tumor TMA with anti-COL20A1 antibodies

In the case of the ovarian sample, both tumor and normal cells are represented on the same image. The antibody stains specifically tumor cells (in dark gray); negative or poor staining is visible in normal cells.

Figure 15:
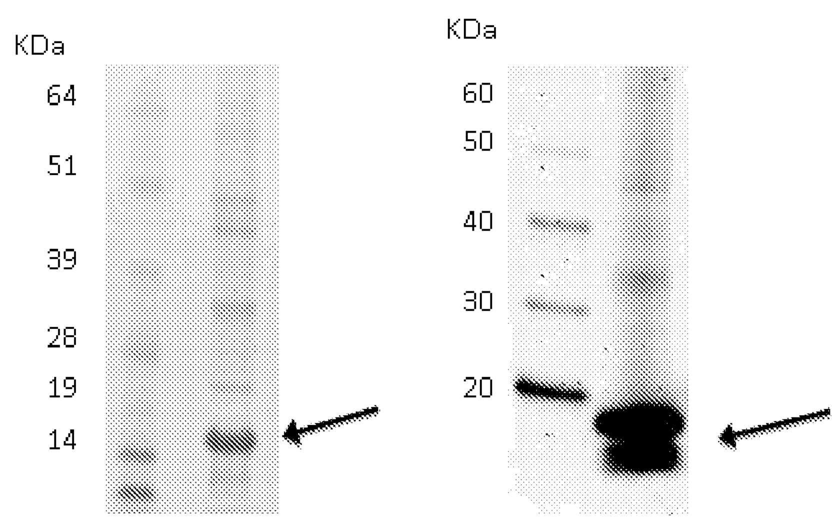

FIG. 15. Analysis of purified GLT25D2 recombinant protein

Left panel: Comassie staining of purified His-tag GLT25D2 fusion protein separated by SDS-PAGE; Right panel: WB on the recombinant GLT25D2 protein stained with anti-GLT25D2 antibody. Arrow marks the protein band of the expected size. Molecular weight markers are reported on the left.

Figure 16:
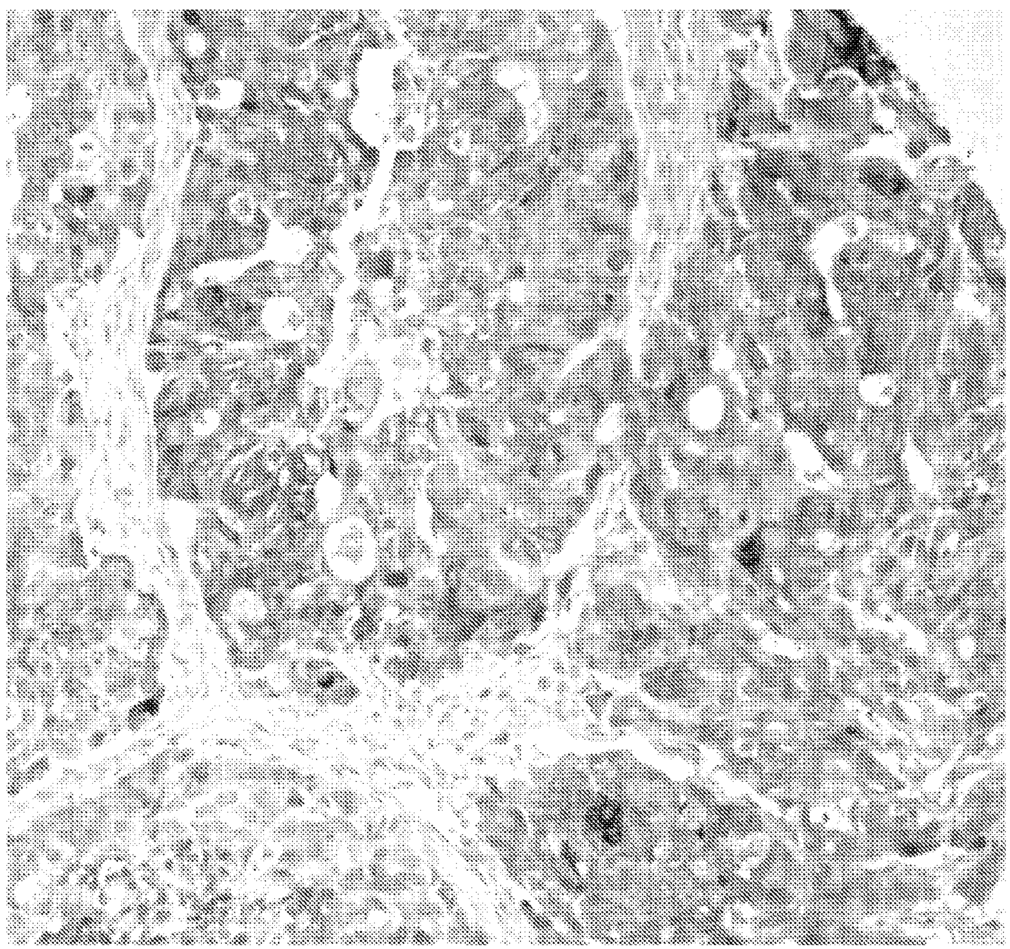

FIG. 16. Staining of ovary tumor TMA with anti-GLT25D2 antibodies

In the case of the ovarian sample, both tumor and normal cells are represented on the same image. The antibody stains specifically tumor cells (in dark gray); negative or poor staining is visible in normal cells.

Figure 17:
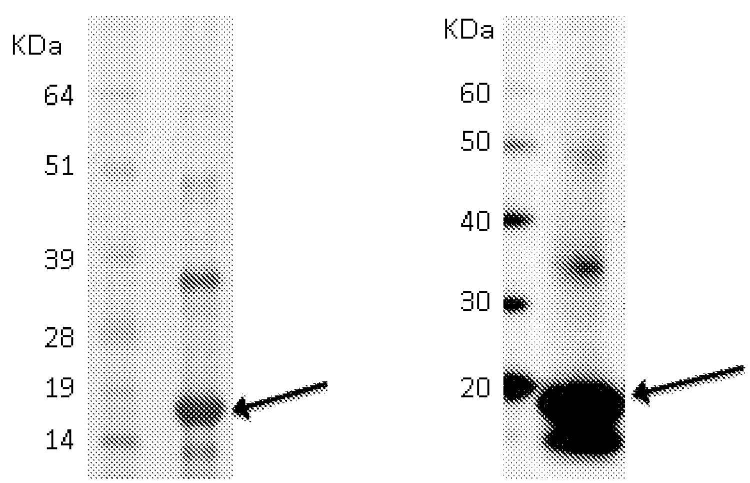

FIG. 17. Analysis of purified SYTL3 recombinant protein

Left panel: Comassie staining of purified His-tag SYTL3 fusion protein expressed; Right panel: WB on the recombinant SYTL3 protein stained with anti-SYTL3 antibody. Arrow marks the protein band of the expected size. Molecular weight markers are reported on the left.

Figure 18:
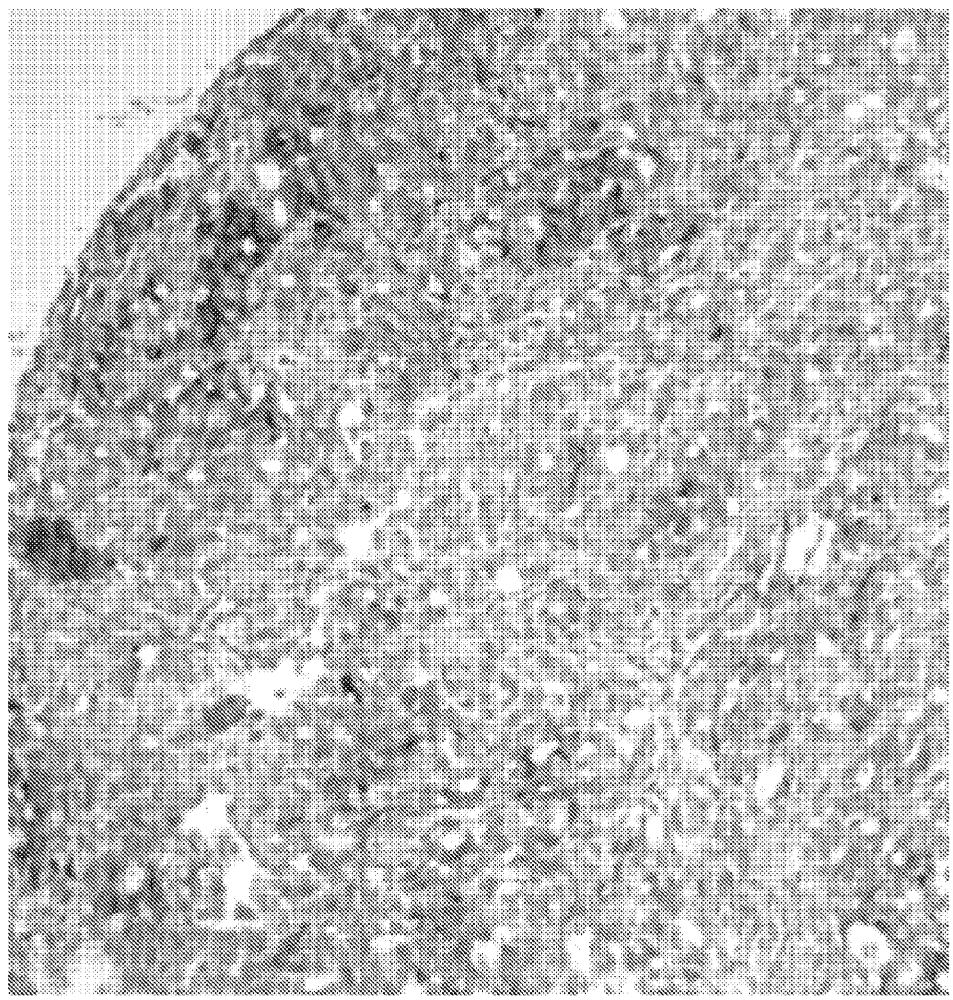

FIG. 18. Staining of ovary tumor TMA with anti-SYTL3 antibodies

In the case of the ovarian sample, both tumor and normal cells are represented on the same image. The antibody stains specifically tumor cells (in dark gray); negative or poor staining is visible in normal cells.

Figure 19:
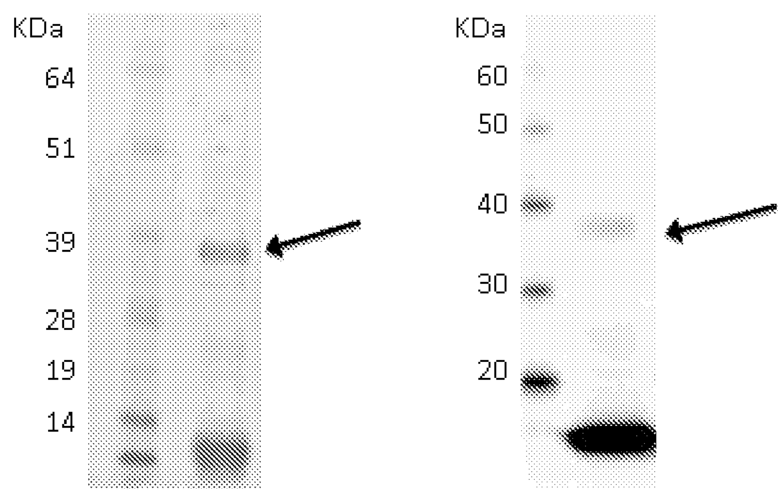

FIG. 19. Analysis of purified DENND1B recombinant protein

Left panel: Comassie staining of purified His-tag DENND1B fusion protein separated by SDS-PAGE; Right panel: WB on the recombinant DENND1B protein stained with anti-DENND1B antibody. Arrow marks the protein band of the expected size. The low molecular weight band corresponds to partially degraded forms of the protein. Molecular weight markers are reported on the left.

Figure 20:
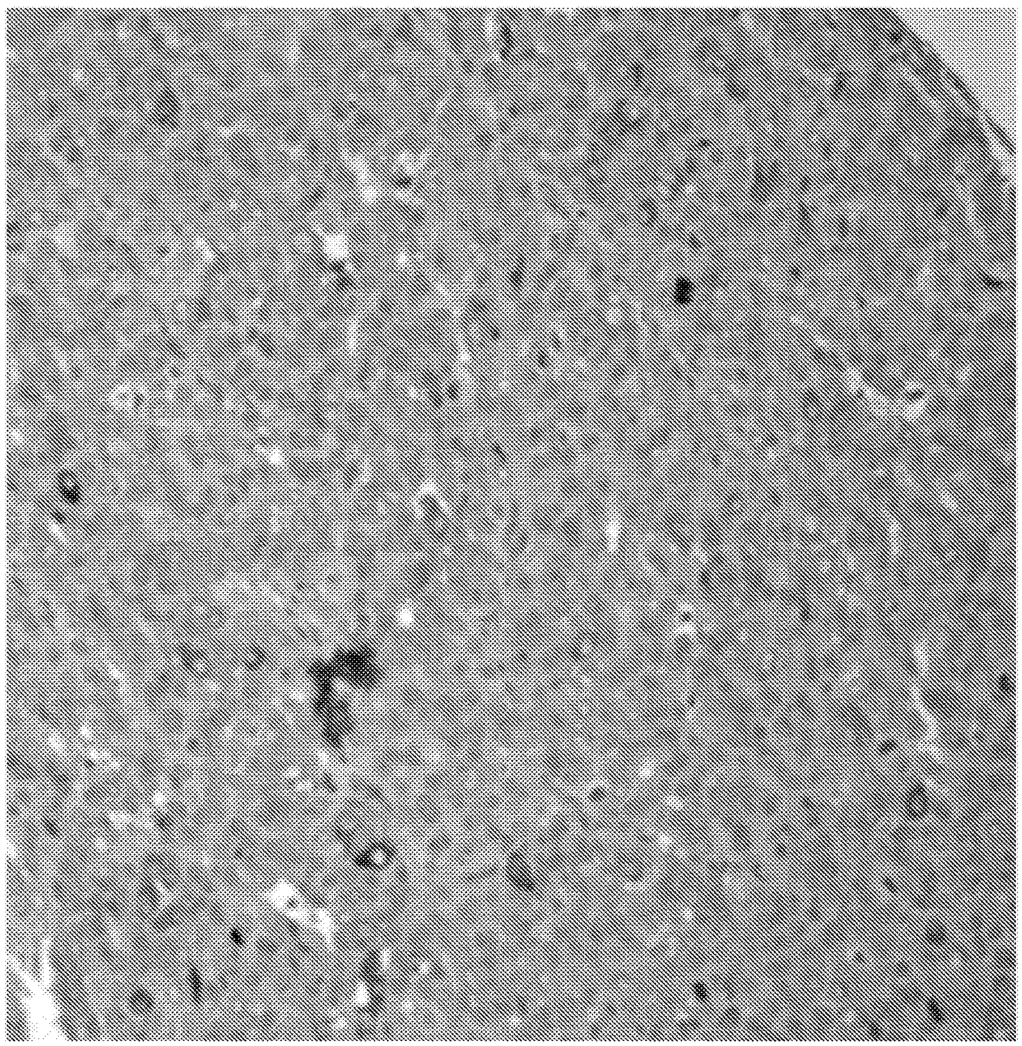

FIG. 20. Staining of ovary tumor TMA with anti DENND1B antibodies

In the case of the ovarian sample, both tumor and normal cells are represented on the same image. The antibody stains specifically tumor cells (in dark gray); negative or poor staining is visible in normal cells.

Figure 21:
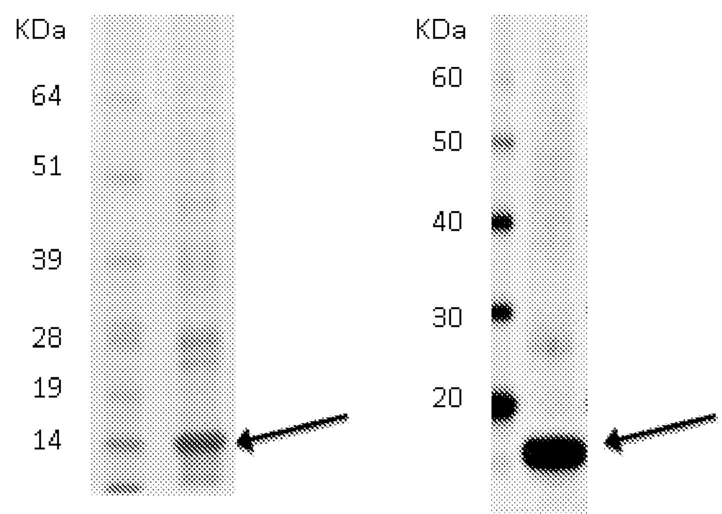

FIG. 21. Analysis of purified FLJ37107 recombinant protein

Left panel: Comassie staining of purified His-tag FLJ37107 fusion protein separated by SDS-PAGE; Right panel: WB on the recombinant protein stained with anti-FLJ37107 antibody. Arrow marks the protein band of the expected size. Molecular weight markers are reported on the left.

Figure 22:
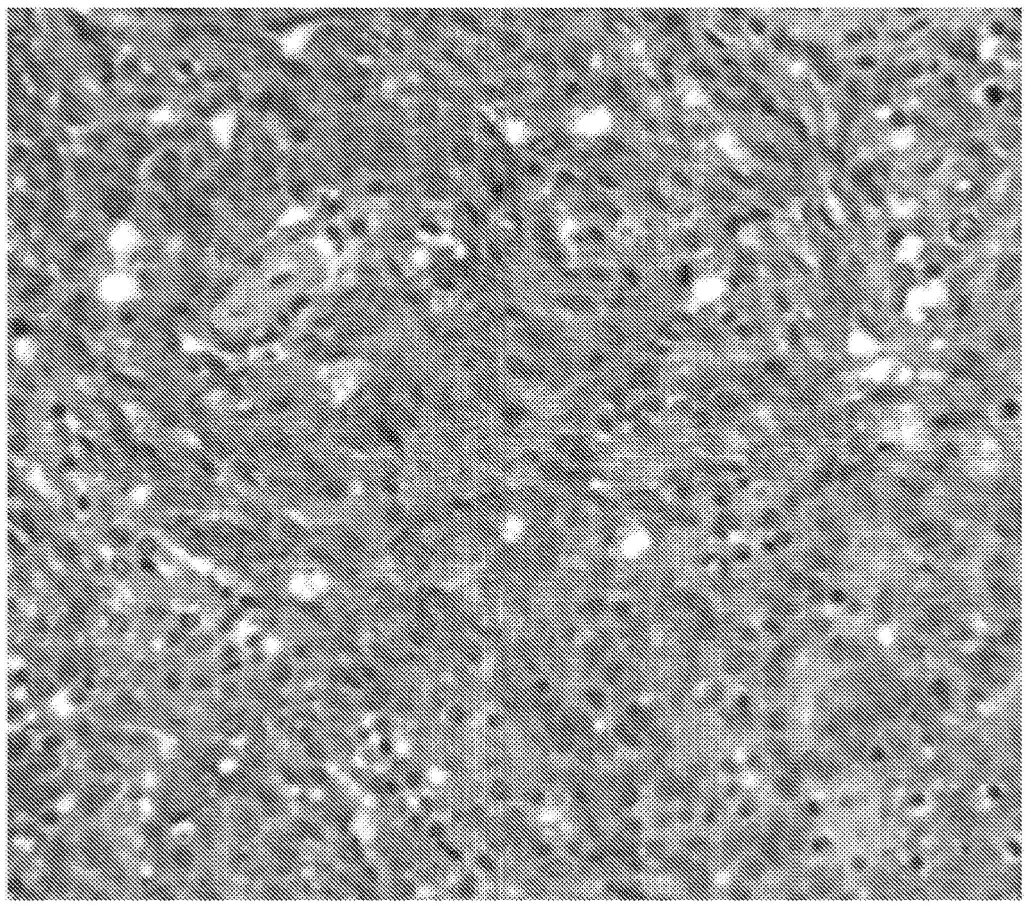

FIG. 22. Staining of ovary tumor TMA with anti-FLJ37107 antibodies

In the case of the ovarian sample, both tumor and normal cells are represented on the same image. The antibody stains specifically tumor cells (in dark gray); negative or poor staining is visible in normal cells.

Figure 23:
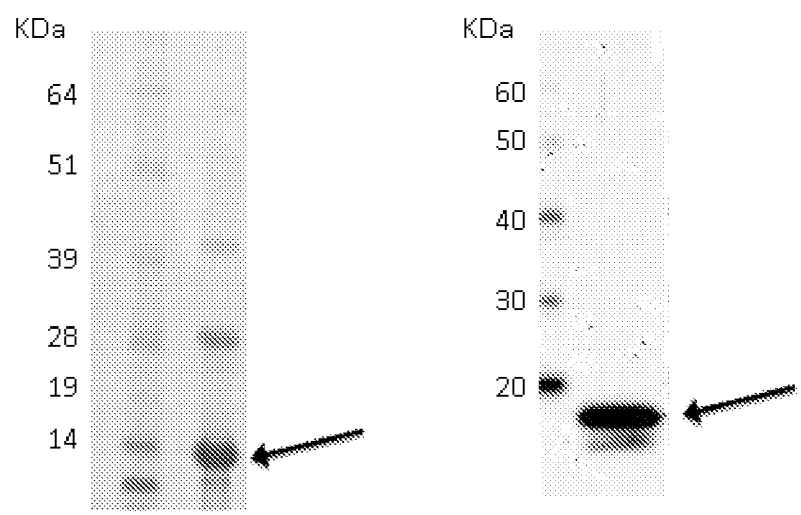

FIG. 23. Analysis of purified C6orf98 recombinant protein

Left panel: Comassie staining of purified His-tag C6orf98 fusion protein separated by SDS-PAGE; Right panel: WB on the recombinant C6orf98 protein stained with anti-C6orf98 antibody. Arrow marks the protein band of the expected size. Molecular weight markers are reported on the left.

Figure 24:
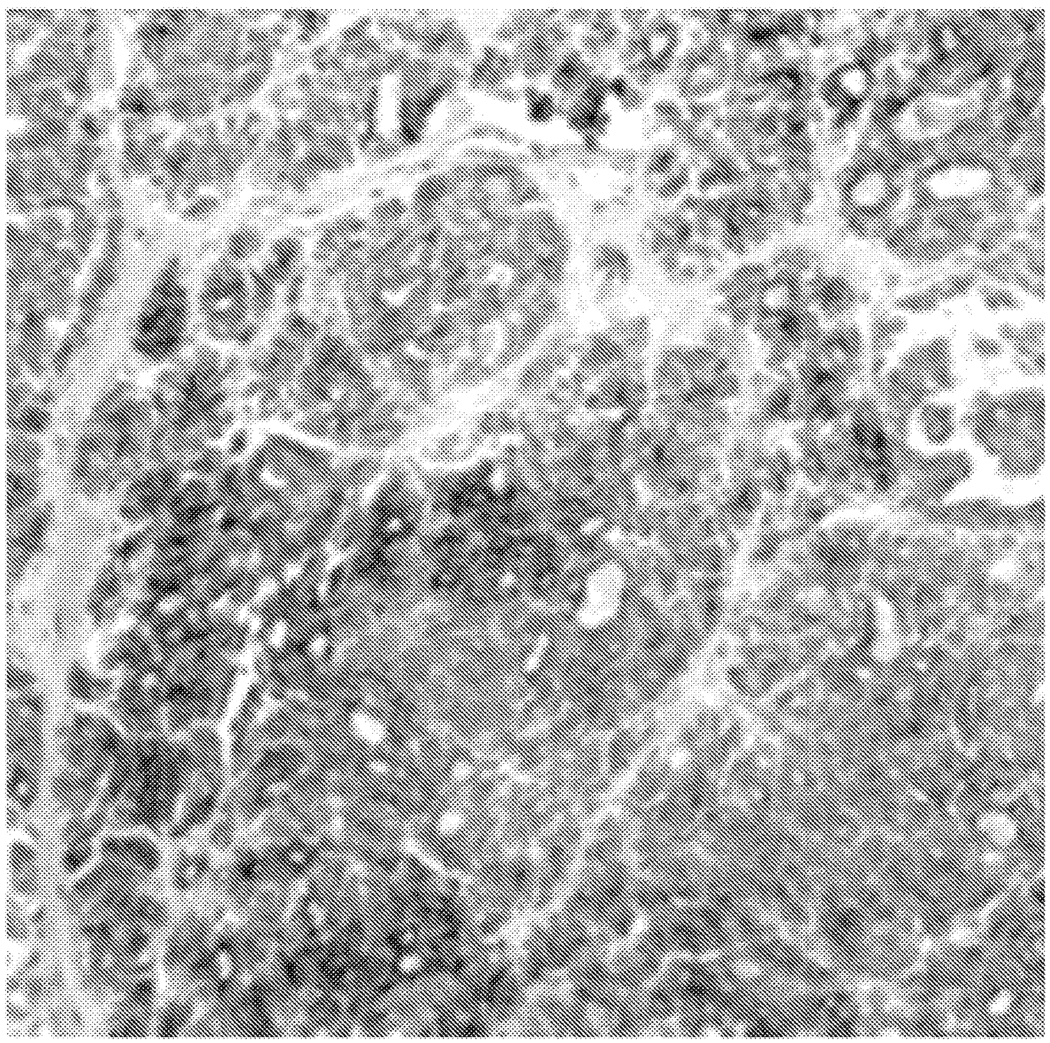

FIG. 24. Staining of ovary tumor TMA with anti-C6orf98 antibodies

In the case of the ovarian sample, both tumor and normal cells are represented on the same image. The antibody stains specifically tumor cells (in dark gray); negative or poor staining is visible in normal cells.

Figure 25:
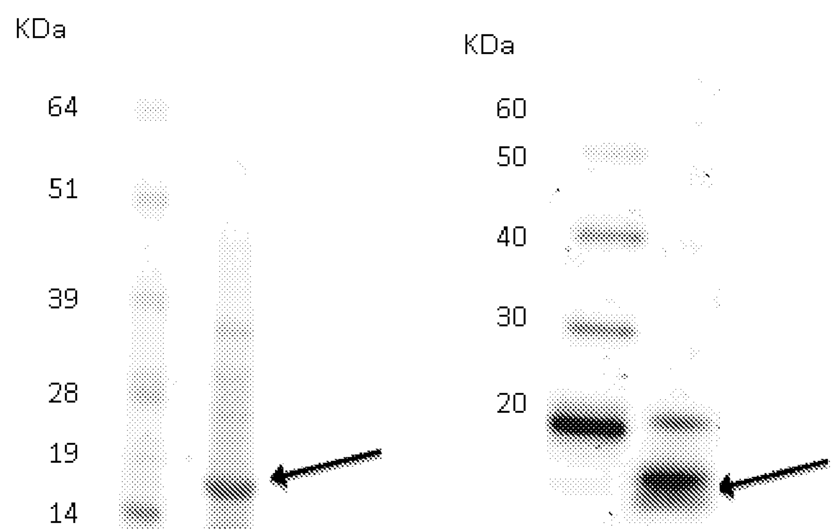

FIG. 25. Analysis of purified Fam69B recombinant protein

Left panel: Comassie staining of purified His-tag Fam69B fusion protein separated by SDS-PAGE; Right panel: WB on the recombinant Fam69B protein stained with anti-Fam69B antibody. Arrow marks the protein band of the expected size. Molecular weight markers are reported on the left.

Figure 26:
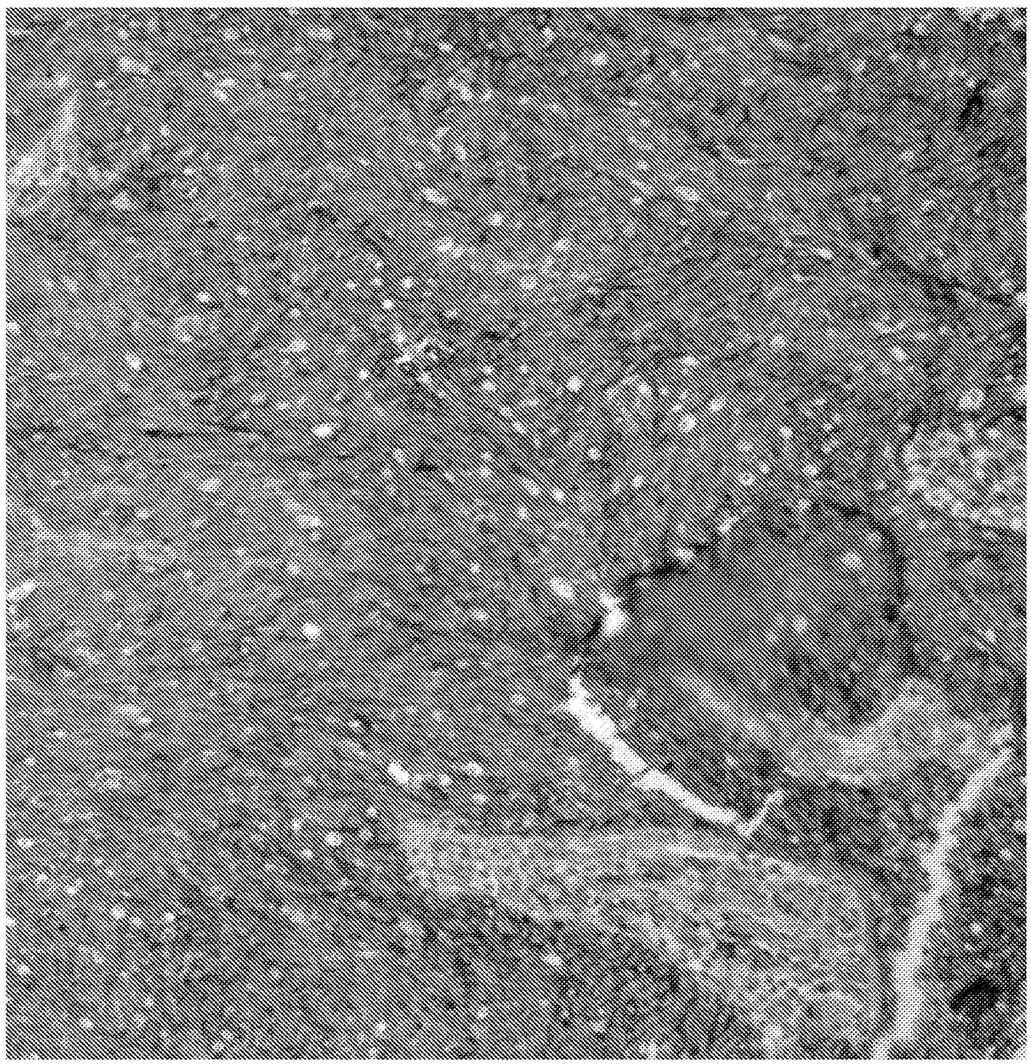

FIG. 26. Staining of ovary tumor TMA with anti-Fam69B antibodies

In the case of the ovarian sample, both tumor and normal cells are represented on the same image. The antibody stains specifically tumor cells (in dark gray); negative or poor staining is visible in normal cells.

Figure 27:
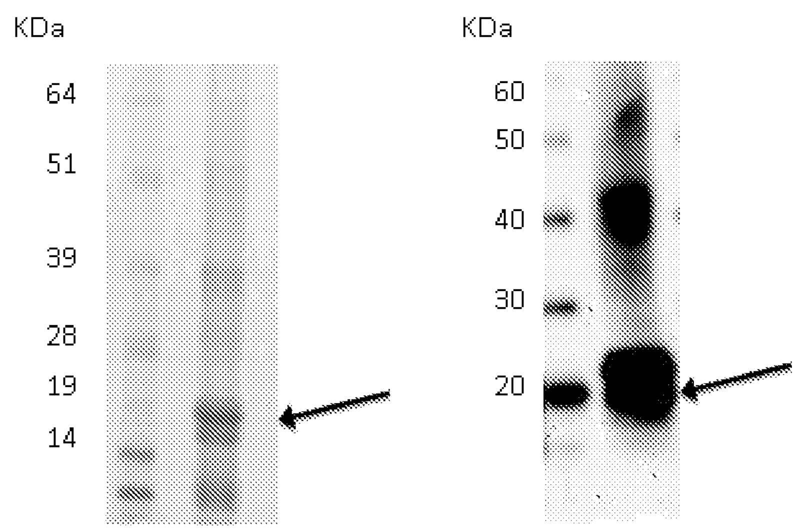

FIG. 27. Analysis of purified EMID1 recombinant protein

Left panel: Comassie staining of purified His-tag EMID1 fusion protein separated by SDS-PAGE; Right panel: WB on the recombinant EMID1 protein stained with anti-EMID1 antibody. Arrow marks the protein band of the expected size. Molecular weight markers are reported on the left.

Figure 28:
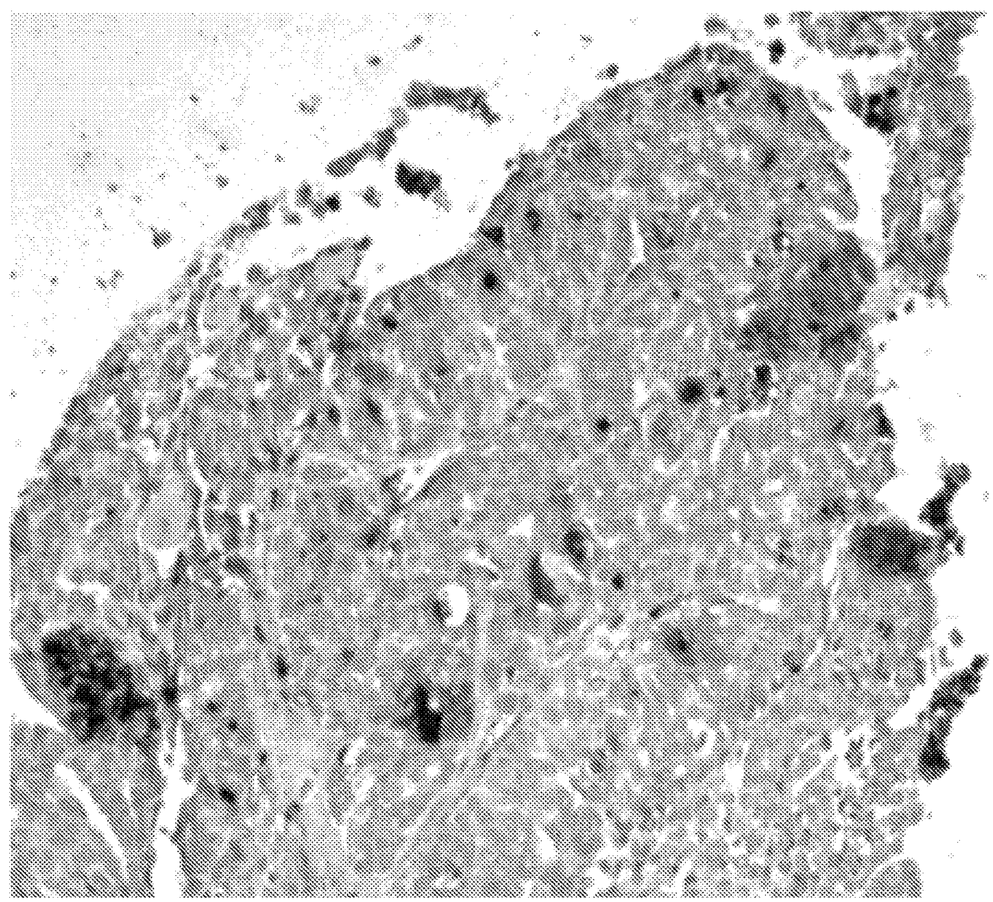

FIG. 28. Staining of ovary tumor TMA with anti-EMID1 antibodies

In the case of the ovarian sample, both tumor and normal cells are represented on the same image. The antibody stains specifically tumor cells (in dark gray); negative or poor staining is visible in normal cells.

Figure 29:
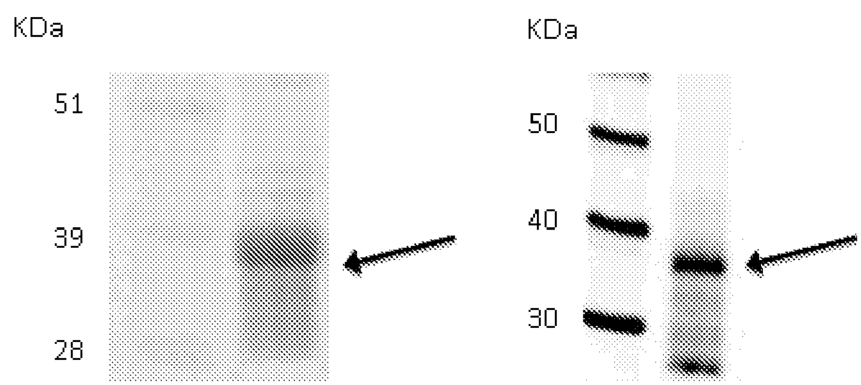

FIG. 29. Analysis of purified KLRG2 recombinant protein

Left panel: Comassie staining of purified His-tag KLRG2 fusion protein separated by SDS-PAGE; Right panel: WB on the recombinant protein stained with anti-KLRG2 antibody. Arrow marks the protein band of the expected size. Molecular weight markers are reported on the left.

Figure 30:
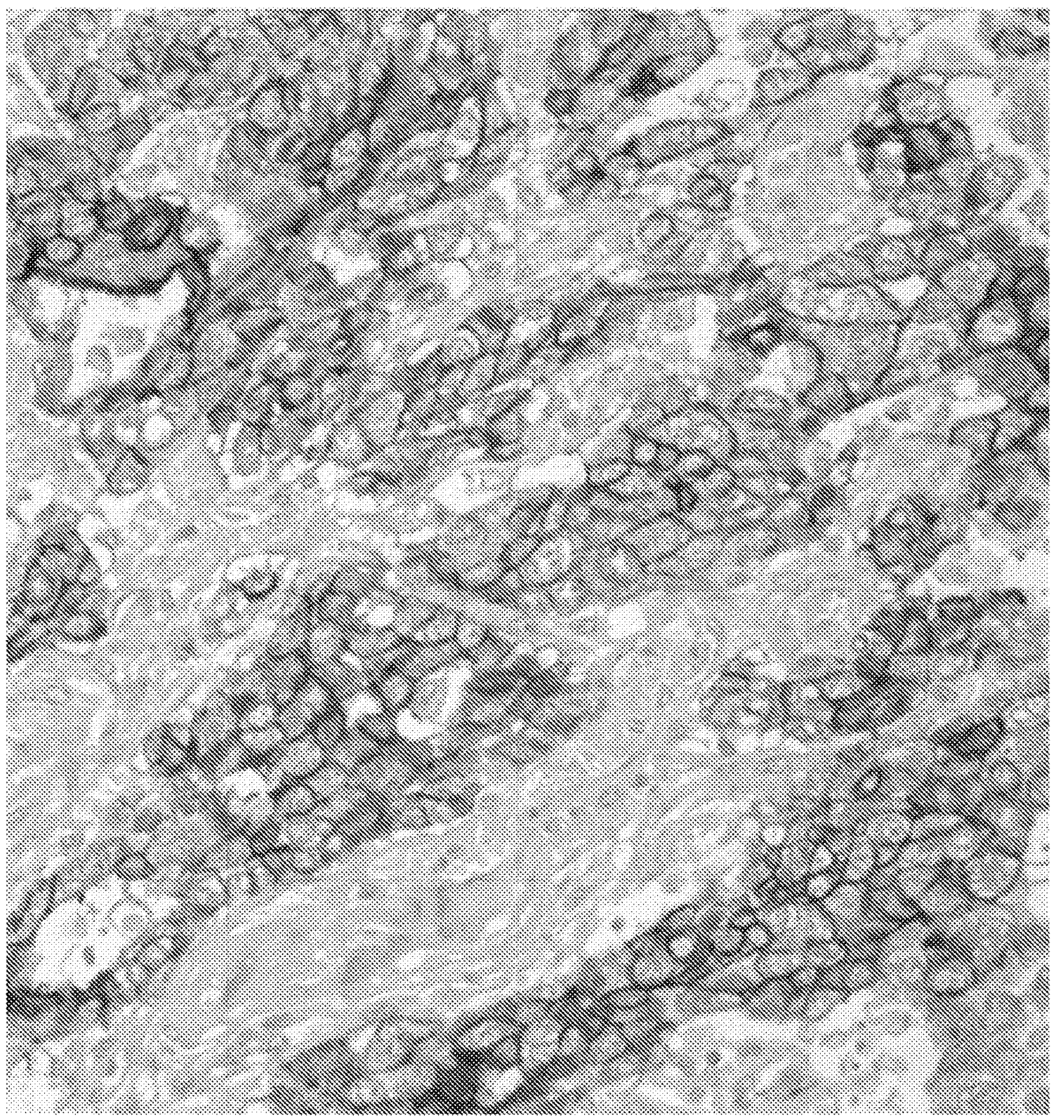

FIG. 30. Staining of ovary tumor TMA with anti-KLRG2 antibodies

In the case of the ovarian sample, both tumor and normal cells are represented on the same image. The antibody stains specifically tumor cells (in dark gray) and the stain clearly delineates the plasma membrane; negative or poor staining is visible in normal cells.

Figure 31:
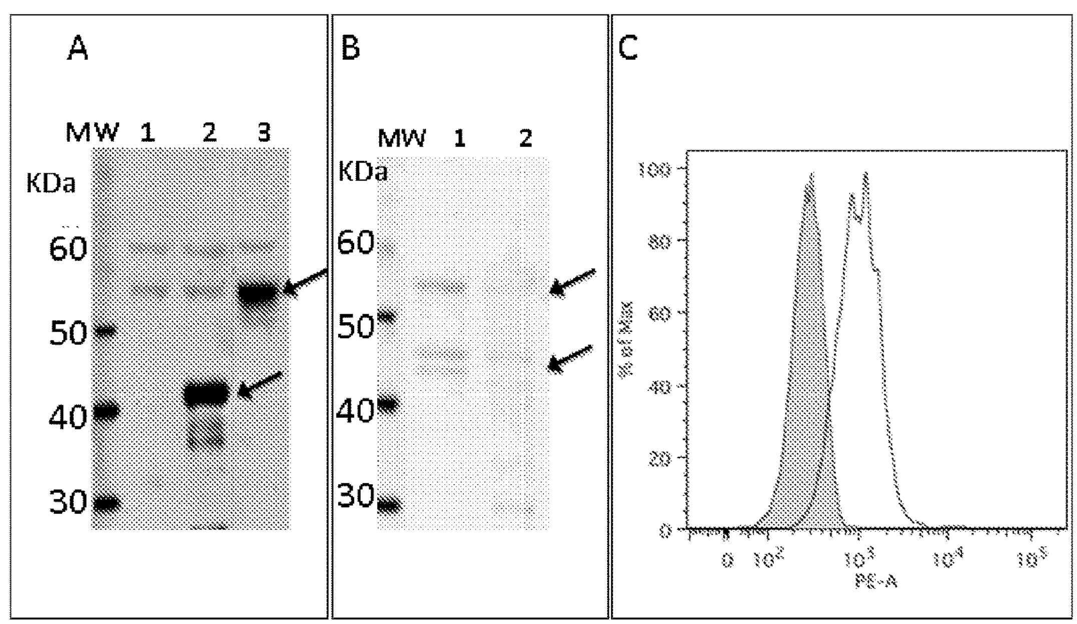

FIG. 31. Expression and localization of KLRG2 in tumor cell lines

Panel A. KLRG2 expression in transfected HeLa cells. Western blot analysis of KLRG2 expression in total protein extracts separated by SDS-PAGE from HeLa cells (corresponding to $2\times10^5$ cells) transfected with the empty pcDNA3 vector (lane 1), with the plasmid construct encoding the isoform 2 of the KLRG2 gene (lane 2); or with the plasmid construct encoding the isoform 1 of the KLRG2 gene (lane 3);

Panel B. KLRG2 expression in ovary-derived tumor cell lines. Western blot analysis of KLRG2 expression in total protein extracts separated by SDS-PAGE from OVCAR-5 (lane 1) and from OVCAR-8 tumor cells (corresponding to $2\times10^5$ cells) (lane 2);

Panel C. Surface exposure of KLRG2 in tumor cell lines. Flow cytometry analysis of KLRG2 cell surface localization in OVCAR-8 cells stained with a negative control antibody (filled curve or with anti-KLRG2 antibody (empty curve). X axis, Fluorescence scale; Y axis, Cells (expressed as percentage relatively to major peaks).

Figure 32:
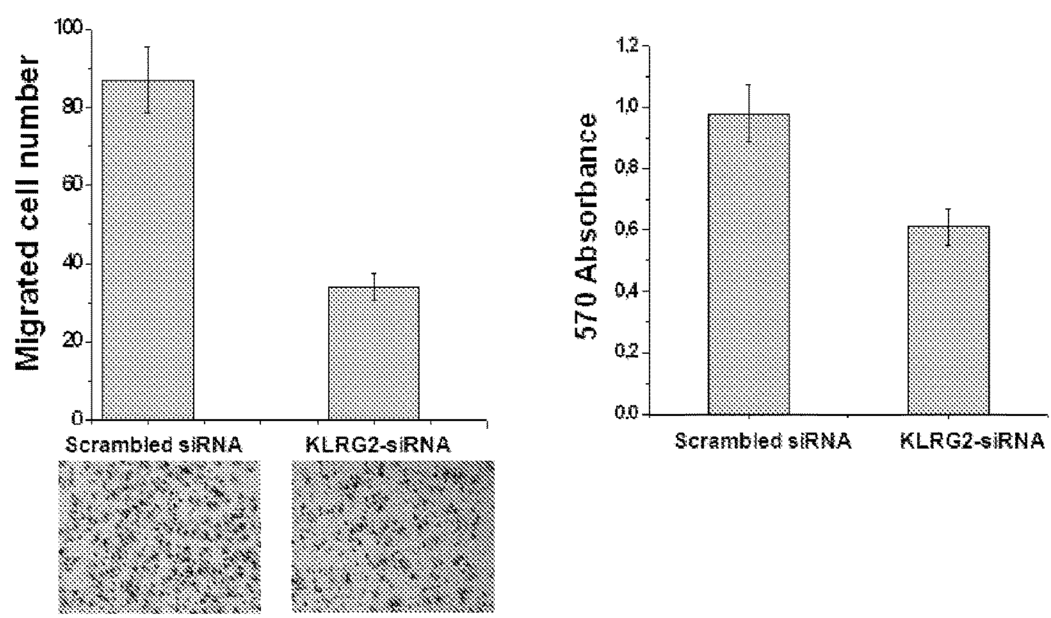

FIG. 32. KLRG2 confer malignant cell phenotypes

The proliferation and the migration/invasive phenotypes of MCF7 cell line were assessed after transfection with KLRG2-siRNA and a scrambled siRNA control using the MTT and the Boyden in vitro invasion assay, respectively.

Panel A. Cell migration/invasiveness measured by the Boyden migration assay. The graph represents the reduced migration/invasiveness of MCF7 treated with the KLRG2 specific siRNA. Small boxes below the columns show the visual counting of the migrated cells.

Panel B. Cell proliferation determined by the MTT incorporation assay. The graph represents the reduced proliferation of the MCF7 tumor cells upon treatment with KLRG2-siRNA, as determined by spectrophotometric reading.

Figure 33:
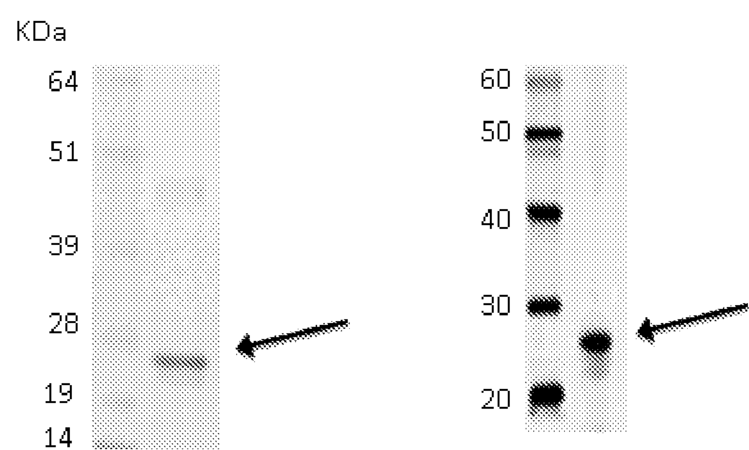

FIG. 33. Analysis of purified ERMP1 recombinant protein

Left panel: Comassie staining of purified His-tag ERMP1 fusion protein separated by SDS-PAGE; Right panel: WB on the recombinant protein stained with anti-ERMP1 antibody. Arrow marks the protein band of the expected size. Molecular weight markers are reported on the left.

Figure 34:
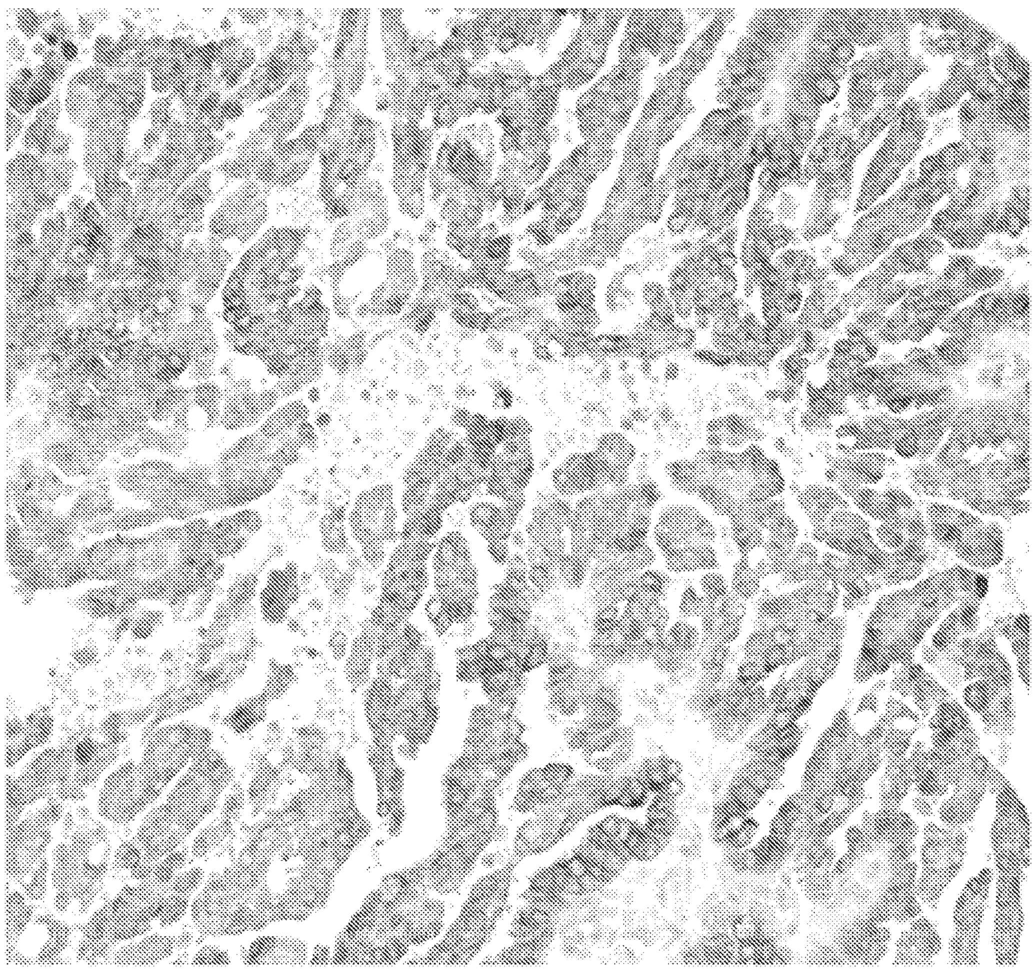

FIG. 34. Staining of ovary tumor TMA with anti-ERMP1 antibodies

In the case of the ovarian sample, both tumor and normal cells are represented on the same image. The antibody stains specifically tumor cells (in dark gray) and the stain clearly delineates the plasma membrane; negative or poor staining is visible in normal cells.

Figure 35:
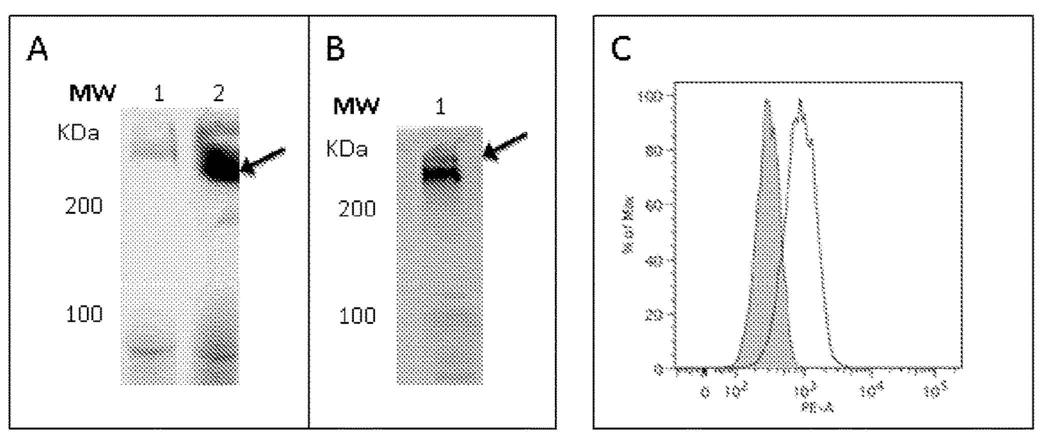

FIG. 35. Expression and localization of ERMP1 in tumor cell lines

Panel A. ERMP1 expression in transfected HEK-293T cells. Western blot analysis of ERMP1 expression in total protein extracts separated by SDS-PAGE from HEK-293T cells (corresponding to $2\times10^5$ cells) transfected with the empty pcDNA3 vector (lane 1) or with the plasmid construct encoding the ERMP1 gene (lane 2).

Panel B. Western blot analysis of ERMP1 expression in total protein extracts separated by SDS-PAGE from OVCAR-4 tumor cells (corresponding to $2\times10^5$ cells) (lane 1). Arrow marks the ERMP1 band. Molecular weight markers are reported on the left.

Panel C. Flow cytometry analysis of ERMP1 cell surface localization in OVCAR-8 tumor cells stained with a negative control antibody (filled curve or with anti-ERMP1 antibody (empty curve). X axis, Fluorescence scale; Y axis, Cells (expressed as % relatively to major peaks).

Figure 36:
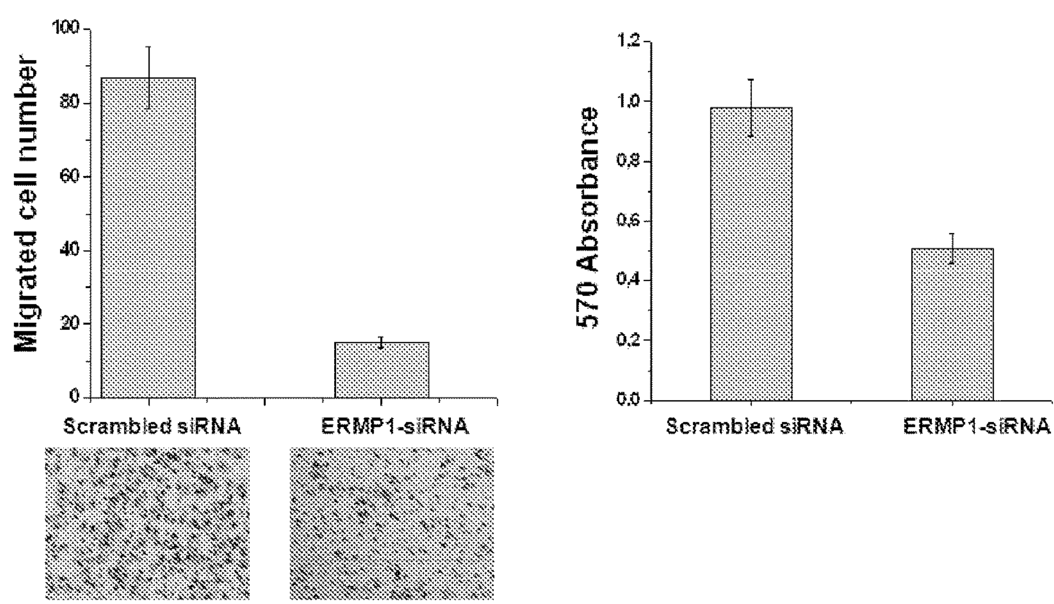

FIG. 36. ERMP1 confers malignant cell phenotypes

The proliferation and the invasive properties of the MCF7 cell line were assessed after transfection with ERMP1-siRNA and a scramble siRNA control using the MTT and the Boyden in vitro invasion assay, respectively.

Panel A. Cell migration/invasiveness measured by the Boyden migration assay. The graph represents the reduced migration/invasiveness of MCF7 treated with the ERMP1-specific siRNA. Small boxes below the columns show the visual counting of the migrated cells.

Panel B. Cell proliferation determined by the MTT incorporation assay. The graph represents the reduced proliferation of the MCF7 tumor cells upon treatment with ERMP1-siRNA, as determined by spectrophotometric reading.

Figure 37:
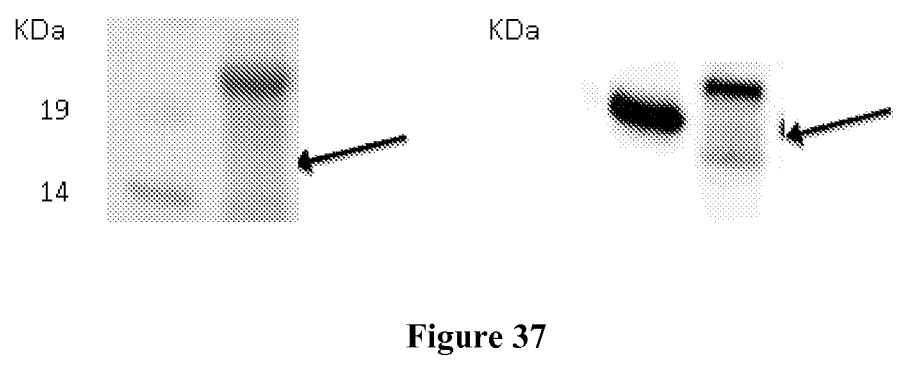

FIG. 37. Analysis of purified VMO1 recombinant protein

Figure 38:
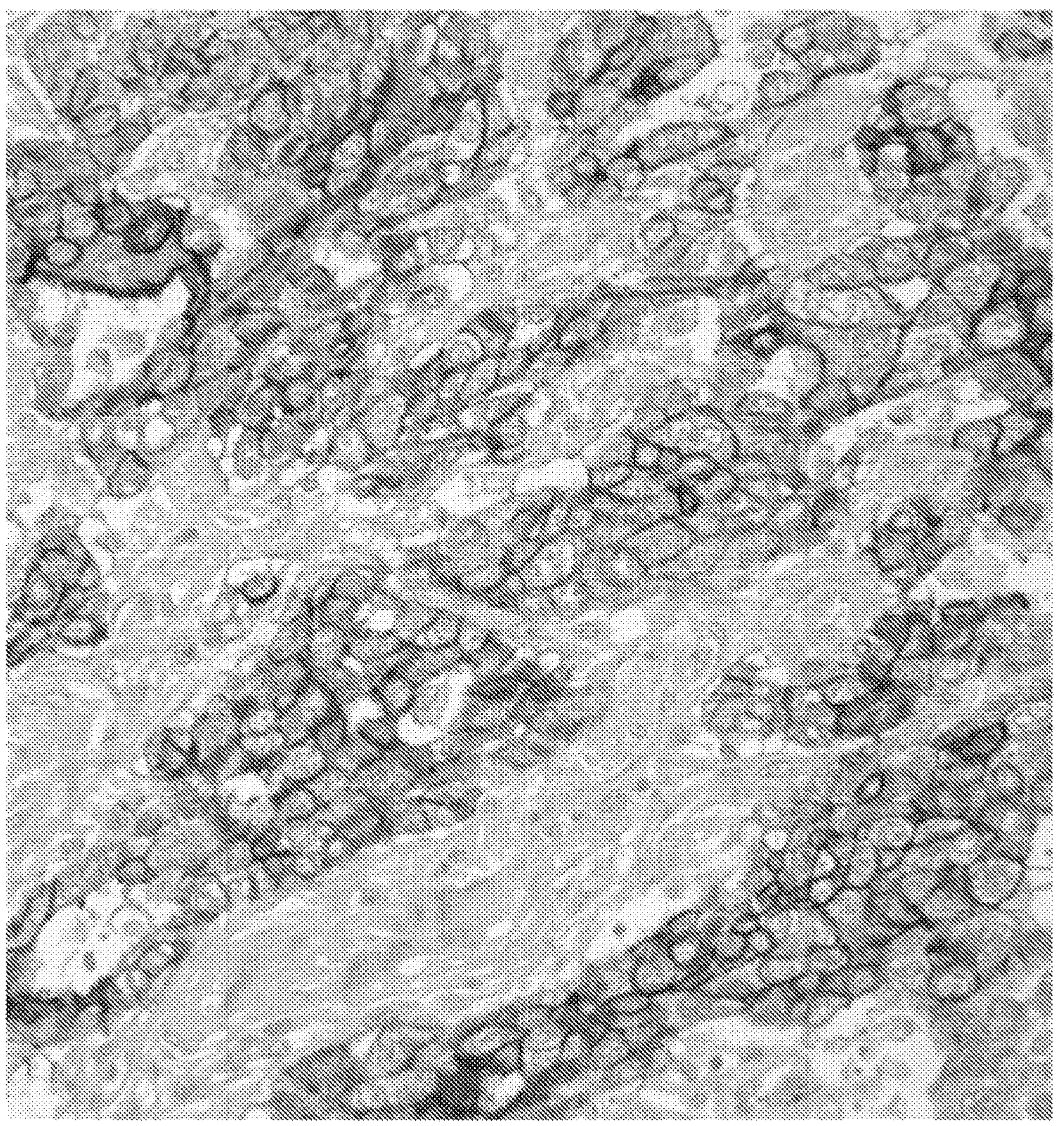

Left panel: Comassie staining of purified His-tag VMO1 fusion protein separated by SDS-PAGE; Right panel: WB on the purified VMO1 protein stained with a specific antibody. Arrow marks the protein band of the expected size. Molecular weight markers are reported on the left FIG. 38. Staining of ovary tumor TMA with anti-VMO1 antibodies In the case of the ovarian sample, both tumor and normal cells are represented on the same image. The antibody stains specifically tumor cells (in dark gray); negative or poor staining is visible in normal cells.

The following examples further illustrate the invention.

EXAMPLES

Example 1. Generation of Recombinant Human Protein Antigens and Antibodies to Identify Tumor Markers Methods The entire coding region or suitable fragments of the genes encoding the target proteins, were designed for cloning and expression using bioinformatic tools with the human genome sequence as template (Lindskog M et al (2005)). Where present, the leader sequence for secretion was replaced with the ATG codon to drive the expression of the recombinant proteins in the cytoplasm of *E. coli*. For cloning, genes were PCR-amplified from clones derived from the Mammalian Gene Collection (mgc.nci.nih.gov/) or from cDNA mixtures generated from pools of total RNA derived from Human testis, Human placenta, Human bone marrow, Human fetal brain, using specific primers. Clonings were designed so as to fuse a 10 histidine tag sequence at the 5' end, annealed to in house developed vectors, derivatives of vector pSP73 (Promega) adapted for the T4 ligation independent cloning method (Nucleic Acids Res. 1990 Oct. 25; 18(20): 6069-6074) and used to transform *E. coli* NovaBlue cells recipient strain. *E. coli* transformants were plated onto selective LB plates containing 100 g/ml ampicillin (LB Amp) and positive *E. coli* clones were identified by restriction enzyme analysis of purified plasmid followed by DNA sequence analysis. For expression, plasmids were used to transform BL21-(DE3) *E. coli* cells and BL21-(DE3) *E. coli* cells harboring the plasmid were inoculated in ZYP-5052 growth medium (Studier, 2005) and grown at 37° C. for 24 hours. Afterwards, bacteria were collected by centrifugation, lysed into B-Per Reagent containing 1 mM MgCl2, 100 units DNAse I (Sigma), and 1 mg/ml lysozyme (Sigma). After 30 min at room temperature under gentle shaking, the lysate was clarified by centrifugation at 30,000 g for 40 min at 4° C. All proteins were purified from the inclusion bodies by resuspending the pellet coming from lysate centrifugation in 40 mM TRIS-HCl, 1 mM TCEP {Tris(2-carboxyethyl)-phosphine hydrochloride, Pierce} and 6M guanidine hydrochloride, pH 8 and performing an IMAC in denaturing conditions. Briefly, the resuspended material was clarified by centrifugation at 30.000 g for 30 min and the supernatant was loaded on 0.5 ml columns of Ni-activated Chelating Sepharose Fast Flow (Pharmacia). The column was washed with 50 mM TRIS-HCl buffer, 1 mM TCEP, 6M urea, 60 mM imidazole, 0.5M NaCl, pH 8. Recombinant proteins were eluted with the same buffer containing 500 mM imidazole. Proteins were analyzed by SDS-Page and their concentration was determined by Bradford assay using the BIORAD reagent (BIORAD) with a bovine serum albumin standard according to the manufacturer's recommendations.

To generate antisera, the purified proteins were used to immunize CD1 mice (6 week-old females, Charles River laboratories, 5 mice per group) intraperitoneally, with 3 protein doses of 20 micrograms each, at 2 week-interval. Freund's complete adjuvant was used for the first immunization, while Freund's incomplete adjuvant was used for the two booster doses. Two weeks after the last immunization animals were bled and sera collected from each animal was pooled.

Results

Gene fragments of the expected size were obtained by PCR from specific clones of the Mammalian Gene Collection or, alternatively, from cDNA generated from pools of total RNA derived from Human testis, Human placenta, Human bone marrow, Human fetal brain, using primers specific for each gene.

In particular, for the SLC39A10 gene, a DNA fragment corresponding to nucleotides 154-1287 of the transcript ENST00000359634 and encoding a protein of 378 residues, corresponding to the amino acid region from 26 to 403 of ENSP00000352656 sequence was obtained.

For the GPR107 gene, a fragment corresponding to nucleotides 291 to 968 of the transcript ENST00000347136 and encoding a protein of 226 residues, corresponding to the amino acid region from 39 to 264 of ENSP00000336988 sequence was obtained.

For the DPY19L3 gene, a fragment corresponding to nucleotides 158 to 463 of the transcript ENST00000392250 and encoding a protein of 102 residues, corresponding to the amino acid region from 1 to 102 of ENSP00000376081 sequence was obtained.

For the FLJ42986 gene, a fragment corresponding to nucleotides 1287 to 1717 of the transcript ENST00000376826 and encoding protein of 144 residues, corresponding to the amino acid region from 30 to 173 of ENSP00000366022 sequence was obtained.

For the COL20A1 gene, a fragment corresponding to nucleotides 577 to 1095 of the transcript ENST00000354338 and encoding a protein of 173 residues, corresponding to the amino acid region from 193 to 365 of ENSP00000346302 sequence was obtained.

For the GLT25D2 gene, a fragment corresponding to nucleotides 454 to 831 of the transcript ENST00000361927 and encoding a protein of 126 residues, corresponding to the amino acid region from 25 to 153 of ENSP00000354960 sequence was obtained.

For the SYTL3 gene, a fragment corresponding to nucleotides 267 to 569 of the transcript ENST00000360448 and encoding a protein of 101 residues, corresponding to the amino acid region from 50 to 150 of ENSP00000353631 sequence was obtained.

For the DENND1B gene, a fragment corresponding to nucleotides 563 to 1468 of the transcript ENST00000235453 and encoding a protein of 302 residues, corresponding to the amino acid region from 95 to 396 of ENSP00000235453 sequence was obtained.

For the FLJ37107 gene, a fragment corresponding to nucleotides 661-972 of the transcript gi|58218993|ref|NM_001010882.1 and encoding a protein of 104 residues, corresponding to the amino acid region from 1 to 104 of gi|58218994|ref|NP_001010882.1 sequence was obtained.

For the C6orf98 gene, a fragment corresponding to nucleotides 67 to 396 of the transcript ENST00000409023 and encoding a protein of 110 residues, corresponding to the amino acid region from 22 to 132 of ENSP00000386324 sequence was obtained.

For the Fam69B gene, a fragment corresponding to nucleotides 233 to 688 of the transcript ENST00000371692 and encoding a protein of 152 residues, corresponding to the amino acid region from 49 to 200 of ENSP00000360757 sequence was obtained.

For the EMID1 gene, a fragment corresponding to nucleotides 203 to 670 of the transcript OTTHUMT00000075712 and encoding a protein of 156 residues, corresponding to the amino acid region from 33 to 188 of OTTHUMP00000028901 sequence was obtained.

For the KLRG2 gene, a fragment corresponding to nucleotides 70 to 849 of the transcript ENST00000340940 and encoding a protein of 260 residues, corresponding to the amino acid region from 1 to 260 of ENSP00000339356 sequence was obtained.

For the ERMP1 gene, a fragment corresponding to nucleotides 55 to 666 of the transcript ENST00000339450 and encoding a protein of 204 residues, corresponding to the amino acid region from 1 to 204 of ENSP00000340427 sequence was obtained.

For the VMO1 gene, a fragment corresponding to nucleotides 157 to 690 of the transcript ENST00000328739 and encoding a protein of 178 residues corresponding to the amino acid region from 25-202 of ENSP00000328397 sequence was obtained.

A clone encoding the correct amino acid sequence was identified for each gene/gene fragment and, upon expression in *E. coli*, a protein of the correct size was produced and subsequently purified using affinity chromatography (FIGS. 1; 5; 8; 11; 13; 15; 17; 19; 21; 23; 25, 27, 29, 33, 37, left panels). As shown in the figures, in some case SDS-PAGE analysis of affinity-purified recombinant proteins revealed the presence of extra bands, of either higher and/or lower masses. Mass spectrometry analysis confirmed that they corresponded to either aggregates or degradation products of the protein under analysis.

Figure 1:
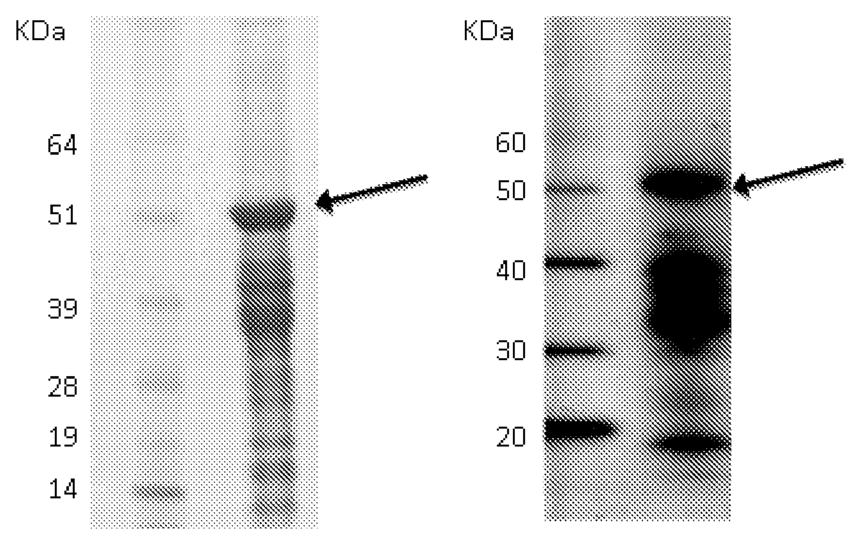
FIG. 1. Analysis of purified SLC39A10 recombinant protein

Antibodies generated by immunization specifically recognized their target proteins in Western blot (WB) (FIGS. 1; 5; 8; 11; 13; 15; 17; 19; 21; 23; 25, 27, 29, 33, 37, right panels).

Example 2. Tissue Profiling by Immune-Histochemistry

Methods

The analysis of the antibodies' capability to recognize their target proteins in tumor samples was carried out by Tissue Micro Array (TMA), a miniaturized immuno-histochemistry technology suitable for HTP analysis that allows to analyze the antibody immuno-reactivity simultaneously on different tissue samples immobilized on a microscope slide.

Since the TMAs include both tumor and healthy tissues, the specificity of the antibodies for the tumors can be immediately appreciated. The use of this technology, differently from approaches based on transcription profile, has the important advantage of giving a first hand evaluation on the potential of the markers in clinics. Conversely, since mRNA levels not always correlate with protein levels (approx. 50% correlation), studies based on transcription profile do not provide solid information regarding the expression of protein markers.

A tissue microarray was prepared containing formalin-fixed paraffin-embedded cores of human tissues from patients affected by ovary cancer and analyzed using the specific antibody sample. In total, the TMA design consisted in 20 ovary tissue samples from 5 well pedigreed patients, each including both tumor and normal epithelium (equal to four tumor samples from each patient) to identify promising target molecules differentially expressed in cancer and normal cells. The direct comparison between tumor and normal epithelium of each patient allowed the identification of antibodies that stain specifically tumor cells and provided indication of target expression in ovary tumor. To confirm the association of each protein with ovary tumors a tissue microarray was prepared containing 100 formalin-fixed paraffin-embedded cores of human ovary tissues from 50 patients (equal to two tissue samples from each patient).

All formalin fixed, paraffin embedded tissues used as donor blocks for TMA production were selected from the archives at the IEO (Istituto Europeo Oncologico, Milan). Corresponding whole tissue sections were examined to confirm diagnosis and tumour classification, and to select representative areas in donor blocks. Normal tissues were defined as microscopically normal (non-neoplastic) and were generally selected from specimens collected from the vicinity of surgically removed tumors. The TMA production was performed essentially as previously described (Kononen J et al (1998) Nature Med. 4:844-847; Kallioniemi O P et al (2001) Hum. MoI. Genet. 10:657-662). Briefly, a hole was made in the recipient TMA block. A cylindrical core tissue sample (1 mm in diameter) from the donor block was acquired and deposited in the recipient TMA block. This was repeated in an automated tissue arrayer "Galileo TMA CK 3500" BioRep (Milan) until a complete TMA design was produced. TMA recipient blocks were baked at 42<0> C for 2 h prior to sectioning. The TMA blocks were sectioned with 2-3 mm thickens using a waterfall microtome (Leica), and placed onto poli-L-lysinated glass slides for immunohistochemical analysis. Automated immunohistochemistry was performed as previously described (Kampf C. et al (2004) Clin. Proteomics 1:285-300). In brief, the glass slides were incubated for 30' min in 60° C., de-paraffinized in xylene (2×15 min) using the Bio-Clear solution (Midway. Scientific, Melbourne, Australia), and re-hydrated in graded alcohols. For antigen retrieval, slides were immersed 0.01 M Na-citrate buffer, pH 6.0 at 99° C. for 30 min Slides were placed in the Autostainer® (DakoCytomation) and endogenous peroxidase was initially blocked with 3% H2O2, for 5 min. Slides were then blocked in Dako Cytomation Wash Buffer containing 5% Bovine serum albumin (BSA) and subsequently incubated with mouse antibodies for 30' (dilution 1:200 in Dako Real™ dilution buffer). After washing with DakoCytomation wash buffer, slides were incubated with the goat anti-mouse peroxidase conjugated Envision® for 30 min each at room temperature (DakoCytomation). Finally, diaminobenzidine (DakoCytomation) was used as chromogen and Harris hematoxylin (Sigma-Aldrich) was used for counterstaining. The slides were mounted with Pertex® (Histolab).

The staining results have been evaluated by a trained pathologist at the light microscope, and scored according to both the percentage of immunostained cells and the intensity of staining. The individual values and the combined score (from 0 to 300) were recorded in a custom-tailored database. Digital images of the immunocytochemical findings have been taken at a Leica DM LB light microscope, equipped with a Leica DFC289 color camera.

Results

The results from tissue profiling showed that the antibodies specific for the recombinant proteins (see Example 1) are strongly immunoreactive on ovary cancer tissues from patients with varying frequencies, indicating the presence of the target proteins in tumors tissues, while no or poor reactivity was detected in normal tissues.

Based on this finding, the detection of target proteins in tissue samples can be associated with the specific tumor/s. In some cases the antibody staining accumulated at the plasma membrane of tumor cells, providing a first indication of the cell localization of target proteins. The capability of target-specific antibodies to stain different tumor tissues is summarized in Table I. Representative examples of microscopic enlargements of tissue samples stained by each antibody are reported in FIGS. 2; 6; 9; 12; 14; 16; 18, 20; 22; 24; 26, 28, 30, 34, 38.

Table I reports the percentage of positive ovarian tumor samples after staining with the target-specific antibodies

TABLE I

| Gene | Percentage of ovary tumor samples showing positive IHC staining |
|---|---|
| SLC39A10 | 80 |
| GPR107 | 40 |
| DPY19L3 | 93 |
| FLJ42986 | 80 |
| COL20A1 | 20 |
| GLT25D2 | 20 |
| SYTL3 | 60 |
| DENND1B | 20 |
| FLJ3710 | 80 |
| C6orf98 | 100 |
| Fam69B | 73 |
| EMID1 | 20* |
| KLRG2 | 29** |
| ERMP1 | 69** |
| VMO1 | 20** |

*The antibody specifically stains secretion products of ovary tumor cells indicating that the corresponding protein is released by tumor cells.
**The antibody stains the plasma membrane of tumor cells

Example 3. Expression of Target Proteins in Transfected Mammalian Cells

Methods

The specificity of the antibodies for each target proteins was assessed by western blot and/or confocal microscopy analysis of eukaryotic cells transiently transfected with a plasmid construct containing the complete sequence of the gene encoding the target proteins. Examples of this type of confocal microscopy experiments are represented for SLC39A10 (corresponding to Transcript ID ENST00000359634), KLRG2 (two cloned sequences corresponding to Transcripts ENST00000340940 and ENST00000393039, corresponding to two transcript variants), ERMP1 (cloned sequence corresponding to Transcripts ENST00000339450).

For cloning, cDNA were generated from pools of total RNA derived from Human testis, Human placenta, Human bone marrow, Human fetal brain, in reverse transcription reactions and the entire coding regions were PCR-amplified with specific primers pairs. PCR products were cloned into plasmid pcDNA3 (Invitrogen). HeLa and Hek-293T cells were grown in DMEM-10% FCS supplemented with 1 mM Glutamine were transiently transfected with preparation of the resulting plasmid and with the empty vector as negative control using the Lipofectamine-2000 transfection reagent (Invitrogen). After 48 hours, cells were collected and analysed by Western blot or confocal microscopy. For Western blot, cells were lysed with PBS buffer containing 1% Triton X100 and total cell extracts (corresponding to $1\times10^6$ cells) were separated on pre-cast SDS-PAGE gradient gels (NuPage 4-12% Bis-Tris gel, Invitrogen) under reducing conditions, followed by electro-transfer to nitrocellulose membranes (Invitrogen) according to the manufacturer's recommendations. The membranes were blocked in blocking buffer composed of 1×PBS-0.1% Tween 20 (PBST) added with 10% dry milk, for 1 h at room temperature, incubated with the antibody diluted 1:2500 in blocking buffer containing 1% dry milk and washed in PBST-1%. The secondary HRP-conjugated antibody (goat anti-mouse immunoglobulin/HRP, Perkin Elmer) was diluted 1:5000 in blocking buffer and chemiluminescence detection was carried out using a Chemidoc-IT UVP CCD camera (UVP) and the Western Lightning™ cheminulescence Reagent Plus (Perkin Elmer), according to the manufacturer's protocol.

For confocal microscopy analysis, the cells were plated on glass cover slips and after 48 h were washed with PBS and fixed with 3% p-formaldehyde solution in PBS for 20 min at RT. For surface staining, cells were incubated overnight at 4° C. with polyclonal antibodies (1:200). The cells were then stained with Alexafluor 488-labeled goat anti-mouse antibodies (Molecular Probes). DAPI (Molecular Probes) was used to visualize nuclei; Live/Dead® red fixable (Molecular Probes) was used to visualize membrane. The cells were mounted with glycerol plastine and observed under a laser-scanning confocal microscope (LeicaSP5).

Results

The selected coding sequences for SLC39A10, KLRG2 and ERMP1 were cloned in a eukaryotic expression vector and the derived plasmids were used for transient transfection of HeLa or HEK293T cell lines. Expression of target proteins KLRG2 and ERMP1 was detected in total protein extracts from HeLa and HEK-293T cells, respectively, by Western blot using the protein-specific antibodies. Overall the data confirmed that the marker-specific antibodies recognized specifically their target proteins while no or marginal staining was visible in cell transfected with the empty pcDNA3. In the case of KLRG2, specific protein bands of expected size were detected in cells transfected with either of the two plasmids encoding the two annotated KLRG2 variants (FIG. 31A). As for cells transfected with ERMP1-encoding plasmid, a band of molecular mass higher than expected (theoretical mass of approximately 100 KDa) was specifically detected by the anti-ERMP1 antibody in transfected cells indicating that the protein forms stable aggregates (FIG. 35A). Expression of protein SLC3910 was carried by confocal microscopy of transfected HeLa cells. The anti-SLC39A10 antibody specifically detected its target protein expressed by transfected cells. In particular, the antibody mainly stained the surface of transfected cells (FIG. 3).

Example 4. Expression and Localization of Target Proteins in Tumor Cell Lines Expression of marker genes was assessed by WB and/or flow cytometry analysis of tumor cell lines. Cells were cultured in under ATCC recommended conditions, and sub-confluent cell monolayers were detached with PBS-0.5 mM EDTA for subsequent analysis. For Western blot analysis, cells were lysed by several freeze-thaw passages in PBS-1% Triton. Total protein extracts were loaded on SDS-PAGE ($2\times10^5$ cells/lane), and subjected to WB with specific antibodies as described above. For flow cytometry analysis, cells ($2\times10^4$ per well) were pelletted in 96 U-bottom microplates by centrifugation at 200×g for 5 min at 4° C. and incubated for 1 hour at 4° C. with the appropriate dilutions of the marker-specific antibodies. Cells were washed twice in PBS-5% FCS and incubated for 20 min with the appropriate dilution of R-Phycoerythrin (PE)-conjugated secondary antibodies (Jackson Immuno Research, PA, USA) at 4° C. After washing, cells were analysed by a FACS Canto II flow cytometer (Becton Dickinson). Data were analyzed with FlowJo 8.3.3 program.

Results

Western blot analysis of tumor cells lines is represented for KLRG2, ERMP1 and DPY19L3. Concerning KLRG2, two major protein bands were detected in the ovary tumor cell lines OVCAR-5 and OVCAR-8, that could be ascribed to the annotated protein variants (FIG. 31B). As regards ERMP1 a band of high molecular mass was detected in the OVCAR-4 cell line (FIG. 35B) showing an electrophoretic pattern similar to that reported in transfected cells (see previous example). This further confirms the existence of stable aggregates for this protein As for DPY19L3, a band of expected size was detected by the antibody on a panel of tumor cells lines (FIG. 10, left panel). Expression and localization analysis was also performed by surface staining and flow cytometry analysis of tumor cell lines. Results, represented for SLC39A10, KLRG2, DPY10L3 and ERMP1, show that these proteins were detected on the surface of ovary tumor cell lines by the marker-specific antibodies (FIGS. 4, 31C, 35C and FIG. 10 right panel).

Example 5. Expression of the Marker Proteins Confer Malignant Cell Phenotype

To verify that the proteins included in the present invention can be exploited as targets for therapeutic applications, the effect of marker depletion was evaluated in vitro in cellular studies generally used to define the role of newly discovered proteins in tumor development. Marker-specific knock-down and control tumor cell lines were assayed for their proliferation and the migration/invasive phenotypes using the MTT assays and the Boyden in vitro invasion assay, respectively.

Method

Expression of marker genes were silenced in tumor cell lines by the siRNA technology and the influence of the reduction of marker expression on cell parameters relevant for tumor development was assessed in in vitro assays. The expression of marker genes was knocked down in a panel of epithelial tumor cell lines previously shown to express the tumor markers using a panel of marker-specific siRNAs (whose target sequence is reported in Table II) using the HiPerfect transfection reagent (QIAGEN) following the manufacturer's protocol. As control, cells treated with irrelevant siRNA (scrambled siRNA) were analysed in parallel. At different time points (ranging from 24 to 72 hours) post transfection, the reduction of gene transcription was assessed by quantitative RT-PCR (Q-RT-PCR) on total RNA, by evaluating the relative marker transcript level, using the beta-actin, GAPDH or MAPK genes as internal normalization control. Afterwards, cell proliferation and migration/invasiveness assays were carried out to assess the effect of the reduced marker expression. Cell proliferation was determined using the MTT assay, a colorimetric assay based on the cellular conversion of a tetrazolium salt into a purple colored formazan product. Absorbance of the colored solution can be quantified using a spectrophotometer to provide an estimate of the number of attached living cells. Approximately $5\times10^3$ cells/100 µl were seeded in 96-well plates in DMEM with 10% FCS to allow cell attachment. After overnight incubation with DMEM without FCS, the cells were treated with 2.5% FBS for 72 hours. Four hours before harvest 15 µL of the MTT dye solution (Promega) were added to each well. After 4-hour incubation at 37° C., the formazan precipitates were solubilized by the addition of 100 µL of solubilization solution (Promega) for 1 h at 37° C. Absorbance at 570 nm was determined on a multiwell plate reader (SpectraMax, Molecular Devices).

Cell migration/invasiveness was tested using the Boyden in vitro invasion assay, as compared to control cell lines treated with a scramble siRNA. This assay is based on a chamber of two medium-filled compartments separated by a microporous membrane. Cells are placed in the upper compartment and are allowed to migrate through the pores of the membrane into the lower compartment, in which chemotactic agents are present. After an appropriate incubation time, the membrane between the two compartments is fixed and stained, and the number of cells that have migrated to the lower side of the membrane is determined. For this assay, a transwell system, equipped with 8-µm pore polyvinylpirrolidone-free polycarbonate filters, was used. The upper sides of the porous polycarbonate filters were coated with 50 µg/cm$^2$ of reconstituted Matrigel basement membrane and placed into six-well culture dishes containing complete growth medium. Cells ($1\times10^4$ cells/well) were loaded into the upper compartment in serum-free growth medium. After 16 h of incubation at 37° C., non-invading cells were removed mechanically using cotton swabs, and the microporous membrane was stained with Diff-Quick solution. Chemotaxis was evaluated by counting the cells migrated to the lower surface of the polycarbonate filters (six randomly chosen fields, mean±SD).

Results

Examples of this analysis are reported for ERMP1 and KLRG2 in MCF7 tumor cell line. Gene silencing experiments with marker-specific siRNA reduced the marker transcripts (approximately 30-40 fold reduction), as determined by Q-RT_PCR. Table II below reports the sequences targeted by the siRNA molecules. The reduction of the expression of either of the two genes expression significantly impairs the proliferation and the invasive phenotype of the MCF7 tumor cell line (FIGS. 32 and 36). This indicates that the proteins are involved in tumor development and are therefore likely targets for the development of anti-cancer therapies.

TABLE II

Sequences of the marker-specific siRNA

| NCBI gene | siRNA Target Sequence |
|---|---|
| KLRG2 | CGAGGACAATCTGGATATCAA<br>CTGGAGCCCTCGAGCAAGAAA |
| ERMP1 | CCCGTGGTTCATCTGATATAA<br>AAGGACTTTGCTCGGCGTTTA<br>TACGTGGATGTTTGTAACGTA<br>CTCGTATTGGCTCAATCATAA |

REFERENCES

1) Anderson, L., and Seilhamer, J. (1997). A comparison of selected mRNA and protein abundances in human liver. Electrophoresis 18, 533-537;

2) Chen, G., Gharib, T. G., Wang, H., Huang, C. C., Kuick, R., Thomas, D. G., Shedden, K. A., Misek, D. E., Taylor, J. M., Giordano, T. J., Kardia, S. L., Iannettoni, M. D., Yee, J., Hogg, P. J., Orringer, M. B., Hanash, S. M., and Beer, D. G. (2003) Protein profiles associated with survival in lung adenocarcinoma. Proc. Natl. Acad. Sci. U.S.A 100, 13537-13542;

3) Ginestier, C., Charafe-Jauffret, E., Bertucci, F., Eisinger, F., Geneix, J., Bechlian, D., Conte, N., Adelaide, J., Toiron, Y., Nguyen, C., Viens, P., Mozziconacci, M. J., Houlgatte, R., Birnbaum, D., and Jacquemier, J. (2002) Distinct and complementary information provided by use of tissue and DNA microarrays in the study of breast tumor markers. Am. J. Pathol. 161, 1223-1233;

4) Gygi, S. P., Rochon, Y., Franza, B. R., and Aebersold, R. (1999) Correlation between protein and mRNA abundance in yeast. Mol. Cell. Biol. 19, 1720-1730; Nishizuka, S., Charboneau, L., Young, L., Major, S., Reinhold, W. C., Waltham, M., Kouros-Mehr, H., Bussey, K. J., Lee, J. K., Espina, V., Munson, P. J., Petricoin, E., III, Liotta, L. A., and Weinstein, J. N. (2003) Proteomic profiling of the NCI-60 cancer cell lines using new high-density reverse-phase lysate microarrays. Proc. Natl. Acad. Sci. U.S. A 100, 14229-14234;

5) Tyers, M., and Mann, M. (2003) From genomics to proteomics. Nature 422, 193-197;

6) Kagara N, Tanaka N, Noguchi S, Hirano T. (2007) Zinc and its transporter ZIP10 are involved in invasive behavior of breast cancer cells. Cancer Sci. 98:692-697;

7) Kasper G, Weiser A A, Rump A, Sparbier K, Dahl E, Hartmann A, Wild P, Schwidetzky U, Castaños-Velez E, Lehmann K. (2005) Expression levels of the putative zinc transporter LIV-1 are associated with a better outcome of breast cancer patients. Int J Cancer. 117:961-973;

8) Sladek R, Rocheleau G, Rung J, Dina C, Shen L, Serre D, Boutin P, Vincent D, Belisle A, Hadjadj S, Balkau B, Heude B, Charpentier G, Hudson T J, Montpetit A, Pshezhetsky A V, Prentki M, Posner B I, Balding D J, Meyre D, Polychronakos C, Froguel P. (2007) A genome-wide association study identifies novel risk loci for type 2 diabetes. Nature. 445:881-885;

9) Garcia-Rudaz, C., Luna, F., Tapia, V., Kerr, B., Colgin, L., Galimi, F., Dissen, G. A., Rawlings, N. D. and Ojeda, S. R. (2007) Fxna, a novel gene differentially expressed in the rat ovary at the time of folliculogenesis, is required for normal ovarian histogenesis. Development. 134, 945-957;

10) Nicholas B, Skipp P, Mould R, Rennard S, Davies D E, O'Connor C D, Djukanovi R. (2006) Shotgun proteomic analysis of human-induced sputum. (2006) Proteomics. 6:4390-4401;

11) Adachi J, Kumar C, Zhang Y, Olsen J V, Mann M. The human urinary proteome contains more than 1500 proteins including a large proportion of membranes proteins. (2006) Genome Biol. 7:R80.

The invention claimed is:

1. A method comprising:

(a) providing a sample of an ovarian tissue from a subject;

(b) detecting in the sample of the ovarian tissue a higher level of expression of a tumor marker selected from a polypeptide comprising a sequence that is at least 95% identical over the full length of the amino acid sequence set forth in SEQ ID NO:85 or SEQ ID NO:86, as compared to expression of the tumor marker in a non-malignant ovarian tissue control sample, wherein the detecting is performed by immunohistochemical analysis using an antibody that specifically binds to the tumor marker; and (c) administering to the subject a therapeutic agent for treatment of an ovarian malignancy, wherein the therapeutic agent comprises a small inhibitory ribonucleic acid (siRNA) molecule that comprises a sequence complementary to SEQ ID NO:103 or 104.

2. The method of claim 1, wherein the sample of the ovarian tissue is from a human subject.

3. A method comprising:

(a) providing a sample of an ovarian tissue from a subject;

(b) detecting in the sample of the ovarian tissue a higher level of expression of KLRG2 protein or mRNA, as compared to a non-malignant ovarian tissue control sample; and (c) administering to the subject a therapeutic agent for treatment of an ovarian malignancy, wherein the therapeutic agent comprises a small inhibitory ribonucleic acid (siRNA) molecule that comprises a sequence complementary to SEQ ID NO:103 or 104.

4. The method of claim 3, wherein the subject is a human subject.

5. The method of claim 3, wherein the expression of KLRG2 protein is detected by an immunoradiometric, immunoenzymatic or immunohistochemical assay.

6. The method of claim 3, wherein the expression of KLRG2 mRNA is detected by polymerase chain reaction (PCR).

7. The method of claim 3, wherein the KLRG2 protein comprises a sequence that is at least 95% identical to the amino acid sequence set forth in SEQ ID NO:85 or 86.

8. The method of claim 3, wherein the siRNA molecule has a sequence complementary to the nucleic acid sequence set forth in SEQ ID NO: 87 or SEQ ID NO: 88.

9. The method of claim 1, wherein the tumor marker is selected from a polypeptide comprising a sequence that is identical over the full length of the amino acid sequence set forth in SEQ ID NO:85 or SEQ ID NO:86.

10. The method of claim 3, wherein the KLRG2 protein comprises a sequence that is at least 95% identical to the amino acid sequence set forth in SEQ ID NO:85 or 86.

11. A method comprising:

(a) providing a sample of an ovarian tissue from a subject;

(b) detecting in the sample of the ovarian tissue a higher level of expression as compared to a non-malignant ovarian tissue control sample, of at least five different tumor markers selected from the group consisting of a polypeptide comprising an amino acid sequence that is at least 95% identical over the full length of:

i) SEQ ID NO:1 or SEQ ID NO:2;

ii) SEQ ID NO:5, SEQ ID NO:6, or SEQ ID NO:7;

iii) SEQ ID NO:11, SEQ ID NO:12, SEQ ID NO:13, or SEQ ID NO:14;

iv) SEQ ID NO:19;

v) SEQ ID NO:21, SEQ ID NO:22, or SEQ ID NO:23;

vi) SEQ ID NO:27, SEQ ID NO:28, SEQ ID NO:29, or SEQ ID NO:30;

vii) SEQ ID NO:35, SEQ ID NO:36, or SEQ ID NO:37;

viii) SEQ ID NO:41, SEQ ID NO:42, SEQ ID NO:43, or SEQ ID NO:44;

ix) SEQ ID NO:49;

x) SEQ ID NO:51;

xi) SEQ ID NO:53 or SEQ ID NO:54;

xii) SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, or SEQ ID NO:70;

xiii) SEQ ID NO:85 or SEQ ID NO:86;

xiv) SEQ ID NO:89, SEQ ID NO:90, or SEQ ID NO:91; and xv) SEQ ID NO:95, SEQ ID NO:96, SEQ ID NO:97, or SEQ ID NO:98, wherein the detecting is performed by immunohistochemical analysis using antibodies that specifically bind to the at least five different tumor markers; and (c) administering to the subject a therapeutic agent for treatment of an ovarian malignancy, wherein the therapeutic agent comprises a small inhibitory ribonucleic acid (siRNA) molecule that comprises a sequence complementary to SEQ ID NO:103 or 104.

* * * * *

SEQUENCE LISTING

<160> NUMBER OF SEQ ID NOS: 108

<210> SEQ ID NO 1
<211> LENGTH: 831
<212> TYPE: PRT
<213> ORGANISM: Homo sapiens

<400> SEQUENCE: 1

Met Lys Val His Met His Thr Lys Phe Cys Leu Ile Cys Leu Leu Thr
1 5 10 15

Phe Ile Phe His His Cys Asn His Cys His Glu Glu His Asp His Gly
20 25 30

Pro Glu Ala Leu His Arg Gln His Arg Gly Met Thr Glu Leu Glu Pro
35 40 45

Ser Lys Phe Ser Lys Gln Ala Ala Glu Asn Glu Lys Lys Tyr Tyr Ile
50 55 60

Glu Lys Leu Phe Glu Arg Tyr Gly Glu Asn Gly Arg Leu Ser Phe Phe
65 70 75 80

Gly Leu Glu Lys Leu Leu Thr Asn Leu Gly Leu Gly Glu Arg Lys Val
85 90 95

Val Glu Ile Asn His Glu Asp Leu Gly His Asp His Val Ser His Leu
100 105 110

Asp Ile Leu Ala Val Gln Glu Gly Lys His Phe His Ser His Asn His
115 120 125

Gln His Ser His Asn His Leu Asn Ser Glu Asn Gln Thr Val Thr Ser
130 135 140

Val Ser Thr Lys Arg Asn His Lys Cys Asp Pro Glu Lys Glu Thr Val
145 150 155 160

Glu Val Ser Val Lys Ser Asp Asp Lys His Met His Asp His Asn His
165 170 175

Arg Leu Arg His His His Arg Leu His His His Leu Asp His Asn Asn
180 185 190

Thr His His Phe His Asn Asp Ser Ile Thr Pro Ser Glu Arg Gly Glu
195 200 205

Pro Ser Asn Glu Pro Ser Thr Glu Thr Asn Lys Thr Gln Glu Gln Ser
210 215 220

Asp Val Lys Leu Pro Lys Gly Lys Arg Lys Lys Lys Gly Arg Lys Ser
225 230 235 240

```
Asn Glu Asn Ser Glu Val Ile Thr Pro Gly Phe Pro Pro Asn His Asp
                245                 250                 255

Gln Gly Glu Gln Tyr Glu His Asn Arg Val His Lys Pro Asp Arg Val
            260                 265                 270

His Asn Pro Gly His Ser His Val His Leu Pro Glu Arg Asn Gly His
        275                 280                 285

Asp Pro Gly Arg Gly His Gln Asp Leu Asp Pro Asp Asn Glu Gly Glu
    290                 295                 300

Leu Arg His Thr Arg Lys Arg Glu Ala Pro His Val Lys Asn Asn Ala
305                 310                 315                 320

Ile Ile Ser Leu Arg Lys Asp Leu Asn Glu Asp Asp His His His Glu
                325                 330                 335

Cys Leu Asn Val Thr Gln Leu Leu Lys Tyr Tyr Gly His Gly Ala Asn
            340                 345                 350

Ser Pro Ile Ser Thr Asp Leu Phe Thr Tyr Leu Cys Pro Ala Leu Leu
        355                 360                 365

Tyr Gln Ile Asp Ser Arg Leu Cys Ile Glu His Phe Asp Lys Leu Leu
    370                 375                 380

Val Glu Asp Ile Asn Lys Asp Lys Asn Leu Val Pro Glu Asp Glu Ala
385                 390                 395                 400

Asn Ile Gly Ala Ser Ala Trp Ile Cys Gly Ile Ile Ser Ile Thr Val
                405                 410                 415

Ile Ser Leu Leu Ser Leu Leu Gly Val Ile Leu Val Pro Ile Ile Asn
            420                 425                 430

Gln Gly Cys Phe Lys Phe Leu Leu Thr Phe Leu Val Ala Leu Ala Val
        435                 440                 445

Gly Thr Met Ser Gly Asp Ala Leu Leu His Leu Leu Pro His Ser Gln
    450                 455                 460

Gly Gly His Asp His Ser His Gln His Ala His Gly His Gly His Ser
465                 470                 475                 480

His Gly His Glu Ser Asn Lys Phe Leu Glu Glu Tyr Asp Ala Val Leu
                485                 490                 495

Lys Gly Leu Val Ala Leu Gly Gly Ile Tyr Leu Leu Phe Ile Ile Glu
            500                 505                 510

His Cys Ile Arg Met Phe Lys His Tyr Lys Gln Gln Arg Gly Lys Gln
        515                 520                 525

Lys Trp Phe Met Lys Gln Asn Thr Glu Glu Ser Thr Ile Gly Arg Lys
    530                 535                 540

Leu Ser Asp His Lys Leu Asn Asn Thr Pro Asp Ser Asp Trp Leu Gln
545                 550                 555                 560

Leu Lys Pro Leu Ala Gly Thr Asp Asp Ser Val Val Ser Glu Asp Arg
                565                 570                 575

Leu Asn Glu Thr Glu Leu Thr Asp Leu Glu Gly Gln Gln Glu Ser Pro
            580                 585                 590

Pro Lys Asn Tyr Leu Cys Ile Glu Glu Glu Lys Ile Ile Asp His Ser
        595                 600                 605

His Ser Asp Gly Leu His Thr Ile His Glu His Asp Leu His Ala Ala
    610                 615                 620

Ala His Asn His His Gly Glu Asn Lys Thr Val Leu Arg Lys His Asn
625                 630                 635                 640

His Gln Trp His His Lys His Ser His His Ser His Gly Pro Cys His
                645                 650                 655
```

```
Ser Gly Ser Asp Leu Lys Glu Thr Gly Ile Ala Asn Ile Ala Trp Met
            660                 665                 670

Val Ile Met Gly Asp Gly Ile His Asn Phe Ser Asp Gly Leu Ala Ile
        675                 680                 685

Gly Ala Ala Phe Ser Ala Gly Leu Thr Gly Gly Ile Ser Thr Ser Ile
    690                 695                 700

Ala Val Phe Cys His Glu Leu Pro His Glu Leu Gly Asp Phe Ala Val
705                 710                 715                 720

Leu Leu Lys Ala Gly Met Thr Val Lys Gln Ala Ile Val Tyr Asn Leu
                725                 730                 735

Leu Ser Ala Met Met Ala Tyr Ile Gly Met Leu Ile Gly Thr Ala Val
            740                 745                 750

Gly Gln Tyr Ala Asn Asn Ile Thr Leu Trp Ile Phe Ala Val Thr Ala
        755                 760                 765

Gly Met Phe Leu Tyr Val Ala Leu Val Asp Met Leu Pro Glu Met Leu
    770                 775                 780

His Gly Asp Gly Asp Asn Glu Glu His Gly Phe Cys Pro Val Gly Gln
785                 790                 795                 800

Phe Ile Leu Gln Asn Leu Gly Leu Leu Phe Gly Phe Ala Ile Met Leu
                805                 810                 815

Val Ile Ala Leu Tyr Glu Asp Lys Ile Val Phe Asp Ile Gln Phe
            820                 825                 830


<210> SEQ ID NO 2
<211> LENGTH: 831
<212> TYPE: PRT
<213> ORGANISM: Homo sapiens

<400> SEQUENCE: 2

Met Lys Val His Met His Thr Lys Phe Cys Leu Ile Cys Leu Leu Thr
1               5                   10                  15

Phe Ile Phe His His Cys Asn His Cys His Glu Glu His Asp His Gly
            20                  25                  30

Pro Glu Ala Leu His Arg Gln His Arg Gly Met Thr Glu Leu Glu Pro
        35                  40                  45

Ser Lys Phe Ser Lys Gln Ala Ala Glu Asn Glu Lys Lys Tyr Tyr Ile
    50                  55                  60

Glu Lys Leu Phe Glu Arg Tyr Gly Glu Asn Gly Arg Leu Ser Phe Phe
65                  70                  75                  80

Gly Leu Glu Lys Leu Leu Thr Asn Leu Gly Leu Gly Glu Arg Lys Val
                85                  90                  95

Val Glu Ile Asn His Glu Asp Leu Gly His Asp His Val Ser His Leu
            100                 105                 110

Asp Ile Leu Ala Val Gln Glu Gly Lys His Phe His Ser His Asn His
        115                 120                 125

Gln His Ser His Asn His Leu Asn Ser Glu Asn Gln Thr Val Thr Ser
    130                 135                 140

Val Ser Thr Lys Arg Asn His Lys Cys Asp Pro Glu Lys Glu Thr Val
145                 150                 155                 160

Glu Val Ser Val Lys Ser Asp Asp Lys His Met His Asp His Asn His
                165                 170                 175

Arg Leu Arg His His His Arg Leu His His His Leu Asp His Asn Asn
            180                 185                 190

Thr His His Phe His Asn Asp Ser Ile Thr Pro Ser Glu Arg Gly Glu
        195                 200                 205
```

```
Pro Ser Asn Glu Pro Ser Thr Glu Thr Asn Lys Thr Gln Glu Gln Ser
    210                 215                 220

Asp Val Lys Leu Pro Lys Gly Lys Arg Lys Lys Lys Gly Arg Lys Ser
225                 230                 235                 240

Asn Glu Asn Ser Glu Val Ile Thr Pro Gly Phe Pro Pro Asn His Asp
                245                 250                 255

Gln Gly Glu Gln Tyr Glu His Asn Arg Val His Lys Pro Asp Arg Val
            260                 265                 270

His Asn Pro Gly His Ser His Val His Leu Pro Glu Arg Asn Gly His
        275                 280                 285

Asp Pro Gly Arg Gly His Gln Asp Leu Asp Pro Asp Asn Glu Gly Glu
    290                 295                 300

Leu Arg His Thr Arg Lys Arg Glu Ala Pro His Val Lys Asn Asn Ala
305                 310                 315                 320

Ile Ile Ser Leu Arg Lys Asp Leu Asn Glu Asp Asp His His His Glu
                325                 330                 335

Cys Leu Asn Val Thr Gln Leu Leu Lys Tyr Tyr Gly His Gly Ala Asn
            340                 345                 350

Ser Pro Ile Ser Thr Asp Leu Phe Thr Tyr Leu Cys Pro Ala Leu Leu
        355                 360                 365

Tyr Gln Ile Asp Ser Arg Leu Cys Ile Glu His Phe Asp Lys Leu Leu
    370                 375                 380

Val Glu Asp Ile Asn Lys Asp Lys Asn Leu Val Pro Glu Asp Glu Ala
385                 390                 395                 400

Asn Ile Gly Ala Ser Ala Trp Ile Cys Gly Ile Ile Ser Ile Thr Val
                405                 410                 415

Ile Ser Leu Leu Ser Leu Leu Gly Val Ile Leu Val Pro Ile Ile Asn
            420                 425                 430

Gln Gly Cys Phe Lys Phe Leu Leu Thr Phe Leu Val Ala Leu Ala Val
        435                 440                 445

Gly Thr Met Ser Gly Asp Ala Leu Leu His Leu Leu Pro His Ser Gln
    450                 455                 460

Gly Gly His Asp His Ser His Gln His Ala His Gly His Gly His Ser
465                 470                 475                 480

His Gly His Glu Ser Asn Lys Phe Leu Glu Glu Tyr Asp Ala Val Leu
                485                 490                 495

Lys Gly Leu Val Ala Leu Gly Gly Ile Tyr Leu Leu Phe Ile Ile Glu
            500                 505                 510

His Cys Ile Arg Met Phe Lys His Tyr Lys Gln Gln Arg Gly Lys Gln
        515                 520                 525

Lys Trp Phe Met Lys Gln Asn Thr Glu Glu Ser Thr Ile Gly Arg Lys
    530                 535                 540

Leu Ser Asp His Lys Leu Asn Asn Thr Pro Asp Ser Asp Trp Leu Gln
545                 550                 555                 560

Leu Lys Pro Leu Ala Gly Thr Asp Asp Ser Val Val Ser Glu Asp Arg
                565                 570                 575

Leu Asn Glu Thr Glu Leu Thr Asp Leu Glu Gly Gln Gln Glu Ser Pro
            580                 585                 590

Pro Lys Asn Tyr Leu Cys Ile Glu Glu Glu Lys Ile Ile Asp His Ser
        595                 600                 605

His Ser Asp Gly Leu His Thr Ile His Glu His Asp Leu His Ala Ala
    610                 615                 620
```

```
Ala His Asn His His Gly Glu Asn Lys Thr Val Leu Arg Lys His Asn
625                 630                 635                 640

His Gln Trp His His Lys His Ser His His Ser His Gly Pro Cys His
                645                 650                 655

Ser Gly Ser Asp Leu Lys Glu Thr Gly Ile Ala Asn Ile Ala Trp Met
            660                 665                 670

Val Ile Met Gly Asp Gly Ile His Asn Phe Ser Asp Gly Leu Ala Ile
        675                 680                 685

Gly Ala Ala Phe Ser Ala Gly Leu Thr Gly Gly Ile Ser Thr Ser Ile
    690                 695                 700

Ala Val Phe Cys His Glu Leu Pro His Glu Leu Gly Asp Phe Ala Val
705                 710                 715                 720

Leu Leu Lys Ala Gly Met Thr Val Lys Gln Ala Ile Val Tyr Asn Leu
                725                 730                 735

Leu Ser Ala Met Met Ala Tyr Ile Gly Met Leu Ile Gly Thr Ala Val
            740                 745                 750

Gly Gln Tyr Ala Asn Asn Ile Thr Leu Trp Ile Phe Ala Val Thr Ala
        755                 760                 765

Gly Met Phe Leu Tyr Val Ala Leu Val Asp Met Leu Pro Glu Met Leu
    770                 775                 780

His Gly Asp Gly Asp Asn Glu Glu His Gly Phe Cys Pro Val Gly Gln
785                 790                 795                 800

Phe Ile Leu Gln Asn Leu Gly Leu Leu Phe Gly Phe Ala Ile Met Leu
                805                 810                 815

Val Ile Ala Leu Tyr Glu Asp Lys Ile Val Phe Asp Ile Gln Phe
            820                 825                 830


<210> SEQ ID NO 3
<211> LENGTH: 5227
<212> TYPE: DNA
<213> ORGANISM: Homo sapiens

<400> SEQUENCE: 3

cacgatttgg tgcagccggg gtttggtacc gagcggagag gagatgcaca cggcactcga      60

gtgtgaggaa aaatagaaat gaaggtacat atgcacacaa aattttgcct catttgtttg     120

ctgacattta tttttcatca ttgcaaccat tgccatgaag aacatgacca tggccctgaa     180

gcgcttcaca gacagcatcg tggaatgaca gaattggagc caagcaaatt ttcaaagcaa     240

gctgctgaaa atgaaaaaaa atactatatt gaaaaacttt ttgagcgtta tggtgaaaat     300

ggaagattat cctttttttgg tttggagaaa cttttaacaa acttgggcct tggagagaga     360

aaagtagttg agattaatca tgaggatctt ggccacgatc atgtttctca tttagatatt     420

ttggcagttc aagagggaaa gcattttcac tcacataacc accagcattc ccataatcat     480

ttaaattcag aaaatcaaac tgtgaccagt gtatccacaa aaagaaacca taaatgtgat     540

ccagagaaag agacagttga agtgtctgta aaatctgatg ataaacatat gcatgaccat     600

aatcaccgcc tacgtcatca ccatcgtttg catcatcatc ttgatcataa caacactcac     660

cattttcata atgattccat tactcccagt gagcgtgggg agcctagcaa tgaaccttca     720

acagagacca ataaaaccca ggaacaatct gatgttaaac taccgaaagg aaagaggaag     780

aaaaaaggga ggaaaagtaa tgaaaattct gaggttatta caccaggttt tcccccctaac     840

catgatcagg gtgaacagta tgagcataat cgggtccaca aacctgatcg tgtacataac     900

ccaggtcatt ctcatgtaca tcttccagaa cgtaatggtc atgatcctgg tcgtggacac     960
```

```
caagatcttg atcctgataa tgaaggtgaa cttcgacata ctagaaagag agaagcacca   1020
catgttaaaa ataatgcaat aatttctttg agaaaagatc taaatgaaga tgaccatcat   1080
catgaatgtt tgaacgtcac tcagttatta aaatactatg gtcatggtgc caactctccc   1140
atctcaactg atttatttac atacctttgc cctgcattgt tatatcaaat cgacagcaga   1200
ctttgtattg agcattttga caaactttta gttgaagata taaataagga taaaaacctg   1260
gttcctgaag atgaggcaaa tataggggca tcagcctgga tttgtggtat catttctatc   1320
actgtcatta gcctgctttc cttgctaggc gtgatcttgg ttcctatcat taaccaagga   1380
tgcttcaaat tccttcttac attccttgtt gcattagctg taggaacaat gagtggagac   1440
gcccttcttc atctactgcc ccattctcag ggtggacatg atcacagtca ccaacatgca   1500
catgggcatg gacattctca tggacatgaa tctaacaagt ttttggaaga atatgatgct   1560
gtattgaaag gacttgttgc tctaggaggc atttacttgc tatttatcat tgaacactgc   1620
attagaatgt ttaagcacta caaacaacaa agaggaaaac agaaatggtt tatgaaacag   1680
aacacagaag aatcaactat tggaagaaag ctttcagatc acaagttaaa caatacacca   1740
gattctgact ggcttcaact caagcctctt gccggaactg atgactcggt tgtttctgaa   1800
gatcgactta atgaaactga actgacagat ttagaaggcc aacaagaatc ccctcctaaa   1860
aattaccttt gtatagaaga ggagaaaatc atagaccatt ctcacagtga tggattacat   1920
accattcatg agcatgatct ccatgctgct gcacataacc accacggcga gaacaaaact   1980
gtgctgagga agcataatca ccagtggcac cacaagcatt ctcatcattc ccatggcccc   2040
tgtcattctg gatccgatct gaaagaaaca ggaatagcta atatagcctg gatggtgatc   2100
atgggggatg gcatccacaa cttcagtgat gggctcgcaa ttggtgcagc tttcagtgct   2160
ggattgacag gaggaatcag tacttctata gccgtcttct gtcatgaact gccacatgaa   2220
ttaggagatt ttgcagttct tcttaaagca ggcatgactg taaagcaagc aattgtatac   2280
aacctcctct ctgccatgat ggcttacata ggcatgctca taggcacagc tgttggtcag   2340
tatgccaata acatcacact ttggatcttt gcagtcactg caggcatgtt cctctatgta   2400
gccttggtgg atatgcttcc agaaatgttg catggtgatg gtgacaatga agaacatggc   2460
ttttgtcctg tggggcaatt catccttcag aatttaggat tgctctttgg atttgccatt   2520
atgctggtga ttgccctcta tgaagataaa attgtgtttg acatccagtt ttgacctttc   2580
ccagtaatca ctgttgatta cgagaatgtt accatgcagc tttgcatctg ttccttgtac   2640
tgtatgcaca ttgctcaaag gaaagtcagt ggcttgcact acttacaagt ttcatagatt   2700
tgagcctaac cacaagaggc tggtgcttag tactgttttc cctgcacgta ggggtctttt   2760
aaaaatataa agcttgtgat aaagagagga gaatatggga ctccatgaac cagtgttgat   2820
atgtttgatt aagacttttc acaaaataat catataaaac actagtctct ttattagtag   2880
aaacttctgt ggctatgcag aaatagagat cgaaccaaaa aaaatcattt aaactttaaa   2940
aatattttaa atggactttg gggagacatt ttttgtgtgt tttaagaatg aattgtagtg   3000
ctctttaatt cagctacata tattcatgtg gtgataggga tcaacttgac acaactttga   3060
aactgcataa agtagacata ggaactagag gaaagctcag gctgcattag agtatgaatt   3120
tagcattggg aaaagccctt attcttgaat ctagagttac tatttttgta tatatttgca   3180
tagtgtttaa acctgcagcc taaactactg aaatttgtga ttgtatgttt gtgtgagctt   3240
cagtttaatg aaagattcat aatggttctt tgtattatta taatacttgg tgttggggtg   3300
ttctttctgt tttgtttttt actttaattt tgttttgatt tttttttttt ttttttggcg   3360
```

```
ggggtaggtg agggtttgga gcatgtggtc tttttaaaaa attgtaaccc tctagaaaat   3420
atcaaagaaa tgaaccagac gtggtttaaa tagttgattt tcctatttta acagtaccaa   3480
ctagttaatt gggaaatgta agttctgaat gttcacattg ctttaccagt ttggcactgg   3540
aaccaagagc acatgtcgtg gctggctaca aggttgtaaa gcagaaaatc gaagtttacc   3600
atgtctgtaa tgtgtacatg aagtgtcaat ttagaacagt tactaggata aactccatta   3660
ttgccatggc tgtcatggta cccaagtgac ttggaagatg catttaaatt actcagctga   3720
aatcacttga tcatcttgtg ccaagatatg ctgttggtgc ctgataggga ttagtctttt   3780
aggtgccctg ttctcctacc ataattgtga atgatttgtg agaagtgcaa gccatgttta   3840
tcctgaattt ttacttaata atttgtatta ctagtcatat gcatgtagct ttctgtttac   3900
atcctatgcc acatggtctt catttatgcc aggtaaactg tatttgaact atgtgcagct   3960
agctttgttt taatctgctt ggcaaccagt gtagctgctg taacaatcta tcttattgtt   4020
caaatatata agagccaaac tcttttccat tccatctaaa atgttttcat ttagtactct   4080
tctttcctcc tactctatga acttcaaaac aaaaacaaaa ctttgagagc agcacatgca   4140
tccaggtatt tatagattat tgccagtgtc ttttctgtat gctataagca agggagctta   4200
ggtgttattt ctttaattta tgcttgaatc tgaaaaatta tttctgactt actccatggc   4260
ctccttataa taagtagaag ttttatatat aattaatttt cagcattggg cactgaatta   4320
ggacagtcct catctcattg cttggccctt caagcaacct agctaaaagg tgctgatatt   4380
ttatttagta ctgccaactt caagtgattt agatatctat ctatctagat ttctgaacca   4440
agatatattt atagttcact tttgggtttt tatacccacg gtaggattct gcattccagc   4500
attaaatctg cttcatttta gaacctttat aaaagcaata gctggaatat actcccagtt   4560
ttaaaataaa tgcctgattg atttaaagca agtaggttat gctgaagtat ataaagaagt   4620
tttatattct ctcaaaaatg gtattatctt tctttatttg ctagattctt acaaatcttt   4680
taagagggct gtaacagttg ctgctagtat tagggttcca catcattcta atgtatagtt   4740
tcaagtctta atagacaatc tgaattccac tacatttctt ttggctccaa cattcctttt   4800
agcttgacca gtctaattta aaatgtgttt gttggaggtc attaacgtta cttgtacaat   4860
gctgtcactg tgtgacatcc atatgaattt tggtatatat caatcaatca atcaatcaca   4920
ttgcattcaa tcaatcagct gtgattgatt gattatgctt agaaatacta tagtaactag   4980
atgcagtgtg aattttttcc attaacaaac aaacaagtca gtggcttaaa tgtgattatg   5040
gtcctgcaag gtgattcttg ctaaaatatc taaacttttg ttttgtttta actgaatcat   5100
tttttaactt aaaaagctgg aaaatatcaa atgctgtttt ttttttttca ttgtcaacag   5160
tggtgtgtca ttttatgtat gttcctaatg cttatggaac tcctccaaaa taaagttact   5220
caaagag                                                             5227
```

<210> SEQ ID NO 4
<211> LENGTH: 5432
<212> TYPE: DNA
<213> ORGANISM: Homo sapiens

<400> SEQUENCE: 4

```
agttgatcac tctgaagctt tttggctaaa gcgtttgggt ttagagcttc cattactcat     60
tcgccttgcc caaggcctca gcaaccgacg ttcgaaagcc aggagaaaag gcgaatgata    120
aagggcgctc cacgcatgcg ttaagaagcc gccccaactc ccccgcggcg ttctttcttg    180
```

```
gaacaaaact agcgcggagc cacggaactc cgcagtttgc gtagacttga atttcctatt    240
cctcggacga tccatgtgga atccgaaaaa tagaaatgaa ggtacatatg cacacaaaat    300
tttgcctcat ttgtttgctg acatttattt ttcatcattg caaccattgc catgaagaac    360
atgaccatgg ccctgaagcg cttcacagac agcatcgtgg aatgacagaa ttggagccaa    420
gcaaatttc aaagcaagct gctgaaaatg aaaaaaaata ctatattgaa aaactttttg    480
agcgttatgg tgaaaatgga agattatcct tttttggttt ggagaaactt ttaacaaact    540
tgggccttgg agagagaaaa gtagttgaga ttaatcatga ggatcttggc cacgatcatg    600
tttctcattt agatattttg gcagttcaag agggaaagca ttttcactca cataaccacc    660
agcattccca taatcattta aattcagaaa atcaaactgt gaccagtgta tccacaaaaa    720
gaaaccataa atgtgatcca gagaaagaga cagttgaagt gtctgtaaaa tctgatgata    780
aacatatgca tgaccataat caccgcctac gtcatcacca tcgtttgcat catcatcttg    840
atcataacaa cactcaccat tttcataatg attccattac tcccagtgag cgtggggagc    900
ctagcaatga accttcaaca gagaccaata aaacccagga acaatctgat gttaaactac    960
cgaaaggaaa gaggaagaaa aaagggagga aaagtaatga aaattctgag gttattacac   1020
caggttttcc ccctaaccat gatcagggtg aacagtatga gcataatcgg gtccacaaac   1080
ctgatcgtgt acataaccca ggtcattctc atgtacatct tccagaacgt aatggtcatg   1140
atcctggtcg tggacaccaa gatcttgatc ctgataatga aggtgaactt cgacatacta   1200
gaaagagaga agcaccacat gttaaaaata atgcaataat ttctttgaga aaagatctaa   1260
atgaagatga ccatcatcat gaatgtttga acgtcactca gttattaaaa tactatggtc   1320
atggtgccaa ctctcccatc tcaactgatt tatttacata cctttgccct gcattgttat   1380
atcaaatcga cagcagactt tgtattgagc attttgacaa acttttagtt gaagatataa   1440
ataaggataa aaacctggtt cctgaagatg aggcaaatat aggggcatca gcctggattt   1500
gtggtatcat ttctatcact gtcattagcc tgctttcctt gctaggcgtg atcttggttc   1560
ctatcattaa ccaaggatgc ttcaaattcc ttcttacatt ccttgttgca ttagctgtag   1620
gaacaatgag tggagacgcc cttcttcatc tactgcccca ttctcagggt ggacatgatc   1680
acagtcacca acatgcacat gggcatggac attctcatgg acatgaatct aacaagtttt   1740
tggaagaata tgatgctgta ttgaaaggac ttgttgctct aggaggcatt tacttgctat   1800
ttatcattga acactgcatt agaatgttta agcactacaa acaacaaaga ggaaaacaga   1860
aatggtttat gaaacagaac acagaagaat caactattgg aagaaagctt tcagatcaca   1920
agttaaacaa tacaccagat tctgactggc ttcaactcaa gcctcttgcc ggaactgatg   1980
actcggttgt ttctgaagat cgacttaatg aaactgaact gacagattta gaaggccaac   2040
aagaatcccc tcctaaaaat tacctttgta tagaagagga gaaaatcata gaccattctc   2100
acagtgatgg attacatacc attcatgagc atgatctcca tgctgctgca cataaccacc   2160
acggcgagaa caaaactgtg ctgaggaagc ataatcacca gtggcaccac aagcattctc   2220
atcattccca tggcccctgt cattctggat ccgatctgaa agaaacagga atagctaata   2280
tagcctggat ggtgatcatg gggatggca tccacaactt cagtgatggg ctcgcaattg    2340
gtgcagcttt cagtgctgga ttgacaggag gaatcagtac ttctatagcc gtcttctgtc   2400
atgaactgcc acatgaatta ggagattttg cagttcttct taaagcaggc atgactgtaa   2460
agcaagcaat tgtatacaac ctcctctctg ccatgatggc ttacataggc atgctcatag   2520
gcacagctgt tggtcagtat gccaataaca tcacactttg gatctttgca gtcactgcag   2580
```

```
gcatgttcct ctatgtagcc ttggtggata tgcttccaga aatgttgcat ggtgatggtg   2640
acaatgaaga acatggcttt tgtcctgtgg ggcaattcat ccttcagaat ttaggattgc   2700
tctttggatt tgccattatg ctggtgattg ccctctatga agataaaatt gtgtttgaca   2760
tccagttttg acctttccca gtaatcactg ttgattacga gaatgttacc atgcagcttt   2820
gcatctgttc cttgtactgt atgcacattg ctcaaaggaa agtcagtggc ttgcactact   2880
tacaagtttc atagatttga gcctaaccac aagaggctgg tgcttagtac tgttttccct   2940
gcacgtaggg gtcttttaaa aatataaagc ttgtgataaa gagaggagaa tatgggactc   3000
catgaaccag tgttgatatg tttgattaag actttttcaca aaataatcat ataaaacact   3060
agtctcttta ttagtagaaa cttctgtggc tatgcagaaa tagagatcga accaaaaaaa   3120
atcatttaaa ctttaaaaat attttaaatg gactttgggg agacattttt tgtgtgtttt   3180
aagaatgaat tgtagtgctc tttaattcag ctacatatat tcatgtggtg atagggatca   3240
acttgacaca actttgaaac tgcataaagt agacatagga actagaggaa agctcaggct   3300
gcattagagt atgaatttag cattgggaaa agcccttatt cttgaatcta gagttactat   3360
ttttgtatat atttgcatag tgtttaaacc tgcagcctaa actactgaaa tttgtgattg   3420
tatgtttgtg tgagcttcag tttaatgaaa gattcataat ggttctttgt attattataa   3480
tacttggtgt tggggtgttc tttctgtttt gttttttact ttaattttgt tttgattttt   3540
ttttttttt tttggcgggg gtaggtgagg gtttggagca tgtggtcttt ttaaaaaatt   3600
gtaaccctct agaaaatatc aaagaaatga accagacgtg gtttaaatag ttgattttcc   3660
tattttaaca gtaccaacta gttaattggg aaatgtaagt tctgaatgtt cacattgctt   3720
taccagtttg gcactggaac caagagcaca tgtcgtggct ggctacaagg ttgtaaagca   3780
gaaaatcgaa gtttaccatg tctgtaatgt gtacatgaag tgtcaattta gaacagttac   3840
taggataaac tccattattg ccatggctgt catggtaccc aagtgacttg gaagatgcat   3900
ttaaattact cagctgaaat cacttgatca tcttgtgcca agatatgctg ttggtgcctg   3960
atagggatta gtcttttagg tgccctgttc tcctaccata attgtgaatg atttgtgaga   4020
agtgcaagcc atgtttatcc tgaattttta cttaataatt tgtattacta gtcatatgca   4080
tgtagctttc tgtttacatc ctatgccaca tggtcttcat ttatgccagg taaactgtat   4140
ttgaactatg tgcagctagc tttgttttaa tctgcttggc aaccagtgta gctgctgtaa   4200
caatctatct tattgttcaa atatataaga gccaaactct tttccattcc atctaaaatg   4260
ttttcattta gtactcttct ttcctcctac tctatgaact tcaaaacaaa aacaaaactt   4320
tgagagcagc acatgcatcc aggtatttat agattattgc cagtgtcttt tctgtatgct   4380
ataagcaagg gagcttaggt gttatttctt taatttatgc ttgaatctga aaaattattt   4440
ctgacttact ccatggcctc cttataataa gtagaagttt tatatataat taattttcag   4500
cattgggcac tgaattagga cagtcctcat ctcattgctt ggcccttcaa gcaacctagc   4560
taaaaggtgc tgatatttta tttagtactg ccaacttcaa gtgatttaga tatctatcta   4620
tctagatttc tgaaccaaga tatatttata gttcactttt gggtttttat acccacggta   4680
ggattctgca ttccagcatt aaatctgctt cattttagaa cctttataaa agcaatagct   4740
ggaatatact cccagtttta aaataaatgc ctgattgatt taaagcaagt aggttatgct   4800
gaagtatata aagaagtttt atattctctc aaaaatggta ttatctttct ttatttgcta   4860
gattcttaca aatcttttaa gagggctgta acagttgctg ctagtattag ggttccacat   4920
```

```
cattctaatg tatagtttca agtcttaata gacaatctga attccactac atttcttttg   4980

gctccaacat tccttttagc ttgaccagtc taatttaaaa tgtgtttgtt ggaggtcatt   5040

aacgttactt gtacaatgct gtcactgtgt gacatccata tgaattttgg tatatatcaa   5100

tcaatcaatc aatcacattg cattcaatca atcagctgtg attgattgat tatgcttaga   5160

aatactatag taactagatg cagtgtgaat tttttccatt aacaaacaaa caagtcagtg   5220

gcttaaatgt gattatggtc ctgcaaggtg attcttgcta aaatatctaa acttttgttt   5280

tgttttaact gaatcatttt ttaacttaaa aagctggaaa atatcaaatg ctgttttttt   5340

tttttcattg tcaacagtgg tgtgtcattt tatgtatgtt cctaatgctt atggaactcc   5400

tccaaaataa agttactcaa agagagcaaa ta                                 5432
```

```
<210> SEQ ID NO 5
<211> LENGTH: 552
<212> TYPE: PRT
<213> ORGANISM: Homo sapiens

<400> SEQUENCE: 5

Met Ala Ala Leu Ala Pro Val Gly Ser Pro Ala Ser Arg Gly Pro Arg
1               5                   10                  15

Leu Ala Ala Gly Leu Arg Leu Leu Pro Met Leu Gly Leu Leu Gln Leu
            20                  25                  30

Leu Ala Glu Pro Gly Leu Gly Arg Val His His Leu Ala Leu Lys Asp
        35                  40                  45

Asp Val Arg His Lys Val His Leu Asn Thr Phe Gly Phe Phe Lys Asp
    50                  55                  60

Gly Tyr Met Val Val Asn Val Ser Ser Leu Ser Leu Asn Glu Pro Glu
65                  70                  75                  80

Asp Lys Asp Val Thr Ile Gly Phe Ser Leu Asp Arg Thr Lys Asn Asp
                85                  90                  95

Gly Phe Ser Ser Tyr Leu Asp Glu Asp Val Asn Tyr Cys Ile Leu Lys
            100                 105                 110

Lys Gln Ser Val Ser Val Thr Leu Leu Ile Leu Asp Ile Ser Arg Ser
        115                 120                 125

Glu Val Arg Val Lys Ser Pro Pro Glu Ala Gly Thr Gln Leu Pro Lys
    130                 135                 140

Ile Ile Phe Ser Arg Asp Glu Lys Val Leu Gly Gln Ser Gln Glu Pro
145                 150                 155                 160

Asn Val Asn Pro Ala Ser Ala Gly Asn Gln Thr Gln Lys Thr Gln Asp
                165                 170                 175

Gly Gly Lys Ser Lys Arg Ser Thr Val Asp Ser Lys Ala Met Gly Glu
            180                 185                 190

Lys Ser Phe Ser Val His Asn Asn Gly Gly Ala Val Ser Phe Gln Phe
        195                 200                 205

Phe Phe Asn Ile Ser Thr Asp Asp Gln Glu Gly Leu Tyr Ser Leu Tyr
    210                 215                 220

Phe His Lys Cys Leu Gly Lys Glu Leu Pro Ser Asp Lys Phe Thr Phe
225                 230                 235                 240

Ser Leu Asp Ile Glu Ile Thr Glu Lys Asn Pro Asp Ser Tyr Leu Ser
                245                 250                 255

Ala Gly Glu Ile Pro Leu Pro Lys Leu Tyr Ile Ser Met Ala Phe Phe
            260                 265                 270

Phe Phe Leu Ser Gly Thr Ile Trp Ile His Ile Leu Arg Lys Arg Arg
        275                 280                 285
```

Asn Asp Val Phe Lys Ile His Trp Leu Met Ala Ala Leu Pro Phe Thr
290 295 300

Lys Ser Leu Ser Leu Val Phe His Ala Ile Asp Tyr His Tyr Ile Ser
305 310 315 320

Ser Gln Gly Phe Pro Ile Glu Gly Trp Ala Val Val Tyr Tyr Ile Thr
325 330 335

His Leu Leu Lys Gly Ala Leu Leu Phe Ile Thr Ile Ala Leu Ile Gly
340 345 350

Thr Gly Trp Ala Phe Ile Lys His Ile Leu Ser Asp Lys Asp Lys Lys
355 360 365

Ile Phe Met Ile Val Ile Pro Leu Gln Val Leu Ala Asn Val Ala Tyr
370 375 380

Ile Ile Ile Glu Ser Thr Glu Glu Gly Thr Thr Glu Tyr Gly Leu Trp
385 390 395 400

Lys Asp Ser Leu Phe Leu Val Asp Leu Leu Cys Cys Gly Ala Ile Leu
405 410 415

Phe Pro Val Val Trp Ser Ile Arg His Leu Gln Glu Ala Ser Ala Thr
420 425 430

Asp Gly Lys Ala Ala Ile Asn Leu Ala Lys Leu Lys Leu Phe Arg His
435 440 445

Tyr Tyr Val Leu Ile Val Cys Tyr Ile Tyr Phe Thr Arg Ile Ile Ala
450 455 460

Phe Leu Leu Lys Leu Ala Val Pro Phe Gln Trp Lys Trp Leu Tyr Gln
465 470 475 480

Leu Leu Asp Glu Thr Ala Thr Leu Val Phe Phe Val Leu Thr Gly Tyr
485 490 495

Lys Phe Arg Pro Ala Ser Asp Asn Pro Tyr Leu Gln Leu Ser Gln Glu
500 505 510

Glu Glu Asp Leu Glu Met Glu Ser Val Val Thr Thr Ser Gly Val Met
515 520 525

Glu Ser Met Lys Lys Val Lys Lys Val Thr Asn Gly Ser Val Glu Pro
530 535 540

Gln Gly Glu Trp Glu Gly Ala Val
545 550

<210> SEQ ID NO 6
<211> LENGTH: 600
<212> TYPE: PRT
<213> ORGANISM: Homo sapiens

<400> SEQUENCE: 6

Met Ala Ala Leu Ala Pro Val Gly Ser Pro Ala Ser Arg Gly Pro Arg
1 5 10 15

Leu Ala Ala Gly Leu Arg Leu Leu Pro Met Leu Gly Leu Leu Gln Leu
20 25 30

Leu Ala Glu Pro Gly Leu Gly Arg Val His His Leu Ala Leu Lys Asp
35 40 45

Asp Val Arg His Lys Val His Leu Asn Thr Phe Gly Phe Phe Lys Asp
50 55 60

Gly Tyr Met Val Val Asn Val Ser Ser Leu Ser Leu Asn Glu Pro Glu
65 70 75 80

Asp Lys Asp Val Thr Ile Gly Phe Ser Leu Asp Arg Thr Lys Asn Asp
85 90 95

Gly Phe Ser Ser Tyr Leu Asp Glu Asp Val Asn Tyr Cys Ile Leu Lys

-continued

```
            100                 105                 110

Lys Gln Ser Val Ser Val Thr Leu Leu Ile Leu Asp Ile Ser Arg Ser
        115                 120                 125

Glu Val Arg Val Lys Ser Pro Pro Glu Ala Gly Thr Gln Leu Pro Lys
    130                 135                 140

Ile Ile Phe Ser Arg Asp Glu Lys Val Leu Gly Gln Ser Gln Glu Pro
145                 150                 155                 160

Asn Val Asn Pro Ala Ser Ala Gly Asn Gln Thr Gln Lys Thr Gln Asp
                165                 170                 175

Gly Gly Lys Ser Lys Arg Ser Thr Val Asp Ser Lys Ala Met Gly Glu
            180                 185                 190

Lys Ser Phe Ser Val His Asn Asn Gly Gly Ala Val Ser Phe Gln Phe
        195                 200                 205

Phe Phe Asn Ile Ser Thr Asp Asp Gln Glu Gly Leu Tyr Ser Leu Tyr
    210                 215                 220

Phe His Lys Cys Leu Gly Lys Glu Leu Pro Ser Asp Lys Phe Thr Phe
225                 230                 235                 240

Ser Leu Asp Ile Glu Ile Thr Glu Lys Asn Pro Asp Ser Tyr Leu Ser
                245                 250                 255

Ala Gly Glu Ile Pro Leu Pro Lys Leu Tyr Ile Ser Met Ala Phe Phe
            260                 265                 270

Phe Phe Leu Ser Gly Thr Ile Trp Ile His Ile Leu Arg Lys Arg Arg
        275                 280                 285

Asn Asp Val Phe Lys Ile His Trp Leu Met Ala Ala Leu Pro Phe Thr
    290                 295                 300

Lys Ser Leu Ser Leu Val Phe His Ala Ile Asp Tyr His Tyr Ile Ser
305                 310                 315                 320

Ser Gln Gly Phe Pro Ile Glu Gly Trp Ala Val Val Tyr Tyr Ile Thr
                325                 330                 335

His Leu Leu Lys Gly Ala Leu Leu Phe Ile Thr Ile Ala Leu Ile Gly
            340                 345                 350

Thr Gly Trp Ala Phe Ile Lys His Ile Leu Ser Asp Lys Asp Lys Lys
        355                 360                 365

Ile Phe Met Ile Val Ile Pro Leu Gln Val Leu Ala Asn Val Ala Tyr
    370                 375                 380

Ile Ile Ile Glu Ser Thr Glu Glu Gly Thr Thr Glu Tyr Gly Leu Trp
385                 390                 395                 400

Lys Asp Ser Leu Phe Leu Val Asp Leu Leu Cys Cys Gly Ala Ile Leu
                405                 410                 415

Phe Pro Val Val Trp Ser Ile Arg His Leu Gln Glu Ala Ser Ala Thr
            420                 425                 430

Asp Gly Lys Gly Asp Ser Met Gly Pro Leu Gln Gln Arg Ala Asn Leu
        435                 440                 445

Arg Ala Gly Ser Arg Ile Glu Ser His His Phe Ala Gln Ala Asp Leu
    450                 455                 460

Glu Leu Leu Ala Ser Ser Cys Pro Pro Ala Ser Val Ser Gln Arg Ala
465                 470                 475                 480

Gly Ile Thr Ala Ala Ile Asn Leu Ala Lys Leu Lys Leu Phe Arg His
                485                 490                 495

Tyr Tyr Val Leu Ile Val Cys Tyr Ile Tyr Phe Thr Arg Ile Ile Ala
            500                 505                 510

Phe Leu Leu Lys Leu Ala Val Pro Phe Gln Trp Lys Trp Leu Tyr Gln
        515                 520                 525
```

```
Leu Leu Asp Glu Thr Ala Thr Leu Val Phe Phe Val Leu Thr Gly Tyr
    530                 535                 540

Lys Phe Arg Pro Ala Ser Asp Asn Pro Tyr Leu Gln Leu Ser Gln Glu
545                 550                 555                 560

Glu Glu Asp Leu Glu Met Glu Ser Val Val Thr Thr Ser Gly Val Met
                565                 570                 575

Glu Ser Met Lys Lys Val Lys Lys Val Thr Asn Gly Ser Val Glu Pro
            580                 585                 590

Gln Gly Glu Trp Glu Gly Ala Val
        595                 600


<210> SEQ ID NO 7
<211> LENGTH: 600
<212> TYPE: PRT
<213> ORGANISM: Homo sapiens

<400> SEQUENCE: 7

Met Ala Ala Leu Ala Pro Val Gly Ser Pro Ala Ser Arg Gly Pro Arg
1               5                   10                  15

Leu Ala Ala Gly Leu Arg Leu Leu Pro Met Leu Gly Leu Leu Gln Leu
            20                  25                  30

Leu Ala Glu Pro Gly Leu Gly Arg Val His His Leu Ala Leu Lys Asp
        35                  40                  45

Asp Val Arg His Lys Val His Leu Asn Thr Phe Gly Phe Phe Lys Asp
    50                  55                  60

Gly Tyr Met Val Val Asn Val Ser Ser Leu Ser Leu Asn Glu Pro Glu
65                  70                  75                  80

Asp Lys Asp Val Thr Ile Gly Phe Ser Leu Asp Arg Thr Lys Asn Asp
                85                  90                  95

Gly Phe Ser Ser Tyr Leu Asp Glu Asp Val Asn Tyr Cys Ile Leu Lys
            100                 105                 110

Lys Gln Ser Val Ser Val Thr Leu Leu Ile Leu Asp Ile Ser Arg Ser
        115                 120                 125

Glu Val Arg Val Lys Ser Pro Pro Glu Ala Gly Thr Gln Leu Pro Lys
    130                 135                 140

Ile Ile Phe Ser Arg Asp Glu Lys Val Leu Gly Gln Ser Gln Glu Pro
145                 150                 155                 160

Asn Val Asn Pro Ala Ser Ala Gly Asn Gln Thr Gln Lys Thr Gln Asp
                165                 170                 175

Gly Gly Lys Ser Lys Arg Ser Thr Val Asp Ser Lys Ala Met Gly Glu
            180                 185                 190

Lys Ser Phe Ser Val His Asn Asn Gly Gly Ala Val Ser Phe Gln Phe
        195                 200                 205

Phe Phe Asn Ile Ser Thr Asp Asp Gln Glu Gly Leu Tyr Ser Leu Tyr
    210                 215                 220

Phe His Lys Cys Leu Gly Lys Glu Leu Pro Ser Asp Lys Phe Thr Phe
225                 230                 235                 240

Ser Leu Asp Ile Glu Ile Thr Glu Lys Asn Pro Asp Ser Tyr Leu Ser
                245                 250                 255

Ala Gly Glu Ile Pro Leu Pro Lys Leu Tyr Ile Ser Met Ala Phe Phe
            260                 265                 270

Phe Phe Leu Ser Gly Thr Ile Trp Ile His Ile Leu Arg Lys Arg Arg
        275                 280                 285

Asn Asp Val Phe Lys Ile His Trp Leu Met Ala Ala Leu Pro Phe Thr
```

```
    290                 295                 300

Lys Ser Leu Ser Leu Val Phe His Ala Ile Asp Tyr His Tyr Ile Ser
305                 310                 315                 320

Ser Gln Gly Phe Pro Ile Glu Gly Trp Ala Val Val Tyr Tyr Ile Thr
                325                 330                 335

His Leu Leu Lys Gly Ala Leu Leu Phe Ile Thr Ile Ala Leu Ile Gly
            340                 345                 350

Thr Gly Trp Ala Phe Ile Lys His Ile Leu Ser Asp Lys Asp Lys Lys
        355                 360                 365

Ile Phe Met Ile Val Ile Pro Leu Gln Val Leu Ala Asn Val Ala Tyr
    370                 375                 380

Ile Ile Ile Glu Ser Thr Glu Glu Gly Thr Thr Glu Tyr Gly Leu Trp
385                 390                 395                 400

Lys Asp Ser Leu Phe Leu Val Asp Leu Leu Cys Cys Gly Ala Ile Leu
                405                 410                 415

Phe Pro Val Val Trp Ser Ile Arg His Leu Gln Glu Ala Ser Ala Thr
            420                 425                 430

Asp Gly Lys Gly Asp Ser Met Gly Pro Leu Gln Gln Arg Ala Asn Leu
        435                 440                 445

Arg Ala Gly Ser Arg Ile Glu Ser His His Phe Ala Gln Ala Asp Leu
    450                 455                 460

Glu Leu Leu Ala Ser Ser Cys Pro Pro Ala Ser Val Ser Gln Arg Ala
465                 470                 475                 480

Gly Ile Thr Ala Ala Ile Asn Leu Ala Lys Leu Lys Leu Phe Arg His
                485                 490                 495

Tyr Tyr Val Leu Ile Val Cys Tyr Ile Tyr Phe Thr Arg Ile Ile Ala
            500                 505                 510

Phe Leu Leu Lys Leu Ala Val Pro Phe Gln Trp Lys Trp Leu Tyr Gln
        515                 520                 525

Leu Leu Asp Glu Thr Ala Thr Leu Val Phe Phe Val Leu Thr Gly Tyr
    530                 535                 540

Lys Phe Arg Pro Ala Ser Asp Asn Pro Tyr Leu Gln Leu Ser Gln Glu
545                 550                 555                 560

Glu Glu Asp Leu Glu Met Glu Ser Val Val Thr Thr Ser Gly Val Met
                565                 570                 575

Glu Ser Met Lys Lys Val Lys Lys Val Thr Asn Gly Ser Val Glu Pro
            580                 585                 590

Gln Gly Glu Trp Glu Gly Ala Val
        595                 600
```

<210> SEQ ID NO 8
<211> LENGTH: 6874
<212> TYPE: DNA
<213> ORGANISM: Homo sapiens

<400> SEQUENCE: 8

```
ccgaggtggg cagcacaggc tcctcgacga cttcctaggt cgcaatctcc aggaaaacga      60

ccacagggtc agcggagcta gccgccgagc cccgctcccc gggccccttcc ggcggctgcg    120

ccctttcacc ccggacgtgg gcgggagagg aagcggctgg tgatgctgga acaaacatgg     180

ccgctctggc gcccgtcggc tccccccgcct cccgcggtcc taggctggcc gcgggcctcc    240

ggctgctccc aatgctgggt ttgctgcagt tgctggccga gcctggcctg ggccgcgtcc     300

atcacctggc actcaaggat gatgtgaggc ataaagttca tctgaacacc tttggcttct     360
```

-continued

```
tcaaggatgg gtacatggtg gtgaatgtca gtagcctctc actgaatgag cctgaagaca    420
aggatgtgac tattggattt agcctagacc gtacaaagaa tgatggcttt tcttcttacc    480
tggatgaaga tgtgaattac tgtattttaa agaaacagtc tgtctctgtc accctttttaa    540
tcctagacat ctccagaagt gaggtaagag taaagtctcc accagaagct ggtacccagt    600
taccaaagat catcttcagc agggatgaga aagtccttgg tcagagccag gagcctaatg    660
ttaaccctgc ttcagcaggc aaccagaccc agaagacaca agatggtgga aagtctaaaa    720
gaagtacagt ggattcaaag gccatgggag agaaatcctt ttctgttcat aataatggtg    780
gggcagtgtc atttcagttt ttctttaaca tcagcactga tgaccaagaa ggcctttaca    840
gtctttattt tcataaatgc cttggaaaag aattgccaag tgacaagttt acattcagcc    900
ttgatattga gatcacagag aagaatcctg acagctacct ctcagcagga gaaattcctc    960
tccccaaatt atacatctca atggcctttt tcttctttct ttctgggacc atctggattc   1020
atatccttcg aaaacgacgg aatgatgtat ttaaaatcca ctggctgatg gcggcccttc   1080
ctttcaccaa gtctctttcc ttggtgttcc atgcaattga ctaccactac atctcctccc   1140
agggcttccc tatcgaaggc tgggctgttg tgtactacat aactcacctt ttgaaagggg   1200
cgctactctt catcaccatt gcactcattg gcactggctg ggctttcatt aagcacatcc   1260
tttctgataa agacaaaaag atcttcatga ttgtcattcc actccaggtc ctggcaaatg   1320
tagcctacat catcatagag tccaccgagg agggcacgac tgaatatggc ttgtggaagg   1380
actctctatt tctggtcgac ctgttgtgtt gtggtgccat cctcttccca gtggtgtggt   1440
caatcagaca tttacaagaa gcatcagcaa cagatggaaa agctgctatt aacttagcaa   1500
agctgaaact tttcagacat tattacgtct tgattgtgtg ttacatatac ttcactagga   1560
tcattgcatt tctcctcaaa ctcgctgttc cattccagtg gaagtggctc taccagctcc   1620
tggatgaaac ggccacactg gtcttctttg ttctaacggg gtataaattc cgtccggctt   1680
cagataaccc ctacctacaa ctttctcagg aagaagaaga cttggaaatg gagtccgttg   1740
tgacaacatc tggggtgatg gaaagtatga agaaagtcaa gaaggtgacc aacggctccg   1800
tggagcccca gggcgagtgg gaaggcgccg tgtgacagag ccgaccctga ggatggcact   1860
gtccaaggaa actgttaact tattcatagt cctattggac agcaggagca gctcctacag   1920
tgaactattg gcaccaccga cagtgacacc agggcacatg gctggagcac agtgccgcgg   1980
aaacctgatt ttgtactctc ttttatggaa acgatctgtg gctgtttaga ggcagctgga   2040
tcctctttca ggcgggaatg ggagggcggg cacagggagg aggagaggaa gagaaaagga   2100
agaattcatt tttaatttag gtttcttttt ttcttcttca tttcggagct ctaaggtgta   2160
tgcagttgtg accccatgtg tggggaagtg tagcaaggac ggctggtgga gggggaagga   2220
gggtgcgagg tgtctgtctg atgctttagg aaatgtctac tgaggaccct gggacttaag   2280
aagaagggcg gggagagtgc cattgcctgt ttgggagaca aaaatgaacg aaaacaggtg   2340
actttggaaa gcaaagtcaa aacccagttt aggatgtagc acctgcccca ggattcctgc   2400
cctcggcttt gccccagacc cttattccag atgctgagag tgaccaggac agcagctcct   2460
gaggcccagt ggtcttcttt ccaacaggaa aagaaggctg tgatgtcgct gtcaggatca   2520
tgccctgtgg cacagcacag gtggtgggag gtggttttct gactgagatg ttgcctgatg   2580
gatggaaaga aatgtatttt taagttcaaa aagcattatc ctgtggcgtt gcctggacat   2640
ccactccctg acagcccaga gcagcactgt ctggcttccc ttcatgcttg tggctttgtt   2700
gtgtttgatc agaattttgg gggaaatgga aagttttcct caaggagcag ctgggggcag   2760
```

```
aataggtagt atttaagcaa atacttaagt ccaagcaaat catccccatt aaaaagcttt   2820
tcctgtaggc tagtaggatt tctaaataga tgaattcaac agacttggtc cccatagtcc   2880
aagagtatgt atgtgaagaa agtgagcatg attcaacagt ttcactctca gggattttag   2940
gatggcaaaa tacttcacag aaactcaatg attaagttcc cttccacact tccagagctt   3000
gaatgaacac aggtagccac ctaaattgag cagtattgca actcagagag aaaatcatct   3060
gaatagtagg acaagctcag aaggtacatt gtgactgagg gcttaaaagg agaccaaaac   3120
atggccccat cagggaagct tcttaatgct tggggggcca gctaggtagg gttgcttcca   3180
aaagctggag cccacccctg cctaggggtt gtcagagagc cacacctgca ggggaacagg   3240
tacctccgag ggtgagagtc gtggtctctg ggagttgttt tctcacctct ggcttagaag   3300
ggtcaggcag aaaccacagg atgtggggtc acactcactg tcccaagttt gggaacctga   3360
aaaagtctcc attcagaaca tggttgttct ccctgtccca tgctatctta tcttcctaaa   3420
tgactaatga ggaagcgggt gttctttttc tgcactttga ttcgccatct gggttctgta   3480
gggtgctctg aaggtgtgat ctgccttctg gctgatgtgg aggaagagca agcgccttcc   3540
caggccacag ctgctcacct ctcggcagat attttaggca agcatccgtg tgtcttccca   3600
tcttcaggag aaaggtaaat gcaccctaag tgttcacttc tggacctttt tcaagttcac   3660
ttgggactgt gtgacagaag ggagttggag ggaggatggg aatattttta acactttgtt   3720
ttcctgtgca gaaacataat accagttttc gcagaaatgt gtctcaatct gtgactacca   3780
aagccctcct cagtccttcc ctcagaggga cacatttgct gtttctcccg caagcagatg   3840
ttgtggatga ggcgatagac tccttggcaa gaacgaaagg tgtgatgaaa cctccctgct   3900
cggaagggtc tccgtggagg tgtcctcatt tcacatgctg ggttttgcaa gcgaggaagc   3960
caggcagtgg aggaactaga gagaggcagg cgtgtgtgtg gacaagcgct ggagccgcag   4020
ccctcagact ggcacgggaa cgccagcgtt gggtgttcag attccacgcg tatgtctggg   4080
ctcactcaca gcatggccga gtgtctgcag tgctggtcct gacccttcca gagcagcagt   4140
ggacagatga gataagactg tttcagaaac aaagatggcc acagccttcc taacaagcag   4200
gtcatctggc catgtctgta ttgtaactgg taaaaggctt caagtcagat tgatgatcaa   4260
gaaaagtcaa aaccccagcc caagattggg aaagcaggtg gtggttccaa gcttttaaaa   4320
aattattgaa gctctccatc ctgttctgtg agtgtgtctt ctctttctcc ttcacgtcat   4380
agccgtgacc caccgttcat ctctgctctt gcgtaaagat gaccgatgga gtccaaagcc   4440
aagtggcttc accagctgac aagccaccct cctgcagcct gagtttcaca gtccactggg   4500
ttcgttgtca tgcggtgttt gaatggttaa gcccttgcag tatttcagat cgggcaaaaa   4560
atatcggatg cacatagcag aaccattggt ggtatttata gctttgcttt gtactcctca   4620
ctgtttctgc ctacgcaaaa tatccatgtt tcctctgaga aatctgttgt ggactgaaag   4680
cgctgctggc tgtgaaattt aataaagtgt gtatgctttg ctagaaaatt atttcttgga   4740
caataggaac agtcattgat ctgtaaatcc tggctcttaa cagtgagtgg ccaaggactt   4800
gatcagccca tttcttggtc cctcagtgct ttaaaattta agtagcactg cattttgtaa   4860
tgttgaatat gactctagtg acttgtagga ggcacttgtg aggagatgct tgcttcagtg   4920
taaaagatgc tcatggcctg agtcagttga gttttctttc aagaaaccac ttcagagtga   4980
aatatccagg gtttccccgc cctggacatg tccagcctgc ccaggcagca cacagccctg   5040
taagtccacc tcgtgtgggt gagatttcct cctgcgtgat gacctcatcg ccatctctgc   5100
```

```
tgtctcattc cacagcctcc ctccctcttc tctcctcctc tgccctcgcc cttcccccctt   5160
ccccatcccc tccccctcct cctctgccct cgcccttacc cctcccccctt cccccttccgc   5220
tcctcctccc tcctccacct ctttctcctc ctccttccct cctcctccct cctcttccct   5280
tctctgccat ctttctcccc gtgcctattg atcccacata ggctcattct gggtacaccg   5340
gctaaaggct ttggtgcatt gcagcgtttt ctcccagcag ctgtgtgaaa gatgcatttt   5400
ctaagctaag gagaattttc tcaagagtgg catactcatg ccaaatatta ttgctctggg   5460
ccatataggc tggtcttcct ccacactaaa atgggtgtct tgttttggta cttaaaacag   5520
tctactccag gcatccagtc cttacagacc aaggaagagc atagcgatgc ctgttggaat   5580
tgcagatgca ttctggcctt ctcccccgtc ctgaaacatt ttctttgagg aaggctctta   5640
gaacattaga tagtctgctg aggttgttgg cccagctcca tacacccagt agaacagtgg   5700
aacaactcat gcttcatgct gccaagctgc tgtacttcaa aggaaacaga tctagcacac   5760
tgctgcaccc ctgcttccac actccacact tcaccccgct gcttttctct gacccgcccc   5820
tggccttgta agactcacgt aagctaagtc caggatgcct gtggcctgcg gcttgattct   5880
tccctttagg attcagcaag ttaatggctt cctcgctata gaagtgagac tttgacttga   5940
tgcctcttgg tatatcaaaa agatattcat ccagaaagta ccaaatgttc tgaaagaccc   6000
gctcttcact ccagttttcc ctagggtgtt tctggcaggg cgtttttaaa aggcatctac   6060
ctgagttgac gctaatactt gtcaccacct ggaacgtagt tatcggtcgg caggctgaac   6120
atactccaga ttccccagag gccacttctg tagcccagcg atgcatctga gcctctctgc   6180
gtggtttatg cttgaaaaat agataatgct tttagatggt tcactgccag gccatgggcc   6240
ccacacatct caggccctgt gtgagggagc acactgagat ggtgcaggag tgaatgggca   6300
tggcttggcc tcgctacctc ggggacctgt tggagttctg gcagcagggt gtctgcaggt   6360
gggacggcgt tctgggcaga gtcagaatgg tcagaatgaa acagaacagc caactcaccc   6420
acaggacagc ttattttgag gcaaggtttt ggattttgga ggaagcagcc agatgaggcg   6480
gtgagcctcc agaaggtcag cctttggagc acgtaagata ctgttacagg gtccagaaat   6540
cgtgttcaca tgggggcttt gactcttcaa acagcttttg cagatcgtaa attgcatttg   6600
cctagtcgtg tgacctcaaa agaagtcaga catatttaat ccagaaatag tttcgtttga   6660
gggagggctt gcaggtctgt aaatagcatt tgctttcctg gttagagatt gggatgcaga   6720
aggagttttc agtatttttt ttaaaacact aatgatcatt gaagagtatt tatgtaaaca   6780
tacaacgtat aatgggtggg ggatccgatc atggtgatgt acggggtgaa ttctcttgcc   6840
gtgttgcaaa tgtgtaaaat aaagattatc tggc                               6874
```

<210> SEQ ID NO 9
<211> LENGTH: 7018
<212> TYPE: DNA
<213> ORGANISM: Homo sapiens

<400> SEQUENCE: 9

```
ccgaggtggg cagcacaggc tcctcgacga cttcctaggt cgcaatctcc aggaaaacga     60
ccacagggtc agcggagcta gccgccgagc cccgctcccc gggcccttcc ggcggctgcg    120
ccctttcacc ccggacgtgg gcgggagagg aagcggctgg tgatgctgga acaaacatgg    180
ccgctctggc gcccgtcggc tccccccgcct cccgcggtcc taggctggcc gcgggcctcc    240
ggctgctccc aatgctgggt ttgctgcagt tgctggccga gcctggcctg ggccgcgtcc    300
atcacctggc actcaaggat gatgtgaggc ataaagttca tctgaacacc tttggcttct    360
```

```
tcaaggatgg gtacatggtg gtgaatgtca gtagcctctc actgaatgag cctgaagaca    420
aggatgtgac tattggattt agcctagacc gtacaaagaa tgatggcttt tcttcttacc    480
tggatgaaga tgtgaattac tgtattttaa agaaacagtc tgtctctgtc acccttttaa    540
tcctagacat ctccagaagt gaggtaagag taaagtctcc accagaagct ggtacccagt    600
taccaaagat catcttcagc agggatgaga aagtccttgg tcagagccag gagcctaatg    660
ttaaccctgc ttcagcaggc aaccagaccc agaagacaca agatggtgga aagtctaaaa    720
gaagtacagt ggattcaaag gccatgggag agaaatcctt ttctgttcat aataatggtg    780
gggcagtgtc atttcagttt ttctttaaca tcagcactga tgaccaagaa ggcctttaca    840
gtctttattt tcataaatgc cttggaaaag aattgccaag tgacaagttt acattcagcc    900
ttgatattga gatcacagag aagaatcctg acagctacct ctcagcagga gaaattcctc    960
tccccaaatt atacatctca atggcctttt tcttctttct ttctgggacc atctggattc   1020
atatccttcg aaaacgacgg aatgatgtat ttaaaatcca ctggctgatg gcggcccttc   1080
ctttcaccaa gtctctttcc ttggtgttcc atgcaattga ctaccactac atctcctccc   1140
agggcttccc tatcgaaggc tgggctgttg tgtactacat aactcacctt ttgaaagggg   1200
cgctactctt catcaccatt gcactcattg gcactggctg ggctttcatt aagcacatcc   1260
tttctgataa agacaaaaag atcttcatga ttgtcattcc actccaggtc ctggcaaatg   1320
tagcctacat catcatagag tccaccgagg agggcacgac tgaatatggc ttgtggaagg   1380
actctctatt tctggtcgac ctgttgtgtt gtggtgccat cctcttccca gtggtgtggt   1440
caatcagaca tttacaagaa gcatcagcaa cagatggaaa aggtgacagc atgggacctc   1500
ttcagcagag agcgaatcta agagcaggaa gtcgcataga gtctcaccat tttgcccagg   1560
ctgatcttga actcctggcc tctagctgtc ctcctgcctc agtctcccaa agggctggga   1620
ttacagctgc tattaactta gcaaagctga aacttttcag acattattac gtcttgattg   1680
tgtgttacat atacttcact aggatcattg catttctcct caaactcgct gttccattcc   1740
agtggaagtg gctctaccag ctcctggatg aaacggccac actggtcttc tttgttctaa   1800
cggggtataa attccgtccg gcttcagata acccctacct acaactttct caggaagaag   1860
aagacttgga aatggagtcc gttgtgacaa catctggggt gatggaaagt atgaagaaag   1920
tcaagaaggt gaccaacggc tccgtggagc cccagggcga gtgggaaggc gccgtgtgac   1980
agagccgacc ctgaggatgg cactgtccaa ggaaactgtt aacttattca tagtcctatt   2040
ggacagcagg agcagctcct acagtgaact attggcacca ccgacagtga caccagggca   2100
catggctgga gcacagtgcc gcggaaacct gattttgtac tctcttttat ggaaacgatc   2160
tgtggctgtt tagaggcagc tggatcctct ttcaggcggg aatgggaggg cgggcacagg   2220
gaggaggaga ggaagagaaa aggaagaatt catttttaat ttaggtttct ttttttcttc   2280
ttcatttcgg agctctaagg tgtatgcagt tgtgacccca tgtgtgggga agtgtagcaa   2340
ggacggctgg tggagggga aggagggtgc gaggtgtctg tctgatgctt taggaaatgt   2400
ctactgagga ccctgggact taagaagaag ggcggggaga gtgccattgc ctgtttggga   2460
gacaaaaatg aacgaaaaca ggtgactttg gaaagcaaag tcaaaaccca gtttaggatg   2520
tagcacctgc cccaggattc ctgccctcgg ctttgcccca gacccttatt ccagatgctg   2580
agagtgacca ggacagcagc tcctgaggcc cagtggtctt ctttccaaca ggaaaagaag   2640
gctgtgatgt cgctgtcagg atcatgccct gtggcacagc acaggtggtg ggaggtggtt   2700
```

```
ttctgactga gatgttgcct gatggatgga aagaaatgta tttttaagtt caaaaagcat   2760
tatcctgtgg cgttgcctgg acatccactc cctgacagcc cagagcagca ctgtctggct   2820
tcccttcatg cttgtggctt tgttgtgttt gatcagaatt ttgggggaaa tggaaagttt   2880
tcctcaagga gcagctgggg gcagaatagg tagtatttaa gcaaatactt aagtccaagc   2940
aaatcatccc cattaaaaag cttttcctgt aggctagtag gatttctaaa tagatgaatt   3000
caacagactt ggtccccata gtccaagagt atgtatgtga agaaagtgag catgattcaa   3060
cagtttcact ctcagggatt ttaggatggc aaaatacttc acagaaactc aatgattaag   3120
ttcccttcca cacttccaga gcttgaatga acacaggtag ccacctaaat tgagcagtat   3180
tgcaactcag agagaaaatc atctgaatag taggacaagc tcagaaggta cattgtgact   3240
gagggcttaa aaggagacca aaacatggcc ccatcaggga agcttcttaa tgcttggggg   3300
gccagctagg tagggttgct tccaaaagct ggagcccacc cctgcctagg ggttgtcaga   3360
gagccacacc tgcaggggaa caggtacctc cgagggtgag agtcgtggtc tctgggagtt   3420
gttttctcac ctctggctta gaagggtcag gcagaaacca caggatgtgg ggtcacactc   3480
actgtcccaa gtttgggaac ctgaaaaagt ctccattcag aacatggttg ttctccctgt   3540
cccatgctat cttatcttcc taaatgacta atgaggaagc gggtgttctt tttctgcact   3600
ttgattcgcc atctgggttc tgtagggtgc tctgaaggtg tgatctgcct tctggctgat   3660
gtggaggaag agcaagcgcc ttcccaggcc acagctgctc acctctcggc agatatttta   3720
ggcaagcatc cgtgtgtctt cccatcttca ggagaaaggt aaatgcaccc taagtgttca   3780
cttctggacc tttttcaagt tcacttggga ctgtgtgaca gaagggagtt ggagggagga   3840
tgggaatatt tttaacactt tgttttcctg tgcagaaaca taataccagt tttcgcagaa   3900
atgtgtctca atctgtgact accaaagccc tcctcagtcc ttccctcaga gggacacatt   3960
tgctgtttct cccgcaagca gatgttgtgg atgaggcgat agactccttg gcaagaacga   4020
aaggtgtgat gaaacctccc tgctcggaag ggtctccgtg gaggtgtcct catttcacat   4080
gctgggtttt gcaagcgagg aagccaggca gtggaggaac tagagagagg caggcgtgtg   4140
tgtggacaag cgctggagcc gcagccctca gactggcacg ggaacgccag cgttgggtgt   4200
tcagattcca cgcgtatgtc tgggctcact cacagcatgg ccgagtgtct gcagtgctgg   4260
tcctgaccct tccagagcag cagtggacag atgagataag actgtttcag aaacaaagat   4320
ggccacagcc ttcctaacaa gcaggtcatc tggccatgtc tgtattgtaa ctggtaaaag   4380
gcttcaagtc agattgatga tcaagaaaag tcaaaacccc agcccaagat tgggaaagca   4440
ggtggtggtt ccaagctttt aaaaaattat tgaagctctc catcctgttc tgtgagtgtg   4500
tcttctcttt ctccttcacg tcatagccgt gacccaccgt tcatctctgc tcttgcgtaa   4560
agatgaccga tggagtccaa agccaagtgg cttcaccagc tgacaagcca ccctcctgca   4620
gcctgagttt cacagtccac tgggttcgtt gtcatgcggt gtttgaatgg ttaagccctt   4680
gcagtatttc agatcgggca aaaaatatcg gatgcacata gcagaaccat tggtggtatt   4740
tatagctttg ctttgtactc ctcactgttt ctgcctacgc aaaatatcca tgtttcctct   4800
gagaaatctg ttgtggactg aaagcgctgc tggctgtgaa atttaataaa gtgtgtatgc   4860
tttgctagaa aattatttct tggacaatag gaacagtcat tgatctgtaa atcctggctc   4920
ttaacagtga gtggccaagg acttgatcag cccatttctt ggtccctcag tgctttaaaa   4980
tttaagtagc actgcatttt gtaatgttga atatgactct agtgacttgt aggaggcact   5040
tgtgaggaga tgcttgcttc agtgtaaaag atgctcatgg cctgagtcag ttgagttttc   5100
```

```
tttcaagaaa ccacttcaga gtgaaatatc cagggtttcc ccgccctgga catgtccagc   5160
ctgcccaggc agcacacagc cctgtaagtc cacctcgtgt gggtgagatt tcctcctgcg   5220
tgatgacctc atcgccatct ctgctgtctc attccacagc ctccctccct cttctctcct   5280
cctctgccct cgcccttccc ccttccccat cccctccccc tcctcctctg ccctcgccct   5340
taccccctccc ccttcccctt ccgctcctcc tccctcctcc acctctttct cctcctcctt   5400
ccctcctcct ccctcctctt cccttctctg ccatctttct ccccgtgcct attgatccca   5460
cataggctca ttctgggtac accggctaaa ggctttggtg cattgcagcg ttttctccca   5520
gcagctgtgt gaaagatgca ttttctaagc taaggagaat ttctcaaga gtggcatact   5580
catgccaaat attattgctc tgggccatat aggctggtct tcctccacac taaaatgggt   5640
gtcttgtttt ggtacttaaa acagtctact ccaggcatcc agtccttaca gaccaaggaa   5700
gagcatagcg atgcctgttg gaattgcaga tgcattctgg ccttctcccc cgtcctgaaa   5760
cattttcttt gaggaaggct cttagaacat tagatagtct gctgaggttg ttggcccagc   5820
tccatacacc cagtagaaca gtggaacaac tcatgcttca tgctgccaag ctgctgtact   5880
tcaaaggaaa cagatctagc acactgctgc accccctgctt ccacactcca cacttcaccc   5940
cgctgctttt ctctgacccg cccctggcct tgtaagactc acgtaagcta agtccaggat   6000
gcctgtggcc tgcggcttga ttcttccctt taggattcag caagttaatg gcttcctcgc   6060
tatagaagtg agactttgac ttgatgcctc ttggtatatc aaaaagatat tcatccagaa   6120
agtaccaaat gttctgaaag acccgctctt cactccagtt ttccctaggg tgtttctggc   6180
agggcgtttt taaaaggcat ctacctgagt tgacgctaat acttgtcacc acctggaacg   6240
tagttatcgg tcggcaggct gaacatactc cagattcccc agaggccact tctgtagccc   6300
agcgatgcat ctgagcctct ctgcgtggtt tatgcttgaa aaatagataa tgcttttaga   6360
tggttcactg ccaggccatg ggccccacac atctcaggcc ctgtgtgagg gagcacactg   6420
agatggtgca ggagtgaatg ggcatggctt ggcctcgcta cctcggggac ctgttggagt   6480
tctggcagca gggtgtctgc aggtgggacg gcgttctggg cagagtcaga atggtcagaa   6540
tgaaacagaa cagccaactc acccacagga cagcttattt tgaggcaagg ttttggattt   6600
tggaggaagc agccagatga ggcggtgagc ctccagaagg tcagcctttg gagcacgtaa   6660
gatactgtta cagggtccag aaatcgtgtt cacatggggg ctttgactct tcaaacagct   6720
tttgcagatc gtaaattgca tttgcctagt cgtgtgacct caaaagaagt cagacatatt   6780
taatccagaa atagtttcgt ttgagggagg gcttgcaggt ctgtaaatag catttgcttt   6840
cctggttaga gattgggatg cagaaggagt tttcagtatt ttttttaaaa cactaatgat   6900
cattgaagag tatttatgta aacatacaac gtataatggg tgggggatcc gatcatggtg   6960
atgtacgggg tgaattctct tgccgtgttg caaatgtgta aaataaagat tatctggc     7018
```

<210> SEQ ID NO 10
<211> LENGTH: 7353
<212> TYPE: DNA
<213> ORGANISM: Homo sapiens

<400> SEQUENCE: 10

```
attattgcaa ccatttcgct tgtatttgag tgtgaagcgc ctagaaaacc acaggacccc     60
tacggcgagc cgggaatttt tagatatttt cctccgagtc aacgctcagt gaaatcagtt    120
caatcagtgg cccgacaccg tgcggctgac acagcttatc cccgaccct gagatcaggg    180
```

```
gtccccggag cccaaggtcg cttccaaagc tcagcgaggc ggaggtgcgg cccgggctgg    240
tctggttcgg ccaccgttgt tatggcaacc gccaataggt tggcttcatc tctaactgaa    300
agtctgcaca ggagcggccg atcgaagggc cccgaggtgg gcagcacagg ctcctcgacg    360
acttcctagg tcgcaatctc caggaaaacg accacagggt cagcggagct agccgccgag    420
ccccgctccc cgggcccttc cggcggctgc gccctttcac cccggacgtg ggcgggagag    480
gaagcggctg gtgatgctgg aacaaacatg gccgctctgg cgcccgtcgg ctcccccgcc    540
tcccgcggtc ctaggctggc cgcgggcctc cggctgctcc caatgctggg tttgctgcag    600
ttgctggccg agcctggcct gggccgcgtc catcacctgg cactcaagga tgatgtgagg    660
cataaagttc atctgaacac ctttggcttc ttcaaggatg ggtacatggt ggtgaatgtc    720
agtagcctct cactgaatga gcctgaagac aaggatgtga ctattggatt tagcctagac    780
cgtacaaaga atgatggctt ttcttcttac ctggatgaag atgtgaatta ctgtatttta    840
aagaaacagt ctgtctctgt caccctttta atcctagaca tctccagaag tgaggtaaga    900
gtaaagtctc caccagaagc tggtacccag ttaccaaaga tcatcttcag cagggatgag    960
aaagtccttg gtcagagcca ggagcctaat gttaaccctg cttcagcagg caaccagacc   1020
cagaagacac aagatggtgg aaagtctaaa agaagtacag tggattcaaa ggccatggga   1080
gagaaatcct tttctgttca taataatggt ggggcagtgt catttcagtt tttctttaac   1140
atcagcactg atgaccaaga aggcctttac agtctttatt ttcataaatg ccttggaaaa   1200
gaattgccaa gtgacaagtt tacattcagc cttgatattg agatcacaga gaagaatcct   1260
gacagctacc tctcagcagg agaaattcct ctccccaaat tatacatctc aatggccttt   1320
ttcttctttc tttctgggac catctggatt catatccttc gaaaacgacg gaatgatgta   1380
tttaaaatcc actggctgat ggcggccctt cctttcacca agtctctttc cttggtgttc   1440
catgcaattg actaccacta catctcctcc cagggcttcc ctatcgaagg ctgggctgtt   1500
gtgtactaca taactcacct tttgaaaggg gcgctactct tcatcaccat tgcactcatt   1560
ggcactggct gggctttcat taagcacatc ctttctgata aagacaaaaa gatcttcatg   1620
attgtcattc cactccaggt cctggcaaat gtagcctaca tcatcataga gtccaccgag   1680
gagggcacga ctgaatatgg cttgtggaag gactctctat ttctggtcga cctgttgtgt   1740
tgtggtgcca tcctcttccc agtggtgtgg tcaatcagac atttacaaga agcatcagca   1800
acagatggaa aaggtgacag catgggacct cttcagcaga gagcgaatct aagagcagga   1860
agtcgcatag agtctcacca ttttgcccag gctgatcttg aactcctggc ctctagctgt   1920
cctcctgcct cagtctccca aagggctggg attacagctg ctattaactt agcaaagctg   1980
aaacttttca gacattatta cgtcttgatt gtgtgttaca tatacttcac taggatcatt   2040
gcatttctcc tcaaactcgc tgttccattc cagtggaagt ggctctacca gctcctggat   2100
gaaacggcca cactggtctt ctttgttcta acggggtata aattccgtcc ggcttcagat   2160
aacccctacc tacaactttc tcaggaagaa gaagacttgg aaatggagtc cgttgtgaca   2220
acatctgggg tgatggaaag tatgaagaaa gtcaagaagg tgaccaacgg ctccgtggag   2280
ccccagggcg agtgggaagg cgccgtgtga cagagccgac cctgaggatg gcactgtcca   2340
aggaaactgt taacttattc atagtcctat tggacagcag gagcagctcc tacagtgaac   2400
tattggcacc accgacagtg acaccagggc acatggctgg agcacagtgc cgcggaaacc   2460
tgattttgta ctctctttta tggaaacgat ctgtggctgt ttagaggcag ctggatcctc   2520
tttcaggcgg gaatgggagg gcgggcacag ggaggaggag aggaagagaa aaggaagaat   2580
```

```
tcatttttaa tttaggtttc tttttttctt cttcatttcg gagctctaag gtgtatgcag   2640
ttgtgacccc atgtgtgggg aagtgtagca aggacggctg gtggaggggg aaggagggtg   2700
cgaggtgtct gtctgatgct ttaggaaatg tctactgagg accctgggac ttaagaagaa   2760
gggcggggag agtgccattg cctgtttggg agacaaaaat gaacgaaaac aggtgacttt   2820
ggaaagcaaa gtcaaaaccc agtttaggat gtagcacctg ccccaggatt cctgccctcg   2880
gctttgcccc agacccttat tccagatgct gagagtgacc aggacagcag ctcctgaggc   2940
ccagtggtct tctttccaac aggaaaagaa ggctgtgatg tcgctgtcag gatcatgccc   3000
tgtggcacag cacaggtggt gggaggtggt tttctgactg agatgttgcc tgatggatgg   3060
aaagaaatgt atttttaagt tcaaaaagca ttatcctgtg gcgttgcctg gacatccact   3120
ccctgacagc ccagagcagc actgtctggc ttcccttcat gcttgtggct ttgttgtgtt   3180
tgatcagaat tttgggggaa atggaaagtt ttcctcaagg agcagctggg ggcagaatag   3240
gtagtattta agcaaatact taagtccaag caaatcatcc ccattaaaaa gcttttcctg   3300
taggctagta ggatttctaa atagatgaat tcaacagact tggtccccat agtccaagag   3360
tatgtatgtg aagaaagtga gcatgattca acagtttcac tctcagggat tttaggatgg   3420
caaaatactt cacagaaact caatgattaa gttcccttcc acacttccag agcttgaatg   3480
aacacaggta gccacctaaa ttgagcagta ttgcaactca gagagaaaat catctgaata   3540
gtaggacaag ctcagaaggt acattgtgac tgagggctta aaaggagacc aaaacatggc   3600
cccatcaggg aagcttctta atgcttgggg ggccagctag gtagggttgc ttccaaaagc   3660
tggagcccac ccctgcctag ggttgtcag agagccacac ctgcagggga acaggtacct    3720
ccgagggtga gagtcgtggt ctctgggagt tgttttctca cctctggctt agaagggtca   3780
ggcagaaacc acaggatgtg gggtcacact cactgtccca agtttgggaa cctgaaaaag   3840
tctccattca gaacatggtt gttctccctg tcccatgcta tcttatcttc ctaaatgact   3900
aatgaggaag cgggtgttct ttttctgcac tttgattcgc catctgggtt ctgtagggtg   3960
ctctgaaggt gtgatctgcc ttctggctga tgtggaggaa gagcaagcgc cttcccaggc   4020
cacagctgct cacctctcgg cagatatttt aggcaagcat ccgtgtgtct tcccatcttc   4080
aggagaaagg taaatgcacc ctaagtgttc acttctggac ctttttcaag ttcacttggg   4140
actgtgtgac agaagggagt tggagggagg atgggaatat ttttaacact ttgttttcct   4200
gtgcagaaac ataataccag ttttcgcaga aatgtgtctc aatctgtgac taccaaagcc   4260
ctcctcagtc cttccctcag agggacacat ttgctgtttc tcccgcaagc agatgttgtg   4320
gatgaggcga tagactcctt ggcaagaacg aaaggtgtga tgaaacctcc ctgctcggaa   4380
gggtctccgt ggaggtgtcc tcatttcaca tgctgggttt tgcaagcgag gaagccaggc   4440
agtggaggaa ctagagagag gcaggcgtgt gtgtggacaa gcgctggagc cgcagccctc   4500
agactggcac gggaacgcca gcgttgggtg ttcagattcc acgcgtatgt ctgggctcac   4560
tcacagcatg gccgagtgtc tgcagtgctg gtcctgaccc ttccagagca gcagtggaca   4620
gatgagataa gactgtttca gaaacaaaga tggccacagc cttcctaaca agcaggtcat   4680
ctggccatgt ctgtattgta actggtaaaa ggcttcaagt cagattgatg atcaagaaaa   4740
gtcaaaaccc cagcccaaga ttgggaaagc aggtggtggt tccaagcttt taaaaaatta   4800
ttgaagctct ccatcctgtt ctgtgagtgt gtcttctctt tctccttcac gtcatagccg   4860
tgacccaccg ttcatctctg ctcttgcgta aagatgaccg atggagtcca aagccaagtg   4920
```

```
gcttcaccag ctgacaagcc accctcctgc agcctgagtt tcacagtcca ctgggttcgt   4980
tgtcatgcgg tgtttgaatg gttaagccct tgcagtattt cagatcgggc aaaaaatatc   5040
ggatgcacat agcagaacca ttggtggtat ttatagcttt gctttgtact cctcactgtt   5100
tctgcctacg caaaatatcc atgtttcctc tgagaaatct gttgtggact gaaagcgctg   5160
ctggctgtga aatttaataa agtgtgtatg ctttgctaga aaattatttc ttggacaata   5220
ggaacagtca ttgatctgta aatcctggct cttaacagtg agtggccaag gacttgatca   5280
gcccatttct tggtccctca gtgctttaaa atttaagtag cactgcattt tgtaatgttg   5340
aatatgactc tagtgacttg taggaggcac ttgtgaggag atgcttgctt cagtgtaaaa   5400
gatgctcatg gcctgagtca gttgagtttt ctttcaagaa accacttcag agtgaaatat   5460
ccagggtttc cccgccctgg acatgtccag cctgcccagg cagcacacag ccctgtaagt   5520
ccacctcgtg tgggtgagat ttcctcctgc gtgatgacct catcgccatc tctgctgtct   5580
cattccacag cctccctccc tcttctctcc tcctctgccc tcgcccttcc cccttcccca   5640
tcccctcccc ctcctcctct gccctcgccc ttacccctcc cccttcccct tccgctcctc   5700
ctccctcctc cacctctttc tcctcctcct tccctcctcc tccctcctct tcccttctct   5760
gccatctttc tccccgtgcc tattgatccc acataggctc attctgggta caccggctaa   5820
aggctttggt gcattgcagc gttttctccc agcagctgtg tgaaagatgc attttctaag   5880
ctaaggagaa ttttctcaag agtggcatac tcatgccaaa tattattgct ctgggccata   5940
taggctggtc ttcctccaca ctaaaatggg tgtcttgttt tggtacttaa aacagtctac   6000
tccaggcatc cagtccttac agaccaagga agagcatagc gatgcctgtt ggaattgcag   6060
atgcattctg gccttctccc ccgtcctgaa acattttctt tgaggaaggc tcttagaaca   6120
ttagatagtc tgctgaggtt gttggcccag ctccatacac ccagtagaac agtggaacaa   6180
ctcatgcttc atgctgccaa gctgctgtac ttcaaaggaa acagatctag cacactgctg   6240
cacccctgct tccacactcc acacttcacc ccgctgcttt tctctgaccc gcccctggcc   6300
ttgtaagact cacgtaagct aagtccagga tgcctgtggc ctgcggcttg attcttccct   6360
ttaggattca gcaagttaat ggcttcctcg ctatagaagt gagactttga cttgatgcct   6420
cttggtatat caaaaagata ttcatccaga aagtaccaaa tgttctgaaa gacccgctct   6480
tcactccagt tttccctagg gtgtttctgg cagggcgttt ttaaaaggca tctacctgag   6540
ttgacgctaa tacttgtcac cacctggaac gtagttatcg gtcggcaggc tgaacatact   6600
ccagattccc cagaggccac ttctgtagcc cagcgatgca tctgagcctc tctgcgtggt   6660
ttatgcttga aaaatagata atgcttttag atggttcact gccaggccat gggccccaca   6720
catctcaggc cctgtgtgag ggagcacact gagatggtgc aggagtgaat gggcatggct   6780
tggcctcgct acctcgggga cctgttggag ttctggcagc agggtgtctg caggtgggac   6840
ggcgttctgg gcagagtcag aatggtcaga atgaaacaga acagccaact cacccacagg   6900
acagcttatt ttgaggcaag gttttggatt ttggaggaag cagccagatg aggcggtgag   6960
cctccagaag gtcagccttt ggagcacgta agatactgtt acagggtcca gaaatcgtgt   7020
tcacatgggg gctttgactc ttcaaacagc ttttgcagat cgtaaattgc atttgcctag   7080
tcgtgtgacc tcaaaagaag tcagacatat ttaatccaga aatagtttcg tttgagggag   7140
ggcttgcagg tctgtaaata gcatttgctt tcctggttag agattgggat gcagaaggag   7200
ttttcagtat ttttttaaa acactaatga tcattgaaga gtatttatgt aaacatacaa   7260
cgtataatgg gtgggggatc cgatcatggt gatgtacggg gtgaattctc ttgccgtgtt   7320
```

gcaaatgtgt aaaataaaga ttatctggca gaa 7353

<210> SEQ ID NO 11
<211> LENGTH: 279
<212> TYPE: PRT
<213> ORGANISM: Homo sapiens

<400> SEQUENCE: 11

```
Met Met Leu Met Gln Ala Leu Val Leu Phe Thr Leu Asp Ser Leu Asp
1               5                   10                  15

Met Leu Pro Ala Val Lys Ala Thr Trp Leu Tyr Gly Ile Gln Ile Thr
            20                  25                  30

Ser Leu Leu Leu Val Cys Ile Leu Gln Phe Phe Asn Ser Met Ile Leu
        35                  40                  45

Gly Ser Leu Leu Ile Ser Phe Asn Leu Ser Val Phe Ile Ala Arg Lys
    50                  55                  60

Leu Gln Lys Asn Leu Lys Thr Gly Ser Phe Leu Asn Arg Leu Gly Lys
65                  70                  75                  80

Leu Leu Leu His Leu Phe Met Val Leu Cys Leu Thr Leu Phe Leu Asn
                85                  90                  95

Asn Ile Ile Lys Lys Ile Leu Asn Leu Lys Ser Asp Glu His Ile Phe
            100                 105                 110

Lys Phe Leu Lys Ala Lys Phe Gly Leu Gly Ala Thr Arg Asp Phe Asp
        115                 120                 125

Ala Asn Leu Tyr Leu Cys Glu Glu Ala Phe Gly Leu Leu Pro Phe Asn
    130                 135                 140

Thr Phe Gly Arg Leu Ser Asp Thr Leu Leu Phe Tyr Ala Tyr Ile Phe
145                 150                 155                 160

Val Leu Ser Ile Thr Val Ile Val Ala Phe Val Val Ala Phe His Asn
                165                 170                 175

Leu Ser Asp Ser Thr Asn Gln Gln Ser Val Gly Lys Met Glu Lys Gly
            180                 185                 190

Thr Val Asp Leu Lys Pro Glu Thr Ala Tyr Asn Leu Ile His Thr Ile
        195                 200                 205

Leu Phe Gly Phe Leu Ala Leu Ser Thr Met Arg Met Lys Tyr Leu Trp
    210                 215                 220

Thr Ser His Met Cys Val Phe Ala Ser Phe Gly Leu Cys Ser Pro Glu
225                 230                 235                 240

Ile Trp Glu Leu Leu Leu Lys Ser Val His Leu Tyr Asn Pro Lys Arg
                245                 250                 255

Ile Cys Ile Met Arg Tyr Ser Val Pro Ile Leu Ile Leu Leu Tyr Leu
            260                 265                 270

Cys Tyr Lys Asn Gln Lys Ser
        275
```

<210> SEQ ID NO 12
<211> LENGTH: 102
<212> TYPE: PRT
<213> ORGANISM: Homo sapiens

<400> SEQUENCE: 12

```
Met Met Ser Ile Arg Gln Arg Arg Glu Ile Arg Ala Thr Glu Val Ser
1               5                   10                  15

Glu Asp Phe Pro Ala Gln Glu Glu Asn Val Lys Leu Glu Asn Lys Leu
            20                  25                  30
```

```
Pro Ser Gly Cys Thr Ser Arg Arg Leu Trp Lys Ile Leu Ser Leu Thr
        35                  40                  45

Ile Gly Gly Thr Ile Ala Leu Cys Ile Gly Leu Leu Thr Ser Val Tyr
    50                  55                  60

Leu Ala Thr Leu His Glu Asn Asp Leu Trp Phe Ser Asn Ile Lys Val
65                  70                  75                  80

Trp Ser Phe Phe Asp His Cys Ile Ile His Ser Val Gly Ser Pro Val
                85                  90                  95

Val Ser His Val Asp Glu
            100


<210> SEQ ID NO 13
<211> LENGTH: 716
<212> TYPE: PRT
<213> ORGANISM: Homo sapiens

<400> SEQUENCE: 13

Met Met Ser Ile Arg Gln Arg Arg Glu Ile Arg Ala Thr Glu Val Ser
1               5                   10                  15

Glu Asp Phe Pro Ala Gln Glu Glu Asn Val Lys Leu Glu Asn Lys Leu
            20                  25                  30

Pro Ser Gly Cys Thr Ser Arg Arg Leu Trp Lys Ile Leu Ser Leu Thr
        35                  40                  45

Ile Gly Gly Thr Ile Ala Leu Cys Ile Gly Leu Leu Thr Ser Val Tyr
    50                  55                  60

Leu Ala Thr Leu His Glu Asn Asp Leu Trp Phe Ser Asn Ile Lys Glu
65                  70                  75                  80

Val Glu Arg Glu Ile Ser Phe Arg Thr Glu Cys Gly Leu Tyr Tyr Ser
                85                  90                  95

Tyr Tyr Lys Gln Met Leu Gln Ala Pro Thr Leu Val Gln Gly Phe His
            100                 105                 110

Gly Leu Ile Tyr Asp Asn Lys Thr Glu Ser Met Lys Thr Ile Asn Leu
        115                 120                 125

Leu Gln Arg Met Asn Ile Tyr Gln Glu Val Phe Leu Ser Ile Leu Tyr
    130                 135                 140

Arg Val Leu Pro Ile Gln Lys Tyr Leu Glu Pro Val Tyr Phe Tyr Ile
145                 150                 155                 160

Tyr Thr Leu Phe Gly Leu Gln Ala Ile Tyr Val Thr Ala Leu Tyr Ile
                165                 170                 175

Thr Ser Trp Leu Leu Ser Gly Thr Trp Leu Ser Gly Leu Leu Ala Ala
            180                 185                 190

Phe Trp Tyr Val Thr Asn Arg Ile Asp Thr Thr Arg Val Glu Phe Thr
        195                 200                 205

Ile Pro Leu Arg Glu Asn Trp Ala Leu Pro Phe Phe Ala Ile Gln Ile
    210                 215                 220

Ala Ala Ile Thr Tyr Phe Leu Arg Pro Asn Leu Gln Pro Leu Ser Glu
225                 230                 235                 240

Arg Leu Thr Leu Leu Ala Ile Phe Ile Ser Thr Phe Leu Phe Ser Leu
                245                 250                 255

Thr Trp Gln Phe Asn Gln Phe Met Met Leu Met Gln Ala Leu Val Leu
            260                 265                 270

Phe Thr Leu Asp Ser Leu Asp Met Leu Pro Ala Val Lys Ala Thr Trp
        275                 280                 285

Leu Tyr Gly Ile Gln Ile Thr Ser Leu Leu Leu Val Cys Ile Leu Gln
    290                 295                 300
```

```
Phe Phe Asn Ser Met Ile Leu Gly Ser Leu Leu Ile Ser Phe Asn Leu
305                 310                 315                 320

Ser Val Phe Ile Ala Arg Lys Leu Gln Lys Asn Leu Lys Thr Gly Ser
                325                 330                 335

Phe Leu Asn Arg Leu Gly Lys Leu Leu Leu His Leu Phe Met Val Leu
            340                 345                 350

Cys Leu Thr Leu Phe Leu Asn Asn Ile Ile Lys Lys Ile Leu Asn Leu
        355                 360                 365

Lys Ser Asp Glu His Ile Phe Lys Phe Leu Lys Ala Lys Phe Gly Leu
    370                 375                 380

Gly Ala Thr Arg Asp Phe Asp Ala Asn Leu Tyr Leu Cys Glu Glu Ala
385                 390                 395                 400

Phe Gly Leu Leu Pro Phe Asn Thr Phe Gly Arg Leu Ser Asp Thr Leu
                405                 410                 415

Leu Phe Tyr Ala Tyr Ile Phe Val Leu Ser Ile Thr Val Ile Val Ala
            420                 425                 430

Phe Val Val Ala Phe His Asn Leu Ser Asp Ser Thr Asn Gln Gln Ser
        435                 440                 445

Val Gly Lys Met Glu Lys Gly Thr Val Asp Leu Lys Pro Glu Thr Ala
    450                 455                 460

Tyr Asn Leu Ile His Thr Ile Leu Phe Gly Phe Leu Ala Leu Ser Thr
465                 470                 475                 480

Met Arg Met Lys Tyr Leu Trp Thr Ser His Met Cys Val Phe Ala Ser
                485                 490                 495

Phe Gly Leu Cys Ser Pro Glu Ile Trp Glu Leu Leu Leu Lys Ser Val
            500                 505                 510

His Leu Tyr Asn Pro Lys Arg Ile Cys Ile Met Arg Tyr Ser Val Pro
        515                 520                 525

Ile Leu Ile Leu Leu Tyr Leu Cys Tyr Lys Phe Trp Pro Gly Met Met
    530                 535                 540

Asp Glu Leu Ser Glu Leu Arg Glu Phe Tyr Asp Pro Asp Thr Val Glu
545                 550                 555                 560

Leu Met Asn Trp Ile Asn Ser Asn Thr Pro Arg Lys Ala Val Phe Ala
                565                 570                 575

Gly Ser Met Gln Leu Leu Ala Gly Val Lys Leu Cys Thr Gly Arg Thr
            580                 585                 590

Leu Thr Asn His Pro His Tyr Glu Asp Ser Ser Leu Arg Glu Arg Thr
        595                 600                 605

Arg Ala Val Tyr Gln Ile Tyr Ala Lys Arg Ala Pro Glu Glu Val His
    610                 615                 620

Ala Leu Leu Arg Ser Phe Gly Thr Asp Tyr Val Ile Leu Glu Asp Ser
625                 630                 635                 640

Ile Cys Tyr Glu Arg Arg His Arg Arg Gly Cys Arg Leu Arg Asp Leu
                645                 650                 655

Leu Asp Ile Ala Asn Gly His Met Met Asp Gly Pro Gly Glu Asn Asp
            660                 665                 670

Pro Asp Leu Lys Pro Ala Asp His Pro Arg Phe Cys Glu Glu Ile Lys
        675                 680                 685

Arg Asn Leu Pro Pro Tyr Val Ala Tyr Phe Thr Arg Val Phe Gln Asn
    690                 695                 700

Lys Thr Phe His Val Tyr Lys Leu Ser Arg Asn Lys
705                 710                 715
```

<210> SEQ ID NO 14
<211> LENGTH: 112
<212> TYPE: PRT
<213> ORGANISM: Homo sapiens

<400> SEQUENCE: 14

```
Met Met Ser Ile Arg Gln Arg Arg Glu Ile Arg Ala Thr Glu Val Ser
1               5                   10                  15

Glu Asp Phe Pro Ala Gln Glu Glu Asn Val Lys Leu Glu Asn Lys Leu
            20                  25                  30

Pro Ser Gly Cys Thr Ser Arg Arg Leu Trp Lys Ile Leu Ser Leu Thr
        35                  40                  45

Ile Gly Gly Thr Pro Phe Ala Leu Asp Phe Leu His Leu Ser Thr Leu
    50                  55                  60

Pro Arg Tyr Met Lys Met Ile Tyr Gly Phe Leu Ile Leu Arg Lys Trp
65                  70                  75                  80

Ser Glu Lys Ser His Ser Glu Gln Ser Val Ala Cys Ile Thr Pro Thr
                85                  90                  95

Thr Ser Arg Cys Cys Arg Leu Gln Pro Ser Cys Lys Val Ile Thr Thr
            100                 105                 110
```

<210> SEQ ID NO 15
<211> LENGTH: 1841
<212> TYPE: DNA
<213> ORGANISM: Homo sapiens

<400> SEQUENCE: 15

```
aagtttgcgg agcggcttct gctcgtcggc cgtgcggcga ggcagggcct gggctgcgac      60

cccggcggcc gctcgcggtc ttgggagagc tggggcgcgt gcctgaactt cccggctgcc     120

cctgtccttg gagacctacc tgatggggac gccaggtgtg caggggcgtg gcgcgtagga     180

gtgatttgga gaacaatgca tgtaagtctg acatcatgat gtccatccgg caaagaagag     240

aaataagagc cacagaagtt tctgaagact ttccagccca agaagaaaat gtgaagttgg     300

aaaataaatt gccatctggt tgtaccagta gaagattatg gaagattttg tcattgacaa     360

ttggtggaac cattgccctt tgcattggac ttcttacatc tgtctacctt gccacgttac     420

atgaaaatga tttatggttt tctaatatta aggaagtgga gcgagaaatc tcattcagaa     480

cagagtgtgg cctgtattac tcctactaca agcagatgct gcaggctcca accctcgtgc     540

aaggttttca tggcctaata tatgataata aaactgaatc tatgaagaca attaacctcc     600

ttcagcgaat gaatatttac caagaggttt ttctcagtat tttatataga gttctaccca     660

tacagaaata tttagagcca gtttattttt atatttacac cttatttggg ctccaggcga     720

tctatgtcac agctctctac ataaccagct ggctactcag tggtacatgg ctgtcaggac     780

tgttggcagc tttctggtat gtcacaaata gaatagatac cacaagagtt gagtttacca     840

tcccactgag ggagaactgg gcgctgccat tctttgcaat tcagatagca gcaattacat     900

atttcctgag accaaactta cagcctcttt ctgaaaggct gacacttctt gccattttca     960

tatcaacttt tctctttagt ctgacatggc aatttaatca atttatgatg ctgatgcaag    1020

cattagtgct gttcacactg gactccctgg acatgctgcc agcagtgaag gcgacatggc    1080

tgtatggaat acagataaca agtttactcc tggtctgcat tcttcagttt tttaattcca    1140

tgattcttgg atcactgctt atcagtttta acctttcagt attcattgca agaaaacttc    1200

agaaaaatct gaaaactgga agcttcctta ataggcttgg gaaacttttg ttacatttat    1260
```

```
ttatggtttt atgtttgaca ctttttctca acaacataat taagaaaatt cttaacctga   1320

agtcagatga acacatattt aaatttctga aggcaaaatt tgggcttgga gcaacaaggg   1380

attttgatgc aaatctctat ctgtgtgaag aagcttttgg cctcctgcct tttaatacat   1440

ttggaaggct ttcagatact ctgctttttt atgcttacat attcgttctg tccatcacag   1500

tgattgtagc attcgttgtt gcctttcata atctcagtga ttctacaaat caacaatccg   1560

tgggtaaaat ggaaaaaggc acagttgacc tgaaaccaga aactgcctac aacttaatac   1620

ataccattct gtttggattc ttggcattga gtacaatgag aatgaagtac ctctggacgt   1680

cacacatgtg tgtgttcgca tcattcggcc tatgtagccc tgaaatatgg gagttacttc   1740

tgaagtcagt ccatctttat aacccaaaga ggatatgtat aatgcgatat tcagtaccga   1800

tattaatact gctgtatcta tgctataaga atcagaaatc t                      1841
```

<210> SEQ ID NO 16
<211> LENGTH: 2206
<212> TYPE: DNA
<213> ORGANISM: Homo sapiens

<400> SEQUENCE: 16

```
cggttctgcc ctccttgtac ccgcggcgcg ctgcggcccg tggcgcggcc ccgttcccgc     60

ctagccccgt cggcctcctt cccctcccgg agccgcgcgt gaggacggct gaggccgcag    120

gagtgatttg gagaacaatg catgtaagtc tgacatcatg atgtccatcc ggcaaagaag    180

agaaataaga gccacagaag tttctgaaga ctttccagcc caagaagaaa atgtgaagtt    240

ggaaaataaa ttgccatctg gttgtaccag tagaagatta tggaagattt tgtcattgac    300

aattggtgga accattgccc tttgcattgg acttcttaca tctgtctacc ttgccacgtt    360

acatgaaaat gatttatggt tttctaatat taaggtatgg agtttctttg accattgtat    420

cattcactca gtgggatctc cagtagtaag ccatgtggat gaatgaccaa ggcaacacag    480

ttttgccata aagaatccaa tctctagaaa ggttggacta tagagtgaaa taacttttgt    540

gtttattatt ttaaaataac atattagaat ctttttttaa atttttcttt attatttatt    600

tatttttgag atggagtctc actctgtcac ccaggctgga gtgcggtggc gcaatcttgg    660

ctcactacaa cctctgcctc gcaggttcag gtgattcttc tggcttagcc tcccaagtag    720

ctgggactat aggtgcgtgc caccacaccc agctaatttt tgtatttttta ctagagacgg    780

ggtttcagca tattgaccag gctgatctcg aactcctgac cttgtgatct gcctgtctca    840

gcctcccaaa gtgctgggat tacaggcgtg agccactgcg tccagccaga atctttattt    900

ttcattttaa ttttttgaga tagggtattg ctctgtcacc caggctagaa tgcagtggtg    960

caaacatggg tcactgcagc ctcaacctcc tgggctcaag tgagtatcct gcctaagctt   1020

cctgtgtcac tgggacccca ggcatgcacc acctcaccaa gctaaatttg atttttttgt   1080

agagacaggg tctcactttg ttgcccatgc tggtctcgaa ctcctgggct caagcgatcc   1140

tactgccctg gtcttccaaa atatgagaat gagccatagc acccagccca gaatttttat   1200

aatcaagtga gttttttctt tttcattaac ttattccatt tatttagcag ttattctaaa   1260

ttagtatttt tcaagttata gattgtgaaa ttagtgcagt aggtcatgag taacattttt   1320

cttaatgaaa tcaaaaagaa agaatactat cacatctagt agggttgagg attgttttgt   1380

gaaactttta attttatata tatatatata tgcacaaact gggtcacagt atacaaggta   1440

cttccttttc tttttttct tgttggctac aacaggaaaa aaaaaaaaca gaaaaggaaa   1500

taaaaaagcc actgctttaa atcatggggt ctaaatgtgg ctccacagag ggtcctcagc   1560
```

```
atgttcatga ctatctaata ctctgtgcaa gtggttttgc agggcatagg gcgatgggga   1620

agccatatgt ttccagggaa aggaactgta attttaatca gattttcagg agggttagcc   1680

gggcgtcacg cctgtaatcc cagcactttg ggaggtcgag gcgggcagat cacttgaagt   1740

caggagttca agaccagcct ggccaacatg gtggaaccct atctctacta aaaatacaaa   1800

aattagccgg gcatggtgac acacacctgt aatctcagct actcaggagg ctgaggcaca   1860

agaatcactt gaactcggga ggaagaggtt gcagtgagct gagatcccac cactgcactc   1920

cagcctgggc aacagagcaa tactctttat caaaaaaaaa aagaaaaaag ttgagggggt   1980

ggtctgtgac tctttaaaca cgtttccttg ttttctttct ctctctcttt ttcaacattt   2040

ctagaactcc tcttggcatt gttttcagaa ctcgtatata acttacatgt ggaaatttgc   2100

atccaaatat accttacatt ttaatctaat atgtcatgat ctttaaccta aactgtggtg   2160

tctaatgact agttgcttgt aaaaataaac aaacaccttc aaagcc                  2206
```

<210> SEQ ID NO 17
<211> LENGTH: 4456
<212> TYPE: DNA
<213> ORGANISM: Homo sapiens

<400> SEQUENCE: 17

```
aagtttgcgg agcggcttct gctcgtcggc cgtgcggcga ggcagggcct gggctgcgac     60

cccggcggcc gctcgcggtc ttgggagagc tggggcgcgt gcctgaactt cccggctgcc    120

cctgtccttg gagacctacc tgatggggac gccaggtgtg caggggcgtg gcgcgtagga    180

gtgatttgga gaacaatgca tgtaagtctg acatcatgat gtccatccgg caaagaagag    240

aaataagagc cacagaagtt tctgaagact ttccagccca agaagaaaat gtgaagttgg    300

aaaataaatt gccatctggt tgtaccagta gaagattatg gaagattttg tcattgacaa    360

ttggtggaac cattgccctt tgcattggac ttcttacatc tgtctacctt gccacgttac    420

atgaaaatga tttatggttt tctaatatta aggaagtgga gcgagaaatc tcattcagaa    480

cagagtgtgg cctgtattac tcctactaca agcagatgct gcaggctcca accctcgtgc    540

aaggttttca tggcctaata tatgataata aaactgaatc tatgaagaca attaacctcc    600

ttcagcgaat gaatatttac caagaggttt ttctcagtat tttatataga gttctaccca    660

tacagaaata tttagagcca gtttattttt atatttacac cttatttggg ctccaggcga    720

tctatgtcac agctctctac ataaccagct ggctactcag tggtacatgg ctgtcaggac    780

tgttggcagc tttctggtat gtcacaaata gaatagatac cacaagagtt gagtttacca    840

tcccactgag ggagaactgg gcgctgccat tctttgcaat tcagatagca gcaattacat    900

atttcctgag accaaactta cagcctcttt ctgaaaggct gacacttctt gccattttca    960

tatcaacttt tctctttagt ctgacatggc aatttaatca atttatgatg ctgatgcaag   1020

cattagtgct gttcacactg gactccctgg acatgctgcc agcagtgaag gcgacatggc   1080

tgtatggaat acagataaca agtttactcc tggtctgcat tcttcagttt tttaattcca   1140

tgattcttgg atcactgctt atcagtttta acctttcagt attcattgca agaaaacttc   1200

agaaaaatct gaaaactgga agcttcctta ataggcttgg gaaacttttg ttacatttat   1260

ttatggtttt atgtttgaca ctttttctca acaacataat taagaaaatt cttaacctga   1320

agtcagatga acacatattt aaatttctga aggcaaaatt tgggcttgga gcaacaaggg   1380

attttgatgc aaatctctat ctgtgtgaag aagcttttgg cctcctgcct tttaatacat   1440
```

```
ttggaaggct ttcagatact ctgctttttt atgcttacat attcgttctg tccatcacag   1500
tgattgtagc attcgttgtt gcctttcata atctcagtga ttctacaaat caacaatccg   1560
tgggtaaaat ggaaaaaggc acagttgacc tgaaaccaga aactgcctac aacttaatac   1620
ataccattct gtttggattc ttggcattga gtacaatgag aatgaagtac ctctggacgt   1680
cacacatgtg tgtgttcgca tcattcggcc tatgtagccc tgaaatatgg gagttacttc   1740
tgaagtcagt ccatctttat aacccaaaga ggatatgtat aatgcgatat tcagtaccga   1800
tattaatact gctgtatcta tgctataagt tctggccagg aatgatggat gaactctccg   1860
agttgagaga attctatgat ccagatacag tggagctgat gaactggatt aactctaaca   1920
ctccaagaaa ggctgtgttt gcgggaagca tgcagttgct ggccggagtc aagctgtgca   1980
cgggaaggac cctaaccaac cacccgcact atgaagacag cagcctgaga gagcggacca   2040
gagcggttta tcagatatat gccaagaggg caccagagga agtgcatgcc ctcctaaggt   2100
ccttcggcac tgactacgta atcctggaag acagcatctg ctacgagcgg aggcaccgcc   2160
ggggctgccg actccgggac ctgctggaca ttgccaacgg ccacatgatg gatggcccag   2220
gagagaatga tcctgatttg aaacctgcag accaccctcg cttctgtgaa gagatcaaaa   2280
gaaacctgcc tccctacgtg gcctacttca ccagagtgtt ccagaacaaa accttccacg   2340
tttacaagct gtccagaaac aagtagcgca gatttctgcc cagtgtctat ttttgatacg   2400
gagaaactgc atcatgatga aactcaatag atgacgtttc ctatgtaagt aggtagccca   2460
aaccttcaag ctgtgatatg agtaagttct acagatgttt acacaagtgt tgccatcttt   2520
gaaagcatct tctacaagca gaagtctttt tcgttgtgtg tctatctttc tcattaatgt   2580
tctttagcct aaatgttaac aactttctaa gagtgaccta gaattatgtt gttggagaga   2640
atgatgtgtg ttccatggat acctggatag gcacataaca tgttggaaga tgagcacctg   2700
ctcaggattt gaaatacgtt taattttcag gtgacttaag acagctatga ttgaatcaac   2760
tagagatgat gatcgactta tttaatatga tttcactggt gaagaccaat tggtagcttt   2820
ttaaaaagca ctttagtgtc ctgttttacc ttaaaatgtt ataatatttt ccagttgtca   2880
tgctgtcaac attaacaaaa aaaatcatgt taaggctttg tatcaaacat tttgttacac   2940
tctgtctgaa atgtaatgtg gagtacttca gcagtatgtg tcatgtattg tgtgtgtctg   3000
tgtgtgtgca tgtgcacaca tgtgttttaa tgctgggcac agaaaagtgt tacaagttcc   3060
atatcgtaag tccttaaagg ggcagaaata tatgtagcca agtagaattt attacatttt   3120
agtgttatta ttttaaaact tactgatact ctttaacctc tcctgcagta atagttttgc   3180
tttatttctt actcatttca atttattggg tttgcaaaat tttgtaaact ttttgtgttt   3240
ttagcctttg tattttttac agcctagaat cttgcaaagt ctgaatattt tttaaatgtt   3300
ctatcttaac tagttcacta atacagtatt tttagcagac agcattttca gacagcattt   3360
tcataccaag tttgacttgt ggtctccaat cttactggga aggccctggt agtgtaattc   3420
ttttccttat taaaaggtaa ccaagtgcct ctaagtcatg cttatttgta aacaacaaag   3480
aagagtatat gtacctgctc aaaatttttt tgataatcgc ttatataatt aatttctaat   3540
gatgaggaca tgtaaaagtt gccagtaaga acatagtatg catttaatta aatcaagatg   3600
gctaatggaa ttaactttct cccctgttct tgccaggtgg aaatgattta agcatttctc   3660
cttgcagttg tattgaagta aattaccata ggcatcaaga tggctgcatc acattttcaa   3720
atgattttat attcagttgc tacttataaa gcagcattca aaaagtcttt tacactgtca   3780
tgttggacac aagcagactc agcttttatc aaaacttgtt taaataaaaa attgacagta   3840
```

```
gctgggttat taaattatgc aactgaaact cctgaattat atcttttctg tatcccttaa   3900

taagattgga gaccactgcc gtttaggata atacaataat aaaacgtttt aatcagtact   3960

aaaactttaa ttaagccaat aatgatgcat gcctgttgta gctgacagca tgggtcagta   4020

catccttcag cgagtgcctt actctaattg aaaccaagca cacgtaaggt acaatatgtt   4080

agactctgtg attttgtttt caaaatcctc tgttatggct atatttaaat ttattttaaa   4140

tattcctgta tgtattcatc taagcatttg ggcatttgga gtcttaatat acaagaaaca   4200

cgtacttaaa tttttatgct tatcaccgca atgatggcaa acagtgattt tttttttcat   4260

agtttaggtg tcattgttgc cagcaccttt agtgctcagt cttcagtgaa aaatataaag   4320

tgccaaaaaa atcttgcaag acagaatcca tacttaacac tctttccaag acactgtgac   4380

catgtacagt agctatttcc tgatgaccaa atctctcaac gaatcatgtt attaataaat   4440

atttttagca ctcatc                                                   4456
```

<210> SEQ ID NO 18
<211> LENGTH: 336
<212> TYPE: DNA
<213> ORGANISM: Homo sapiens

<400> SEQUENCE: 18

```
atgatgtcca tccggcaaag aagagaaata agagccacag aagtttctga agactttcca     60

gcccaagaag aaaatgtgaa gttggaaaat aaattgccat ctggttgtac cagtagaaga    120

ttatggaaga ttttgtcatt gacaattggt ggaacccccct ttgcattgga cttcttacat    180

ctgtctacct tgccacgtta catgaaaatg atttatggtt ttctaatatt aaggaagtgg    240

agcgagaaat ctcattcaga acagagtgtg gcctgtatta ctcctactac aagcagatgc    300

tgcaggctcc aaccctcgtg caaggtaatt acaact                              336
```

<210> SEQ ID NO 19
<211> LENGTH: 173
<212> TYPE: PRT
<213> ORGANISM: Homo sapiens

<400> SEQUENCE: 19

```
Met Thr Leu Cys His Arg Asp Ser Phe Gly Ser Trp His Leu Phe His
1               5                   10                  15

Leu Leu Leu Leu Glu Tyr Met Ile His Ile Leu Gln Ser Cys Leu Glu
            20                  25                  30

Glu Glu Glu Glu Glu Glu Asp Met Gly Thr Val Lys Glu Met Leu Pro
        35                  40                  45

Asp Asp Pro Thr Leu Gly Gln Pro Asp Gln Ala Leu Phe His Ser Leu
    50                  55                  60

Asn Ser Ser Leu Ser Gln Ala Cys Ala Ser Pro Ser Met Glu Pro Leu
65                  70                  75                  80

Gly Val Met Pro Thr His Met Gly Gln Gly Arg Tyr Pro Val Gly Val
                85                  90                  95

Ser Asn Met Val Leu Arg Ile Leu Gly Phe Leu Val Asp Thr Ala Met
            100                 105                 110

Gly Asn Lys Leu Ile Gln Val Leu Leu Glu Asp Glu Thr Thr Glu Ser
        115                 120                 125

Ala Val Lys Leu Ser Leu Pro Met Gly Gln Glu Ala Leu Ile Thr Leu
    130                 135                 140

Lys Asp Gly Gln Gln Phe Val Ile Gln Ile Ser Asp Val Pro Gln Ser
```

```
145                 150                 155                 160

Ser Glu Asp Ile Tyr Phe Arg Glu Asn Asn Ala Asn Val
                165                 170


<210> SEQ ID NO 20
<211> LENGTH: 1907
<212> TYPE: DNA
<213> ORGANISM: Homo sapiens

<400> SEQUENCE: 20

ataactccaa cgctcaagca agtcaaggac acccacggac tcaacaccgc gaccagattg      60

gaaaaggtgt tggtcgacaa cttctgcatt tgcgaagagt gcagcgtccc tcgctgtctc     120

atgtatgaga tttacgtgga gacctgtggg caaaacactg agaaccaagt caacccggcc     180

acctttggga agcttgtgag attggttttt ccggaccttg gcacccggag gctgggcact     240

agaggaagtg ccaggtatca ttatgatgga atctgtatca agaaaagctc tttcttctat     300

gcccagtatt gctacctgat aggtgaaaaa aggtatcaca gtggagatgc cattgccttt     360

gaaaaatcta ctaattataa cagcattatc caacaagaag caacatgtga agatcattca     420

ccgatgaaga cagacccagt tggatcccct ttgtctgaat tcaggagatg tccatttctg     480

gagcaagaac aggcaaagaa atactcctgt aatatgatgg ccttccttgc tgacgaatac     540

tgcaactatt gtcgagacat tttacgaaat gtgaggaact gagaacttga gagggtggag     600

gacttgctta cttccttctg gaagtctctg cagcaagaca cagtcatgct gatgtcattg     660

cctgacgtgt gccagctctt taaatgctac gacgtccagc tgtacaaggg aattgaggat     720

gttctccttc atgacttctt ggaagatgtt tctattcagt acctgaaatc tgtgcagtta     780

tttagtaaga aatttaagct gtggctcctt aatgctttgg aaggtgttcc agccctcttg     840

cagatctcca aactcaaaga ctatgcgaat ggtattgaaa agtaagaggc gtgtcagcgt     900

tttgaagtca gatctacagg ccatcatcaa tcaaggcact ttggctactt ctaagaaagc     960

cctggcaagt gaccggagtg gcgcagatga actggagaac aacccagaga tgaaatgttt    1020

aagaaactta atttctttgc tgggaacatc aacagatctc agggtattcc tcagctgtct    1080

gtcttcacat ctccaagcat ttgtgttcca gacaagcaga agcaaagaag agtttaccaa    1140

attggccgcc agcttccagc tgagatggaa tcttcttctc actgctgtaa gcaaagccat    1200

gaccctctgc cacagagata gttttggctc ctggcatctg tttcacttgt tgcttttgga    1260

atatatgatt catatacttc agtcatgcct agaggaggaa gaggaggagg aggacatggg    1320

gactgtcaag gaaatgctac cagatgaccc gactctcggc cagccagacc aggcactttt    1380

ccattctctg aattcctcac tgtcgcaggc gtgtgccagc cccagcatgg agccactggg    1440

ggtgatgccc acacacatgg gccagggccg atatcccgtg ggtgtgagca acatggtcct    1500

caggatcctg ggcttcctgg tggacactgc catgggcaat aagctcatcc aggtgctgtt    1560

ggaagatgaa accactgaaa gcgcagttaa actcagcctt cctatgggac aagaagccct    1620

cataacccta aaagatggac aacaatttgt gattcagata tcagatgtac cccaaagctc    1680

tgaagatatt tatttcagag aaaacaatgc taatgtgtga gattatttat ttgaatagag    1740

aataagaaaa ctgatagact tgcattctta aaaatattaa atactaaagt tttctattg     1800

acgaaagatg atgttatgta tataatagat gtagcattgt ctattttatg tttatatgta    1860

tttcaaggag gtggtttcga taaaatatgt aaactgattt ggagaat                  1907


<210> SEQ ID NO 21
```

<211> LENGTH: 1328
<212> TYPE: PRT
<213> ORGANISM: Homo sapiens

<400> SEQUENCE: 21

```
Met Ser Ser Gly Asp Pro Ala His Leu Gly Leu Cys Leu Trp Leu Trp
1               5                   10                  15

Leu Gly Ala Thr Leu Gly Arg Glu Gln Val Gln Ala Ser Gly Leu Leu
            20                  25                  30

Arg Leu Ala Val Leu Pro Glu Asp Arg Leu Gln Met Lys Trp Arg Glu
        35                  40                  45

Ser Glu Gly Ser Gly Leu Gly Tyr Leu Val Gln Val Lys Pro Met Ala
    50                  55                  60

Gly Asp Ser Glu Gln Glu Val Ile Leu Thr Thr Lys Thr Pro Lys Ala
65                  70                  75                  80

Thr Val Gly Gly Leu Ser Pro Ser Lys Gly Tyr Thr Leu Gln Ile Phe
                85                  90                  95

Glu Leu Thr Gly Ser Gly Arg Phe Leu Leu Ala Arg Arg Glu Phe Val
            100                 105                 110

Ile Glu Asp Leu Lys Ser Ser Ser Leu Asp Arg Ser Ser Gln Arg Pro
        115                 120                 125

Leu Gly Ser Gly Ala Pro Glu Pro Thr Pro Ser His Thr Gly Ser Pro
    130                 135                 140

Asp Pro Glu Gln Ala Ser Glu Pro Gln Val Ala Phe Thr Pro Ser Gln
145                 150                 155                 160

Asp Pro Arg Thr Pro Gly Gly Ser Glu Trp Arg Glu Thr Gly Pro Gln
                165                 170                 175

Phe Arg Cys Leu Pro Pro Val Pro Ala Asp Met Val Phe Leu Val Asp
            180                 185                 190

Gly Ser Trp Ser Ile Gly His Ser His Phe Gln Gln Val Lys Asp Phe
        195                 200                 205

Leu Ala Ser Val Ile Ala Pro Phe Glu Ile Gly Pro Asp Lys Val Gln
    210                 215                 220

Val Gly Leu Thr Gln Tyr Ser Gly Asp Ala Gln Thr Glu Trp Asp Leu
225                 230                 235                 240

Asn Ser Leu Ser Thr Lys Glu Gln Val Leu Ala Ala Val Arg Arg Leu
                245                 250                 255

Arg Tyr Lys Gly Gly Asn Thr Phe Thr Gly Leu Ala Leu Thr His Val
            260                 265                 270

Leu Gly Gln Asn Leu Gln Pro Ala Ala Gly Leu Arg Pro Glu Ala Ala
        275                 280                 285

Lys Val Val Ile Leu Val Thr Asp Gly Lys Ser Gln Asp Asp Val His
    290                 295                 300

Thr Ala Ala Arg Val Leu Lys Asp Leu Gly Val Asn Val Phe Ala Val
305                 310                 315                 320

Gly Val Lys Asn Ala Asp Glu Ala Glu Leu Arg Leu Leu Ala Ser Pro
                325                 330                 335

Pro Arg Asp Ile Thr Val His Ser Val Leu Asp Phe Leu Gln Leu Gly
            340                 345                 350

Ala Leu Ala Gly Leu Leu Ser Arg Leu Ile Cys Gln Arg Leu Gln Gly
        355                 360                 365

Gly Ser Pro Arg Gln Gly Pro Ala Ala Ala Pro Ala Leu Asp Thr Leu
    370                 375                 380

Pro Ala Pro Thr Ser Leu Val Leu Ser Gln Val Thr Ser Ser Ser Ile
```

```
385                 390                 395                 400

Arg Leu Ser Trp Thr Pro Ala Pro Arg His Pro Leu Lys Tyr Leu Ile
                405                 410                 415

Val Trp Arg Ala Ser Arg Gly Gly Thr Pro Arg Glu Val Val Val Glu
            420                 425                 430

Gly Pro Ala Ala Ser Thr Glu Leu His Asn Leu Ala Ser Arg Thr Glu
        435                 440                 445

Tyr Leu Val Ser Val Phe Pro Ile Tyr Glu Gly Gly Val Gly Glu Gly
    450                 455                 460

Leu Arg Gly Leu Val Thr Thr Ala Pro Leu Pro Pro Pro Arg Ala Leu
465                 470                 475                 480

Thr Leu Ala Ala Val Thr Pro Arg Thr Val His Leu Thr Trp Gln Pro
                485                 490                 495

Ser Ala Gly Ala Thr His Tyr Leu Val Arg Cys Ser Pro Ala Ser Pro
            500                 505                 510

Lys Gly Glu Glu Glu Glu Arg Glu Val Gln Val Gly Arg Pro Glu Val
        515                 520                 525

Leu Leu Asp Gly Leu Glu Pro Gly Arg Asp Tyr Glu Val Ser Val Gln
    530                 535                 540

Ser Leu Arg Gly Pro Glu Gly Ser Glu Ala Arg Gly Ile Arg Ala Arg
545                 550                 555                 560

Thr Pro Thr Leu Ala Pro Pro Arg His Leu Gly Phe Ser Asp Val Ser
                565                 570                 575

His Asp Ala Ala Arg Val Phe Trp Glu Gly Ala Pro Arg Pro Val Arg
            580                 585                 590

Leu Val Arg Val Thr Tyr Val Ser Ser Glu Gly Gly His Ser Gly Gln
        595                 600                 605

Thr Glu Ala Pro Gly Asn Ala Thr Ser Ala Thr Leu Gly Pro Leu Ser
    610                 615                 620

Ser Ser Thr Thr Tyr Thr Val Arg Val Thr Cys Leu Tyr Pro Gly Gly
625                 630                 635                 640

Gly Ser Ser Thr Leu Thr Gly Arg Val Thr Thr Lys Lys Ala Pro Ser
                645                 650                 655

Pro Ser Gln Leu Ser Met Thr Glu Leu Pro Gly Asp Ala Val Gln Leu
            660                 665                 670

Ala Trp Val Ala Ala Ala Pro Ser Gly Val Leu Val Tyr Gln Ile Thr
        675                 680                 685

Trp Thr Pro Leu Gly Glu Gly Lys Ala His Glu Ile Ser Val Pro Gly
    690                 695                 700

Asn Leu Gly Thr Ala Val Leu Pro Gly Leu Gly Arg His Thr Glu Tyr
705                 710                 715                 720

Asp Val Thr Ile Leu Ala Tyr Tyr Arg Asp Gly Ala Arg Ser Asp Pro
                725                 730                 735

Val Ser Leu Arg Tyr Thr Pro Ser Thr Val Ser Arg Ser Pro Pro Ser
            740                 745                 750

Asn Leu Ala Leu Ala Ser Glu Thr Pro Asp Ser Leu Gln Val Ser Trp
        755                 760                 765

Thr Pro Pro Leu Gly Arg Val Leu His Tyr Trp Leu Thr Tyr Ala Pro
    770                 775                 780

Ala Ser Gly Leu Gly Pro Glu Lys Ser Val Ser Val Pro Gly Ala Arg
785                 790                 795                 800

Ser His Val Thr Leu Pro Asp Leu Gln Ala Ala Thr Lys Tyr Arg Val
                805                 810                 815
```

```
Leu Val Ser Ala Ile Tyr Ala Ala Gly Arg Ser Glu Ala Val Ser Ala
            820                 825                 830

Thr Gly Gln Thr Ala Cys Pro Ala Leu Arg Pro Asp Gly Ser Leu Pro
        835                 840                 845

Gly Phe Asp Leu Met Val Ala Phe Ser Leu Val Glu Lys Ala Tyr Ala
    850                 855                 860

Ser Ile Arg Gly Val Ala Met Glu Pro Ser Ala Phe Gly Gly Thr Pro
865                 870                 875                 880

Thr Phe Thr Leu Phe Lys Asp Ala Gln Leu Thr Arg Arg Val Ser Asp
                885                 890                 895

Val Tyr Pro Ala Pro Leu Pro Pro Glu His Thr Ile Val Phe Leu Val
            900                 905                 910

Arg Leu Leu Pro Glu Thr Pro Arg Glu Ala Phe Ala Leu Trp Gln Met
        915                 920                 925

Thr Ala Glu Asp Phe Gln Pro Leu Leu Gly Val Leu Leu Asp Ala Gly
    930                 935                 940

Lys Lys Ser Leu Thr Tyr Phe His Arg Asp Pro Arg Ala Ala Leu Gln
945                 950                 955                 960

Glu Ala Thr Phe Asp Pro Gln Glu Val Arg Lys Ile Phe Phe Gly Ser
                965                 970                 975

Phe His Lys Val His Val Ala Val Gly Arg Ser Lys Val Arg Leu Tyr
            980                 985                 990

Val Asp Cys Arg Lys Val Ala Glu  Arg Pro Leu Gly Glu  Met Gly Ser
        995                 1000                1005

Pro Pro  Ala Ala Gly Phe Val  Thr Leu Gly Arg Leu  Ala Lys Ala
    1010                 1015                1020

Arg Gly  Pro Arg Ser Ser Ser  Ala Ala Phe Gln Leu  Gln Met Leu
    1025                 1030                1035

Gln Ile  Val Cys Ser Asp Thr  Trp Ala Asp Glu Asp  Arg Cys Cys
    1040                 1045                1050

Glu Leu  Pro Ala Ser Arg Asp  Gly Glu Thr Cys Pro  Ala Phe Val
    1055                 1060                1065

Ser Ala  Cys Ser Cys Ser Ser  Glu Thr Pro Gly Pro  Pro Gly Pro
    1070                 1075                1080

Gln Gly  Pro Pro Gly Leu Pro  Gly Arg Asn Gly Thr  Pro Gly Glu
    1085                 1090                1095

Gln Gly  Phe Pro Gly Pro Arg  Gly Glu Pro Gly Pro  Pro Gly Gln
    1100                 1105                1110

Met Gly  Pro Glu Gly Pro Gly  Gly Gln Gln Gly Ser  Pro Gly Thr
    1115                 1120                1125

Gln Gly  Arg Ala Val Gln Gly  Pro Val Gly Pro Pro  Gly Val Lys
    1130                 1135                1140

Gly Glu  Lys Gly Asp His Gly  Leu Pro Gly Leu Gln  Gly His Pro
    1145                 1150                1155

Gly His  Gln Gly Ile Pro Gly  Arg Val Gly Leu Gln  Gly Pro Lys
    1160                 1165                1170

Gly Met  Arg Gly Leu Glu Gly  Thr Ala Gly Leu Pro  Gly Pro Gly
    1175                 1180                1185

Pro Arg  Gly Phe Gln Gly Met  Ala Gly Ala Arg Gly  Thr Ser Gly
    1190                 1195                1200

Glu Arg  Gly Pro Pro Gly Thr  Val Gly Pro Thr Gly  Leu Pro Gly
    1205                 1210                1215
```

```
Pro Lys  Gly Glu Arg Gly Glu  Lys Gly Glu Pro Gln  Ser Leu Ala
    1220                 1225                 1230

Thr Leu  Tyr Gln Leu Val Ser  Gln Ala Cys Glu Ser  Ala Ile Gln
    1235                 1240                 1245

Thr His  Val Ser Lys Phe Asp  Ser Phe His Glu Asn  Thr Arg Pro
    1250                 1255                 1260

Pro Met  Pro Ile Leu Glu Gln  Lys Leu Glu Pro Gly  Thr Glu Pro
    1265                 1270                 1275

Leu Gly  Ser Pro Gly Thr Arg  Ser Lys Ala Leu Val  Pro Gly Glu
    1280                 1285                 1290

Trp Gly  Arg Gly Gly Arg His  Leu Glu Gly Arg Gly  Glu Pro Gly
    1295                 1300                 1305

Ala Val  Gly Gln Met Gly Ser  Pro Gly Gln Gln Gly  Ala Ser Thr
    1310                 1315                 1320

Gln Gly  Leu Trp Glu
    1325


<210> SEQ ID NO 22
<211> LENGTH: 1278
<212> TYPE: PRT
<213> ORGANISM: Homo sapiens

<400> SEQUENCE: 22

Met Ser Ser Gly Asp Pro Ala His Leu Gly Leu Cys Leu Trp Leu Trp
1               5                   10                  15

Leu Gly Ala Thr Leu Gly Arg Glu Gln Val Gln Ala Ser Gly Leu Leu
            20                  25                  30

Arg Leu Ala Val Leu Pro Glu Asp Arg Leu Gln Met Lys Trp Arg Glu
        35                  40                  45

Ser Glu Gly Ser Gly Leu Gly Tyr Leu Val Gln Val Lys Pro Met Ala
    50                  55                  60

Gly Asp Ser Glu Gln Glu Val Ile Leu Thr Thr Lys Thr Pro Lys Ala
65                  70                  75                  80

Thr Val Gly Gly Leu Ser Pro Ser Lys Gly Tyr Thr Leu Gln Ile Phe
                85                  90                  95

Glu Leu Thr Gly Ser Gly Arg Phe Leu Leu Ala Arg Arg Glu Phe Val
            100                 105                 110

Ile Glu Asp Leu Lys Ser Ser Ser Leu Asp Arg Ser Ser Gln Arg Pro
        115                 120                 125

Leu Gly Ser Gly Ala Pro Glu Pro Thr Pro Ser His Thr Gly Ser Pro
    130                 135                 140

Asp Pro Glu Gln Ala Ser Glu Pro Gln Val Ala Phe Thr Pro Ser Gln
145                 150                 155                 160

Asp Pro Arg Thr Pro Gly Gly Ser Glu Trp Arg Glu Thr Gly Pro Gln
                165                 170                 175

Phe Arg Cys Leu Pro Pro Val Pro Ala Asp Met Val Phe Leu Val Asp
            180                 185                 190

Gly Ser Trp Ser Ile Gly His Ser His Phe Gln Gln Val Lys Asp Phe
        195                 200                 205

Leu Ala Ser Val Ile Ala Pro Phe Glu Ile Gly Pro Asp Lys Val Gln
    210                 215                 220

Val Gly Leu Thr Gln Tyr Ser Gly Asp Ala Gln Thr Glu Trp Asp Leu
225                 230                 235                 240

Asn Ser Leu Ser Thr Lys Glu Gln Val Leu Ala Ala Val Arg Arg Leu
                245                 250                 255
```

```
Arg Tyr Lys Gly Gly Asn Thr Phe Thr Gly Leu Ala Leu Thr His Val
            260                 265                 270

Leu Gly Gln Asn Leu Gln Pro Ala Ala Gly Leu Arg Pro Glu Ala Ala
        275                 280                 285

Lys Val Val Ile Leu Val Thr Asp Gly Lys Ser Gln Asp Asp Val His
    290                 295                 300

Thr Ala Ala Arg Val Leu Lys Asp Leu Gly Val Asn Val Phe Ala Val
305                 310                 315                 320

Gly Val Lys Asn Ala Asp Glu Ala Glu Leu Arg Leu Leu Ala Ser Pro
                325                 330                 335

Pro Arg Asp Ile Thr Val His Ser Val Leu Asp Phe Leu Gln Leu Gly
            340                 345                 350

Ala Leu Ala Gly Leu Leu Ser Arg Leu Ile Cys Gln Arg Leu Gln Gly
        355                 360                 365

Gly Ser Pro Arg Gln Gly Pro Ala Ala Ala Pro Ala Leu Asp Thr Leu
    370                 375                 380

Pro Ala Pro Thr Ser Leu Val Leu Ser Gln Val Thr Ser Ser Ser Ile
385                 390                 395                 400

Arg Leu Ser Trp Thr Pro Ala Pro Arg His Pro Leu Lys Tyr Leu Ile
                405                 410                 415

Val Trp Arg Ala Ser Arg Gly Gly Thr Pro Arg Glu Val Val Val Glu
            420                 425                 430

Gly Pro Ala Ala Ser Thr Glu Leu His Asn Leu Ala Ser Arg Thr Glu
        435                 440                 445

Tyr Leu Val Ser Val Phe Pro Ile Tyr Glu Gly Gly Val Gly Glu Gly
    450                 455                 460

Leu Arg Gly Leu Val Thr Thr Ala Pro Leu Pro Pro Pro Arg Ala Leu
465                 470                 475                 480

Thr Leu Ala Ala Val Thr Pro Arg Thr Val His Leu Thr Trp Gln Pro
                485                 490                 495

Ser Ala Gly Ala Thr His Tyr Leu Val Arg Cys Ser Pro Ala Ser Pro
            500                 505                 510

Lys Gly Glu Glu Glu Glu Arg Glu Val Gln Val Gly Arg Pro Glu Val
        515                 520                 525

Leu Leu Asp Gly Leu Glu Pro Gly Arg Asp Tyr Glu Val Ser Val Gln
    530                 535                 540

Ser Leu Arg Gly Pro Glu Gly Ser Glu Ala Arg Gly Ile Arg Ala Arg
545                 550                 555                 560

Thr Pro Thr Leu Ala Pro Pro Arg His Leu Gly Phe Ser Asp Val Ser
                565                 570                 575

His Asp Ala Ala Arg Val Phe Trp Glu Gly Ala Pro Arg Pro Val Arg
            580                 585                 590

Leu Val Arg Val Thr Tyr Val Ser Ser Glu Gly Gly His Ser Gly Gln
        595                 600                 605

Thr Glu Ala Pro Gly Asn Ala Thr Ser Ala Thr Leu Gly Pro Leu Ser
    610                 615                 620

Ser Ser Thr Thr Tyr Thr Val Arg Val Thr Cys Leu Tyr Pro Gly Gly
625                 630                 635                 640

Gly Ser Ser Thr Leu Thr Gly Arg Val Thr Thr Lys Lys Ala Pro Ser
                645                 650                 655

Pro Ser Gln Leu Ser Met Thr Glu Leu Pro Gly Asp Ala Val Gln Leu
            660                 665                 670
```

```
Ala Trp Val Ala Ala Ala Pro Ser Gly Val Leu Val Tyr Gln Ile Thr
        675                 680                 685

Trp Thr Pro Leu Gly Glu Gly Lys Ala His Glu Ile Ser Val Pro Gly
    690                 695                 700

Asn Leu Gly Thr Ala Val Leu Pro Gly Leu Gly Arg His Thr Glu Tyr
705                 710                 715                 720

Asp Val Thr Ile Leu Ala Tyr Tyr Arg Asp Gly Ala Arg Ser Asp Pro
                725                 730                 735

Val Ser Leu Arg Tyr Thr Pro Ser Thr Val Ser Arg Ser Pro Pro Ser
            740                 745                 750

Asn Leu Ala Leu Ala Ser Glu Thr Pro Asp Ser Leu Gln Val Ser Trp
        755                 760                 765

Thr Pro Pro Leu Gly Arg Val Leu His Tyr Trp Leu Thr Tyr Ala Pro
    770                 775                 780

Ala Ser Gly Leu Gly Pro Glu Lys Ser Val Ser Val Pro Gly Ala Arg
785                 790                 795                 800

Ser His Val Thr Leu Pro Asp Leu Gln Ala Ala Thr Lys Tyr Arg Val
                805                 810                 815

Leu Val Ser Ala Ile Tyr Ala Ala Gly Arg Ser Glu Ala Val Ser Ala
            820                 825                 830

Thr Gly Gln Thr Ala Cys Pro Ala Leu Arg Pro Asp Gly Ser Leu Pro
        835                 840                 845

Gly Phe Asp Leu Met Val Ala Phe Ser Leu Val Glu Lys Ala Tyr Ala
    850                 855                 860

Ser Ile Arg Gly Val Ala Met Glu Pro Ser Ala Phe Gly Gly Thr Pro
865                 870                 875                 880

Thr Phe Thr Leu Phe Lys Asp Ala Gln Leu Thr Arg Arg Val Ser Asp
                885                 890                 895

Val Tyr Pro Ala Pro Leu Pro Pro Glu His Thr Ile Val Phe Leu Val
            900                 905                 910

Arg Leu Leu Pro Glu Thr Pro Arg Glu Ala Phe Ala Leu Trp Gln Met
        915                 920                 925

Thr Ala Glu Asp Phe Gln Pro Leu Leu Gly Val Leu Leu Asp Ala Gly
    930                 935                 940

Lys Lys Ser Leu Thr Tyr Phe His Arg Asp Pro Arg Ala Ala Leu Gln
945                 950                 955                 960

Glu Ala Thr Phe Asp Pro Gln Glu Val Arg Lys Ile Phe Phe Gly Ser
                965                 970                 975

Phe His Lys Val His Val Ala Val Gly Arg Ser Lys Val Arg Leu Tyr
            980                 985                 990

Val Asp Cys Arg Lys Val Ala Glu  Arg Pro Leu Gly Glu  Met Gly Ser
        995                 1000                1005

Pro Pro  Ala Ala Gly Phe Val  Thr Leu Gly Arg Leu  Ala Lys Ala
    1010                1015                1020

Arg Gly  Pro Arg Ser Ser Ser  Ala Ala Phe Gln Leu  Gln Met Leu
    1025                1030                1035

Gln Ile  Val Cys Ser Asp Thr  Trp Ala Asp Glu Asp  Arg Cys Cys
    1040                1045                1050

Glu Leu  Pro Ala Ser Arg Asp  Gly Glu Thr Cys Pro  Ala Phe Val
    1055                1060                1065

Ser Ala  Cys Ser Cys Ser Ser  Glu Thr Pro Gly Pro  Pro Gly Pro
    1070                1075                1080

Gln Gly  Pro Pro Gly Pro Pro  Gly Val Lys Gly Glu  Lys Gly Asp
```

```
    1085                1090                1095

His Gly  Leu Pro Gly Leu Gln  Gly His Pro Gly His  Gln Gly Ile
    1100                1105                1110

Pro Gly  Arg Val Gly Leu Gln  Gly Pro Lys Gly Met  Arg Gly Leu
    1115                1120                1125

Glu Gly  Thr Ala Gly Leu Pro  Gly Pro Gly Pro Arg  Gly Phe Gln
    1130                1135                1140

Gly Met  Ala Gly Ala Arg Gly  Thr Ser Gly Glu Arg  Gly Pro Pro
    1145                1150                1155

Gly Thr  Val Gly Pro Thr Gly  Leu Pro Gly Pro Lys  Gly Glu Arg
    1160                1165                1170

Gly Glu  Lys Gly Glu Pro Gln  Ser Leu Ala Thr Leu  Tyr Gln Leu
    1175                1180                1185

Val Ser  Gln Ala Cys Glu Ser  Ala Ile Gln Thr His  Val Ser Lys
    1190                1195                1200

Phe Asp  Ser Phe His Glu Asn  Thr Arg Pro Pro Met  Pro Ile Leu
    1205                1210                1215

Glu Gln  Lys Leu Glu Pro Gly  Thr Glu Pro Leu Gly  Ser Pro Gly
    1220                1225                1230

Thr Arg  Ser Lys Ala Leu Val  Pro Gly Glu Trp Gly  Arg Gly Gly
    1235                1240                1245

Arg His  Leu Glu Gly Arg Gly  Glu Pro Gly Ala Val  Gly Gln Met
    1250                1255                1260

Gly Ser  Pro Gly Gln Gln Gly  Ala Ser Thr Gln Gly  Leu Trp Glu
    1265                1270                1275


<210> SEQ ID NO 23
<211> LENGTH: 1283
<212> TYPE: PRT
<213> ORGANISM: Homo sapiens

<400> SEQUENCE: 23

Met Ser Ser Gly Asp Pro Ala His Leu Gly Leu Cys Leu Trp Leu Trp
1               5                   10                  15

Leu Gly Ala Thr Leu Gly Arg Glu Gln Val Gln Ala Ser Gly Leu Leu
            20                  25                  30

Arg Leu Ala Val Leu Pro Glu Asp Arg Leu Gln Met Lys Trp Arg Glu
        35                  40                  45

Ser Glu Gly Ser Gly Leu Gly Tyr Leu Val Gln Val Lys Pro Met Ala
    50                  55                  60

Gly Asp Ser Glu Gln Glu Val Ile Leu Thr Thr Lys Thr Pro Lys Ala
65                  70                  75                  80

Thr Val Gly Gly Leu Ser Pro Ser Lys Gly Tyr Thr Leu Gln Ile Phe
                85                  90                  95

Glu Leu Thr Gly Ser Gly Arg Phe Leu Leu Ala Arg Arg Glu Phe Val
            100                 105                 110

Ile Glu Asp Leu Lys Ser Ser Ser Leu Asp Arg Ser Ser Gln Arg Pro
        115                 120                 125

Leu Gly Ser Gly Ala Pro Glu Pro Thr Pro Ser His Thr Gly Ser Pro
    130                 135                 140

Asp Pro Glu Gln Ala Ser Glu Pro Gln Val Ala Phe Thr Pro Ser Gln
145                 150                 155                 160

Asp Pro Arg Thr Pro Ala Gly Pro Gln Phe Arg Cys Leu Pro Pro Val
                165                 170                 175
```

```
Pro Ala Asp Met Val Phe Leu Val Asp Gly Ser Trp Ser Ile Gly His
            180                 185                 190

Ser His Phe Gln Gln Val Lys Asp Phe Leu Ala Ser Val Ile Ala Pro
        195                 200                 205

Phe Glu Ile Gly Pro Asp Lys Val Gln Val Gly Leu Thr Gln Tyr Ser
    210                 215                 220

Gly Asp Ala Gln Thr Glu Trp Asp Leu Asn Ser Leu Ser Thr Lys Glu
225                 230                 235                 240

Gln Val Leu Ala Ala Val Arg Arg Leu Arg Tyr Lys Gly Gly Asn Thr
                245                 250                 255

Phe Thr Gly Leu Ala Leu Thr His Val Leu Gly Gln Asn Leu Gln Pro
            260                 265                 270

Ala Ala Gly Leu Arg Pro Glu Ala Ala Lys Val Val Ile Leu Val Thr
        275                 280                 285

Asp Gly Lys Ser Gln Asp Asp Val His Thr Ala Ala Arg Val Leu Lys
    290                 295                 300

Asp Leu Gly Val Asn Val Phe Ala Val Gly Val Lys Asn Ala Asp Glu
305                 310                 315                 320

Ala Glu Leu Arg Leu Leu Ala Ser Pro Pro Arg Asp Ile Thr Val His
                325                 330                 335

Ser Val Leu Asp Phe Leu Gln Leu Gly Ala Leu Ala Gly Leu Leu Ser
            340                 345                 350

Arg Leu Ile Cys Gln Arg Leu Gln Gly Gly Ser Pro Arg Gln Gly Pro
        355                 360                 365

Ala Ala Ala Pro Ala Leu Asp Thr Leu Pro Ala Pro Thr Ser Leu Val
    370                 375                 380

Leu Ser Gln Val Thr Ser Ser Ser Ile Arg Leu Ser Trp Thr Pro Ala
385                 390                 395                 400

Pro Arg His Pro Leu Lys Tyr Leu Ile Val Trp Arg Ala Ser Arg Gly
                405                 410                 415

Gly Thr Pro Arg Glu Val Val Val Glu Gly Pro Ala Ala Ser Thr Glu
            420                 425                 430

Leu His Asn Leu Ala Ser Arg Thr Glu Tyr Leu Val Ser Val Phe Pro
        435                 440                 445

Ile Tyr Glu Gly Gly Val Gly Glu Gly Leu Arg Gly Leu Val Thr Thr
    450                 455                 460

Ala Pro Leu Pro Pro Pro Arg Ala Leu Thr Leu Ala Ala Val Thr Pro
465                 470                 475                 480

Arg Thr Val His Leu Thr Trp Gln Pro Ser Ala Gly Ala Thr His Tyr
                485                 490                 495

Leu Val Arg Cys Ser Pro Ala Ser Pro Lys Gly Glu Glu Glu Glu Arg
            500                 505                 510

Glu Val Gln Val Gly Arg Pro Glu Val Leu Leu Asp Gly Leu Glu Pro
        515                 520                 525

Gly Arg Asp Tyr Glu Val Ser Val Gln Ser Leu Arg Gly Pro Glu Gly
    530                 535                 540

Ser Glu Ala Arg Gly Ile Arg Ala Arg Thr Pro Thr Leu Ala Pro Pro
545                 550                 555                 560

Arg His Leu Gly Phe Ser Asp Val Ser His Asp Ala Ala Arg Val Phe
                565                 570                 575

Trp Glu Gly Ala Pro Arg Pro Val Arg Leu Val Arg Val Thr Tyr Val
            580                 585                 590

Ser Ser Glu Gly Gly His Ser Gly Gln Thr Glu Ala Pro Gly Asn Ala
```

```
        595                 600                 605

Thr Ser Ala Thr Leu Gly Pro Leu Ser Ser Ser Thr Thr Tyr Thr Val
    610                 615                 620

Arg Val Thr Cys Leu Tyr Pro Gly Gly Gly Ser Ser Thr Leu Thr Gly
625                 630                 635                 640

Arg Val Thr Thr Lys Lys Ala Pro Ser Pro Ser Gln Leu Ser Met Thr
                645                 650                 655

Glu Leu Pro Gly Asp Ala Val Gln Leu Ala Trp Val Ala Ala Ala Pro
            660                 665                 670

Ser Gly Val Leu Val Tyr Gln Ile Thr Trp Thr Pro Leu Gly Glu Gly
        675                 680                 685

Lys Ala His Glu Ile Ser Val Pro Gly Asn Leu Gly Thr Ala Val Leu
    690                 695                 700

Pro Gly Leu Gly Arg His Thr Glu Tyr Asp Val Thr Ile Leu Ala Tyr
705                 710                 715                 720

Tyr Arg Asp Gly Ala Arg Ser Asp Pro Val Ser Leu Arg Tyr Thr Pro
                725                 730                 735

Ser Thr Val Ser Arg Ser Pro Pro Ser Asn Leu Ala Leu Ala Ser Glu
            740                 745                 750

Thr Pro Asp Ser Leu Gln Val Ser Trp Thr Pro Pro Leu Gly Arg Val
        755                 760                 765

Leu His Tyr Trp Leu Thr Tyr Ala Pro Ala Ser Gly Leu Gly Pro Glu
    770                 775                 780

Lys Ser Val Ser Val Pro Gly Ala Arg Ser His Val Thr Leu Pro Asp
785                 790                 795                 800

Leu Gln Ala Ala Thr Lys Tyr Arg Val Leu Val Ser Ala Ile Tyr Ala
                805                 810                 815

Ala Gly Arg Ser Glu Ala Val Ser Ala Thr Gly Gln Thr Ala Cys Pro
            820                 825                 830

Ala Leu Arg Pro Asp Gly Ser Leu Pro Gly Phe Asp Leu Met Val Ala
        835                 840                 845

Phe Ser Leu Val Glu Lys Ala Tyr Ala Ser Ile Arg Gly Val Ala Met
    850                 855                 860

Glu Pro Ser Ala Phe Gly Gly Thr Pro Thr Phe Thr Leu Phe Lys Asp
865                 870                 875                 880

Ala Gln Leu Thr Arg Arg Val Ser Asp Val Tyr Pro Ala Pro Leu Pro
                885                 890                 895

Pro Glu His Thr Ile Val Phe Leu Val Arg Leu Leu Pro Glu Thr Pro
            900                 905                 910

Arg Glu Ala Phe Ala Leu Trp Gln Met Thr Ala Glu Asp Phe Gln Pro
        915                 920                 925

Leu Leu Gly Val Leu Leu Asp Ala Gly Lys Lys Ser Leu Thr Tyr Phe
    930                 935                 940

His Arg Asp Pro Arg Ala Ala Leu Gln Glu Ala Thr Phe Asp Pro Gln
945                 950                 955                 960

Glu Val Arg Lys Ile Phe Phe Gly Ser Phe His Lys Val His Val Ala
                965                 970                 975

Val Gly Arg Ser Lys Val Arg Leu Tyr Val Asp Cys Arg Lys Val Ala
            980                 985                 990

Glu Arg Pro Leu Gly Glu Met Gly  Ser Pro Pro Ala Ala  Gly Phe Val
        995                 1000                1005

Thr Leu  Gly Arg Leu Ala Lys  Ala Arg Gly Pro Arg  Ser Ser Ser
    1010                1015                1020
```

```
Ala Ala  Phe Gln Leu Gln Met  Leu Gln Ile Val Cys  Ser Asp Thr
    1025                 1030                 1035

Trp Ala  Asp Glu Asp Arg Cys  Cys Glu Leu Pro Ala  Ser Arg Asp
    1040                 1045                 1050

Gly Glu  Thr Cys Pro Ala Phe  Val Ser Ala Cys Ser  Cys Ser Ser
    1055                 1060                 1065

Glu Thr  Pro Gly Pro Pro Gly  Pro Gln Gly Pro Pro  Gly Leu Pro
    1070                 1075                 1080

Gly Arg  Asn Gly Thr Pro Gly  Glu Gln Gly Phe Pro  Gly Pro Arg
    1085                 1090                 1095

Gly Pro  Pro Gly Val Lys Gly  Glu Lys Gly Asp His  Gly Leu Pro
    1100                 1105                 1110

Gly Leu  Gln Gly His Pro Gly  His Gln Gly Ile Pro  Gly Arg Val
    1115                 1120                 1125

Gly Leu  Gln Gly Pro Lys Gly  Met Arg Gly Leu Glu  Gly Thr Ala
    1130                 1135                 1140

Gly Leu  Pro Gly Pro Gly Pro  Arg Gly Phe Gln Gly  Met Ala Gly
    1145                 1150                 1155

Ala Arg  Gly Thr Ser Gly Glu  Arg Gly Pro Pro Gly  Thr Val Gly
    1160                 1165                 1170

Pro Thr  Gly Leu Pro Gly Pro  Lys Gly Glu Arg Gly  Glu Lys Gly
    1175                 1180                 1185

Glu Pro  Gln Ser Leu Ala Thr  Leu Tyr Gln Leu Val  Ser Gln Ala
    1190                 1195                 1200

Ser His  Val Ser Lys Phe Asp  Ser Phe His Glu Asn  Thr Arg Pro
    1205                 1210                 1215

Pro Met  Pro Ile Leu Glu Gln  Lys Leu Glu Pro Gly  Thr Glu Pro
    1220                 1225                 1230

Leu Gly  Ser Pro Gly Thr Arg  Ser Lys Ala Leu Val  Pro Gly Glu
    1235                 1240                 1245

Trp Gly  Arg Gly Gly Arg His  Leu Glu Gly Arg Gly  Glu Pro Gly
    1250                 1255                 1260

Ala Val  Gly Gln Met Gly Ser  Pro Gly Gln Gln Gly  Ala Ser Thr
    1265                 1270                 1275

Gln Gly  Leu Trp Glu
    1280
```

<210> SEQ ID NO 24
<211> LENGTH: 3987
<212> TYPE: DNA
<213> ORGANISM: Homo sapiens

<400> SEQUENCE: 24

```
atgagctccg gagaccctgc acacctcggc ctctgcctct ggctgtggct gggcgccacc     60

ctgggaagag agcaagttca agcaagcggt ctcctgaggc tggctgtgct gcctgaggac    120

cggctgcaga tgaagtggag agagtcggag gggagcggcc tcggctacct ggtgcaggtg    180

aagcccatgg caggggactc ggaacaggag gtgatactga ccaccaagac ccctaaggcc    240

acagtggggg gcctgagccc ctccaagggc tacaccttgc agatcttcga gctcactggc    300

tctgggcgct tcctgctagc tcggagggag tttgtgattg aggatctgaa gagtagctcc    360

ctggacagga gcagccagag gcccctcggc tctggagccc cggagcccac cccctcccac    420

acggggagcc cagaccctga gcaggcttct gagccccaag ttgccttcac accaagccag    480
```

```
gatccgcgca ctcctggtgg gtcagagtgg agagagaccg gcccccagtt ccgctgcctg    540

ccccccgtgc ctgctgacat ggtcttcctg gtggacgggt cctggagcat tggccacagt    600

cacttccagc aggtcaagga cttcctggcc agtgtcatcg caccctttga aatcgggccg    660

gataaggtcc aagtaggcct gactcagtac agcggggatg ctcagactga gtgggacctg    720

aactccctca gcaccaagga acaggtgctg gcagctgtgc gccgcctccg ctacaagggg    780

gggaacacgt tcacaggcct tgccctgacc cacgtgctgg ggcagaacct gcagccggcg    840

gctggcctcc gtccagaggc agccaaggtg gtgattctgg tgacggacgg caagtcccag    900

gacgatgtgc acactgctgc ccgtgtcctc aaggacctgg gcgtgaacgt cttcgctgtg    960

ggtgtgaaga acgccgatga ggctgagctg aggctcctgg cgtccccgcc gagggacatc   1020

accgtccaca gcgtgctgga cttcctgcag ctcggcgcgc tggctggcct gctcagccgt   1080

ctcatctgcc agaggctcca gggtgggagc ccgcggcagg gcccagcagc ggctccagcc   1140

ctggacaccc tccctgcccc caccagcctg gtcctgagcc aggtgacctc ctccagcatc   1200

cgcctgtcct ggactccagc cccccggcac cccctcaagt atctgatcgt ttggcgagcc   1260

tctagaggtg gcacccccag ggaggtggtg gtggagggac ccgccgcctc cacggagctg   1320

cacaacctgg cctcccgcac agagtacctg gtctccgtgt tccccatcta tgagggcggg   1380

gttggcgaag gcctgcgggg cctggtgacc acagcacctc tgcctccgcc ccgggcgctg   1440

accctggccg cagtgacgcc cagaaccgtc cacctcacct ggcagccctc ggccggggcc   1500

acccactacc tggtgcgatg ttctcctgct tcccccaagg gtgaagagga ggagcgagag   1560

gtgcaggtcg ggcggcccga ggtgctgctg gatggcctgg aacctggcag ggactatgag   1620

gtctcggtgc agagcctgcg aggccctgag ggcagcgagg cccggggcat ccgtgccagg   1680

acccccaccc tggccccccc gagacacctg ggcttctcag acgtgagcca cgacgcggca   1740

cgagtgttct gggagggtgc cccgaggcct gtgcgcctgg tcagggtcac ctatgtgtcc   1800

agcgagggtg gacactcggg gcagacagag gctcctggga acgccacctc ggccacgctg   1860

gggcctctct cttcctccac cacctacact gtccgtgtca cctgcctcta ccctgggggt   1920

ggctcctcta cgctgactgg ccgggtgacc accaagaaag ctcccagccc aagccagctg   1980

tccatgacgg agctgccagg ggatgcagtc cagctggcgt gggtggccgc agccccgtct   2040

ggcgtgcttg tctaccagat cacgtggacg cccctgggag aggggaaggc tcacgagatc   2100

tctgtcccag ggaacctcgg cacggccgtc ctgcctggcc tagggaggca cacagagtac   2160

gacgtcacca tcttggccta ctacagggac ggggcccgca gtgaccctgt gtccctccgc   2220

tatacccccct ccacggtgag caggagccca ccctccaacc tggccctggc ctcggagacc   2280

cccgacagcc tgcaggtcag ctggacgccc ccgcttggcc gcgtgctcca ttactggctc   2340

acctacgccc ccgcctctgg cttgggaccc gagaaatccg tctctgtgcc aggagccagg   2400

agccacgtga cactgcccga cctgcaggca gccacgaagt acagggtcct ggtctcagct   2460

atctatgcag caggcaggag tgaggctgtg tctgccacgg gccagacagc ctgcccagcc   2520

ctccgccctg acggctccct cccagggttt gacctgatgg tggccttcag cctggtggaa   2580

aaggcttatg cgtccatccg gggcgtggcc atggagccct ctgccttcgg tgggaccccg   2640

accttcacgc tcttcaagga cgcccagctg acaagacggg tcagtgacgt ctacccagcc   2700

cccctacctc cagagcacac catcgtcttc cttgtgcgcc tacttcccga gacaccccgt   2760

gaggccttcg cgctgtggca gatgacagcc gaggacttcc agcccctcct tggggttctg   2820

ctggatgccg ggaagaagtc cctgacctac ttccaccgtg accccagggc tgccttgcag   2880
```

```
gaggccacct tcgacccgca ggaagtgagg aagattttct tcgggagctt ccacaaggtg   2940

cacgtggctg tgggccgctc caaggtcagg ctctatgtgg actgccggaa ggtggctgag   3000

cggcccottg gggagatggg cagcccaccc gctgcgggct tcgtcacgct ggggaggctg   3060

gccaaggcca ggggccccg gagcagttcg gccgcgtttc agctccagat gctgcagatc    3120

gtgtgcagtg acacctgggc cgatgaggac cggtgctgtg agctccctgc ctcgagggat   3180

ggagagacct gccccgcctt cgtgtctgcc tgttcctgtt cctcagagac ccctgggccc   3240

ccaggacctc aaggaccccc aggcctccct gggaggaatg gcaccccagg agagcagggc   3300

ttcccagggc ccaggggaga gcccgggcca cccggacaga tgggaccaga aggtcctgga   3360

ggccagcagg gctcgccggg gacccagggc cgtgcagtcc aggggcctgt gggtccacca   3420

ggggtcaaag gagagaaggg agaccatggg cttccaggct tgcagggcca ccccggccac   3480

cagggcatcc ccgggagagt tggcctccag ggaccaaagg gaatgagagg cctggaggga   3540

actgctggcc tgcctggacc cggccccagg gggttccagg gcatggcagg ggccaggggc   3600

actagtggag agcgaggacc tccagggacc gtggggccca caggactgcc agggcccaaa   3660

ggggaacgag gagagaaggg cgagccgcag tcccttgcca ccctctacca gcttgtgagc   3720

caggcctgtg agtctgccat tcagacacac gtgtcaaagt tcgactcctt ccacgagaac   3780

accaggcccc ccatgcccat cttggagcag aagctggagc cgggcactga gcccctgggg   3840

tcccctggca cccgcagcaa ggccctggtt cctggagaat gggggcgtgg tggccgccac   3900

cttgagggca gaggggagcc tggagctgtt ggtcagatgg gcagccctgg gcagcagggg   3960

gctagcaccc agggcctctg ggagtga                                       3987
```

<210> SEQ ID NO 25
<211> LENGTH: 3837
<212> TYPE: DNA
<213> ORGANISM: Homo sapiens

<400> SEQUENCE: 25

```
atgagctccg gagaccctgc acacctcggc ctctgcctct ggctgtggct gggcgccacc     60

ctgggaagag agcaagttca agcaagcggt ctcctgaggc tggctgtgct gcctgaggac    120

cggctgcaga tgaagtggag agagtcggag gggagcggcc tcggctacct ggtgcaggtg    180

aagcccatgg caggggactc ggaacaggag gtgatactga ccaccaagac ccctaaggcc    240

acagtggggg gcctgagccc ctccaagggc tacaccttgc agatcttcga gctcactggc    300

tctgggcgct tcctgctagc tcggagggag tttgtgattg aggatctgaa gagtagctcc    360

ctggacagga gcagccagag gcccctcggc tctggagccc cggagcccac cccctcccac    420

acggggagcc cagaccctga gcaggcttct gagccccaag ttgccttcac accaagccag    480

gatccgcgca ctcctggtgg gtcagagtgg agagagaccg gcccccagtt ccgctgcctg    540

ccccccgtgc ctgctgacat ggtcttcctg gtggacgggt cctggagcat tggccacagt    600

cacttccagc aggtcaagga cttcctggcc agtgtcatcg caccctttga aatcgggccg    660

gataaggtcc aagtaggcct gactcagtac agcggggatg ctcagactga gtgggacctg    720

aactccctca gcaccaagga acaggtgctg gcagctgtgc gccgcctccg ctacaagggg    780

gggaacacgt tcacaggcct tgccctgacc cacgtgctgg ggcagaacct gcagccggcg    840

gctggcctcc gtccagaggc agccaaggtg gtgattctgg tgacggacgg caagtcccag    900

gacgatgtgc acactgctgc ccgtgtcctc aaggacctgg gcgtgaacgt cttcgctgtg    960
```

```
ggtgtgaaga acgccgatga ggctgagctg aggctcctgg cgtccccgcc gagggacatc   1020
accgtccaca gcgtgctgga cttcctgcag ctcggcgcgc tggctggcct gctcagccgt   1080
ctcatctgcc agaggctcca gggtgggagc ccgcggcagg gcccagcagc ggctccagcc   1140
ctggacaccc tccctgcccc caccagcctg gtcctgagcc aggtgacctc ctccagcatc   1200
cgcctgtcct ggactccagc cccccggcac cccctcaagt atctgatcgt ttggcgagcc   1260
tctagaggtg gcacccccag ggaggtggtg gtggagggac ccgccgcctc cacggagctg   1320
cacaacctgg cctcccgcac agagtacctg gtctccgtgt tccccatcta tgagggcggg   1380
gttggcgaag gcctgcgggg cctggtgacc acagcacctc tgcctccgcc ccgggcgctg   1440
accctggccg cagtgacgcc cagaaccgtc cacctcacct ggcagccctc ggccggggcc   1500
acccactacc tggtgcgatg ttctcctgct tcccccaagg gtgaagagga ggagcgagag   1560
gtgcaggtcg ggcggcccga ggtgctgctg gatggcctgg aacctggcag ggactatgag   1620
gtctcggtgc agagcctgcg aggccctgag ggcagcgagg cccggggcat ccgtgccagg   1680
acccccaccc tggccccccc gagacacctg ggcttctcag acgtgagcca cgacgcggca   1740
cgagtgttct gggagggtgc cccgaggcct gtgcgcctgg tcagggtcac ctatgtgtcc   1800
agcgagggtg gacactcggg gcagacagag gctcctggga acgccacctc ggccacgctg   1860
gggcctctct cttcctccac cacctacact gtccgtgtca cctgcctcta ccctgggggt   1920
ggctcctcta cgctgactgg ccgggtgacc accaagaaag ctcccagccc aagccagctg   1980
tccatgacgg agctgccagg ggatgcagtc cagctggcgt gggtggccgc agccccgtct   2040
ggcgtgcttg tctaccagat cacgtggacg cccctgggag aggggaaggc tcacgagatc   2100
tctgtcccag ggaacctcgg cacggccgtc ctgcctggcc tagggaggca cacagagtac   2160
gacgtcacca tcttggccta ctacagggac ggggcccgca gtgaccctgt gtccctccgc   2220
tatacccccct ccacggtgag caggagccca ccctccaacc tggccctggc ctcggagacc   2280
cccgacagcc tgcaggtcag ctggacgccc ccgcttggcc gcgtgctcca ttactggctc   2340
acctacgccc ccgcctctgg cttgggaccc gagaaatccg tctctgtgcc aggagccagg   2400
agccacgtga cactgcccga cctgcaggca gccacgaagt acagggtcct ggtctcagct   2460
atctatgcag caggcaggag tgaggctgtg tctgccacgg gccagacagc ctgcccagcc   2520
ctccgccctg acggctccct cccagggttt gacctgatgg tggccttcag cctggtggaa   2580
aaggcttatg cgtccatccg gggcgtggcc atggagccct ctgccttcgg tgggaccccg   2640
accttcacgc tcttcaagga cgcccagctg acaagacggg tcagtgacgt ctacccagcc   2700
cccctacctc cagagcacac catcgtcttc cttgtgcgcc tacttcccga gacaccccgt   2760
gaggccttcg cgctgtggca gatgacagcc gaggacttcc agcccctcct tggggttctg   2820
ctggatgccg ggaagaagtc cctgacctac ttccaccgtg accccagggc tgccttgcag   2880
gaggccacct tcgacccgca ggaagtgagg aagattttct tcgggagctt ccacaaggtg   2940
cacgtggctg tgggccgctc caaggtcagg ctctatgtgg actgccggaa ggtggctgag   3000
cggcccettg gggagatggg cagcccaccc gctgcgggct tcgtcacgct ggggaggctg   3060
gccaaggcca ggggcccccg gagcagttcg gccgcgtttc agctccagat gctgcagatc   3120
gtgtgcagtg acacctgggc cgatgaggac cggtgctgtg agctccctgc ctcgagggat   3180
ggagagacct gccccgcctt cgtgtctgcc tgttcctgtt cctcagagac ccctgggccc   3240
ccaggacctc aaggaccccc aggtccacca ggggtcaaag gagagaaggg agaccatggg   3300
cttccaggct tgcagggcca ccccggccac cagggcatcc ccgggagagt tggcctccag   3360
```

```
ggaccaaagg gaatgagagg cctggaggga actgctggcc tgcctggacc tggccccagg   3420

gggttccagg gcatggcagg ggccaggggc actagtggag agcgaggacc tccagggacc   3480

gtggggccca caggactgcc agggcccaaa ggggaacgag gagagaaggg cgagccgcag   3540

tcccttgcca ccctctacca gcttgtgagc caggcctgtg agtctgccat tcagacacac   3600

gtgtcaaagt tcgactcctt ccacgagaac accaggcccc ccatgcccat cttggagcag   3660

aagctggagc cgggcactga gcccctgggg tcccctggca cccgcagcaa ggccctggtt   3720

cctggagaat gggggcgtgg tggccgccac cttgagggca gaggggagcc tggagctgtt   3780

ggtcagatgg gcagccctgg gcagcagggg gctagcaccc agggcctctg ggagtga      3837


<210> SEQ ID NO 26
<211> LENGTH: 4168
<212> TYPE: DNA
<213> ORGANISM: Homo sapiens

<400> SEQUENCE: 26

ataagctcca gccttcctgt ggccacagca ggaccagagt ggaccagcac accccaggag     60

agaggactgg ggtcccagga gtaggaggag cccgagcacc atgagctccg gagaccctgc    120

acacctcggc ctctgcctct ggctgtggct gggcgccacc ctgggaagag agcaagttca    180

agcaagcggt ctcctgaggc tggctgtgct gcctgaggac cggctgcaga tgaagtggag    240

agagtcggag gggagcggcc tcggctacct ggtgcaggtg aagcccatgg caggggactc    300

ggaacaggag gtgatactga ccaccaagac ccctaaggcc acagtggggg gcctgagccc    360

ctccaagggc tacaccttgc agatcttcga gctcactggc tctgggcgct tcctgctagc    420

tcggagggag tttgtgattg aggatctgaa gagtagctcc ctggacagga gcagccagag    480

gcccctcggc tctggagccc cggagcccac cccctcccac acggggagcc cagaccctga    540

gcaggcttct gagccccaag ttgccttcac accaagccag gatccgcgca ctcctgccgg    600

cccccagttc cgctgcctgc cccccgtgcc tgctgacatg gtcttcctgg tggacgggtc    660

ctggagcatt ggccacagtc acttccagca ggtcaaggac ttcctggcca gtgtcatcgc    720

acccttttgaa atcgggccgg ataaggtcca agtaggcctg actcagtaca gcggggatgc    780

tcagactgag tgggacctga actccctcag caccaaggaa caggtgctgg cagctgtgcg    840

ccgcctccgc tacaaggggg ggaacacgtt cacaggcctt gccctgaccc acgtgctggg    900

gcagaacctg cagccggcgg ctggcctccg tccagaggca gccaaggtgg tgattctggt    960

gacggacggc aagtcccagg acgatgtgca cactgctgcc cgtgtcctca aggacctggg   1020

cgtgaacgtc ttcgctgtgg gtgtgaagaa cgccgatgag gctgagctga ggctcctggc   1080

gtccccgccg agggacatca ccgtccacag cgtgctggac ttcctgcagc tcggcgcgct   1140

ggctggcctg ctcagccgtc tcatctgcca gaggctccag ggtgggagcc cgcggcaggg   1200

cccagcagcg gctccagccc tggacaccct ccctgccccc accagcctgg tcctgagcca   1260

ggtgacctcc tccagcatcc gcctgtcctg gactccagcc ccccggcacc ccctcaagta   1320

tctgatcgtt tggcgagcct ctagaggtgg cacccccagg gaggtggtgg tggagggacc   1380

cgccgcctcc acggagctgc acaacctggc ctcccgcaca gagtacctgg tctccgtgtt   1440

ccccatctat gagggcgggg ttggcgaagg cctgcggggc ctggtgacca cagcacctct   1500

gcctccgccc cgggcgctga ccctggccgc agtgacgccc agaaccgtcc acctcacctg   1560

gcagccctcg gccggggcca cccactacct ggtgcgatgt tctcctgctt cccccaaggg   1620
```

```
tgaagaggag gagcgagagg tgcaggtcgg gcggcccgag gtgctgctgg atggcctgga   1680
acctggcagg gactatgagg tctcggtgca gagcctgcga ggccctgagg gcagcgaggc   1740
ccggggcatc cgtgccagga cccccaccct ggcccccccg agacacctgg gcttctcaga   1800
cgtgagccac gacgcggcac gagtgttctg ggagggtgcc ccgaggcctg tgcgcctggt   1860
cagggtcacc tatgtgtcca gcgagggtgg acactcgggg cagacagagg ctcctgggaa   1920
cgccacctcg gccacgctgg ggcctctctc ttcctccacc acctacactg tccgtgtcac   1980
ctgcctctac cctgggggtg gctcctctac gctgactggc cgggtgacca ccaagaaagc   2040
tcccagccca agccagctgt ccatgacgga gctgccaggg gatgcagtcc agctggcgtg   2100
ggtggccgca gccccgtctg gcgtgcttgt ctaccagatc acgtggacgc ccctgggaga   2160
ggggaaggct cacgagatct ctgtcccagg gaacctcggc acggccgtcc tgcctggcct   2220
agggaggcac acagagtacg acgtcaccat cttggcctac tacagggacg gggcccgcag   2280
tgaccctgtg tccctccgct ataccccctc cacggtgagc aggagcccac cctccaacct   2340
ggccctggcc tcggagaccc ccgacagcct gcaggtcagc tggacgcccc cgcttggccg   2400
cgtgctccat tactggctca cctacgcccc cgcctctggc ttgggacccg agaaatccgt   2460
ctctgtgcca ggagccagga gccacgtgac actgcccgac ctgcaggcag ccacgaagta   2520
cagggtcctg gtctcagcta tctatgcagc aggcaggagt gaggctgtgt ctgccacggg   2580
ccagacagcc tgcccagccc tccgccctga cggctccctc ccagggtttg acctgatggt   2640
ggccttcagc ctggtggaaa aggcttatgc gtccatccgg ggcgtggcca tggagccctc   2700
tgccttcggt gggaccccga ccttcacgct cttcaaggac gcccagctga caagacgggt   2760
cagtgacgtc tacccagccc ccctacctcc agagcacacc atcgtcttcc ttgtgcgcct   2820
acttcccgag acaccccgtg aggccttcgc gctgtggcag atgacagccg aggacttcca   2880
gcccctcctt ggggttctgc tggatgccgg gaagaagtcc ctgacctact tccaccgtga   2940
ccccagggct gccttgcagg aggccacctt cgacccgcag gaagtgagga agattttctt   3000
cgggagcttc cacaaggtgc acgtggctgt gggccgctcc aaggtcaggc tctatgtgga   3060
ctgccggaag gtggctgagc ggccccttgg ggagatgggc agcccacccg ctgcgggctt   3120
cgtcacgctg gggaggctgg ccaaggccag ggggcccccgg agcagttcgg ccgcgtttca   3180
gctccagatg ctgcagatcg tgtgcagtga cacctgggcc gatgaggacc ggtgctgtga   3240
gctccctgcc tcgagggatg gagagacctg ccccgccttc gtgtctgcct gttcctgttc   3300
ctcagagacc cctgggcccc caggacctca aggaccccca ggcctccctg ggaggaatgg   3360
caccccagga gagcagggct tcccagggcc caggggtcca ccaggggtca aaggagagaa   3420
gggagaccat gggcttccag gcttgcaggg ccaccccggc caccagggca tccccgggag   3480
agttggcctc cagggaccaa agggaatgag aggcctggag ggaactgctg gcctgcctgg   3540
acctggcccc agggggttcc agggcatggc aggggccagg ggcactagtg gagagcgagg   3600
acctccaggg accgtggggc ccacaggact gccagggccc aaaggggaac gaggagagaa   3660
gggcgagccg cagtcccttg ccaccctcta ccagcttgtg agccaggcct cacacgtgtc   3720
aaagttcgac tccttccacg agaacaccag gcccccccatg cccatcttgg agcagaagct   3780
ggagccgggc actgagcccc tggggtcccc tggcacccgc agcaaggccc tggttcctgg   3840
agaatggggg cgtggtggcc gccaccttga gggcagaggg gagcctggag ctgttggtca   3900
gatgggcagc cctgggcagc agggggctag cacccagggc ctctgggagt gacaggacat   3960
tttctgcact gccccgagga acgctgagcc ttcctccctg ggtttgtctg gacaccgaga   4020
```

```
gcgaccacat cctggagaag ccaggagaaa agctcaggaa gagcctgcag gtggaaggag   4080

agggaagcag cggcctcggc caaggcccac cccatactct tggctctgta gcatttccaa   4140

gttcagataa acccctgagt gctcaccc                                       4168


<210> SEQ ID NO 27
<211> LENGTH: 740
<212> TYPE: PRT
<213> ORGANISM: Homo sapiens

<400> SEQUENCE: 27

Ala Val Arg Ala Glu Pro Gly Leu Glu Glu Leu Ser Ser Gly Leu Arg
1               5                   10                  15

Ala His Ser Pro Ser Ala Thr Thr Val Cys Glu Pro Glu Ala Gln Gly
            20                  25                  30

Ser Ala Ser Gly Cys Arg Tyr Ala Ala His Pro His Trp Gly Leu Gly
        35                  40                  45

Gly Ala Ala Ala Ala Gly Gly Ser Trp Glu Pro Gln Pro Pro Arg Pro
    50                  55                  60

Val Cys Glu Pro Ala Gly Arg Gly Lys Pro His Pro Pro Ala Ala Pro
65                  70                  75                  80

Arg Ser Pro Leu Leu Pro Gly Ser Arg Arg Arg Pro Gln Ala Ala Gln
                85                  90                  95

Pro Gly Ala Arg Ala Arg Thr Ser Pro Pro Pro Ala Ser Ala Arg Asn
            100                 105                 110

Met Ala Ala Arg Pro Ala Ala Thr Leu Ala Trp Ser Leu Leu Leu Leu
        115                 120                 125

Ser Ser Ala Leu Leu Arg Glu Gly Cys Arg Ala Arg Phe Val Ala Glu
    130                 135                 140

Arg Asp Ser Glu Asp Asp Gly Glu Glu Pro Val Val Phe Pro Glu Ser
145                 150                 155                 160

Pro Leu Gln Ser Pro Thr Val Leu Val Ala Val Leu Ala Arg Asn Ala
                165                 170                 175

Ala His Thr Leu Pro His Phe Leu Gly Cys Leu Glu Arg Leu Asp Tyr
            180                 185                 190

Pro Lys Ser Arg Met Ala Ile Trp Ala Ala Thr Asp His Asn Val Asp
        195                 200                 205

Asn Thr Thr Glu Ile Phe Arg Glu Trp Leu Lys Asn Val Gln Arg Leu
    210                 215                 220

Tyr His Tyr Val Glu Trp Arg Pro Met Asp Glu Pro Glu Ser Tyr Pro
225                 230                 235                 240

Asp Glu Ile Gly Pro Lys His Trp Pro Thr Ser Arg Phe Ala His Val
                245                 250                 255

Met Lys Leu Arg Gln Ala Ala Leu Arg Thr Ala Arg Glu Lys Trp Ser
            260                 265                 270

Asp Tyr Ile Leu Phe Ile Asp Val Asp Asn Phe Leu Thr Asn Pro Gln
        275                 280                 285

Thr Leu Asn Leu Leu Ile Ala Glu Asn Lys Thr Ile Val Ala Pro Met
    290                 295                 300

Leu Glu Ser Arg Gly Leu Tyr Ser Asn Phe Trp Cys Gly Ile Thr Pro
305                 310                 315                 320

Lys Ala Lys Gly Phe Tyr Lys Arg Thr Pro Asp Tyr Val Gln Ile Arg
                325                 330                 335

Glu Trp Lys Arg Thr Gly Cys Phe Pro Val Pro Met Val His Ser Thr
```

```
            340                 345                 350

Phe Leu Ile Asp Leu Arg Lys Glu Ala Ser Asp Lys Leu Thr Phe Tyr
        355                 360                 365

Pro Pro His Gln Asp Tyr Thr Trp Thr Phe Asp Asp Ile Ile Val Phe
    370                 375                 380

Ala Phe Ser Ser Arg Gln Ala Gly Ile Gln Met Tyr Leu Cys Asn Arg
385                 390                 395                 400

Glu His Tyr Gly Tyr Leu Pro Ile Pro Leu Lys Pro His Gln Thr Leu
                405                 410                 415

Gln Glu Asp Ile Glu Asn Leu Ile His Val Gln Ile Glu Ala Met Ile
            420                 425                 430

Asp Arg Pro Pro Met Glu Pro Ser Gln Tyr Val Ser Val Val Pro Lys
        435                 440                 445

Tyr Pro Asp Lys Met Gly Phe Asp Glu Ile Phe Met Ile Asn Leu Lys
    450                 455                 460

Arg Arg Lys Asp Arg Arg Asp Arg Met Leu Arg Thr Leu Tyr Glu Gln
465                 470                 475                 480

Glu Ile Glu Val Lys Ile Val Glu Ala Val Asp Gly Lys Ala Leu Asn
                485                 490                 495

Thr Ser Gln Leu Lys Ala Leu Asn Ile Glu Met Leu Pro Gly Tyr Arg
            500                 505                 510

Asp Pro Tyr Ser Ser Arg Pro Leu Thr Arg Gly Glu Ile Gly Cys Phe
        515                 520                 525

Leu Ser His Tyr Ser Val Trp Lys Glu Val Ile Asp Arg Glu Leu Glu
    530                 535                 540

Lys Thr Leu Val Ile Glu Asp Asp Val Arg Phe Glu His Gln Phe Lys
545                 550                 555                 560

Lys Lys Leu Met Lys Leu Met Asp Asn Ile Asp Gln Ala Gln Leu Asp
                565                 570                 575

Trp Glu Leu Ile Tyr Ile Gly Arg Lys Arg Met Gln Val Lys Glu Pro
            580                 585                 590

Glu Lys Ala Val Pro Asn Val Ala Asn Leu Val Glu Ala Asp Tyr Ser
        595                 600                 605

Tyr Trp Thr Leu Gly Tyr Val Ile Ser Leu Glu Gly Ala Gln Lys Leu
    610                 615                 620

Val Gly Ala Asn Pro Phe Gly Lys Met Leu Pro Val Asp Glu Phe Leu
625                 630                 635                 640

Pro Val Met Tyr Asn Lys His Pro Val Ala Glu Tyr Lys Glu Tyr Tyr
                645                 650                 655

Glu Ser Arg Asp Leu Lys Ala Phe Ser Ala Glu Pro Leu Leu Ile Tyr
            660                 665                 670

Pro Thr His Tyr Thr Gly Gln Pro Gly Tyr Leu Ser Asp Thr Glu Thr
        675                 680                 685

Ser Thr Ile Trp Asp Asn Glu Thr Val Ala Thr Asp Trp Asp Arg Thr
    690                 695                 700

His Ala Trp Lys Ser Arg Lys Gln Ser Arg Ile Tyr Ser Asn Ala Lys
705                 710                 715                 720

Asn Thr Glu Ala Leu Pro Pro Pro Thr Ser Leu Asp Thr Val Pro Ser
                725                 730                 735

Arg Asp Glu Leu
            740


<210> SEQ ID NO 28
```

```
<211> LENGTH: 626
<212> TYPE: PRT
<213> ORGANISM: Homo sapiens

<400> SEQUENCE: 28

Met Ala Ala Arg Pro Ala Ala Thr Leu Ala Trp Ser Leu Leu Leu Leu
1               5                   10                  15

Ser Ser Ala Leu Leu Arg Glu Gly Cys Arg Ala Arg Phe Val Ala Glu
            20                  25                  30

Arg Asp Ser Glu Asp Asp Gly Glu Glu Pro Val Val Phe Pro Glu Ser
        35                  40                  45

Pro Leu Gln Ser Pro Thr Val Leu Val Ala Val Leu Ala Arg Asn Ala
    50                  55                  60

Ala His Thr Leu Pro His Phe Leu Gly Cys Leu Glu Arg Leu Asp Tyr
65                  70                  75                  80

Pro Lys Ser Arg Met Ala Ile Trp Ala Ala Thr Asp His Asn Val Asp
                85                  90                  95

Asn Thr Thr Glu Ile Phe Arg Glu Trp Leu Lys Asn Val Gln Arg Leu
            100                 105                 110

Tyr His Tyr Val Glu Trp Arg Pro Met Asp Glu Pro Glu Ser Tyr Pro
        115                 120                 125

Asp Glu Ile Gly Pro Lys His Trp Pro Thr Ser Arg Phe Ala His Val
    130                 135                 140

Met Lys Leu Arg Gln Ala Ala Leu Arg Thr Ala Arg Glu Lys Trp Ser
145                 150                 155                 160

Asp Tyr Ile Leu Phe Ile Asp Val Asp Asn Phe Leu Thr Asn Pro Gln
                165                 170                 175

Thr Leu Asn Leu Leu Ile Ala Glu Asn Lys Thr Ile Val Ala Pro Met
            180                 185                 190

Leu Glu Ser Arg Gly Leu Tyr Ser Asn Phe Trp Cys Gly Ile Thr Pro
        195                 200                 205

Lys Gly Phe Tyr Lys Arg Thr Pro Asp Tyr Val Gln Ile Arg Glu Trp
    210                 215                 220

Lys Arg Thr Gly Cys Phe Pro Val Pro Met Val His Ser Thr Phe Leu
225                 230                 235                 240

Ile Asp Leu Arg Lys Glu Ala Ser Asp Lys Leu Thr Phe Tyr Pro Pro
                245                 250                 255

His Gln Asp Tyr Thr Trp Thr Phe Asp Asp Ile Ile Val Phe Ala Phe
            260                 265                 270

Ser Ser Arg Gln Ala Gly Ile Gln Met Tyr Leu Cys Asn Arg Glu His
        275                 280                 285

Tyr Gly Tyr Leu Pro Ile Pro Leu Lys Pro His Gln Thr Leu Gln Glu
    290                 295                 300

Asp Ile Glu Asn Leu Ile His Val Gln Ile Glu Ala Met Ile Asp Arg
305                 310                 315                 320

Pro Pro Met Glu Pro Ser Gln Tyr Val Ser Val Val Pro Lys Tyr Pro
                325                 330                 335

Asp Lys Met Gly Phe Asp Glu Ile Phe Met Ile Asn Leu Lys Arg Arg
            340                 345                 350

Lys Asp Arg Arg Asp Arg Met Leu Arg Thr Leu Tyr Glu Gln Glu Ile
        355                 360                 365

Glu Val Lys Ile Val Glu Ala Val Asp Gly Lys Ala Leu Asn Thr Ser
    370                 375                 380

Gln Leu Lys Ala Leu Asn Ile Glu Met Leu Pro Gly Tyr Arg Asp Pro
```

```
385                 390                 395                 400

Tyr Ser Ser Arg Pro Leu Thr Arg Gly Glu Ile Gly Cys Phe Leu Ser
                405                 410                 415

His Tyr Ser Val Trp Lys Glu Val Ile Asp Arg Glu Leu Glu Lys Thr
            420                 425                 430

Leu Val Ile Glu Asp Asp Val Arg Phe Glu His Gln Phe Lys Lys Lys
        435                 440                 445

Leu Met Lys Leu Met Asp Asn Ile Asp Gln Ala Gln Leu Asp Trp Glu
    450                 455                 460

Leu Ile Tyr Ile Gly Arg Lys Arg Met Gln Val Lys Glu Pro Glu Lys
465                 470                 475                 480

Ala Val Pro Asn Val Ala Asn Leu Val Glu Ala Asp Tyr Ser Tyr Trp
                485                 490                 495

Thr Leu Gly Tyr Val Ile Ser Leu Glu Gly Ala Gln Lys Leu Val Gly
            500                 505                 510

Ala Asn Pro Phe Gly Lys Met Leu Pro Val Asp Glu Phe Leu Pro Val
        515                 520                 525

Met Tyr Asn Lys His Pro Val Ala Glu Tyr Lys Glu Tyr Tyr Glu Ser
    530                 535                 540

Arg Asp Leu Lys Ala Phe Ser Ala Glu Pro Leu Leu Ile Tyr Pro Thr
545                 550                 555                 560

His Tyr Thr Gly Gln Pro Gly Tyr Leu Ser Asp Thr Glu Thr Ser Thr
                565                 570                 575

Ile Trp Asp Asn Glu Thr Val Ala Thr Asp Trp Asp Arg Thr His Ala
            580                 585                 590

Trp Lys Ser Arg Lys Gln Ser Arg Ile Tyr Ser Asn Ala Lys Asn Thr
        595                 600                 605

Glu Ala Leu Pro Pro Pro Thr Ser Leu Asp Thr Val Pro Ser Arg Asp
    610                 615                 620

Glu Leu
625


<210> SEQ ID NO 29
<211> LENGTH: 363
<212> TYPE: PRT
<213> ORGANISM: Homo sapiens

<400> SEQUENCE: 29

Met Phe Ser Asp Cys Trp Leu Cys Pro Ser Leu Gly Ser Ser Gly Ile
1               5                   10                  15

Gln Met Tyr Leu Cys Asn Arg Glu His Tyr Gly Tyr Leu Pro Ile Pro
            20                  25                  30

Leu Lys Pro His Gln Thr Leu Gln Glu Asp Ile Glu Asn Leu Ile His
        35                  40                  45

Val Gln Ile Glu Ala Met Ile Asp Arg Pro Pro Met Glu Pro Ser Gln
    50                  55                  60

Tyr Val Ser Val Val Pro Lys Tyr Pro Asp Lys Met Gly Phe Asp Glu
65                  70                  75                  80

Ile Phe Met Ile Asn Leu Lys Arg Arg Lys Asp Arg Arg Asp Arg Met
                85                  90                  95

Leu Arg Thr Leu Tyr Glu Gln Glu Ile Glu Val Lys Ile Val Glu Ala
            100                 105                 110

Val Asp Gly Lys Ala Leu Asn Thr Ser Gln Leu Lys Ala Leu Asn Ile
        115                 120                 125
```

```
Glu Met Leu Pro Gly Tyr Arg Asp Pro Tyr Ser Ser Arg Pro Leu Thr
    130                 135                 140

Arg Gly Glu Ile Gly Cys Phe Leu Ser His Tyr Ser Val Trp Lys Glu
145                 150                 155                 160

Val Ile Asp Arg Glu Leu Glu Lys Thr Leu Val Ile Glu Asp Asp Val
                165                 170                 175

Arg Phe Glu His Gln Phe Lys Lys Lys Leu Met Lys Leu Met Asp Asn
            180                 185                 190

Ile Asp Gln Ala Gln Leu Asp Trp Glu Leu Ile Tyr Ile Gly Arg Lys
        195                 200                 205

Arg Met Gln Val Lys Glu Pro Glu Lys Ala Val Pro Asn Val Ala Asn
    210                 215                 220

Leu Val Glu Ala Asp Tyr Ser Tyr Trp Thr Leu Gly Tyr Val Ile Ser
225                 230                 235                 240

Leu Glu Gly Ala Gln Lys Leu Val Gly Ala Asn Pro Phe Gly Lys Met
                245                 250                 255

Leu Pro Val Asp Glu Phe Leu Pro Val Met Tyr Asn Lys His Pro Val
            260                 265                 270

Ala Glu Tyr Lys Glu Tyr Tyr Glu Ser Arg Asp Leu Lys Ala Phe Ser
        275                 280                 285

Ala Glu Pro Leu Leu Ile Tyr Pro Thr His Tyr Thr Gly Gln Pro Gly
    290                 295                 300

Tyr Leu Ser Asp Thr Glu Thr Ser Thr Ile Trp Asp Asn Glu Thr Val
305                 310                 315                 320

Ala Thr Asp Trp Asp Arg Thr His Ala Trp Lys Ser Arg Lys Gln Ser
                325                 330                 335

Arg Ile Tyr Ser Asn Ala Lys Asn Thr Glu Ala Leu Pro Pro Pro Thr
            340                 345                 350

Ser Leu Asp Thr Val Pro Ser Arg Asp Glu Leu
        355                 360


<210> SEQ ID NO 30
<211> LENGTH: 234
<212> TYPE: PRT
<213> ORGANISM: Homo sapiens

<400> SEQUENCE: 30

Met Leu Pro Gly Tyr Arg Asp Pro Tyr Ser Ser Arg Pro Leu Thr Arg
1               5                   10                  15

Gly Glu Ile Gly Cys Phe Leu Ser His Tyr Ser Val Trp Lys Glu Val
            20                  25                  30

Ile Asp Arg Glu Leu Glu Lys Thr Leu Val Ile Glu Asp Asp Val Arg
        35                  40                  45

Phe Glu His Gln Phe Lys Lys Lys Leu Met Lys Leu Met Asp Asn Ile
    50                  55                  60

Asp Gln Ala Gln Leu Asp Trp Glu Leu Ile Tyr Ile Gly Arg Lys Arg
65                  70                  75                  80

Met Gln Val Lys Glu Pro Glu Lys Ala Val Pro Asn Val Ala Asn Leu
                85                  90                  95

Val Glu Ala Asp Tyr Ser Tyr Trp Thr Leu Gly Tyr Val Ile Ser Leu
            100                 105                 110

Glu Gly Ala Gln Lys Leu Val Gly Ala Asn Pro Phe Gly Lys Met Leu
        115                 120                 125

Pro Val Asp Glu Phe Leu Pro Val Met Tyr Asn Lys His Pro Val Ala
    130                 135                 140
```

```
Glu Tyr Lys Glu Tyr Tyr Glu Ser Arg Asp Leu Lys Ala Phe Ser Ala
145                 150                 155                 160

Glu Pro Leu Leu Ile Tyr Pro Thr His Tyr Thr Gly Gln Pro Gly Tyr
                165                 170                 175

Leu Ser Asp Thr Glu Thr Ser Thr Ile Trp Asp Asn Glu Thr Val Ala
            180                 185                 190

Thr Asp Trp Asp Arg Thr His Ala Trp Lys Ser Arg Lys Gln Ser Arg
        195                 200                 205

Ile Tyr Ser Asn Ala Lys Asn Thr Glu Ala Leu Pro Pro Pro Thr Ser
    210                 215                 220

Leu Asp Thr Val Pro Ser Arg Asp Glu Leu
225                 230


<210> SEQ ID NO 31
<211> LENGTH: 5188
<212> TYPE: DNA
<213> ORGANISM: Homo sapiens

<400> SEQUENCE: 31

cacaactcgc ggctctaggg aaggccacag acctcagctg tacgagcgga acctggacta      60

gaggaacttt cctcaggact cagggcacac agcccctcgg ccactactgt ctgcgagccc     120

gaggcgcagg ggagcgccag cggctgcagg tacgctgcgc acccgcactg gggcctgggc     180

ggtgcagcgg cggcgggagg gtcctgggaa ccgcagccgc cgaggccagt gtgtgagccg     240

gccggccgcg gcaagccgca tcccccggcc gcccctcgca gccccttgct ccccggcagc     300

cgccgccgcc ctcaggcagc ccagccgggc gctcgcgcca ggacttcccc gccgcccgcc     360

tcggcccgga acatggctgc gcgccctgct gccaccctcg cctggtcgct actgctcctc     420

tcctcagccc tgctccgcga aggctgccga gcgcgcttcg tcgccgagcg ggactcggag     480

gacgacggag aggagccggt ggttttcccg gagtcgcccc tgcagagccc cacggtgctc     540

gtggcggtcc tcgcccgcaa cgcggcgcac acgctgccgc acttcctcgg ctgcctggag     600

cggctggact accccaagag caggatggcc atctgggcag ccactgatca caatgtggat     660

aatacaacag aaatattcag ggagtggttg aaaaatgtac agagactcta tcactatgtg     720

gagtggaggc ctatggatga accagagtct taccctgatg aaattggacc aaagcactgg     780

ccaacctccc ggtttgccca tgtgatgaaa ctacgacagg cagcccttcg aactgcgagg     840

gaaaaatggt cagactacat tctgttcata gatgttgaca atttcctgac taatccacag     900

accctcaatc tactgattgc agaaaacaaa actattgtgg cccccatgct ggagtctcgg     960

ggcctgtatt ctaatttctg gtgcggaatc accccctaagg caaagggctt ctataagagg   1020

accccagact acgttcagat tcgagaatgg aagaggacag gctgcttccc cgtccccatg    1080

gtccactcca ccttcctaat tgacctcagg aaggaggcct cggacaagct gactttctac    1140

cccccacacc aggactacac ctggaccttt gatgacatca ttgtctttgc cttctccagc    1200

aggcaagcag gcatccagat gtacctctgc aacagagagc actatggcta cctgcccatc    1260

cccctgaagc cccatcagac actgcaggaa gacatcgaga acctcatcca tgtgcagatt    1320

gaagcaatga ttgaccgtcc tccaatggaa ccctcccagt atgtctcagt tgtccctaaa    1380

tatccagaca agatgggatt tgatgagatt ttcatgataa acctcaaacg cagaaaggac    1440

aggcgggacc ggatgctgcg cacactgtat gaacaggaga ttgaggtcaa gattgtcgag    1500

gctgtggatg gaaaggcact caacacaagc cagctgaagg cactgaatat tgaaatgctg    1560
```

```
cctggctatc gagatcccta ttcctccagg cctctaacaa ggggtgaaat cggctgcttt   1620
ctcagccact actcagtctg gaaagaggta attgatcgag agctagagaa gactcttgta   1680
attgaagacg atgtgcgttt tgagcatcag tttaagaaga agctgatgaa gctgatggat   1740
aacattgacc aggctcagct ggactgggaa ctgatttata ttggtaggaa gaggatgcaa   1800
gtaaaggagc cagagaaagc agtgcccaat gtggcaaacc tggtcgaagc cgactattcc   1860
tactggaccc tgggctacgt catctctctg gaaggagcac agaagctggt tggagccaat   1920
ccttttggga agatgctgcc agtggatgag tttctgccag tcatgtacaa caagcatccc   1980
gtagccgagt acaaggagta ttatgaatcc agggacctga aagccttctc tgcagaaccc   2040
ttgctcatct accctacgca ctacacaggc cagccggggt acctgagtga cacggagacc   2100
tccaccatct gggacaatga gacagtggcc accgactggg ataggacaca tgcctggaag   2160
tcccggaagc aaagccgcat ctacagcaat gccaagaaca cagaggccct gccaccgcca   2220
acctccctgg acactgtgcc ttcaagggat gagctatgaa ggctccctgg gagtgtggcc   2280
cacatcagtt caacatcctc tggtttttct aaagggctat tcatctgttt gctccagttt   2340
tctgttttgt tttgttctta gtggtcacag tcatctaacc aaagtgatct agtgtgatag   2400
atcgaaatta acatattttt gaccatggaa ggaaataagg aaattcaacc caaatttccc   2460
aagacggctg aaagacaggt tttttggaaa ctgttaagat aaactgtaat ccagacacct   2520
aattcttcag ttcactactc atgtgatact gattcccaca ttaaggttga acaacatggc   2580
tcagagtctt gttcaagaga aagtgatcac cgagctgtca catcagcaaa tatgtagtca   2640
aggcagccag gccaactaga ccacacttat tggtctagtt tgtccgtttt atatgacatt   2700
gaaaacttgt gtgtgcaact tttgggggac aggaatcact taaaatcata tttatttggc   2760
tttttattta aaggattctg tcacaagtct tattgaaaag tagatttttt aaaaaaaaaa   2820
aatcttagtc cctgttatcc agtaggggtg ggtatttggg tccgactgag acttggcctg   2880
tgaccatcat ggcagttgga gttctcatat agaggtgacc agtttgccat gtggatataa   2940
tttagtagat atttgacagt ttgtgtaggt atttgaggga aaaaactcaa tgtttggctt   3000
ttttattatg gccactcgag tcaggatgct ctatttataa agataaatgt aatatataaa   3060
gggtgaggac tggctgtgca tcctgccctg tcccgggttt gcgcgctgct acagagcttc   3120
acgctctccg ctccacccct tagcctggga acccaccgca ggtgtgagtt ctgtgagtca   3180
ctgctaagag acagagcaca ttttcaggcc agcaactatc cttgccagag ttttttcatt   3240
atattttgaa ttatttattt tacaaaatgg gcgaagatat tgtctttagg ataaggcaga   3300
gaaacagatg ttgcagactt ccacggcacc cgggggagtg gtgggtgtgg acacattggt   3360
tcggcaatct gattctcctg aatttcccag ccaggctctt gtggggaggc ctgtggatgg   3420
ggggatttga actatttgga aacaaatgat tctctatctc aggtgagaaa cctggtcaga   3480
aacaaagggc tggtcacctg atttaggcca gcaaccaggg aagctcttag aatcccaggc   3540
ggacaccctt tctcaaaaga tatcccctaa gagtcctttc tgctttcttc acagattgat   3600
tttatgtaaa atgcagagtt ggactacacg atttcttccc actccacaat ctgtcatcct   3660
agtatagatc atggtggttt ccctcaagtt tatgttctca tgccctcaat ctgtaaattt   3720
ttgtctccag aaaaaccctc ccaggcatcc cataccagca ccgttcctca tcactgtcca   3780
tgcaccatgc agccatatgg ggggccgtgc acaccccaaa ccctgagctt cacacttaaa   3840
ctcatgggga gggcccttca gagcagagtc cacaggcggg tggtgctaca tacacaagct   3900
tagtgtacga gtgtaagata cactttaagc cagacaccta attcttcagt tcactgccca   3960
```

```
tgtgatactg attgccacat taaggttgaa cagcatggct cagagtctag agaaagtgat   4020

caccaagctg tctcatcacc aaataggtag tcaaggcagc ctcatctccc caggtgaggg   4080

gcgggtcccc actttaggac aagaggcagc ttgccttcca ccagacgcca gcctcggcct   4140

tccttcccga ctcactgtgg gtacccttct acactgacca gcaagctagg ccgctggagg   4200

aaagggaact cacccaactc taaattgtgc cgcttagact tagctgtcag tgtgacttcc   4260

tttcccaccc acccccagaa aaacagaaag agcatctggg gagcgagtga aaattcctta   4320

ggtgattcct aagatttcct tgggtatctg gtttttgttt tcatatttga gtgtgtgcat   4380

gtgtgcatga ctttaatgac ttttttaatg gggtgggagg tggctggggt gctggggttg   4440

aaggaagttt gggttgattt ttgtggtgtt ttgtttaata gagaattttt tttttcctgt   4500

tcccctgtca gctggtctga cagatttaag aactctcatt cttaaaagac tttggactta   4560

aattctagca ttttagacta ggactgttct actgtgaaga aagttctgtc tcctttagcc   4620

cggtttgttt ctccctgctc aggtctagaa tcccaagcag tgttcttttc tggtgaacac   4680

tgtgagccgc agatgtgact ttttttttaa agtcatctct tcagcaatcc agaggttcct   4740

tgacctcatt atttgtccta tctctccctt atagtcctaa gccaagacat ttgacctttg   4800

acatttgacc tttgcagtgt catgtgaggg cgtcagtata gaggcctttg catctgggcc   4860

tggcacccgc tctctgcctc tggaggctaa accctgtctg gatttctctt gggatctaac   4920

gtgggatctt ctggacagac aaccgtgaca tcagcagtgc tggtgctgct gtgtgtggac   4980

tgaacacctg cactttgcag aggacacgct gcatgggccc cgcttgcggt tcattcaggc   5040

ctgctgcagg agctctgaga acaagaaaga gtggacaccc gttcccctgc atcatctgtc   5100

ttgcgtgcta tttcagagtg gggaagtgat aaactatttg ccttctggag ctctttgtga   5160

aaaattaaaa aaaaacttag ctcaaaga                                      5188
```

<210> SEQ ID NO 32
<211> LENGTH: 5182
<212> TYPE: DNA
<213> ORGANISM: Homo sapiens

<400> SEQUENCE: 32

```
cacaactcgc ggctctaggg aaggccacag acctcagctg tacgagcgga acctggacta     60

gaggaacttt cctcaggact cagggcacac agcccctcgg ccactactgt ctgcgagccc    120

gaggcgcagg ggagcgccag cggctgcagg tacgctgcgc acccgcactg gggcctgggc    180

ggtgcagcgg cggcgggagg gtcctgggaa ccgcagccgc cgaggccagt gtgtgagccg    240

gccggccgcg gcaagccgca tcccccggcc gcccctcgca gcccccttgct ccccggcagc    300

cgccgccgcc ctcaggcagc ccagccgggc gctcgcgcca ggacttcccc gccgcccgcc    360

tcggcccgga acatggctgc gcgccctgct gccaccctcg cctggtcgct actgctcctc    420

tcctcagccc tgctccgcga aggctgccga gcgcgcttcg tcgccgagcg ggactcggag    480

gacgacggag aggagccggt ggttttcccg gagtcgcccc tgcagagccc cacggtgctc    540

gtggcggtcc tcgcccgcaa cgcggcgcac acgctgccgc acttcctcgg ctgcctggag    600

cggctggact accccaagag caggatggcc atctgggcag ccactgatca caatgtggat    660

aatacaacag aaatattcag ggagtggttg aaaaatgtac agagactcta tcactatgtg    720

gagtggaggc ctatggatga accagagtct taccctgatg aaattggacc aaagcactgg    780

ccaacctccc ggtttgccca tgtgatgaaa ctacgacagg cagcccttcg aactgcgagg    840
```

```
gaaaaatggt cagactacat tctgttcata gatgttgaca atttcctgac taatccacag    900
accctcaatc tactgattgc agaaaacaaa actattgtgg cccccatgct ggagtctcgg    960
ggcctgtatt ctaatttctg gtgcggaatc acccctaagg gcttctataa gaggacccca   1020
gactacgttc agattcgaga atggaagagg acaggctgct tccccgtccc catggtccac   1080
tccaccttcc taattgacct caggaaggag gcctcggaca agctgacttt ctacccccca   1140
caccaggact acacctggac ctttgatgac atcattgtct ttgccttctc cagcaggcaa   1200
gcaggcatcc agatgtacct ctgcaacaga gagcactatg gctacctgcc catccccctg   1260
aagccccatc agacactgca ggaagacatc gagaacctca tccatgtgca gattgaagca   1320
atgattgacc gtcctccaat ggaaccctcc cagtatgtct cagttgtccc taaatatcca   1380
gacaagatgg gatttgatga gattttcatg ataaacctca aacgcagaaa ggacaggcgg   1440
gaccggatgc tgcgcacact gtatgaacag gagattgagg tcaagattgt cgaggctgtg   1500
gatggaaagg cactcaacac aagccagctg aaggcactga atattgaaat gctgcctggc   1560
tatcgagatc cctattcctc caggcctcta acaaggggtg aaatcggctg ctttctcagc   1620
cactactcag tctggaaaga ggtaattgat cgagagctag agaagactct tgtaattgaa   1680
gacgatgtgc gttttgagca tcagtttaag aagaagctga tgaagctgat ggataacatt   1740
gaccaggctc agctggactg ggaactgatt tatattggta ggaagaggat gcaagtaaag   1800
gagccagaga aagcagtgcc caatgtggca aacctggtcg aagccgacta ttcctactgg   1860
accctgggct acgtcatctc tctggaagga gcacagaagc tggttggagc caatcctttt   1920
gggaagatgc tgccagtgga tgagtttctg ccagtcatgt acaacaagca tcccgtagcc   1980
gagtacaagg agtattatga atccagggac ctgaaagcct tctctgcaga acccttgctc   2040
atctacccta cgcactacac aggccagccg gggtacctga gtgacacgga gacctccacc   2100
atctgggaca atgagacagt ggccaccgac tgggatagga cacatgcctg gaagtcccgg   2160
aagcaaagcc gcatctacag caatgccaag aacacagagg ccctgccacc gccaacctcc   2220
ctggacactg tgccttcaag ggatgagcta tgaaggctcc ctgggagtgt ggcccacatc   2280
agttcaacat cctctggttt ttctaaaggg ctattcatct gtttgctcca gttttctgtt   2340
ttgttttgtt cttagtggtc acagtcatct aaccaaagtg atctagtgtg atagatcgaa   2400
attaacatat ttttgaccat ggaaggaaat aaggaaattc aacccaaatt tcccaagacg   2460
gctgaaagac aggtttttg gaaactgtta agataaactg taatccagac acctaattct   2520
tcagttcact actcatgtga tactgattcc cacattaagg ttgaacaaca tggctcagag   2580
tcttgttcaa gagaaagtga tcaccgagct gtcacatcag caaatatgta gtcaaggcag   2640
ccaggccaac tagaccacac ttattggtct agtttgtccg ttttatatga cattgaaaac   2700
ttgtgtgtgc aacttttggg ggacaggaat cacttaaaat catatttatt tggcttttta   2760
tttaaaggat tctgtcacaa gtcttattga aaagtagatt ttttaaaaaa aaaaaatctt   2820
agtccctgtt atccagtagg ggtgggtatt tgggtccgac tgagacttgg cctgtgacca   2880
tcatggcagt tggagttctc atatagaggt gaccagtttg ccatgtggat ataatttagt   2940
agatatttga cagtttgtgt aggtatttga gggaaaaaac tcaatgtttg gcttttttat   3000
tatggccact cgagtcagga tgctctattt ataaagataa atgtaatata taaagggtga   3060
ggactggctg tgcatcctgc cctgtcccgg gtttgcgcgc tgctacagag cttcacgctc   3120
tccgctccac cccttagcct gggaacccac cgcaggtgtg agttctgtga gtcactgcta   3180
agagacagag cacattttca ggccagcaac tatccttgcc agagtttttt cattatattt   3240
```

```
tgaattattt attttacaaa atgggcgaag atattgtctt taggataagg cagagaaaca   3300
gatgttgcag acttccacgg cacccggggg agtggtgggt gtggacacat tggttcggca   3360
atctgattct cctgaatttc ccagccaggc tcttgtgggg aggcctgtgg atggggggat   3420
ttgaactatt tggaaacaaa tgattctcta tctcaggtga gaaacctggt cagaaacaaa   3480
gggctggtca cctgatttag gccagcaacc agggaagctc ttagaatccc aggcggacac   3540
cctttctcaa aagatatccc ctaagagtcc tttctgcttt cttcacagat tgattttatg   3600
taaaatgcag agttggacta cacgatttct tcccactcca caatctgtca tcctagtata   3660
gatcatggtg gtttccctca agtttatgtt ctcatgccct caatctgtaa atttttgtct   3720
ccagaaaaac cctcccaggc atcccatacc agcaccgttc ctcatcactg tccatgcacc   3780
atgcagccat atgggggggcc gtgcacaccc caaaccctga gcttcacact taaactcatg   3840
gggagggccc ttcagagcag agtccacagg cgggtggtgc tacatacaca agcttagtgt   3900
acgagtgtaa gatacacttt aagccagaca cctaattctt cagttcactg cccatgtgat   3960
actgattgcc acattaaggt tgaacagcat ggctcagagt ctagagaaag tgatcaccaa   4020
gctgtctcat caccaaatag gtagtcaagg cagcctcatc tccccaggtg aggggcgggt   4080
ccccacttta ggacaagagg cagcttgcct tccaccagac gccagcctcg gccttccttc   4140
ccgactcact gtgggtaccc ttctacactg accagcaagc taggccgctg gaggaaaggg   4200
aactcaccca actctaaatt gtgccgctta gacttagctg tcagtgtgac ttcctttccc   4260
acccaccccc agaaaaacag aaagagcatc tggggagcga gtgaaaattc cttaggtgat   4320
tcctaagatt tccttgggta tctggttttt gttttcatat ttgagtgtgt gcatgtgtgc   4380
atgactttaa tgactttttt aatggggtgg gaggtggctg ggtgctgggg gttgaaggaa   4440
gtttgggttg atttttgtgg tgttttgttt aatagagaat ttttttttc ctgttcccct   4500
gtcagctggt ctgacagatt taagaactct cattcttaaa agactttgga cttaaattct   4560
agcattttag actaggactg ttctactgtg aagaaagttc tgtctccttt agcccggttt   4620
gtttctccct gctcaggtct agaatcccaa gcagtgttct tttctggtga acactgtgag   4680
ccgcagatgt gacttttttt ttaaagtcat ctcttcagca atccagaggt tccttgacct   4740
cattatttgt cctatctctc ccttatagtc ctaagccaag acatttgacc tttgacattt   4800
gacctttgca gtgtcatgtg agggcgtcag tatagaggcc tttgcatctg ggcctggcac   4860
ccgctctctg cctctggagg ctaaaccctg tctggatttc tcttgggatc taacgtggga   4920
tcttctggac agacaaccgt gacatcagca gtgctggtgc tgctgtgtgt ggactgaaca   4980
cctgcacttt gcagaggaca cgctgcatgg gccccgcttg cggttcattc aggcctgctg   5040
caggagctct gagaacaaga aagagtggac acccgttccc ctgcatcatc tgtcttgcgt   5100
gctatttcag agtggggaag tgataaacta tttgccttct ggagctcttt gtgaaaaatt   5160
aaaaaaaaac ttagctcaaa ga                                             5182
```

<210> SEQ ID NO 33
<211> LENGTH: 2325
<212> TYPE: DNA
<213> ORGANISM: Homo sapiens

<400> SEQUENCE: 33

```
ttttcgtttt tttgttctat gtatgcctag atttagcttt aataatctgt cagcgttaca     60
gaattttcct gtttgctttc atatcaaatg tggatttcat tcctcatttt cttgttattt    120
```

```
cctgtaggtg gattacagtg ttccattctg ctctccagaa tgggaattcc ttgcctccct    180
tttgatcctt tcatgccttt tttgttcatt ccaggccatg agtttgcttt ttcttcagag    240
ggaaaaaatc aatttcctct gggctgaaga atagccgagt gtttttatta gtccccaatg    300
ctgtgtttta ctttttttaat aaaggagcat tttttaggtc tatagacata cctgaaacaa    360
ccacttattt aattgcagtg tcaaactcag catcagacac agttcaggtt ccttctcctc    420
gcttgtcact cagcagtatg ttttctgatt gttggctttg tccctctctt ggatcctcag    480
gcatccagat gtacctctgc aacagagagc actatggcta cctgcccatc cccctgaagc    540
cccatcagac actgcaggaa gacatcgaga acctcatcca tgtgcagatt gaagcaatga    600
ttgaccgtcc tccaatggaa ccctcccagt atgtctcagt tgtccctaaa tatccagaca    660
agatgggatt tgatgagatt ttcatgataa acctcaaacg cagaaaggac aggcgggacc    720
ggatgctgcg cacactgtat gaacaggaga ttgaggtcaa gattgtcgag gctgtggatg    780
gaaaggcact caacacaagc cagctgaagg cactgaatat tgaaatgctg cctggctatc    840
gagatcccta ttcctccagg cctctaacaa ggggtgaaat cggctgcttt ctcagccact    900
actcagtctg gaaagaggta attgatcgag agctagagaa gactcttgta attgaagacg    960
atgtgcgttt tgagcatcag tttaagaaga agctgatgaa gctgatggat aacattgacc   1020
aggctcagct ggactgggaa ctgatttata ttggtaggaa gaggatgcaa gtaaaggagc   1080
cagagaaagc agtgcccaat gtggcaaacc tggtcgaagc cgactattcc tactggaccc   1140
tgggctacgt catctctctg gaaggagcac agaagctggt tggagccaat ccttttggga   1200
agatgctgcc agtggatgag tttctgccag tcatgtacaa caagcatccc gtagccgagt   1260
acaaggagta ttatgaatcc agggacctga aagccttctc tgcagaaccc ttgctcatct   1320
accctacgca ctacacaggc cagccggggt acctgagtga cacggagacc tccaccatct   1380
gggacaatga gacagtggcc accgactggg ataggacaca tgcctggaag tcccggaagc   1440
aaagccgcat ctacagcaat gccaagaaca cagaggccct gccaccgcca acctccctgg   1500
acactgtgcc ttcaagggat gagctatgaa ggctccctgg gagtgtggcc cacatcagtt   1560
caacatcctc tggtttttct aaagggctat tcatctgttt gctccagttt tctgttttgt   1620
tttgttctta gtggtcacag tcatctaacc aaagtgatct agtgtgatag atcgaaatta   1680
acatattttt gaccatggaa ggaaataagg aaattcaacc caaatttccc aagacggctg   1740
aaagacaggt tttttggaaa ctgttaagat aaactgtaat ccagacacct aattcttcag   1800
ttcactactc atgtgatact gattcccaca ttaaggttga acaacatggc tcagagtctt   1860
gttcaagaga aagtgatcac cgagctgtca catcagcaaa tatgtagtca aggcagccag   1920
gccaactaga ccacacttat tggtctagtt tgtccgtttt atatgacatt gaaaacttgt   1980
gtgtgcaact tttgggggac aggaatcact taaaatcata tttatttggc tttttattta   2040
aaggattctg tcacaagtct tattgaaaag tagatttttt aaaaaaaaaa aatcttagtc   2100
cctgttatcc agtaggggtg ggtatttggg tccgactgag acttggcctg tgaccatcat   2160
ggcagttgga gttctcatat agaggtgacc agtttgccat gtggatataa tttagtagat   2220
atttgacagt ttgtgtaggt atttgaggga aaaaactcaa tgtttggctt ttttattatg   2280
gccactcgag tcaggatgct ctatttataa agataaatgt aatat                   2325
```

<210> SEQ ID NO 34
<211> LENGTH: 4723
<212> TYPE: DNA
<213> ORGANISM: Homo sapiens

<400> SEQUENCE: 34

```
ttttctattc ttttactttc aacctatttt tgtcttttaa tctaaaggct gcctcttata     60
gataccacat ggttgtatta atttttaaaa cttactatgc caaattcttc cttcattgca    120
gtgttttatt catttgcctt cactacattt ttttccagat ccttaaggtc agccagaggt    180
gagagactag ggacttctca agtttttcct gggcgtgtgg acagccctga atatgcctgg    240
ggccttctag attctcaggg atattttgga gcaaatcaaa ctccctatgg acctcttatt    300
ccttggtttt tccttttaag tttttggtg ggcttcttgt tagcatcagc tgataatgct     360
tctcaaacag ctgtaatgtt aaacagttgt tgctcatggg ttttgacaaa tgacctgcag    420
atagtgctgt tcacagaaaa tgaactctga gtcaggtcaa atcaagacaa gctctgagaa    480
tgtagctttt caaggagcta ctagacaggt tgaatagaga ttattttctg ggggcaggtc    540
tttaagggag tctcagtcca ttttgtccct gccagtggct tctgggttgg tggggtttgc    600
cgctctctta gttgtgaggc tactggtttt caaggctttt gtagggctgg ggtgaacagg    660
ttaggattag ggcagctgtg aacttcacaa agctcactgt gttaacagag attcagcagt    720
aggtcttgat caaacactcc ttggattatt gcagtacttt aactaatttc cataggagtg    780
tacttattaa atcttgtcaa aaaactgatg atgcttagaa ctatgttggg cactatgagg    840
gatacacaaa aatatgatac cctcttgtct tcccagacct cataatacta gtgtgacaca    900
ttagcctgga ggaacttcta aggaataaag ggaagcctct ctgtctttgt ctgtgtgggg    960
gaggggtgtt tgcagaacta actctctctt tctctggcct ttgtggtggg gacctttgac   1020
ttgttaatct ccagacgtgt tttatgtgat gcagggcact caacacaagc cagctgaagg   1080
cactgaatat tgaaatgctg cctggctatc gagatcccta ttcctccagg cctctaacaa   1140
ggggtgaaat cggctgcttt ctcagccact actcagtctg gaaagaggta attgatcgag   1200
agctagagaa gactcttgta attgaagacg atgtgcgttt tgagcatcag tttaagaaga   1260
agctgatgaa gctgatggat aacattgacc aggctcagct ggactgggaa ctgatttata   1320
ttggtaggaa gaggatgcaa gtaaaggagc cagagaaagc agtgcccaat gtggcaaacc   1380
tggtcgaagc cgactattcc tactggaccc tgggctacgt catctctctg gaaggagcac   1440
agaagctggt tggagccaat ccttttggga agatgctgcc agtggatgag tttctgccag   1500
tcatgtacaa caagcatccc gtagccgagt acaaggagta ttatgaatcc agggacctga   1560
aagccttctc tgcagaaccc ttgctcatct accctacgca ctacacaggc cagccggggt   1620
acctgagtga cacggagacc tccaccatct gggacaatga gacagtggcc accgactggg   1680
ataggacaca tgcctggaag tcccggaagc aaagccgcat ctacagcaat gccaagaaca   1740
cagaggccct gccaccgcca acctccctgg acactgtgcc ttcaagggat gagctatgaa   1800
ggctccctgg gagtgtggcc cacatcagtt caacatcctc tggtttttct aaagggctat   1860
tcatctgttt gctccagttt tctgttttgt tttgttctta gtggtcacag tcatctaacc   1920
aaagtgatct agtgtgatag atcgaaatta acatattttt gaccatggaa ggaaataagg   1980
aaattcaacc caaatttccc aagacggctg aaagacaggt tttttggaaa ctgttaagat   2040
aaactgtaat ccagacacct aattcttcag ttcactactc atgtgatact gattcccaca   2100
ttaaggttga acaacatggc tcagagtctt gttcaagaga aagtgatcac cgagctgtca   2160
catcagcaaa tatgtagtca aggcagccag gccaactaga ccacacttat tggtctagtt   2220
tgtccgtttt atatgacatt gaaaacttgt gtgtgcaact tttgggggac aggaatcact   2280
```

```
taaaatcata tttatttggc tttttattta aaggattctg tcacaagtct tattgaaaag   2340
tagattttt  aaaaaaaaaa aatcttagtc cctgttatcc agtaggggtg ggtatttggg   2400
tccgactgag acttggcctg tgaccatcat ggcagttgga gttctcatat agaggtgacc   2460
agtttgccat gtggatataa tttagtagat atttgacagt ttgtgtaggt atttgaggga   2520
aaaaactcaa tgtttggctt ttttattatg gccactcgag tcaggatgct ctatttataa   2580
agataaatgt aatatataaa gggtgaggac tggctgtgca tcctgccctg tcccgggttt   2640
gcgcgctgct acagagcttc acgctctccg ctccacccct tagcctggga acccaccgca   2700
ggtgtgagtt ctgtgagtca ctgctaagag acagagcaca ttttcaggcc agcaactatc   2760
cttgccagag tttttcatt  atattttgaa ttatttattt tacaaaatgg gcgaagatat   2820
tgtctttagg ataaggcaga gaaacagatg ttgcagactt ccacggcacc cgggggagtg   2880
gtgggtgtgg acacattggt tcggcaatct gattctcctg aatttcccag ccaggctctt   2940
gtggggaggc ctgtggatgg ggggatttga actatttgga aacaaatgat tctctatctc   3000
aggtgagaaa cctggtcaga aacaaagggc tggtcacctg atttaggcca gcaaccaggg   3060
aagctcttag aatcccaggc ggacaccctt tctcaaaaga tatcccctaa gagtcctttc   3120
tgctttcttc acagattgat tttatgtaaa atgcagagtt ggactacacg atttcttccc   3180
actccacaat ctgtcatcct agtatagatc atggtggttt ccctcaagtt tatgttctca   3240
tgccctcaat ctgtaaattt ttgtctccag aaaaaccctc ccaggcatcc cataccagca   3300
ccgttcctca tcactgtcca tgcaccatgc agccatatgg ggggccgtgc acaccccaaa   3360
ccctgagctt cacacttaaa ctcatgggga gggcccttca gagcagagtc cacaggcggg   3420
tggtgctaca tacacaagct tagtgtacga gtgtaagata cactttaagc cagacaccta   3480
attcttcagt tcactgccca tgtgatactg attgccacat taaggttgaa cagcatggct   3540
cagagtctag agaaagtgat caccaagctg tctcatcacc aaataggtag tcaaggcagc   3600
ctcatctccc caggtgaggg gcgggtcccc actttaggac aagaggcagc ttgccttcca   3660
ccagacgcca gcctcggcct tccttcccga ctcactgtgg gtacccttct acactgacca   3720
gcaagctagg ccgctggagg aaagggaact cacccaactc taaattgtgc cgcttagact   3780
tagctgtcag tgtgacttcc tttcccaccc acccccagaa aaacagaaag agcatctggg   3840
gagcgagtga aaattcctta ggtgattcct aagatttcct tgggtatctg gtttttgttt   3900
tcatatttga gtgtgtgcat gtgtgcatga ctttaatgac ttttttaatg gggtgggagg   3960
tggctggggt gctggggttg aaggaagttt gggttgattt ttgtggtgtt ttgtttaata   4020
gagaattttt tttttcctgt tcccctgtca gctggtctga cagatttaag aactctcatt   4080
cttaaaagac tttggactta aattctagca ttttagacta ggactgttct actgtgaaga   4140
aagttctgtc tcctttagcc cggtttgttt ctccctgctc aggtctagaa tcccaagcag   4200
tgttcttttc tggtgaacac tgtgagccgc agatgtgact ttttttttaa agtcatctct   4260
tcagcaatcc agaggttcct tgacctcatt atttgtccta tctctccctt atagtcctaa   4320
gccaagacat ttgacctttg acatttgacc tttgcagtgt catgtgaggg cgtcagtata   4380
gaggcctttg catctgggcc tggcacccgc tctctgcctc tggaggctaa accctgtctg   4440
gatttctctt gggatctaac gtgggatctt ctggacagac aaccgtgaca tcagcagtgc   4500
tggtgctgct gtgtgtggac tgaacacctg cactttgcag aggacacgct gcatgggccc   4560
cgcttgcggt tcattcaggc ctgctgcagg agctctgaga acaagaaaga gtggacaccc   4620
gttcccctgc atcatctgtc ttgcgtgcta tttcagagtg ggaagtgat  aaactatttg   4680
```

ccttctggag ctctttgtga aaaattaaaa aaaaacttag ctc 4723

<210> SEQ ID NO 35
<211> LENGTH: 542
<212> TYPE: PRT
<213> ORGANISM: Homo sapiens

<400> SEQUENCE: 35

Met Ala Gln Glu Ile Asp Leu Ser Ala Leu Lys Glu Leu Glu Arg Glu
1 5 10 15

Ala Ile Leu Gln Val Leu Tyr Arg Asp Gln Ala Val Gln Asn Thr Glu
20 25 30

Glu Glu Arg Thr Arg Lys Leu Lys Thr His Leu Gln His Leu Arg Trp
35 40 45

Lys Gly Ala Lys Asn Thr Asp Trp Glu His Lys Glu Lys Cys Cys Ala
50 55 60

Arg Cys Gln Gln Val Leu Gly Phe Leu Leu His Arg Gly Ala Val Cys
65 70 75 80

Arg Gly Cys Ser His Arg Val Cys Ala Gln Cys Arg Val Phe Leu Arg
85 90 95

Gly Thr His Ala Trp Lys Cys Thr Val Cys Phe Glu Asp Arg Asn Val
100 105 110

Lys Ile Lys Thr Gly Glu Trp Phe Tyr Glu Glu Arg Ala Lys Lys Phe
115 120 125

Pro Thr Gly Gly Lys His Glu Thr Val Gly Gly Gln Leu Leu Gln Ser
130 135 140

Tyr Gln Lys Leu Ser Lys Ile Ser Val Val Pro Pro Thr Pro Pro Pro
145 150 155 160

Val Ser Glu Ser Gln Cys Ser Arg Ser Pro Gly Arg Lys Val Ser Ala
165 170 175

Pro Asp Ile Leu Lys Pro Leu Asn Gln Glu Asp Pro Lys Cys Ser Thr
180 185 190

Asn Pro Ile Leu Lys Gln Gln Asn Leu Pro Ser Ser Pro Ala Pro Ser
195 200 205

Thr Ile Phe Ser Gly Gly Phe Arg His Gly Ser Leu Ile Ser Ile Asp
210 215 220

Ser Thr Cys Thr Glu Met Gly Asn Phe Asp Asn Ala Asn Val Thr Gly
225 230 235 240

Glu Ile Glu Phe Ala Ile His Tyr Cys Phe Lys Thr His Ser Leu Glu
245 250 255

Ile Cys Ile Lys Ala Cys Lys Asn Leu Ala Tyr Gly Glu Glu Lys Lys
260 265 270

Lys Lys Cys Asn Pro Tyr Val Lys Thr Tyr Leu Leu Pro Asp Arg Ser
275 280 285

Ser Gln Gly Lys Arg Lys Thr Gly Val Gln Arg Asn Thr Val Asp Pro
290 295 300

Thr Phe Gln Glu Thr Leu Lys Tyr Gln Val Ala Pro Ala Gln Leu Val
305 310 315 320

Thr Arg Gln Leu Gln Val Ser Val Trp His Leu Gly Thr Leu Ala Arg
325 330 335

Arg Val Phe Leu Gly Glu Val Ile Ile Pro Leu Ala Thr Trp Asp Phe
340 345 350

Glu Asp Ser Thr Thr Gln Ser Phe Arg Trp His Pro Leu Arg Ala Lys
355 360 365

```
Ala Glu Lys Tyr Glu Asp Ser Val Pro Gln Ser Asn Gly Glu Leu Thr
    370                 375                 380

Val Arg Ala Lys Leu Val Leu Pro Ser Arg Pro Arg Lys Leu Gln Glu
385                 390                 395                 400

Ala Gln Glu Gly Thr Asp Gln Pro Ser Leu His Gly Gln Leu Cys Leu
                405                 410                 415

Val Val Leu Gly Ala Lys Asn Leu Pro Val Arg Pro Asp Gly Thr Leu
            420                 425                 430

Asn Ser Phe Val Lys Gly Cys Leu Thr Leu Pro Asp Gln Gln Lys Leu
        435                 440                 445

Arg Leu Lys Ser Pro Val Leu Arg Lys Gln Ala Cys Pro Gln Trp Lys
    450                 455                 460

His Ser Phe Val Phe Ser Gly Val Thr Pro Ala Gln Leu Arg Gln Ser
465                 470                 475                 480

Ser Leu Glu Leu Thr Val Trp Asp Gln Ala Leu Phe Gly Met Asn Asp
                485                 490                 495

Arg Leu Leu Gly Gly Thr Arg Leu Gly Ser Lys Gly Asp Thr Ala Val
            500                 505                 510

Gly Gly Asp Ala Cys Ser Leu Ser Lys Leu Gln Trp Gln Lys Val Leu
        515                 520                 525

Ser Ser Pro Asn Leu Trp Thr Asp Met Thr Leu Val Leu His
    530                 535                 540


<210> SEQ ID NO 36
<211> LENGTH: 610
<212> TYPE: PRT
<213> ORGANISM: Homo sapiens

<400> SEQUENCE: 36

Met Ala Gln Glu Ile Asp Leu Ser Ala Leu Lys Glu Leu Glu Arg Glu
1               5                   10                  15

Ala Ile Leu Gln Val Leu Tyr Arg Asp Gln Ala Val Gln Asn Thr Glu
            20                  25                  30

Glu Glu Arg Thr Arg Lys Leu Lys Thr His Leu Gln His Leu Arg Trp
        35                  40                  45

Lys Gly Ala Lys Asn Thr Asp Trp Glu His Lys Glu Lys Cys Cys Ala
    50                  55                  60

Arg Cys Gln Gln Val Leu Gly Phe Leu Leu His Arg Gly Ala Val Cys
65                  70                  75                  80

Arg Gly Cys Ser His Arg Val Cys Ala Gln Cys Arg Val Phe Leu Arg
                85                  90                  95

Gly Thr His Ala Trp Lys Cys Thr Val Cys Phe Glu Asp Arg Asn Val
            100                 105                 110

Lys Ile Lys Thr Gly Glu Trp Phe Tyr Glu Glu Arg Ala Lys Lys Phe
        115                 120                 125

Pro Thr Gly Gly Lys His Glu Thr Val Gly Gly Gln Leu Leu Gln Ser
    130                 135                 140

Tyr Gln Lys Leu Ser Lys Ile Ser Val Val Pro Pro Thr Pro Pro Pro
145                 150                 155                 160

Val Ser Glu Ser Gln Cys Ser Arg Ser Pro Gly Arg Leu Gln Glu Phe
                165                 170                 175

Gly Gln Phe Arg Gly Phe Asn Lys Ser Val Glu Asn Leu Phe Leu Ser
            180                 185                 190

Leu Ala Thr His Val Lys Lys Leu Ser Lys Ser Gln Asn Asp Met Thr
```

```
        195                 200                 205

Ser Glu Lys His Leu Leu Ala Thr Gly Pro Arg Gln Cys Val Gly Gln
    210                 215                 220

Thr Glu Arg Arg Ser Gln Ser Asp Thr Ala Val Asn Val Thr Thr Arg
225                 230                 235                 240

Lys Val Ser Ala Pro Asp Ile Leu Lys Pro Leu Asn Gln Glu Asp Pro
                245                 250                 255

Lys Cys Ser Thr Asn Pro Ile Leu Lys Gln Gln Asn Leu Pro Ser Ser
            260                 265                 270

Pro Ala Pro Ser Thr Ile Phe Ser Gly Gly Phe Arg His Gly Ser Leu
        275                 280                 285

Ile Ser Ile Asp Ser Thr Cys Thr Glu Met Gly Asn Phe Asp Asn Ala
    290                 295                 300

Asn Val Thr Gly Glu Ile Glu Phe Ala Ile His Tyr Cys Phe Lys Thr
305                 310                 315                 320

His Ser Leu Glu Ile Cys Ile Lys Ala Cys Lys Asn Leu Ala Tyr Gly
                325                 330                 335

Glu Glu Lys Lys Lys Lys Cys Asn Pro Tyr Val Lys Thr Tyr Leu Leu
            340                 345                 350

Pro Asp Arg Ser Ser Gln Gly Lys Arg Lys Thr Gly Val Gln Arg Asn
        355                 360                 365

Thr Val Asp Pro Thr Phe Gln Glu Thr Leu Lys Tyr Gln Val Ala Pro
    370                 375                 380

Ala Gln Leu Val Thr Arg Gln Leu Gln Val Ser Val Trp His Leu Gly
385                 390                 395                 400

Thr Leu Ala Arg Arg Val Phe Leu Gly Glu Val Ile Ile Pro Leu Ala
                405                 410                 415

Thr Trp Asp Phe Glu Asp Ser Thr Thr Gln Ser Phe Arg Trp His Pro
            420                 425                 430

Leu Arg Ala Lys Ala Glu Lys Tyr Glu Asp Ser Val Pro Gln Ser Asn
        435                 440                 445

Gly Glu Leu Thr Val Arg Ala Lys Leu Val Leu Pro Ser Arg Pro Arg
    450                 455                 460

Lys Leu Gln Glu Ala Gln Glu Gly Thr Asp Gln Pro Ser Leu His Gly
465                 470                 475                 480

Gln Leu Cys Leu Val Val Leu Gly Ala Lys Asn Leu Pro Val Arg Pro
                485                 490                 495

Asp Gly Thr Leu Asn Ser Phe Val Lys Gly Cys Leu Thr Leu Pro Asp
            500                 505                 510

Gln Gln Lys Leu Arg Leu Lys Ser Pro Val Leu Arg Lys Gln Ala Cys
        515                 520                 525

Pro Gln Trp Lys His Ser Phe Val Phe Ser Gly Val Thr Pro Ala Gln
    530                 535                 540

Leu Arg Gln Ser Ser Leu Glu Leu Thr Val Trp Asp Gln Ala Leu Phe
545                 550                 555                 560

Gly Met Asn Asp Arg Leu Leu Gly Gly Thr Arg Leu Gly Ser Lys Gly
                565                 570                 575

Asp Thr Ala Val Gly Gly Asp Ala Cys Ser Leu Ser Lys Leu Gln Trp
            580                 585                 590

Gln Lys Val Leu Ser Ser Pro Asn Leu Trp Thr Asp Met Thr Leu Val
        595                 600                 605

Leu His
    610
```

```
<210> SEQ ID NO 37
<211> LENGTH: 542
<212> TYPE: PRT
<213> ORGANISM: Homo sapiens

<400> SEQUENCE: 37

Met Ala Gln Glu Ile Asp Leu Ser Ala Leu Lys Glu Leu Glu Arg Glu
1               5                   10                  15

Ala Ile Leu Gln Val Leu Tyr Arg Asp Gln Ala Val Gln Asn Thr Glu
            20                  25                  30

Glu Glu Arg Thr Arg Lys Leu Lys Thr His Leu Gln His Leu Arg Trp
        35                  40                  45

Lys Gly Ala Lys Asn Thr Asp Trp Glu His Lys Glu Lys Cys Cys Ala
    50                  55                  60

Arg Cys Gln Gln Val Leu Gly Phe Leu Leu His Arg Gly Ala Val Cys
65                  70                  75                  80

Arg Gly Cys Ser His Arg Val Cys Ala Gln Cys Arg Val Phe Leu Arg
                85                  90                  95

Gly Thr His Ala Trp Lys Cys Thr Val Cys Phe Glu Asp Arg Asn Val
            100                 105                 110

Lys Ile Lys Thr Gly Glu Trp Phe Tyr Glu Glu Arg Ala Lys Lys Phe
        115                 120                 125

Pro Thr Gly Gly Lys His Glu Thr Val Gly Gly Gln Leu Leu Gln Ser
    130                 135                 140

Tyr Gln Lys Leu Ser Lys Ile Ser Val Val Pro Pro Thr Pro Pro Pro
145                 150                 155                 160

Val Ser Glu Ser Gln Cys Ser Arg Ser Pro Gly Arg Lys Val Ser Ala
                165                 170                 175

Pro Asp Ile Leu Lys Pro Leu Asn Gln Glu Asp Pro Lys Cys Ser Thr
            180                 185                 190

Asn Pro Ile Leu Lys Gln Gln Asn Leu Pro Ser Ser Pro Ala Pro Ser
        195                 200                 205

Thr Ile Phe Ser Gly Gly Phe Arg His Gly Ser Leu Ile Ser Ile Asp
    210                 215                 220

Ser Thr Cys Thr Glu Met Gly Asn Phe Asp Asn Ala Asn Val Thr Gly
225                 230                 235                 240

Glu Ile Glu Phe Ala Ile His Tyr Cys Phe Lys Thr His Ser Leu Glu
                245                 250                 255

Ile Cys Ile Lys Ala Cys Lys Asn Leu Ala Tyr Gly Glu Glu Lys Lys
            260                 265                 270

Lys Lys Cys Asn Pro Tyr Val Lys Thr Tyr Leu Leu Pro Asp Arg Ser
        275                 280                 285

Ser Gln Gly Lys Arg Lys Thr Gly Val Gln Arg Asn Thr Val Asp Pro
    290                 295                 300

Thr Phe Gln Glu Thr Leu Lys Tyr Gln Val Ala Pro Ala Gln Leu Val
305                 310                 315                 320

Thr Arg Gln Leu Gln Val Ser Val Trp His Leu Gly Thr Leu Ala Arg
                325                 330                 335

Arg Val Phe Leu Gly Glu Val Ile Ile Pro Leu Ala Thr Trp Asp Phe
            340                 345                 350

Glu Asp Ser Thr Thr Gln Ser Phe Arg Trp His Pro Leu Arg Ala Lys
        355                 360                 365

Ala Glu Lys Tyr Glu Asp Ser Val Pro Gln Ser Asn Gly Glu Leu Thr
```

```
    370                 375                 380

Val Arg Ala Lys Leu Val Leu Pro Ser Arg Pro Arg Lys Leu Gln Glu
385                 390                 395                 400

Ala Gln Glu Gly Thr Asp Gln Pro Ser Leu His Gly Gln Leu Cys Leu
                405                 410                 415

Val Val Leu Gly Ala Lys Asn Leu Pro Val Arg Pro Asp Gly Thr Leu
            420                 425                 430

Asn Ser Phe Val Lys Gly Cys Leu Thr Leu Pro Asp Gln Gln Lys Leu
        435                 440                 445

Arg Leu Lys Ser Pro Val Leu Arg Lys Gln Ala Cys Pro Gln Trp Lys
    450                 455                 460

His Ser Phe Val Phe Ser Gly Val Thr Pro Ala Gln Leu Arg Gln Ser
465                 470                 475                 480

Ser Leu Glu Leu Thr Val Trp Asp Gln Ala Leu Phe Gly Met Asn Asp
                485                 490                 495

Arg Leu Leu Gly Gly Thr Arg Leu Gly Ser Lys Gly Asp Thr Ala Val
            500                 505                 510

Gly Gly Asp Ala Cys Ser Leu Ser Lys Leu Gln Trp Gln Lys Val Leu
        515                 520                 525

Ser Ser Pro Asn Leu Trp Thr Asp Met Thr Leu Val Leu His
    530                 535                 540


<210> SEQ ID NO 38
<211> LENGTH: 2277
<212> TYPE: DNA
<213> ORGANISM: Homo sapiens

<400> SEQUENCE: 38

aagaagaatt gacttccttc tctgcagagc cggctctggt ctcttctctt gaagcagatg     60

cgaaggctcc ccgaatgaga aagaatactc ggaatcagcg gtgaattgca gtgatctttc    120

agagaaagcg cctgttcaac tttgtcctct ctcagagact cagagccttg gggcactgag    180

ggatgccagt tctgcctgtt catctggaac ctggatctaa ggagggaaga ggcgttgccc    240

ctgctggcat agtcaggtat tgaacgggct gagcttttca tgatggttcc tgctgacctg    300

gaaacatctt aaatggaagg gcgtgagcgc ttggtccatg cagtgaagct cttccaacct    360

gggtcaacga aaacggagaa gaaatggccc aagaaataga tctgagtgct ctcaaggagt    420

tagaacgcga ggccattctc caggtcctgt accgagacca ggcggttcaa aacacagagg    480

aggagaggac acggaaactg aaaacacacc tgcagcatct ccggtggaaa ggagcgaaga    540

acacggactg ggagcacaaa gagaagtgct gtgcgcgctg ccagcaggtg ctggggttcc    600

tgctgcaccg ggcgccgtg tgccggggct gcagccaccg cgtgtgtgcc cagtgccgag    660

tgttcctgag ggggacccat gcctggaagt gcacggtgtg cttcgaggac aggaatgtca    720

aaataaaaac tggagaatgg ttctatgagg aacgagccaa gaaatttcca actggaggca    780

aacatgagac agttggaggg cagctcttgc aatcttatca gaagctgagc aaaatttctg    840

tggttcctcc tactccacct cctgtcagcg agagccagtg cagccgcagt cctggcagga    900

aggtcagtgc accagatatt ctgaaacctc tcaatcaaga ggatcccaaa tgctctacta    960

accctatttt gaagcaacag aatctcccat ccagtccggc acccagtacc atattctctg   1020

gaggttttag acacggaagt ttaattagca ttgacagcac ctgtacagag atgggcaatt   1080

ttgacaatgc taatgtcact ggagaaatag aatttgccat tcattattgc ttcaaaaccc   1140

attctttaga aatatgcatc aaggcctgta agaaccttgc ctatggagaa gaaaagaaga   1200
```

```
aaaagtgcaa tccgtatgtg aagacctacc tgttgcccga cagatcctcc cagggaaagc   1260
gcaagactgg agtccaaagg aacaccgtgg acccgacctt tcaggagacc ttgaagtatc   1320
aggtggcccc tgcccagctg gtgacccggc agctgcaggt ctcggtgtgg catctgggca   1380
cgctggcccg gagagtgttt cttggagaag tgatcattcc tctggccacg tgggactttg   1440
aagacagcac aacacagtcc ttccgctggc atccgctccg ggccaaggcg gagaaatacg   1500
aagacagcgt tcctcagagt aatggagagc tcacagtccg ggctaagctg gttctccctt   1560
cacggcccag aaaactccaa gaggctcaag aagggacaga tcagccatca cttcatggtc   1620
aactttgttt ggtagtgcta ggagccaaga atttacctgt gcggccagat ggcaccttga   1680
actcatttgt taagggctgt ctcactctgc cagaccaaca aaaactgaga ctgaagtcgc   1740
cagtcctgag gaagcaggct tgcccccagt ggaaacactc atttgtcttc agtggcgtaa   1800
ccccagctca gctgaggcag tcaagcttgg agttaactgt ctgggatcag gccctctttg   1860
gaatgaacga ccgcttgctt ggaggaacca gacttggttc aaagggagac acagctgttg   1920
gcggggatgc atgctcacta tcgaagctcc agtggcagaa agtcctttcc agccccaatc   1980
tatggacaga catgactctt gtcctgcact gacatgaagg cctcaaggtt ccaggttgca   2040
gcaggcgtga ggcactgtgc gtctgcagag gggctacgaa ccaggtgcag ggtcccagct   2100
ggagacccct ttgaccttga gcagtctcca tctgcggccc tgtcccatgg cttaaccgcc   2160
tattggtatc tgtgtatatt tacgttaaac acaattatgt tacctaagcc tctggtgggt   2220
tatctcctct ttgagatgta gaaaatggcc agattttaat aaacgttgtt acccatg      2277
```

<210> SEQ ID NO 39
<211> LENGTH: 2131
<212> TYPE: DNA
<213> ORGANISM: Homo sapiens

<400> SEQUENCE: 39

```
aggagggaag aggcgttgcc cctgctggca tagtcaggta ccagcccagc caggtattga     60
acgggctgag cttttcatga tggttcctgc tgacctggaa acatcttaaa tggaagggcg    120
tgagcgcttg gtccatgcag tgaagctctt ccaacctggg tcaacgaaaa cggagaagaa    180
atggcccaag aaatagatct gagtgctctc aaggagttag aacgcgaggc cattctccag    240
gtcctgtacc gagaccaggc ggttcaaaac acagaggagg agaggacacg gaaactgaaa    300
acacacctgc agcatctccg gtggaaagga gcgaagaaca cggactggga gcacaaagag    360
aagtgctgtg cgcgctgcca gcaggtgctg ggttcctgc  tgcaccgggg cgccgtgtgc    420
cggggctgca gccaccgcgt gtgtgcccag tgccgagtgt tcctgagggg gacccatgcc    480
tggaagtgca cggtgtgctt cgaggacagg aatgtcaaaa taaaaactgg agaatggttc    540
tatgaggaac gagccaagaa atttccaact ggaggcaaac atgagacagt tggagggcag    600
ctcttgcaat cttatcagaa gctgagcaaa atttctgtgg ttcctcctac tccacctcct    660
gtcagcgaga gccagtgcag ccgcagtcct ggcaggttac aggaatttgg tcagtttaga    720
ggatttaata agtccgtgga aaatttgttt ctgtctcttg ctacccacgt gaaaaagctc    780
tccaaatccc agaatgatat gacttctgag aagcatcttc tcgccacggg ccccaggcag    840
tgtgtgggac agacagagag acggagccag tctgacactg cggtcaacgt caccaccagg    900
aaggtcagtg caccagatat tctgaaacct ctcaatcaag aggatcccaa atgctctact    960
aaccctattt tgaagcaaca gaatctccca tccagtccgg cacccagtac catattctct   1020
```

```
ggaggtttta gacacggaag tttaattagc attgacagca cctgtacaga gatgggcaat   1080

tttgacaatg ctaatgtcac tggagaaata gaatttgcca ttcattattg cttcaaaacc   1140

cattctttag aaatatgcat caaggcctgt aagaaccttg cctatggaga agaaaagaag   1200

aaaaagtgca atccgtatgt gaagacctac ctgttgcccg acagatcctc ccagggaaag   1260

cgcaagactg gagtccaaag gaacaccgtg gacccgacct ttcaggagac cttgaagtat   1320

caggtggccc ctgcccagct ggtgacccgg cagctgcagg tctcggtgtg gcatctgggc   1380

acgctggccc ggagagtgtt tcttggagaa gtgatcattc ctctggccac gtgggacttt   1440

gaagacagca caacacagtc cttccgctgg catccgctcc gggccaaggc ggagaaatac   1500

gaagacagcg ttcctcagag taatggagag ctcacagtcc gggctaagct ggttctccct   1560

tcacggccca gaaaactcca agaggctcaa gaagggacag atcagccatc acttcatggt   1620

caactttgtt tggtagtgct aggagccaag aatttacctg tgcggccaga tggcaccttg   1680

aactcatttg ttaagggctg tctcactctg ccagaccaac aaaaactgag actgaagtcg   1740

ccagtcctga ggaagcaggc ttgcccccag tggaaacact catttgtctt cagtggcgta   1800

accccagctc agctgaggca gtcaagcttg gagttaactg tctgggatca ggccctcttt   1860

ggaatgaacg accgcttgct tggaggaacc agacttggtt caaagggaga cacagctgtt   1920

ggcggggatg catgctcact atcgaagctc cagtggcaga aagtcctttc cagccccaat   1980

ctatggacag acatgactct tgtcctgcac tgacatgaag gcctcaaggt tccaggttgc   2040

agcaggcgtg aggcactgtg cgtctgcaga ggggctacga accaggtgca gggtcccagc   2100

tggagacccc tttgaccttg agcagtctcc a                                  2131
```

<210> SEQ ID NO 40
<211> LENGTH: 1927
<212> TYPE: DNA
<213> ORGANISM: Homo sapiens

<400> SEQUENCE: 40

```
aggagggaag aggcgttgcc cctgctggca tagtcaggta ccagcccagc caggtattga     60

acgggctgag cttttcatga tggttcctgc tgacctggaa acatcttaaa tggaagggcg    120

tgagcgcttg gtccatgcag tgaagctctt ccaacctggg tcaacgaaaa cggagaagaa    180

atggcccaag aaatagatct gagtgctctc aaggagttag aacgcgaggc cattctccag    240

gtcctgtacc gagaccaggc ggttcaaaac acagaggagg agaggacacg gaaactgaaa    300

acacacctgc agcatctccg gtggaaagga gcgaagaaca cggactggga gcacaaagag    360

aagtgctgtg cgcgctgcca gcaggtgctg ggtttcctgc tgcaccgggg cgccgtgtgc    420

cggggctgca gccaccgcgt gtgtgcccag tgccgagtgt tcctgagggg gacccatgcc    480

tggaagtgca cggtgtgctt cgaggacagg aatgtcaaaa taaaaactgg agaatggttc    540

tatgaggaac gagccaagaa atttccaact ggaggcaaac atgagacagt tggagggcag    600

ctcttgcaat cttatcagaa gctgagcaaa atttctgtgg ttcctcctac tccacctcct    660

gtcagcgaga gccagtgcag ccgcagtcct ggcaggaagg tcagtgcacc agatattctg    720

aaacctctca atcaagagga tcccaaatgc tctactaacc ctattttgaa gcaacagaat    780

ctcccatcca gtccggcacc cagtaccata ttctctggag gttttagaca cggaagttta    840

attagcattg acagcacctg tacagagatg ggcaattttg acaatgctaa tgtcactgga    900

gaaatagaat ttgccattca ttattgcttc aaaacccatt ctttagaaat atgcatcaag    960

gcctgtaaga accttgccta tggagaagaa aagaagaaaa agtgcaatcc gtatgtgaag   1020
```

```
acctacctgt tgcccgacag atcctcccag ggaaagcgca agactggagt ccaaaggaac   1080

accgtggacc cgacctttca ggagaccttg aagtatcagg tggcccctgc ccagctggtg   1140

acccggcagc tgcaggtctc ggtgtggcat ctgggcacgc tggcccggag agtgtttctt   1200

ggagaagtga tcattcctct ggccacgtgg gactttgaag acagcacaac acagtccttc   1260

cgctggcatc cgctccgggc caaggcggag aaatacgaag acagcgttcc tcagagtaat   1320

ggagagctca cagtccgggc taagctggtt ctcccttcac ggcccagaaa actccaagag   1380

gctcaagaag ggacagatca gccatcactt catggtcaac tttgtttggt agtgctagga   1440

gccaagaatt tacctgtgcg gccagatggc accttgaact catttgttaa gggctgtctc   1500

actctgccag accaacaaaa actgagactg aagtcgccag tcctgaggaa gcaggcttgc   1560

ccccagtgga aacactcatt tgtcttcagt ggcgtaaccc cagctcagct gaggcagtca   1620

agcttggagt taactgtctg ggatcaggcc ctctttggaa tgaacgaccg cttgcttgga   1680

ggaaccagac ttggttcaaa gggagacaca gctgttggcg gggatgcatg ctcactatcg   1740

aagctccagt ggcagaaagt cctttccagc cccaatctat ggacagacat gactcttgtc   1800

ctgcactgac atgaaggcct caaggttcca ggttgcagca ggcgtgaggc actgtgcgtc   1860

tgcagagggg ctacgaacca ggtgcagggt cccagctgga gacccctttg accttgagca   1920

gtctcca                                                             1927
```

<210> SEQ ID NO 41
<211> LENGTH: 406
<212> TYPE: PRT
<213> ORGANISM: Homo sapiens

<400> SEQUENCE: 41

```
Met Asp Cys Arg Thr Lys Ala Asn Pro Asp Arg Thr Phe Asp Leu Val
1               5                   10                  15

Leu Lys Val Lys Cys His Ala Ser Glu Asn Glu Asp Pro Val Val Leu
            20                  25                  30

Trp Lys Phe Pro Glu Asp Phe Gly Asp Gln Glu Ile Leu Gln Ser Val
        35                  40                  45

Pro Lys Phe Cys Phe Pro Phe Asp Val Glu Arg Val Ser Gln Asn Gln
    50                  55                  60

Val Gly Gln His Phe Thr Phe Val Leu Thr Asp Ile Glu Ser Lys Gln
65                  70                  75                  80

Arg Phe Gly Phe Cys Arg Leu Thr Ser Gly Gly Thr Ile Cys Leu Cys
                85                  90                  95

Ile Leu Ser Tyr Leu Pro Trp Phe Glu Val Tyr Tyr Lys Leu Leu Asn
            100                 105                 110

Thr Leu Ala Asp Tyr Leu Ala Lys Glu Leu Glu Asn Asp Leu Asn Glu
        115                 120                 125

Thr Leu Arg Ser Leu Tyr Asn His Pro Val Pro Lys Ala Asn Thr Pro
    130                 135                 140

Val Asn Leu Ser Val His Ser Tyr Phe Ile Ala Pro Asp Val Thr Gly
145                 150                 155                 160

Leu Pro Thr Ile Pro Glu Ser Arg Asn Leu Thr Glu Tyr Phe Val Ala
                165                 170                 175

Val Asp Val Asn Asn Met Leu Gln Leu Tyr Ala Ser Met Leu His Glu
            180                 185                 190

Arg Arg Ile Val Ile Ile Ser Ser Lys Leu Ser Thr Leu Thr Ala Cys
        195                 200                 205
```

```
Ile His Gly Ser Ala Ala Leu Leu Tyr Pro Met Tyr Trp Gln His Ile
    210                 215                 220

Tyr Ile Pro Val Leu Pro Pro His Leu Leu Asp Tyr Cys Cys Ala Pro
225                 230                 235                 240

Met Pro Tyr Leu Ile Gly Ile His Ser Ser Leu Ile Glu Arg Val Lys
                245                 250                 255

Asn Lys Ser Leu Glu Asp Val Val Met Leu Asn Val Asp Thr Asn Thr
            260                 265                 270

Leu Glu Ser Pro Phe Ser Asp Leu Asn Asn Leu Pro Ser Asp Val Val
        275                 280                 285

Ser Ala Leu Lys Asn Lys Leu Lys Lys Gln Ser Thr Ala Thr Gly Asp
    290                 295                 300

Gly Val Ala Arg Ala Phe Leu Arg Ala Gln Ala Ala Leu Phe Gly Ser
305                 310                 315                 320

Tyr Arg Asp Ala Leu Arg Tyr Lys Pro Gly Glu Pro Ile Thr Phe Cys
                325                 330                 335

Glu Glu Ser Phe Val Lys His Arg Ser Ser Val Met Lys Gln Phe Leu
            340                 345                 350

Glu Thr Ala Ile Asn Leu Gln Leu Phe Lys Gln Phe Ile Asp Gly Arg
        355                 360                 365

Leu Ala Lys Leu Asn Ala Gly Arg Gly Phe Ser Asp Val Phe Glu Glu
    370                 375                 380

Glu Ile Thr Ser Gly Gly Phe Cys Gly Gly Lys Asp Lys Leu Gln Tyr
385                 390                 395                 400

Asp Tyr Pro Phe Ser Gln
                405


<210> SEQ ID NO 42
<211> LENGTH: 426
<212> TYPE: PRT
<213> ORGANISM: Homo sapiens

<400> SEQUENCE: 42

Met Asp Cys Arg Thr Lys Ala Asn Pro Asp Arg Thr Phe Asp Leu Val
1               5                   10                  15

Leu Lys Val Lys Cys His Ala Ser Glu Asn Glu Asp Pro Val Val Leu
            20                  25                  30

Trp Lys Phe Pro Glu Asp Phe Gly Asp Gln Glu Ile Leu Gln Ser Val
        35                  40                  45

Pro Lys Phe Cys Phe Pro Phe Asp Val Glu Arg Val Ser Gln Asn Gln
    50                  55                  60

Val Gly Gln His Phe Thr Phe Val Leu Thr Asp Ile Glu Ser Lys Gln
65                  70                  75                  80

Arg Phe Gly Phe Cys Arg Leu Thr Ser Gly Gly Thr Ile Cys Leu Cys
                85                  90                  95

Ile Leu Ser Tyr Leu Pro Trp Phe Glu Val Tyr Tyr Lys Leu Leu Asn
            100                 105                 110

Thr Leu Ala Asp Tyr Leu Ala Lys Glu Leu Glu Asn Asp Leu Asn Glu
        115                 120                 125

Thr Leu Arg Ser Leu Tyr Asn His Pro Val Pro Lys Ala Asn Thr Pro
    130                 135                 140

Val Asn Leu Ser Val Asn Gln Glu Ile Phe Ile Ala Cys Glu Gln Val
145                 150                 155                 160

Leu Lys Asp Gln Pro Ala Leu Val Pro His Ser Tyr Phe Ile Ala Pro
```

```
                165                 170                 175

Asp Val Thr Gly Leu Pro Thr Ile Pro Glu Ser Arg Asn Leu Thr Glu
            180                 185                 190

Tyr Phe Val Ala Val Asp Val Asn Asn Met Leu Gln Leu Tyr Ala Ser
        195                 200                 205

Met Leu His Glu Arg Arg Ile Val Ile Ile Ser Ser Lys Leu Ser Thr
    210                 215                 220

Leu Thr Ala Cys Ile His Gly Ser Ala Ala Leu Leu Tyr Pro Met Tyr
225                 230                 235                 240

Trp Gln His Ile Tyr Ile Pro Val Leu Pro Pro His Leu Leu Asp Tyr
                245                 250                 255

Cys Cys Ala Pro Met Pro Tyr Leu Ile Gly Ile His Ser Ser Leu Ile
            260                 265                 270

Glu Arg Val Lys Asn Lys Ser Leu Glu Asp Val Val Met Leu Asn Val
        275                 280                 285

Asp Thr Asn Thr Leu Glu Ser Pro Phe Ser Asp Leu Asn Asn Leu Pro
    290                 295                 300

Ser Asp Val Val Ser Ala Leu Lys Asn Lys Leu Lys Lys Gln Ser Thr
305                 310                 315                 320

Ala Thr Gly Asp Gly Val Ala Arg Ala Phe Leu Arg Ala Gln Ala Ala
                325                 330                 335

Leu Phe Gly Ser Tyr Arg Asp Ala Leu Arg Tyr Lys Pro Gly Glu Pro
            340                 345                 350

Ile Thr Phe Cys Glu Glu Ser Phe Val Lys His Arg Ser Ser Val Met
        355                 360                 365

Lys Gln Phe Leu Glu Thr Ala Ile Asn Leu Gln Leu Phe Lys Gln Phe
    370                 375                 380

Ile Asp Gly Arg Leu Ala Lys Leu Asn Ala Gly Arg Gly Phe Ser Asp
385                 390                 395                 400

Val Phe Glu Glu Glu Ile Thr Ser Gly Gly Phe Cys Gly Gly Lys Asp
                405                 410                 415

Lys Leu Gln Tyr Asp Tyr Pro Phe Ser Gln
            420                 425


<210> SEQ ID NO 43
<211> LENGTH: 426
<212> TYPE: PRT
<213> ORGANISM: Homo sapiens

<400> SEQUENCE: 43

Ile Glu Thr Lys Thr Arg Ala Asn Pro Asp Arg Thr Phe Asp Leu Val
1               5                   10                  15

Leu Lys Val Lys Cys His Ala Ser Glu Asn Glu Asp Pro Val Val Leu
            20                  25                  30

Trp Lys Phe Pro Glu Asp Phe Gly Asp Gln Glu Ile Leu Gln Ser Val
        35                  40                  45

Pro Lys Phe Cys Phe Pro Phe Asp Val Glu Arg Val Ser Gln Asn Gln
    50                  55                  60

Val Gly Gln His Phe Thr Phe Val Leu Thr Asp Ile Glu Ser Lys Gln
65                  70                  75                  80

Arg Phe Gly Phe Cys Arg Leu Thr Ser Gly Gly Thr Ile Cys Leu Cys
                85                  90                  95

Ile Leu Ser Tyr Leu Pro Trp Phe Glu Val Tyr Tyr Lys Leu Leu Asn
            100                 105                 110
```

```
Thr Leu Ala Asp Tyr Leu Ala Lys Glu Leu Glu Asn Asp Leu Asn Glu
        115                 120                 125

Thr Leu Arg Ser Leu Tyr Asn His Pro Val Pro Lys Ala Asn Thr Pro
    130                 135                 140

Val Asn Leu Ser Val Asn Gln Glu Ile Phe Ile Ala Cys Glu Gln Val
145                 150                 155                 160

Leu Lys Asp Gln Pro Ala Leu Val Pro His Ser Tyr Phe Ile Ala Pro
                165                 170                 175

Asp Val Thr Gly Leu Pro Thr Ile Pro Glu Ser Arg Asn Leu Thr Glu
            180                 185                 190

Tyr Phe Val Ala Val Asp Val Asn Asn Met Leu Gln Leu Tyr Ala Ser
        195                 200                 205

Met Leu His Glu Arg Arg Ile Val Ile Ile Ser Ser Lys Leu Ser Thr
    210                 215                 220

Leu Thr Ala Cys Ile His Gly Ser Ala Ala Leu Leu Tyr Pro Met Tyr
225                 230                 235                 240

Trp Gln His Ile Tyr Ile Pro Val Leu Pro Pro His Leu Leu Asp Tyr
                245                 250                 255

Cys Cys Ala Pro Met Pro Tyr Leu Ile Gly Ile His Ser Ser Leu Ile
            260                 265                 270

Glu Arg Val Lys Asn Lys Ser Leu Glu Asp Val Val Met Leu Asn Val
        275                 280                 285

Asp Thr Asn Thr Leu Glu Ser Pro Phe Ser Asp Leu Asn Asn Leu Pro
    290                 295                 300

Ser Asp Val Val Ser Ala Leu Lys Asn Lys Leu Lys Lys Gln Ser Thr
305                 310                 315                 320

Ala Thr Gly Asp Gly Val Ala Arg Ala Phe Leu Arg Ala Gln Ala Ala
                325                 330                 335

Leu Phe Gly Ser Tyr Arg Asp Ala Leu Arg Tyr Lys Pro Gly Glu Pro
            340                 345                 350

Ile Thr Phe Cys Glu Glu Ser Phe Val Lys His Arg Ser Ser Val Met
        355                 360                 365

Lys Gln Phe Leu Glu Thr Ala Ile Asn Leu Gln Leu Phe Lys Gln Phe
    370                 375                 380

Ile Asp Gly Arg Leu Ala Lys Leu Asn Ala Gly Arg Gly Phe Ser Asp
385                 390                 395                 400

Val Phe Glu Glu Glu Ile Thr Ser Gly Gly Phe Cys Gly Gly Lys Asp
                405                 410                 415

Lys Leu Gln Tyr Asp Tyr Pro Phe Ser Gln
            420                 425


<210> SEQ ID NO 44
<211> LENGTH: 396
<212> TYPE: PRT
<213> ORGANISM: Homo sapiens

<400> SEQUENCE: 44

Met Ala Ala Ala Pro Arg Glu Glu Lys Arg Trp Pro Gln Pro Val Phe
1               5                   10                  15

Ser Asn Pro Val Val Leu Trp Lys Phe Pro Glu Asp Phe Gly Asp Gln
            20                  25                  30

Glu Ile Leu Gln Ser Val Pro Lys Phe Cys Phe Pro Phe Asp Val Glu
        35                  40                  45

Arg Val Ser Gln Asn Gln Val Gly Gln His Phe Thr Phe Val Leu Thr
    50                  55                  60
```

```
Asp Ile Glu Ser Lys Gln Arg Phe Gly Phe Cys Arg Leu Thr Ser Gly
65                  70                  75                  80

Gly Thr Ile Cys Leu Cys Ile Leu Ser Tyr Leu Pro Trp Phe Glu Val
                85                  90                  95

Tyr Tyr Lys Leu Leu Asn Thr Leu Ala Asp Tyr Leu Ala Lys Glu Leu
            100                 105                 110

Glu Asn Asp Leu Asn Glu Thr Leu Arg Ser Leu Tyr Asn His Pro Val
        115                 120                 125

Pro Lys Ala Asn Thr Pro Val Asn Leu Ser Val His Ser Tyr Phe Ile
    130                 135                 140

Ala Pro Asp Val Thr Gly Leu Pro Thr Ile Pro Glu Ser Arg Asn Leu
145                 150                 155                 160

Thr Glu Tyr Phe Val Ala Val Asp Val Asn Asn Met Leu Gln Leu Tyr
                165                 170                 175

Ala Ser Met Leu His Glu Arg Arg Ile Val Ile Ile Ser Ser Lys Leu
            180                 185                 190

Ser Thr Leu Thr Ala Cys Ile His Gly Ser Ala Ala Leu Leu Tyr Pro
        195                 200                 205

Met Tyr Trp Gln His Ile Tyr Ile Pro Val Leu Pro Pro His Leu Leu
    210                 215                 220

Asp Tyr Cys Cys Ala Pro Met Pro Tyr Leu Ile Gly Ile His Ser Ser
225                 230                 235                 240

Leu Ile Glu Arg Val Lys Asn Lys Ser Leu Glu Asp Val Val Met Leu
                245                 250                 255

Asn Val Asp Thr Asn Thr Leu Glu Ser Pro Phe Ser Asp Leu Asn Asn
            260                 265                 270

Leu Pro Ser Asp Val Val Ser Ala Leu Lys Asn Lys Leu Lys Lys Gln
        275                 280                 285

Ser Thr Ala Thr Gly Asp Gly Val Ala Arg Ala Phe Leu Arg Ala Gln
    290                 295                 300

Ala Ala Leu Phe Gly Ser Tyr Arg Asp Ala Leu Arg Tyr Lys Pro Gly
305                 310                 315                 320

Glu Pro Ile Thr Phe Cys Glu Glu Ser Phe Val Lys His Arg Ser Ser
                325                 330                 335

Val Met Lys Gln Phe Leu Glu Thr Ala Ile Asn Leu Gln Leu Phe Lys
            340                 345                 350

Gln Phe Ile Asp Gly Arg Leu Ala Lys Leu Asn Ala Gly Arg Gly Phe
        355                 360                 365

Ser Asp Val Phe Glu Glu Glu Ile Thr Ser Gly Gly Phe Cys Gly Gly
    370                 375                 380

Lys Asp Lys Leu Gln Tyr Asp Tyr Pro Phe Ser Gln
385                 390                 395
```

<210> SEQ ID NO 45
<211> LENGTH: 2117
<212> TYPE: DNA
<213> ORGANISM: Homo sapiens

<400> SEQUENCE: 45

```
gccgggggcg cagccgacat gggcccgccg ccacggctgc tgtgagcagc ctctttccct      60

gtgtggccgc cggcgtgggc ggggacggcg cgaccctcgc gcggccgggc tgcgggcttc     120

caggccagcg cgcgggggcc ggacggacag ccccacaccg acatgtaacc atggactgca     180

ggaccaaggc aaatccagac agaacctttg acttggtgtt gaaagtgaaa tgtcatgcct     240
```

```
ctgaaaatga agatcctgtg gtattgtgga aattcccaga ggactttgga gaccaggaaa    300
tactacagag tgtgccaaag ttctgttttc cctttgacgt tgaaagggtg tctcagaatc    360
aagttggaca gcactttacc tttgtactga cagacattga aagtaaacag agatttggat    420
tctgcagact gacgtcagga ggcacaattt gtttatgcat ccttagttac cttccctggt    480
ttgaagtgta ttacaagctt ctaaatactc ttgcagatta cttggctaag gaactggaaa    540
atgatttgaa tgaaactctc agatcactgt ataaccaccc agtaccaaag gcaaatactc    600
ctgtaaattt gagtgtgcat tcctacttca ttgcccctga tgtaactgga ctcccaacaa    660
tacccgagag tagaaatctt acagaatatt ttgttgccgt ggatgtgaac aacatgctgc    720
agctgtatgc cagtatgctg catgaaaggc gcatcgtgat tatctcgagc aaattaagca    780
ctttaactgc ctgtatccat ggatcagctg ctcttctata cccaatgtat tggcaacaca    840
tatacatccc agtgcttcct ccacacctgc tggactactg ctgtgcccca atgccatacc    900
tgattggaat acactccagc ctcatagaga gagtgaaaaa caaatcattg gaagatgttg    960
ttatgttaaa tgttgataca aacacattag aatcaccatt tagtgacttg aacaacctac   1020
caagtgatgt ggtctcggcc ttgaaaaata aactgaagaa gcagtctaca gctacgggtg   1080
atggagtagc tagggccttt cttagagcac aggctgcttt gtttggatcc tacagagatg   1140
cactgagata caaacctggt gagcccatca ctttctgtga ggagagtttt gtaaagcacc   1200
gctcaagcgt gatgaaacag ttcctggaaa ctgccattaa cctccagctt tttaagcagt   1260
ttatcgatgg tcgactggca aaactaaatg caggaagggg tttctctgat gtatttgaag   1320
aagagatcac ttcaggtggc ttttgtggag gtaaagacaa gttacaatat gattatccat   1380
tttctcaata acaattttct tggtctttgc acttgtgtct gataaaacct atttcataaa   1440
caactaatga tttcctccta aatatgtaat gtcttaaata catttttcat cttataaaag   1500
ctatggaatt agcttatttt gcctgatacc tgttactcaa ggcattaagt tggcctcctg   1560
aattggcagc tgttggcctc gataatctct taatattgct ggaaattagt aatacagaaa   1620
tccaatcaac tcatatcttc ctgtctttcc ttctgaatag tagtattctc tgctagaaaa   1680
ctactagtga tggttattac tgagtatgaa tttaagaact gaggttatga ttggtaatac   1740
aatccaaaaa gaagggtctg aacaccaaaa ttctttatac atatttaagt aactgtatta   1800
ttattataca gatgtcttta ccctttttgac tttatagatc actgcagcat taagaaagtt   1860
tccagtttac cattccataa gtacaattaa tccttctagt gtaaatgttc aaatactgtt   1920
ataattatct aggcaattaa taatttacaa actgatattt ttgcacgatt gtagtggtgt   1980
atagtcttga cttgcagagc attttgcttg agtccttgaa atgtcgtgtt cattcattat   2040
ttgctgagtg cttacaatgt attaggcact gttctaaata ttaagtgtac taaataaaca   2100
aaaatccttg tattctg                                                  2117
```

```
<210> SEQ ID NO 46
<211> LENGTH: 2177
<212> TYPE: DNA
<213> ORGANISM: Homo sapiens

<400> SEQUENCE: 46
```

```
gccgggggcg cagccgacat gggcccgccg ccacggctgc tgtgagcagc ctctttccct     60
gtgtggccgc cggcgtgggc ggggacggcg cgaccctcgc gcggccgggc tgcgggcttc    120
caggccagcg cgcgggggcc ggacggacag ccccacaccg acatgtaacc atggactgca    180
```

```
ggaccaaggc aaatccagac agaacctttg acttggtgtt gaaagtgaaa tgtcatgcct    240

ctgaaaatga agatcctgtg gtattgtgga aattcccaga ggactttgga gaccaggaaa    300

tactacagag tgtgccaaag ttctgttttc cctttgacgt tgaaagggtg tctcagaatc    360

aagttggaca gcactttacc tttgtactga cagacattga aagtaaacag agatttggat    420

tctgcagact gacgtcagga ggcacaattt gtttatgcat ccttagttac cttccctggt    480

ttgaagtgta ttacaagctt ctaaatactc ttgcagatta cttggctaag gaactggaaa    540

atgatttgaa tgaaactctc agatcactgt ataaccaccc agtaccaaag gcaaatactc    600

ctgtaaattt gagtgtgaac caagagatat ttattgcctg tgagcaagtt ctgaaagatc    660

agcctgctct agtaccgcat tcctacttca ttgcccctga tgtaactgga ctcccaacaa    720

tacccgagag tagaaatctt acagaatatt ttgttgccgt ggatgtgaac aacatgctgc    780

agctgtatgc cagtatgctg catgaaaggc gcatcgtgat tatctcgagc aaattaagca    840

ctttaactgc ctgtatccat ggatcagctg ctcttctata cccaatgtat tggcaacaca    900

tatacatccc agtgcttcct ccacacctgc tggactactg ctgtgcccca atgccatacc    960

tgattggaat acactccagc ctcatagaga gagtgaaaaa caaatcattg gaagatgttg   1020

ttatgttaaa tgttgataca aacacattag aatcaccatt tagtgacttg aacaacctac   1080

caagtgatgt ggtctcggcc ttgaaaaata aactgaagaa gcagtctaca gctacgggtg   1140

atggagtagc tagggccttt cttagagcac aggctgcttt gtttggatcc tacagagatg   1200

cactgagata caaacctggt gagcccatca ctttctgtga ggagagtttt gtaaagcacc   1260

gctcaagcgt gatgaaacag ttcctggaaa ctgccattaa cctccagctt tttaagcagt   1320

ttatcgatgg tcgactggca aaactaaatg caggaagggg tttctctgat gtatttgaag   1380

aagagatcac ttcaggtggc ttttgtggag gtaaagacaa gttacaatat gattatccat   1440

tttctcaata acaattttct tggtctttgc acttgtgtct gataaaacct atttcataaa   1500

caactaatga tttcctccta aatatgtaat gtcttaaata catttttcat cttataaaag   1560

ctatggaatt agcttatttt gcctgatacc tgttactcaa ggcattaagt tggcctcctg   1620

aattggcagc tgttggcctc gataatctct taatattgct ggaaattagt aatacagaaa   1680

tccaatcaac tcatatcttc ctgtctttcc ttctgaatag tagtattctc tgctagaaaa   1740

ctactagtga tggttattac tgagtatgaa tttaagaact gaggttatga ttggtaatac   1800

aatccaaaaa gaagggtctg aacaccaaaa ttctttatac atatttaagt aactgtatta   1860

ttattataca gatgtcttta cctttttgac tttatagatc actgcagcat taagaaagtt   1920

tccagtttac cattccataa gtacaattaa tccttctagt gtaaatgttc aaatactgtt   1980

ataattatct aggcaattaa taatttacaa actgatattt ttgcacgatt gtagtggtgt   2040

atagtcttga cttgcagagc attttgcttg agtccttgaa atgtcgtgtt cattcattat   2100

ttgctgagtg cttacaatgt attaggcact gttctaaata ttaagtgtac taaataaaca   2160

aaaatccttg tattctg                                                  2177
```

```
<210> SEQ ID NO 47
<211> LENGTH: 2007
<212> TYPE: DNA
<213> ORGANISM: Homo sapiens

<400> SEQUENCE: 47

attgagacaa aaacaagggc aaatccagac agaacctttg acttggtgtt gaaagtgaaa     60

tgtcatgcct ctgaaaatga agatcctgtg gtattgtgga aattcccaga ggactttgga    120
```

```
gaccaggaaa tactacagag tgtgccaaag ttctgttttc cctttgacgt tgaaagggtg    180

tctcagaatc aagttggaca gcactttacc tttgtactga cagacattga aagtaaacag    240

agatttggat tctgcagact gacgtcagga ggcacaattt gtttatgcat ccttagttac    300

cttccctggt ttgaagtgta ttacaagctt ctaaatactc ttgcagatta cttggctaag    360

gaactggaaa atgatttgaa tgaaactctc agatcactgt ataaccaccc agtaccaaag    420

gcaaatactc ctgtaaattt gagtgtgaac caagagatat ttattgcctg tgagcaagtt    480

ctgaaagatc agcctgctct agtaccgcat tcctacttca ttgcccctga tgtaactgga    540

ctcccaacaa tacccgagag tagaaatctt acagaatatt ttgttgccgt ggatgtgaac    600

aacatgctgc agctgtatgc cagtatgctg catgaaaggc gcatcgtgat tatctcgagc    660

aaattaagca ctttaactgc ctgtatccat ggatcagctg ctcttctata cccaatgtat    720

tggcaacaca tatacatccc agtgcttcct ccacacctgc tggactactg ctgtgcccca    780

atgccatacc tgattggaat acactccagc ctcatagaga gagtgaaaaa caaatcattg    840

gaagatgttg ttatgttaaa tgttgataca aacacattag aatcaccatt tagtgacttg    900

aacaacctac caagtgatgt ggtctcggcc ttgaaaaata aactgaagaa gcagtctaca    960

gctacgggtg atggagtagc tagggccttt cttagagcac aggctgcttt gtttggatcc   1020

tacagagatg cactgagata caaacctggt gagcccatca ctttctgtga ggagagtttt   1080

gtaaagcacc gctcaagcgt gatgaaacag ttcctggaaa ctgccattaa cctccagctt   1140

tttaagcagt ttatcgatgg tcgactggca aaactaaatg caggaagggg tttctctgat   1200

gtatttgaag aagagatcac ttcaggtggc ttttgtggag gtaaagacaa gttacaatat   1260

gattatccat tttctcaata acaattttct tggtctttgc acttgtgtct gataaaacct   1320

atttcataaa caactaatga tttcctccta aatatgtaat gtcttaaata catttttcat   1380

cttataaaag ctatggaatt agcttatttt gcctgatacc tgttactcaa ggcattaagt   1440

tggcctcctg aattggcagc tgttggcctc gataatctct taatattgct ggaaattagt   1500

aatacagaaa tccaatcaac tcatatcttc ctgtctttcc ttctgaatag tagtattctc   1560

tgctagaaaa ctactagtga tggttattac tgagtatgaa tttaagaact gaggttatga   1620

ttggtaatac aatccaaaaa gaagggtctg aacaccaaaa ttctttatac atatttaagt   1680

aactgtatta ttattataca gatgtcttta cctttttgac tttatagatc actgcagcat   1740

taagaaagtt tccagtttac cattccataa gtacaattaa tccttctagt gtaaatgttc   1800

aaatactgtt ataattatct aggcaattaa taatttacaa actgatattt ttgcacgatt   1860

gtagtggtgt atagtcttga cttgcagagc attttgcttg agtccttgaa atgtcgtgtt   1920

cattcattat ttgctgagtg cttacaatgt attaggcact gttctaaata ttaagtgtac   1980

taaataaaca aaaatccttg tattctg                                       2007
```

<210> SEQ ID NO 48
<211> LENGTH: 2197
<212> TYPE: DNA
<213> ORGANISM: Homo sapiens

<400> SEQUENCE: 48

```
gcgggggccg gacggacagc cccacaccga catgtaacca tggactgcag gaccaaggca     60

aatccagaca gaacctttga cttggtgttg aaagtgaaat gtcatgcctc tgaaaatgaa    120

gaggacagtc cagcttatct gccgaggatt ccccctggaa aagtacgccg attcgcattt    180
```

```
tgcattaaga aactggaaaa ctttcctgtc ggtcctggcg tagcgcctcc cgtgtccggg    240

gtagaccttg taccggctga aaccgcatag ctcgaccttc atggcggcag ctccacggga    300

ggagaaaaga tggccccaac ctgtattttc gaatcctgtg gtattgtgga aattcccaga    360

ggactttgga gaccaggaaa tactacagag tgtgccaaag ttctgttttc cctttgacgt    420

tgaaagggtg tctcagaatc aagttggaca gcactttacc tttgtactga cagacattga    480

aagtaaacag agatttggat tctgcagact gacgtcagga ggcacaattt gtttatgcat    540

ccttagttac cttccctggt ttgaagtgta ttacaagctt ctaaatactc ttgcagatta    600

cttggctaag gaactggaaa atgatttgaa tgaaactctc agatcactgt ataaccaccc    660

agtaccaaag gcaaatactc ctgtaaattt gagtgtgcat tcctacttca ttgcccctga    720

tgtaactgga ctcccaacaa tacccgagag tagaaatctt acagaatatt ttgttgccgt    780

ggatgtgaac aacatgctgc agctgtatgc cagtatgctg catgaaaggc gcatcgtgat    840

tatctcgagc aaattaagca ctttaactgc ctgtatccat ggatcagctg ctcttctata    900

cccaatgtat tggcaacaca tatacatccc agtgcttcct ccacacctgc tggactactg    960

ctgtgcccca atgccatacc tgattggaat acactccagc ctcatagaga gagtgaaaaa   1020

caaatcattg gaagatgttg ttatgttaaa tgttgataca aacacattag aatcaccatt   1080

tagtgacttg aacaacctac caagtgatgt ggtctcggcc ttgaaaaata aactgaagaa   1140

gcagtctaca gctacgggtg atggagtagc tagggccttt cttagagcac aggctgcttt   1200

gtttggatcc tacagagatg cactgagata caaacctggt gagcccatca ctttctgtga   1260

ggagagtttt gtaaagcacc gctcaagcgt gatgaaacag ttcctggaaa ctgccattaa   1320

cctccagctt tttaagcagt ttatcgatgg tcgactggca aaactaaatg caggaagggg   1380

tttctctgat gtatttgaag aagagatcac ttcaggtggc ttttgtggag gtaaagacaa   1440

gttacaatat gattatccat tttctcaata acaattttct tggtctttgc acttgtgtct   1500

gataaaacct atttcataaa caactaatga tttcctccta aatatgtaat gtcttaaata   1560

catttttcat cttataaaag ctatggaatt agcttatttt gcctgatacc tgttactcaa   1620

ggcattaagt tggcctcctg aattggcagc tgttggcctc gataatctct taatattgct   1680

ggaaattagt aatacagaaa tccaatcaac tcatatcttc ctgtctttcc ttctgaatag   1740

tagtattctc tgctagaaaa ctactagtga tggttattac tgagtatgaa tttaagaact   1800

gaggttatga ttggtaatac aatccaaaaa gaagggtctg aacaccaaaa ttctttatac   1860

atatttaagt aactgtatta ttattataca gatgtcttta cctttttgac tttatagatc   1920

actgcagcat taagaaagtt tccagtttac cattccataa gtacaattaa tccttctagt   1980

gtaaatgttc aaatactgtt ataattatct aggcaattaa taatttacaa actgatattt   2040

ttgcacgatt gtagtggtgt atagtcttga cttgcagagc attttgcttg agtccttgaa   2100

atgtcgtgtt cattcattat ttgctgagtg cttacaatgt attaggcact gttctaaata   2160

ttaagtgtac taaataaaca aaaatccttg tattctg                            2197
```

<210> SEQ ID NO 49
<211> LENGTH: 131
<212> TYPE: PRT
<213> ORGANISM: Homo sapiens

<400> SEQUENCE: 49

```
Met Phe Leu Gly Leu Val Gly Leu Arg Thr Lys Gly Arg Arg Trp Ile
1               5                   10                  15
```

```
Ser Ser Trp Ser Glu Gly Glu Asp Arg Gly Gln Ser Pro Glu Gly Val
            20                  25                  30

Leu Leu Thr Trp Val Phe Gly Thr Lys Cys Val Met His Pro Cys Glu
        35                  40                  45

Glu Thr Thr Lys Gln Ala Leu Cys Glu Gln Gln Gly Cys Leu Phe His
    50                  55                  60

Leu Gly Ala Asp Glu Leu Ser Pro Lys Arg Glu Ser Ala Gln Ser Ile
65                  70                  75                  80

Ser Phe Lys Trp Glu Asn Ser Ile Tyr Leu His Ala Thr Leu Phe Leu
                85                  90                  95

Ile Gly Glu Tyr Leu His Leu Ala Phe Tyr Tyr Phe Leu Leu Val Leu
            100                 105                 110

Tyr Ile Leu Cys Ser Phe Leu Ser Tyr Cys Leu Leu Leu Trp Leu Gly
        115                 120                 125

Ser Phe Leu
    130


<210> SEQ ID NO 50
<211> LENGTH: 2950
<212> TYPE: DNA
<213> ORGANISM: Homo sapiens

<400> SEQUENCE: 50

attatctagg tctcggagga tggagaaatc aaaagtgcca ttttctggcc atttagaacc      60

attgtcgagt ttgtattggg gccaagcagt gttgcagaag aaaataagac atttagattt     120

tagttcaggt gatagttgaa gaaattttaa gttcttgaga acacaggcta agggagaaga     180

aggaggaatg gagggtggaa gtttgcccat agtgaaggag gcaagtttaa agagaaaggt     240

agagacatgg agaaagggtt ggggagcagc cctgggctgc aatgtgggtg agcagccaaa     300

gcaggcatcc ccgcaattga cttgccacca agggaatgtg gttgaatgac caaggcaggc     360

atccctgaag atatcagacg ccaatggaat gtgggtgaat aatcaggcag gcatccccgg     420

aatgattaaa cactaaggga aggctgcctt cctgagtaca tgaccagcac cagagttttg     480

ggtccatgga taaaatgtgt ctcctttgtc tctactagaa aatgaaagga attgaaatta     540

agagaagaga gggagtgaag ggtggcacca agaatgaaag gagaaagagg ttgagggata     600

gtgagaaagg ttggagaaga gagtaaaaag aggccactta cccgatttaa aatttgtgag     660

atgttccttg ggctggttgg tctgaggacc aaaggtcgta ggtggatctc ttcatggagt     720

gagggtgagg acaggggaca gtctcctgaa ggagtcctgc tgacctgggt ctttggcacc     780

aaatgtgtca tgcatccatg tgaagagacc accaaacagg ctttgtgtga gcaacagggc     840

tgtttgtttc acctgggtgc agacgagttg agtccaaaaa gagagtcagc ccagtctata     900

tcttttaaat gggaaaattc aatctattta catgcaacgt tattcttgat aggtgagtac     960

ttacatctag cattctatta ttttctgctt gttttgtata tcctttgttc cttcctctct    1020

tactgtttac ttttgtggtt gggcagtttt ctgtagggat aagatttgag tcttatctct    1080

ttctccctat gtgttagctt taccagtgag tttttatagt ttcacatatt tttatgatgc    1140

tggttatcat cttctctgtg gggaacaggc cccccaaaac ctggccataa actggcccca    1200

aaactggcca taaacaaaat ctctgcagca ctgtgacatg tacatgatgg tcttaacgcc    1260

cacgctggaa ggttgtgggt ttaccagaat gagggcaagg aacacctggc ccacccaggg    1320

tggaaaaccg cttaaaggca ttcttaaacc acaaacaata gcatgagtga tctgtgcctt    1380

aaggccatgc tcctgctgca gatagctagt ccaacccatc cctttatttc agcccatctc    1440
```

```
ttcatttccc ataaggaata attttagtta atctaatatc tatagaaaga atgctaatga   1500

ctagcttgct gttaataaat acatgggtaa acctctgttg gaggctctca gctctgaagg   1560

ctgtgagacc cttgatttcc tacttcactc ctctatattt ctgtgtcttt aattcctcta   1620

gtgccactgg gttagagtct ccccgaccaa gctggtctca gcaagtggtc tccatcatgg   1680

gggctcgaat ccaggttgaa gggtcaccag agtgatggtt ggagaacatg gaactagctg   1740

gaggacacct gagtactctt aaagcaaacc ccgtggtgag taagaagggg agctcagaag   1800

catcagggta acaatgggac aagtgtgggg tctggttcgt tccatcttgg aactttttca   1860

cactgatgat gaggaagaag gagagtataa tgaagtaaca gaagaggtta tagagcaggt   1920

ttatttgcca gctaaagcta aagtggcaaa ggagggagag gttcatccct acccttctgc   1980

acccctcat tattattttg aagaaaaaga gtggcctgac cctccagatc tttcttttcc   2040

agaggacagt gggcaaaaat tagttgcccc agtgactgtt caagcagcac ctcgagcgac   2100

tgctcttagt tctattcagt caggaattca gcaagctaga tgagaaggtg attaagaggc   2160

ttggcagttc cctgttagac tacactgccc agaccaacag ggaaatattg tagctacatt   2220

tgagcctttt tgttttaaat tactcaaaga atttaaacaa gctattaatc agtatggacc   2280

aggttctcct tttgtaatgg gactattaaa gaacattgct gtttccagtc agatgattcc   2340

tactgactgg gacgctctta ctcaagcttg tctaactcct gcttagttct tacaatttaa   2400

aacttggtgg gcagatgaag cttccattca ggcttctcac aacacgcagg accaacctca   2460

aattaatata actgcagacc aacttttggg ggttggcagt tgggctggtt tagatgcaca   2520

aatggtcatg caggatgatg ccatagaaca gcttagagga gcgtgcatta gagcttgggg   2580

aaaaaaaatc acttcaagtg gagaacaata ccctttcttt agtgctataa aacagggacc   2640

agaagaatca tatgtggatt ttatagctca gttacaggag tctcttaaaa agatgactgc   2700

agatttggct gctcaggata tagtgttgca attattagct ttcaacaatg ctaatcctga   2760

ttgccaggct gctctgtgac ctatcagagg gaaagcacat ttagttgatt atatcaaggc   2820

ctgtggtggt atcagaggta atctgcatca ggccacctgc tagcacgggc aatggcagga   2880

ctgagagtgg atacagaaag tactccattt cctggagctt gttttaactg tgggaagcat   2940

ggtcatactg                                                          2950
```

<210> SEQ ID NO 51
<211> LENGTH: 132
<212> TYPE: PRT
<213> ORGANISM: Homo sapiens

<400> SEQUENCE: 51

```
Met Ser Gln Gly Arg His Leu Leu Glu Phe Leu Pro Leu Tyr Ile Ala
1               5                   10                  15

Phe Met Leu Arg Gly Val Cys Arg Ile Asp Ala Gly Ser Leu Asn Pro
            20                  25                  30

Glu Leu Phe Leu Pro Met Leu His Glu Glu Asp Trp Cys Trp Glu Ile
        35                  40                  45

Ala Gly His Val Asp Ser Gln Glu Leu Phe Val Gly Leu Phe Ser Ser
    50                  55                  60

Thr Ser Thr Gly His Ala Glu Leu Asp Lys Lys Val Asn Gly Leu Tyr
65                  70                  75                  80

Tyr Asp Ser Val Phe Gln Leu Ser Leu Asp Arg Met Arg His Thr Arg
                85                  90                  95
```

```
Ser Met Ala Arg Val Glu Arg Leu Arg His Arg Lys Ala Ile Gln Lys
            100                 105                 110

Lys Thr Gln Leu Val His His Leu Leu Phe Lys Gly Trp Ala Ser Asp
        115                 120                 125

Glu Thr Glu Ile
    130


<210> SEQ ID NO 52
<211> LENGTH: 399
<212> TYPE: DNA
<213> ORGANISM: Homo sapiens

<400> SEQUENCE: 52

atgtcacaag gcaggcatct tcttgagttt cttccattgt acatagcttt catgttacgt      60

ggggtttgta ggatagacgc tggaagcctt aatccagaac tgtttttgcc aatgttacat     120

gaagaggatt ggtgttggga gatagctggc catgtggact cccaagagtt attcgttggt     180

ttgttttcta gtacctctac tgggcatgca gagctggaca aaaaggttaa tggactttat     240

tatgactctg tattccagtt gtctctggac cgtatgcgtc atacaaggag tatggctaga     300

gtagagaggc tgagacacag gaaagcgatc cagaaaaaga ctcagttagt ccatcatctg     360

ctatttaaag gatgggcttc tgatgaaact gaaatttag                            399


<210> SEQ ID NO 53
<211> LENGTH: 431
<212> TYPE: PRT
<213> ORGANISM: Homo sapiens

<400> SEQUENCE: 53

Met Arg Arg Leu Arg Arg Leu Ala His Leu Val Leu Phe Cys Pro Phe
1               5                   10                  15

Ser Lys Arg Leu Gln Gly Arg Leu Pro Gly Leu Arg Val Arg Cys Ile
            20                  25                  30

Phe Leu Ala Trp Leu Gly Val Phe Ala Gly Ser Trp Leu Val Tyr Val
        35                  40                  45

His Tyr Ser Ser Tyr Ser Glu Arg Cys Arg Gly His Val Cys Gln Val
    50                  55                  60

Val Ile Cys Asp Gln Tyr Arg Lys Gly Ile Ile Ser Gly Ser Val Cys
65                  70                  75                  80

Gln Asp Leu Cys Glu Leu His Met Val Glu Trp Arg Thr Cys Leu Ser
                85                  90                  95

Val Ala Pro Gly Gln Gln Val Tyr Ser Gly Leu Trp Arg Asp Lys Asp
            100                 105                 110

Val Thr Ile Lys Cys Gly Ile Glu Glu Thr Leu Asp Ser Lys Ala Arg
        115                 120                 125

Ser Asp Ala Ala Pro Arg Arg Glu Leu Val Leu Phe Asp Lys Pro Thr
    130                 135                 140

Arg Gly Thr Ser Ile Lys Glu Phe Arg Glu Met Thr Leu Ser Phe Leu
145                 150                 155                 160

Lys Ala Asn Leu Gly Asp Leu Pro Ser Leu Pro Ala Leu Val Gly Gln
                165                 170                 175

Val Leu Leu Met Ala Asp Phe Asn Lys Asp Asn Arg Val Ser Leu Ala
            180                 185                 190

Glu Ala Lys Ser Val Trp Ala Leu Leu Gln Arg Asn Glu Phe Leu Leu
        195                 200                 205

Leu Leu Ser Leu Gln Glu Lys Glu His Ala Ser Arg Leu Leu Gly Tyr
```

```
    210                 215                 220

Cys Gly Asp Leu Tyr Leu Thr Glu Gly Val Pro His Gly Ala Trp His
225                 230                 235                 240

Ala Ala Ala Leu Pro Pro Leu Leu Arg Pro Leu Leu Pro Pro Ala Leu
                245                 250                 255

Gln Gly Ala Leu Gln Gln Trp Leu Gly Pro Ala Trp Pro Trp Arg Ala
            260                 265                 270

Lys Ile Ala Ile Gly Leu Leu Glu Phe Val Glu Glu Leu Phe His Gly
        275                 280                 285

Ser Tyr Gly Thr Phe Tyr Met Cys Glu Thr Thr Leu Ala Asn Val Gly
    290                 295                 300

Tyr Thr Ala Thr Tyr Asp Phe Lys Met Ala Asp Leu Gln Gln Val Ala
305                 310                 315                 320

Pro Glu Ala Thr Val Arg Arg Phe Leu Gln Gly Arg Arg Cys Glu His
                325                 330                 335

Ser Thr Asp Cys Thr Tyr Gly Arg Asp Cys Arg Ala Pro Cys Asp Arg
            340                 345                 350

Leu Met Arg Gln Cys Lys Gly Asp Leu Ile Gln Pro Asn Leu Ala Lys
        355                 360                 365

Val Cys Ala Leu Leu Arg Gly Tyr Leu Leu Pro Gly Ala Pro Ala Asp
    370                 375                 380

Leu Arg Glu Glu Leu Gly Thr Gln Leu Arg Thr Cys Thr Thr Leu Ser
385                 390                 395                 400

Gly Leu Ala Ser Gln Val Glu Ala His His Ser Leu Val Leu Ser His
                405                 410                 415

Leu Lys Thr Leu Leu Trp Lys Lys Ile Ser Asn Thr Lys Tyr Ser
            420                 425                 430


<210> SEQ ID NO 54
<211> LENGTH: 344
<212> TYPE: PRT
<213> ORGANISM: Homo sapiens

<400> SEQUENCE: 54

Met Val Glu Trp Arg Thr Cys Leu Ser Val Ala Pro Gly Gln Gln Val
1               5                   10                  15

Tyr Ser Gly Leu Trp Arg Asp Lys Asp Val Thr Ile Lys Cys Gly Ile
            20                  25                  30

Glu Glu Thr Leu Asp Ser Lys Ala Arg Ser Asp Ala Ala Pro Arg Arg
        35                  40                  45

Glu Leu Val Leu Phe Asp Lys Pro Thr Arg Gly Thr Ser Ile Lys Glu
    50                  55                  60

Phe Arg Glu Met Thr Leu Ser Phe Leu Lys Ala Asn Leu Gly Asp Leu
65                  70                  75                  80

Pro Ser Leu Pro Ala Leu Val Gly Gln Val Leu Leu Met Ala Asp Phe
                85                  90                  95

Asn Lys Asp Asn Arg Val Ser Leu Ala Glu Ala Lys Ser Val Trp Ala
            100                 105                 110

Leu Leu Gln Arg Asn Glu Phe Leu Leu Leu Leu Ser Leu Gln Glu Lys
        115                 120                 125

Glu His Ala Ser Arg Leu Leu Gly Tyr Cys Gly Asp Leu Tyr Leu Thr
    130                 135                 140

Glu Gly Val Pro His Gly Ala Trp His Ala Ala Ala Leu Pro Pro Leu
145                 150                 155                 160
```

-continued

Leu Arg Pro Leu Leu Pro Pro Ala Leu Gln Gly Ala Leu Gln Gln Trp
165 170 175

Leu Gly Pro Ala Trp Pro Trp Arg Ala Lys Ile Ala Ile Gly Leu Leu
180 185 190

Glu Phe Val Glu Glu Leu Phe His Gly Ser Tyr Gly Thr Phe Tyr Met
195 200 205

Cys Glu Thr Thr Leu Ala Asn Val Gly Tyr Thr Ala Thr Tyr Asp Phe
210 215 220

Lys Met Ala Asp Leu Gln Gln Val Ala Pro Glu Ala Thr Val Arg Arg
225 230 235 240

Phe Leu Gln Gly Arg Arg Cys Glu His Ser Thr Asp Cys Thr Tyr Gly
245 250 255

Arg Asp Cys Arg Ala Pro Cys Asp Arg Leu Met Arg Gln Cys Lys Gly
260 265 270

Asp Leu Ile Gln Pro Asn Leu Ala Lys Val Cys Ala Leu Leu Arg Gly
275 280 285

Tyr Leu Leu Pro Gly Ala Pro Ala Asp Leu Arg Glu Glu Leu Gly Thr
290 295 300

Gln Leu Arg Thr Cys Thr Thr Leu Ser Gly Leu Ala Ser Gln Val Glu
305 310 315 320

Ala His His Ser Leu Val Leu Ser His Leu Lys Thr Leu Leu Trp Lys
325 330 335

Lys Ile Ser Asn Thr Lys Tyr Ser
340

<210> SEQ ID NO 55
<211> LENGTH: 1645
<212> TYPE: DNA
<213> ORGANISM: Homo sapiens

<400> SEQUENCE: 55
agggagcggc ggccgctgcg ggccgggccg ggccggggct gaggccgagc gagccgcggg 60
gcccgcgcag ccccggccgg agcccaccat gcggcggctg cggcgcctgg cgcacctggt 120
gctcttctgc cccttctcca agcgcctgca gggccggctc ccaggcctca gggtccgctg 180
catcttcctg gcctggctgg gcgtctttgc aggcagctgg ctggtgtacg tgcactactc 240
gtcctactcg gagcgctgtc gcggccatgt ctgccaggtg gtcatttgtg accagtaccg 300
caaggggatc atctcgggct ccgtctgcca ggacctgtgt gagctgcata tggtggagtg 360
gaggacctgc ctctcggtgg ccccgggcca gcaggtgtac agcgggctct ggcgggacaa 420
ggatgtaacc atcaagtgtg gcattgagga gaccctcgac tccaaggccc ggtcggatgc 480
ggcccccggg cgggagctgg tactgtttga caagcccacc cggggcacct ccatcaagga 540
attccgggag atgaccctca gcttcctcaa ggcgaacctg ggagacctgc cttccctgcc 600
ggcgctggtt ggccaggtcc tgctcatggc tgacttcaac aaggacaacc gggtgtccct 660
ggcggaagcc aagtccgtgt gggccctgct gcagcgtaac gagttcctgc tgctgctgtc 720
cctgcaggag aaggagcacg cctccagact gctgggctac tgtggggacc tctacctcac 780
cgagggcgtg ccgcatggcg cctggcacgc ggccgccctt ccacccctgt tgcgcccact 840
gctgccgcct gccctgcagg gtgctctcca gcagtggctg gggcctgcgt ggccttggcg 900
ggccaagatc gccatcggcc tgctggagtt cgtggaggag ctcttccacg gctcttacgg 960
gactttctac atgtgtgaga ccacactggc caacgtgggc tacacagcca cctacgactt 1020
caagatggcc gacctgcagc aggtggcacc cgaggccacc gtgcgccgct tcctgcaggg 1080

```
ccgccgctgc gagcacagca ccgactgcac ctacgggcgc gactgcaggg ccccgtgtga   1140

caggctcatg aggcagtgca agggcgacct catccagccc aacctggcca aggtgtgcgc   1200

actgctacgg ggctacctgc tgcctggcgc gcccgccgac ctccgcgagg agctgggcac   1260

acagctgcgc acctgtacca cgctgagcgg gctggccagc caggtggagg cccatcactc   1320

gctggtgctc agccacctca agactctgct ctggaagaag atctccaaca ccaagtactc   1380

ttgatggggc agtgaggggc ctggccaccc ttcctggagc tggccaggtg ccagggtcca   1440

accctccctc aaggaatcct gtcagaagat gtgaaatgca actgtgttgc aaaatcactc   1500

ccctaccgtc agggctctgg attccagcac cacagacatg agaccccagc tcggagcaaa   1560

ggcggacatg gacatcccgg caggagagtc ctccaagggg gtttgttact ctgaagaacg   1620

taatgtcaat aaacagcttt tatgt                                         1645
```

<210> SEQ ID NO 56
<211> LENGTH: 2410
<212> TYPE: DNA
<213> ORGANISM: Homo sapiens

<400> SEQUENCE: 56

```
ggccgcagcc tgtcctcctg cctcagcctg gggaaggctg ggccgggcca aagagggagg     60

ccaagtcctt gggacaggag gagacccaca cctgagatta gtggaaaccc agccagaagc    120

tgccatgcag gtgtggctct gggcatcagg atctgtcgtg agagccccca tgagtgccca    180

gtgcagaatg gctggcagcc cgccctgacg gggagcagag gggctggacg cggtgccctt    240

cacgggatga cacccagctg tttgccctgt gtccaggggg ttgcttctct gacagaggcc    300

ctatggctcg tgtctgactc ctgtccaggt tctgccagcc tgaccatcca tcgctctggc    360

accaagagcc caccctttg ttcttcctgg cgtcccaggg aaagccctgc ctgggtgggg    420

cagctcctgg cccttcagat ggaagacgca gtccagtcag caccatcata ggaaacaagt    480

tcagaaatgt ctcacttact attccgggca gggagggcgc catgagtcag ggggtgcatc    540

ctccctcctg gcgtcacccg aggcaggaat gaagagtcag gcagagagcg cgcgtgtggc    600

agctggtggt gtagatatta gggactagtg tgaattctag ttcaccggcc aatgcctgga    660

tggtccagag ctgggtcggc tgggcggaga gctgcctcca ggttcctgcc tctggccctg    720

gcgtggggtc gacactgggt gtggtgtgtg tctcatgtcc aggcagtggc ctttgctgtg    780

ccgtcctgtt acaggagcca ggatggtggg gacgggaccg gaccggaggg ttggcggggc    840

tgcccctgca gccgacagcc ccatcctgca gccaccaatg gcatgaccca gggccccggc    900

actgcctgtg tgaggggctg gcagctttcc aactgcagca agtggaggcc cctgccagct    960

tcgggcctgt gggcaggggc tcagtggggc aggggtgtgg ctgccccgcc cggcacgcct   1020

gcacctgtct cctcagtgtg accagtaccg caaggggatc atctcgggct ccgtctgcca   1080

ggacctgtgt gagctgcata tggtggagtg gaggacctgc ctctcggtgg ccccgggcca   1140

gcaggtgtac agcgggctct ggcgggacaa ggatgtaacc atcaagtgtg gcattgagga   1200

gaccctcgac tccaaggccc ggtcggatgc ggcccccggg cgggagctgg tactgtttga   1260

caagcccacc cggggcacct ccatcaagga attccgggag atgaccctca gcttcctcaa   1320

ggcgaacctg ggagacctgc cttccctgcc ggcgctggtt ggccaggtcc tgctcatggc   1380

tgacttcaac aaggacaacc gggtgtccct ggcggaagcc aagtccgtgt gggccctgct   1440

gcagcgtaac gagttcctgc tgctgctgtc cctgcaggag aaggagcacg cctccagact   1500
```

```
gctgggctac tgtggggacc tctacctcac cgagggcgtg ccgcatggcg cctggcacgc   1560

ggccgccctt ccacccctgt tgcgcccact gctgccgcct gccctgcagg gtgctctcca   1620

gcagtggctg gggcctgcgt ggccttggcg ggccaagatc gccatcggcc tgctggagtt   1680

cgtggaggag ctcttccacg gctcttacgg gactttctac atgtgtgaga ccacactggc   1740

caacgtgggc tacacagcca cctacgactt caagatggcc gacctgcagc aggtggcacc   1800

cgaggccacc gtgcgccgct tcctgcaggg ccgccgctgc gagcacagca ccgactgcac   1860

ctacgggcgc gactgcaggg ccccgtgtga caggctcatg aggcagtgca agggcgacct   1920

catccagccc aacctggcca aggtgtgcgc actgctacgg ggctacctgc tgcctggcgc   1980

gcccgccgac ctccgcgagg agctgggcac acagctgcgc acctgtacca cgctgagcgg   2040

gctggccagc caggtggagg cccatcactc gctggtgctc agccacctca agactctgct   2100

ctggaagaag atctccaaca ccaagtactc ttgatggggc agtgaggggc ctggccaccc   2160

ttcctggagc tggccaggtg ccagggtcca accctccctc aaggaatcct gtcagaagat   2220

gtgaaatgca actgtgttgc aaaatcactc ccctaccgtc agggctctgg attccagcac   2280

cacagacatg agaccccagc tcggagcaaa ggcggacatg gacatcccgg caggagagtc   2340

ctccaagggg gtttgttact ctgaagaacg taatgtcaat aaacagcttt tatgtaatgc   2400

ccagggctga                                                          2410
```

<210> SEQ ID NO 57
<211> LENGTH: 423
<212> TYPE: PRT
<213> ORGANISM: Homo sapiens

<400> SEQUENCE: 57

```
Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Arg Thr Val Val Arg Pro Thr Tyr Lys
65                  70                  75                  80

Val Met Tyr Lys Ile Val Thr Ala Pro Ser Ser Ala Ser Leu Glu Pro
                85                  90                  95

Met Trp Ser Gly Ser Thr Met Arg Arg Met Ala Leu Arg Pro Thr Ala
            100                 105                 110

Phe Ser Gly Cys Leu Asn Cys Ser Lys Val Ser Glu Leu Thr Glu Arg
        115                 120                 125

Leu Lys Val Leu Glu Ala Lys Met Thr Met Leu Thr Val Ile Glu Gln
    130                 135                 140

Pro Val Pro Pro Thr Pro Ala Thr Pro Glu Asp Pro Ala Pro Leu Trp
145                 150                 155                 160

Gly Pro Pro Pro Ala Gln Gly Ser Pro Gly Asp Gly Gly Leu Gln Asp
                165                 170                 175

Gln Val Gly Ala Trp Gly Leu Pro Gly Pro Thr Gly Pro Lys Gly Asp
            180                 185                 190

Ala Gly Ser Arg Gly Pro Met Gly Met Arg Gly Pro Pro Gly Pro Gln
        195                 200                 205
```

```
Gly Pro Pro Gly Ser Pro Gly Arg Ala Gly Ala Val Gly Thr Pro Gly
    210                 215                 220

Glu Arg Gly Pro Pro Gly Pro Pro Gly Pro Pro Gly Pro Pro Gly Pro
225                 230                 235                 240

Pro Ala Pro Val Gly Pro Pro His Ala Arg Ile Ser Gln His Gly Asp
                245                 250                 255

Pro Leu Leu Ser Asn Thr Phe Thr Glu Thr Asn Asn His Trp Pro Gln
            260                 265                 270

Gly Pro Thr Gly Pro Pro Gly Pro Pro Gly Pro Met Gly Pro Pro Gly
        275                 280                 285

Pro Pro Gly Pro Thr Gly Val Pro Gly Ser Pro Gly His Ile Gly Pro
    290                 295                 300

Pro Gly Pro Thr Gly Pro Lys Gly Ile Ser Gly His Pro Gly Glu Lys
305                 310                 315                 320

Gly Glu Arg Gly Leu Arg Gly Glu Pro Gly Pro Gln Gly Ser Ala Gly
                325                 330                 335

Gln Arg Gly Glu Pro Gly Pro Lys Gly Asp Pro Gly Glu Lys Ser His
            340                 345                 350

Trp Gly Glu Gly Leu His Gln Leu Arg Glu Ala Leu Lys Ile Leu Ala
        355                 360                 365

Glu Arg Val Leu Ile Leu Glu Thr Met Ile Gly Leu Tyr Glu Pro Glu
    370                 375                 380

Leu Gly Ser Gly Ala Gly Pro Ala Gly Thr Gly Thr Pro Ser Leu Leu
385                 390                 395                 400

Arg Gly Lys Arg Gly Gly His Ala Thr Asn Tyr Arg Ile Val Ala Pro
                405                 410                 415

Arg Ser Arg Asp Glu Arg Gly
            420


<210> SEQ ID NO 58
<211> LENGTH: 212
<212> TYPE: PRT
<213> ORGANISM: Homo sapiens

<400> SEQUENCE: 58

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Val Ala Ala Ser Ser Ala
            100                 105                 110

Ser Leu Glu Pro Met Trp Ser Gly Ser Thr Met Arg Arg Met Ala Leu
        115                 120                 125

Arg Pro Thr Ala Phe Ser Gly Cys Leu Asn Cys Ser Lys Val Ser Glu
    130                 135                 140

Leu Thr Glu Arg Leu Lys Val Leu Glu Ala Lys Met Thr Met Leu Thr
145                 150                 155                 160
```

```
Val Ile Glu Gln Pro Val Pro Pro Thr Pro Ala Thr Pro Glu Asp Pro
                165                 170                 175

Ala Pro Leu Trp Gly Pro Pro Pro Ala Gln Gly Ser Pro Gly Asp Gly
            180                 185                 190

Gly Leu Gln Gly Asp Pro Leu Leu Ser Asn Thr Phe Thr Glu Thr Asn
        195                 200                 205

Asn His Trp Pro
    210


<210> SEQ ID NO 59
<211> LENGTH: 175
<212> TYPE: PRT
<213> ORGANISM: Homo sapiens

<400> SEQUENCE: 59

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Gly Cys Leu Asn Cys Ser
            100                 105                 110

Lys Val Ser Glu Leu Thr Glu Arg Leu Lys Val Leu Glu Ala Lys Met
        115                 120                 125

Thr Met Leu Thr Val Ile Glu Gln Pro Val Pro Pro Thr Pro Ala Thr
    130                 135                 140

Pro Glu Asp Pro Ala Pro Leu Trp Gly Pro Pro Pro Ala Gln Gly Ser
145                 150                 155                 160

Pro Gly Asp Gly Gly Leu Gln Asp Gln Val Gly Ala Trp Gly Leu
                165                 170                 175


<210> SEQ ID NO 60
<211> LENGTH: 34
<212> TYPE: PRT
<213> ORGANISM: Homo sapiens

<400> SEQUENCE: 60

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg


<210> SEQ ID NO 61
<211> LENGTH: 445
<212> TYPE: PRT
<213> ORGANISM: Homo sapiens

<400> SEQUENCE: 61

Met Gly Gly Pro Arg Ala Trp Ala Leu Leu Cys Leu Gly Leu Leu Leu
```

-continued

```
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Val Ala Ala Ser Ser Ala
            100                 105                 110

Ser Leu Glu Pro Met Trp Ser Gly Ser Thr Met Arg Arg Met Ala Leu
        115                 120                 125

Arg Pro Thr Ala Phe Ser Gly Cys Leu Asn Cys Ser Lys Val Ser Glu
    130                 135                 140

Leu Thr Glu Arg Leu Lys Val Leu Glu Ala Lys Met Thr Met Leu Thr
145                 150                 155                 160

Val Ile Glu Gln Pro Val Pro Pro Thr Pro Ala Thr Pro Glu Asp Pro
                165                 170                 175

Ala Pro Leu Trp Gly Pro Pro Pro Ala Gln Gly Ser Pro Gly Asp Gly
            180                 185                 190

Gly Leu Gln Asp Gln Val Gly Ala Trp Gly Leu Pro Gly Pro Thr Gly
        195                 200                 205

Pro Lys Gly Asp Ala Gly Ser Arg Gly Pro Met Gly Met Arg Gly Pro
    210                 215                 220

Pro Gly Pro Gln Gly Pro Pro Gly Ser Pro Gly Arg Ala Gly Ala Val
225                 230                 235                 240

Gly Thr Pro Gly Glu Arg Gly Pro Pro Gly Pro Pro Gly Pro Pro Gly
                245                 250                 255

Pro Pro Gly Pro Pro Ala Pro Val Gly Pro Pro His Ala Arg Ile Ser
            260                 265                 270

Gln His Gly Asp Pro Leu Leu Ser Asn Thr Phe Thr Glu Thr Asn Asn
        275                 280                 285

His Trp Pro Gln Gly Pro Thr Gly Pro Pro Gly Pro Pro Gly Pro Met
    290                 295                 300

Gly Pro Pro Gly Pro Pro Gly Pro Thr Gly Val Pro Gly Ser Pro Gly
305                 310                 315                 320

His Ile Gly Pro Pro Gly Pro Thr Gly Pro Lys Gly Ile Ser Gly His
                325                 330                 335

Pro Gly Glu Lys Gly Glu Arg Gly Leu Arg Gly Glu Pro Gly Pro Gln
            340                 345                 350

Gly Ser Ala Gly Gln Arg Gly Glu Pro Gly Pro Lys Gly Asp Pro Gly
        355                 360                 365

Glu Lys Ser His Trp Ala Pro Ser Leu Gln Ser Phe Leu Gln Gln Gln
    370                 375                 380

Ala Gln Leu Glu Leu Leu Ala Arg Arg Val Thr Leu Leu Glu Ala Ile
385                 390                 395                 400

Ile Trp Pro Glu Pro Glu Leu Gly Ser Gly Ala Gly Pro Ala Gly Thr
                405                 410                 415

Gly Thr Pro Ser Leu Leu Arg Gly Lys Arg Gly Gly His Ala Thr Asn
            420                 425                 430
```

```
Tyr Arg Ile Val Ala Pro Arg Ser Arg Asp Glu Arg Gly
        435                 440                 445


<210> SEQ ID NO 62
<211> LENGTH: 443
<212> TYPE: PRT
<213> ORGANISM: Homo sapiens

<400> SEQUENCE: 62

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Val Ala Ala Ser Ser Ala
            100                 105                 110

Ser Leu Glu Pro Met Trp Ser Gly Ser Thr Met Arg Arg Met Ala Leu
        115                 120                 125

Arg Pro Thr Ala Phe Ser Gly Cys Leu Asn Cys Ser Lys Val Ser Glu
    130                 135                 140

Leu Thr Glu Arg Leu Lys Val Leu Glu Ala Lys Met Thr Met Leu Thr
145                 150                 155                 160

Val Ile Glu Gln Pro Val Pro Pro Thr Pro Ala Thr Pro Glu Asp Pro
                165                 170                 175

Ala Pro Leu Trp Gly Pro Pro Pro Ala Gln Gly Ser Pro Gly Asp Gly
            180                 185                 190

Gly Leu Gln Asp Gln Val Gly Ala Trp Gly Leu Pro Gly Pro Thr Gly
        195                 200                 205

Pro Lys Gly Asp Ala Gly Ser Arg Gly Pro Met Gly Met Arg Gly Pro
    210                 215                 220

Pro Gly Pro Gln Gly Pro Pro Gly Ser Pro Gly Arg Ala Gly Ala Val
225                 230                 235                 240

Gly Thr Pro Gly Glu Arg Gly Pro Pro Gly Pro Pro Gly Pro Pro Gly
                245                 250                 255

Pro Pro Gly Pro Pro Ala Pro Val Gly Pro Pro His Ala Arg Ile Ser
            260                 265                 270

Gln His Gly Asp Pro Leu Leu Ser Asn Thr Phe Thr Glu Thr Asn Asn
        275                 280                 285

His Trp Pro Gln Gly Pro Thr Gly Pro Pro Gly Pro Pro Gly Pro Met
    290                 295                 300

Gly Pro Pro Gly Pro Pro Gly Pro Thr Gly Val Pro Gly Ser Pro Gly
305                 310                 315                 320

His Ile Gly Pro Pro Gly Pro Thr Gly Pro Lys Gly Ile Ser Gly His
                325                 330                 335

Pro Gly Glu Lys Gly Glu Arg Gly Leu Arg Gly Glu Pro Gly Pro Gln
            340                 345                 350

Gly Ser Ala Gly Gln Arg Gly Glu Pro Gly Pro Lys Gly Asp Pro Gly
```

```
        355                 360                 365

Glu Lys Ser His Trp Gly Glu Gly Leu His Gln Leu Arg Glu Ala Leu
    370                 375                 380

Lys Ile Leu Ala Glu Arg Val Leu Ile Leu Glu Thr Met Ile Gly Leu
385                 390                 395                 400

Tyr Glu Pro Glu Leu Gly Ser Gly Ala Gly Pro Ala Gly Thr Gly Thr
                405                 410                 415

Pro Ser Leu Leu Arg Gly Lys Arg Gly Gly His Ala Thr Asn Tyr Arg
            420                 425                 430

Ile Val Ala Pro Arg Ser Arg Asp Glu Arg Gly
        435                 440


<210> SEQ ID NO 63
<211> LENGTH: 441
<212> TYPE: PRT
<213> ORGANISM: Homo sapiens

<400> SEQUENCE: 63

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Ala Ser Ser Ala Ser Leu
            100                 105                 110

Glu Pro Met Trp Ser Gly Ser Thr Met Arg Arg Met Ala Leu Arg Pro
        115                 120                 125

Thr Ala Phe Ser Gly Cys Leu Asn Cys Ser Lys Val Ser Glu Leu Thr
    130                 135                 140

Glu Arg Leu Lys Val Leu Glu Ala Lys Met Thr Met Leu Thr Val Ile
145                 150                 155                 160

Glu Gln Pro Val Pro Pro Thr Pro Ala Thr Pro Glu Asp Pro Ala Pro
                165                 170                 175

Leu Trp Gly Pro Pro Pro Ala Gln Gly Ser Pro Gly Asp Gly Gly Leu
            180                 185                 190

Gln Asp Gln Val Gly Ala Trp Gly Leu Pro Gly Pro Thr Gly Pro Lys
        195                 200                 205

Gly Asp Ala Gly Ser Arg Gly Pro Met Gly Met Arg Gly Pro Pro Gly
    210                 215                 220

Pro Gln Gly Pro Pro Gly Ser Pro Gly Arg Ala Gly Ala Val Gly Thr
225                 230                 235                 240

Pro Gly Glu Arg Gly Pro Pro Gly Pro Pro Gly Pro Pro Gly Pro Pro
                245                 250                 255

Gly Pro Pro Ala Pro Val Gly Pro Pro His Ala Arg Ile Ser Gln His
            260                 265                 270

Gly Asp Pro Leu Leu Ser Asn Thr Phe Thr Glu Thr Asn Asn His Trp
        275                 280                 285
```

```
Pro Gln Gly Pro Thr Gly Pro Pro Gly Pro Pro Gly Pro Met Gly Pro
    290                 295                 300

Pro Gly Pro Pro Gly Pro Thr Gly Val Pro Gly Ser Pro Gly His Ile
305                 310                 315                 320

Gly Pro Pro Gly Pro Thr Gly Pro Lys Gly Ile Ser Gly His Pro Gly
                325                 330                 335

Glu Lys Gly Glu Arg Gly Leu Arg Gly Glu Pro Gly Pro Gln Gly Ser
            340                 345                 350

Ala Gly Gln Arg Gly Glu Pro Gly Pro Lys Gly Asp Pro Gly Glu Lys
        355                 360                 365

Ser His Trp Gly Glu Gly Leu His Gln Leu Arg Glu Ala Leu Lys Ile
    370                 375                 380

Leu Ala Glu Arg Val Leu Ile Leu Glu Thr Met Ile Gly Leu Tyr Glu
385                 390                 395                 400

Pro Glu Leu Gly Ser Gly Ala Gly Pro Ala Gly Thr Gly Thr Pro Ser
                405                 410                 415

Leu Leu Arg Gly Lys Arg Gly Gly His Ala Thr Asn Tyr Arg Ile Val
            420                 425                 430

Ala Pro Arg Ser Arg Asp Glu Arg Gly
        435                 440


<210> SEQ ID NO 64
<211> LENGTH: 439
<212> TYPE: PRT
<213> ORGANISM: Homo sapiens

<400> SEQUENCE: 64

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Arg Thr Val Val Arg Pro Thr Tyr Lys
65                  70                  75                  80

Val Met Tyr Lys Ile Val Thr Ala Arg Glu Trp Arg Cys Cys Pro Gly
                85                  90                  95

His Ser Gly Val Ser Cys Glu Glu Ala Ser Ser Ala Ser Leu Glu Pro
            100                 105                 110

Met Trp Ser Gly Ser Thr Met Arg Arg Met Ala Leu Arg Pro Thr Ala
        115                 120                 125

Phe Ser Gly Cys Leu Asn Cys Ser Lys Val Ser Glu Leu Thr Glu Arg
    130                 135                 140

Leu Lys Val Leu Glu Ala Lys Met Thr Met Leu Thr Val Ile Glu Gln
145                 150                 155                 160

Pro Val Pro Pro Thr Pro Ala Thr Pro Glu Asp Pro Ala Pro Leu Trp
                165                 170                 175

Gly Pro Pro Pro Ala Gln Gly Ser Pro Gly Asp Gly Gly Leu Gln Asp
            180                 185                 190

Gln Val Gly Ala Trp Gly Leu Pro Gly Pro Thr Gly Pro Lys Gly Asp
        195                 200                 205

Ala Gly Ser Arg Gly Pro Met Gly Met Arg Gly Pro Pro Gly Pro Gln
    210                 215                 220
```

```
Gly Pro Pro Gly Ser Pro Gly Arg Ala Gly Ala Val Gly Thr Pro Gly
225                 230                 235                 240

Glu Arg Gly Pro Pro Gly Pro Pro Gly Pro Pro Gly Pro Pro Gly Pro
                245                 250                 255

Pro Ala Pro Val Gly Pro Pro His Ala Arg Ile Ser Gln His Gly Asp
            260                 265                 270

Pro Leu Leu Ser Asn Thr Phe Thr Glu Thr Asn Asn His Trp Pro Gln
        275                 280                 285

Gly Pro Thr Gly Pro Pro Gly Pro Pro Gly Pro Met Gly Pro Pro Gly
    290                 295                 300

Pro Pro Gly Pro Thr Gly Val Pro Gly Ser Pro Gly His Ile Gly Pro
305                 310                 315                 320

Pro Gly Pro Thr Gly Pro Lys Gly Ile Ser Gly His Pro Gly Glu Lys
                325                 330                 335

Gly Glu Arg Gly Leu Arg Gly Glu Pro Gly Pro Gln Gly Ser Ala Gly
            340                 345                 350

Gln Arg Gly Glu Pro Gly Pro Lys Gly Asp Pro Gly Glu Lys Ser His
        355                 360                 365

Trp Gly Glu Gly Leu His Gln Leu Arg Glu Ala Leu Lys Ile Leu Ala
    370                 375                 380

Glu Arg Val Leu Ile Leu Glu Thr Met Ile Gly Leu Tyr Glu Pro Glu
385                 390                 395                 400

Leu Gly Ser Gly Ala Gly Pro Ala Gly Thr Gly Thr Pro Ser Leu Leu
                405                 410                 415

Arg Gly Lys Arg Gly Gly His Ala Thr Asn Tyr Arg Ile Val Ala Pro
            420                 425                 430

Arg Ser Arg Asp Glu Arg Gly
        435


<210> SEQ ID NO 65
<211> LENGTH: 422
<212> TYPE: PRT
<213> ORGANISM: Homo sapiens

<400> SEQUENCE: 65

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Val Ala Ala Ser Ser Ala
            100                 105                 110

Ser Leu Glu Pro Met Trp Ser Gly Ser Thr Met Arg Arg Met Ala Leu
        115                 120                 125

Arg Pro Thr Ala Phe Ser Gly Cys Leu Asn Cys Ser Lys Val Ser Glu
    130                 135                 140

Leu Thr Glu Arg Leu Lys Val Leu Glu Ala Lys Met Thr Met Leu Thr
```

```
145                 150                 155                 160

Val Ile Glu Gln Pro Val Pro Pro Thr Pro Ala Thr Pro Glu Asp Pro
                165                 170                 175

Ala Pro Leu Trp Gly Pro Pro Pro Ala Gln Gly Ser Pro Gly Asp Gly
            180                 185                 190

Gly Leu Gln Asp Gln Val Gly Ala Trp Gly Leu Pro Gly Pro Thr Gly
        195                 200                 205

Pro Lys Gly Asp Ala Gly Ser Arg Gly Pro Met Gly Met Arg Gly Pro
    210                 215                 220

Pro Gly Pro Gln Gly Pro Pro Gly Ser Pro Gly Arg Ala Gly Ala Val
225                 230                 235                 240

Gly Thr Pro Gly Glu Arg Gly Pro Pro Gly Pro Pro Gly Pro Pro Gly
                245                 250                 255

Pro Pro Gly Pro Pro Ala Pro Val Gly Pro Pro His Ala Arg Ile Ser
            260                 265                 270

Gln His Gly Asp Pro Leu Leu Ser Asn Thr Phe Thr Glu Thr Asn Asn
        275                 280                 285

His Trp Pro Gln Gly Pro Thr Gly Pro Pro Gly Pro Pro Gly Pro Met
    290                 295                 300

Gly Pro Pro Gly Pro Pro Gly Pro Thr Gly Val Pro Gly Ser Pro Gly
305                 310                 315                 320

His Ile Gly Leu Arg Gly Glu Pro Gly Pro Gln Gly Ser Ala Gly Gln
                325                 330                 335

Arg Gly Glu Pro Gly Pro Lys Gly Asp Pro Gly Glu Lys Ser His Trp
            340                 345                 350

Gly Glu Gly Leu His Gln Leu Arg Glu Ala Leu Lys Ile Leu Ala Glu
        355                 360                 365

Arg Val Leu Ile Leu Glu Thr Met Ile Gly Leu Tyr Glu Pro Glu Leu
    370                 375                 380

Gly Ser Gly Ala Gly Pro Ala Gly Thr Gly Thr Pro Ser Leu Leu Arg
385                 390                 395                 400

Gly Lys Arg Gly Gly His Ala Thr Asn Tyr Arg Ile Val Ala Pro Arg
                405                 410                 415

Ser Arg Asp Glu Arg Gly
            420


<210> SEQ ID NO 66
<211> LENGTH: 212
<212> TYPE: PRT
<213> ORGANISM: Homo sapiens

<400> SEQUENCE: 66

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95
```

```
Pro Gly His Ser Gly Val Ser Cys Glu Glu Val Ala Ala Ser Ser Ala
            100                 105                 110

Ser Leu Glu Pro Met Trp Ser Gly Ser Thr Met Arg Arg Met Ala Leu
        115                 120                 125

Arg Pro Thr Ala Phe Ser Gly Cys Leu Asn Cys Ser Lys Val Ser Glu
    130                 135                 140

Leu Thr Glu Arg Leu Lys Val Leu Glu Ala Lys Met Thr Met Leu Thr
145                 150                 155                 160

Val Ile Glu Gln Pro Val Pro Pro Thr Pro Ala Thr Pro Glu Asp Pro
                165                 170                 175

Ala Pro Leu Trp Gly Pro Pro Pro Ala Gln Gly Ser Pro Gly Asp Gly
            180                 185                 190

Gly Leu Gln Gly Asp Pro Leu Leu Ser Asn Thr Phe Thr Glu Thr Asn
        195                 200                 205

Asn His Trp Pro
    210
```

<210> SEQ ID NO 67
<211> LENGTH: 175
<212> TYPE: PRT
<213> ORGANISM: Homo sapiens

<400> SEQUENCE: 67

```
Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Gly Cys Leu Asn Cys Ser
            100                 105                 110

Lys Val Ser Glu Leu Thr Glu Arg Leu Lys Val Leu Glu Ala Lys Met
        115                 120                 125

Thr Met Leu Thr Val Ile Glu Gln Pro Val Pro Pro Thr Pro Ala Thr
    130                 135                 140

Pro Glu Asp Pro Ala Pro Leu Trp Gly Pro Pro Pro Ala Gln Gly Ser
145                 150                 155                 160

Pro Gly Asp Gly Gly Leu Gln Asp Gln Val Gly Ala Trp Gly Leu
                165                 170                 175
```

<210> SEQ ID NO 68
<211> LENGTH: 236
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 68

```
Xaa Met Thr Met Leu Thr Val Ile Glu Gln Pro Val Pro Pro Thr Pro
1               5                   10                  15
```

```
Ala Thr Pro Glu Asp Pro Ala Pro Leu Trp Gly Pro Pro Pro Ala Gln
            20                  25                  30

Gly Ser Pro Gly Asp Gly Gly Leu Gln Gly Leu Pro Gly Ala Ile Glu
        35                  40                  45

Ser Val Arg Val Pro Leu Leu Pro Arg Asn Asp Gln Val Gly Ala Trp
    50                  55                  60

Gly Leu Pro Gly Pro Thr Gly Pro Lys Gly Asp Ala Gly Ser Arg Gly
65                  70                  75                  80

Pro Met Gly Met Arg Gly Pro Pro Gly Pro Gln Gly Pro Pro Gly Ser
                85                  90                  95

Pro Gly Arg Ala Gly Ala Val Gly Thr Pro Gly Glu Arg Gly Pro Pro
            100                 105                 110

Gly Pro Pro Gly Pro Pro Gly Pro Pro Gly Pro Pro Ala Pro Val Gly
        115                 120                 125

Pro Pro His Ala Arg Ile Ser Gln His Gly Asp Pro Leu Leu Ser Asn
    130                 135                 140

Thr Phe Thr Glu Thr Asn Asn His Trp Pro Gln Gly Pro Thr Gly Pro
145                 150                 155                 160

Pro Gly Pro Pro Gly Pro Met Gly Pro Pro Gly Pro Pro Gly Pro Thr
                165                 170                 175

Gly Val Pro Gly Ser Pro Gly His Ile Gly Pro Pro Gly Pro Thr Gly
            180                 185                 190

Pro Lys Gly Ile Ser Gly His Pro Gly Glu Lys Gly Glu Arg Gly Leu
        195                 200                 205

Arg Gly Glu Pro Gly Pro Gln Gly Ser Ala Gly Gln Arg Gly Glu Pro
    210                 215                 220

Gly Pro Lys Gly Asp Pro Gly Glu Lys Ser His Trp
225                 230                 235


<210> SEQ ID NO 69
<211> LENGTH: 305
<212> TYPE: PRT
<213> ORGANISM: Homo sapiens

<400> SEQUENCE: 69

Met Thr Met Leu Thr Val Ile Glu Gln Pro Val Pro Pro Thr Pro Ala
1               5                   10                  15

Thr Pro Glu Asp Pro Ala Pro Leu Trp Gly Pro Pro Pro Ala Gln Gly
            20                  25                  30

Ser Pro Gly Asp Gly Gly Leu Gln Gly Leu Pro Gly Ala Ile Glu Ser
        35                  40                  45

Val Arg Val Pro Leu Leu Pro Arg Asn Asp Gln Val Gly Ala Trp Gly
    50                  55                  60

Leu Pro Gly Pro Thr Gly Pro Lys Gly Asp Ala Gly Ser Arg Gly Pro
65                  70                  75                  80

Met Gly Met Arg Gly Pro Pro Gly Pro Gln Gly Pro Pro Gly Ser Pro
                85                  90                  95

Gly Arg Ala Gly Ala Val Gly Thr Pro Gly Glu Arg Gly Pro Pro Gly
            100                 105                 110

Pro Pro Gly Pro Pro Gly Pro Pro Gly Pro Pro Ala Pro Val Gly Pro
        115                 120                 125

Pro His Ala Arg Ile Ser Gln His Gly Asp Pro Leu Leu Ser Asn Thr
    130                 135                 140

Phe Thr Glu Thr Asn Asn His Trp Pro Gln Gly Pro Thr Gly Pro Pro
```

```
145                 150                 155                 160

Gly Pro Pro Gly Pro Met Gly Pro Pro Gly Pro Pro Gly Pro Thr Gly
                165                 170                 175

Val Pro Gly Ser Pro Gly His Ile Gly Pro Pro Gly Pro Thr Gly Pro
            180                 185                 190

Lys Gly Ile Ser Gly His Pro Gly Glu Lys Gly Glu Arg Gly Leu Arg
        195                 200                 205

Gly Glu Pro Gly Pro Gln Gly Ser Ala Gly Gln Arg Gly Glu Pro Gly
    210                 215                 220

Pro Lys Gly Asp Pro Gly Glu Lys Ser His Trp Gly Glu Gly Leu His
225                 230                 235                 240

Gln Leu Arg Glu Ala Leu Lys Ile Leu Ala Glu Arg Val Leu Ile Leu
                245                 250                 255

Glu Thr Met Ile Gly Leu Tyr Glu Pro Glu Leu Gly Ser Gly Ala Gly
            260                 265                 270

Pro Ala Gly Thr Gly Thr Pro Ser Leu Leu Arg Gly Lys Arg Gly Gly
        275                 280                 285

His Ala Thr Asn Tyr Arg Ile Val Ala Pro Arg Ser Arg Asp Glu Arg
    290                 295                 300

Gly
305


<210> SEQ ID NO 70
<211> LENGTH: 226
<212> TYPE: PRT
<213> ORGANISM: Homo sapiens

<400> SEQUENCE: 70

Met Lys Ser Ser Leu Met Phe Thr Asp Pro His Ser Leu Gly Thr Tyr
1               5                   10                  15

Thr Tyr Gln Ala Leu Ser Trp Ala Leu Gly Gly Val Arg His Val Pro
            20                  25                  30

Ala Leu Leu Glu Leu Pro Cys Cys Trp Glu Gln Gly Trp Ala Glu Glu
        35                  40                  45

Lys Gln Gln Cys Leu Pro His Val Thr Arg Val Ser Met Arg Gly Phe
    50                  55                  60

Gly Gly Leu Gly Ala Pro Arg Lys Glu Asp Ser Ala Trp Thr Arg Trp
65                  70                  75                  80

Arg Thr Arg Cys Cys Ala His Pro Pro Val Arg Leu Pro Gly Ser Leu
                85                  90                  95

Gly Leu Trp Thr Pro Gly Pro Ser Leu Met Pro Thr Ala Pro Gly Cys
            100                 105                 110

Leu Val Leu Ser Leu Lys Ala Thr Leu Gly Leu Leu Ala Ser Cys Ile
        115                 120                 125

Pro Thr Asn Pro Cys Asp Ser Ile Ala Gly Pro Gln Gly Pro Pro Gly
    130                 135                 140

Ser Pro Gly Arg Ala Gly Ala Val Gly Thr Pro Gly Glu Arg Gly Pro
145                 150                 155                 160

Pro Gly Pro Pro Gly Pro Pro Gly Pro Pro Gly Pro Pro Ala Pro Val
                165                 170                 175

Gly Pro Pro His Ala Arg Ile Ser Gln His Gly Glu Ser Pro Trp Asp
            180                 185                 190

Pro Ser Arg Trp Arg Trp Gly Trp Ser Ser His Gln His Ser Ala Arg
        195                 200                 205
```

```
Tyr His Leu Pro Arg Ala Phe Cys Val Pro Ala Leu Leu Thr Ile Gly
    210                 215                 220

His Met
225


<210> SEQ ID NO 71
<211> LENGTH: 2031
<212> TYPE: DNA
<213> ORGANISM: Homo sapiens

<400> SEQUENCE: 71

gggctccgcg cgtccggggc ggctggcggc gcgggcaggc aggcggggag gacaggctgg     60

gggcggcgac cgcgaggggc cgcgcgcgga gggcgcctgg tgcagcatgg gcggcccgcg    120

ggcttgggcg ctgctctgcc tcgggctcct gctcccggga ggcggcgctg cgtggagcat    180

cggggcagct ccgttctccg gacgcaggaa ctggtgctcc tatgtggtga cccgcaccat    240

ctcatgccat gtgcagaatg gcacctacct tcagcgagtg ctgcagaact gcccctggcc    300

catgagctgt ccggggagca gaactgtggt gagacccaca tacaaggtga tgtacaagat    360

agtgaccgcc ccttcctctg cctccttgga gcccatgtgg tcgggcagta ccatgcggcg    420

gatggcgctt cggcccacag ccttctcagg ttgtctcaac tgcagcaaag tgtcagagct    480

gacagagcgg ctgaaggtgc tggaggccaa gatgaccatg ctgactgtca tagagcagcc    540

agtacctcca acaccagcta cccctgagga ccctgccccg ctctggggtc cccctcctgc    600

ccagggcagc ccggagatg gaggcctcca ggaccaagtc ggtgcttggg ggcttcccgg    660

gcccaccggc cccaagggag atgccggcag tcggggccca atggggatga gaggcccacc    720

aggtccacag ggcccccag ggagccctgg ccgggctgga gctgtgggca cccctggaga    780

gaggggacct cctgggccac cagggcctcc tggcccccct gggcccccag cccctgttgg    840

gccaccccat gcccggatct cccagcatgg agacccattg ctgtccaaca ccttcactga    900

gaccaacaac cactggcccc agggacccac tgggcctcca ggccctccag ggcccatggg    960

tccccctggg cctcctggcc ccacaggtgt ccctgggagt cctggtcaca taggaccccc   1020

aggccccact ggacccaaag gaatctctgg ccacccagga gagaagggcg agagaggact   1080

gcgtggggag cctggccccc aaggctctgc tgggcagcgg ggggaacctg gccctaaggg   1140

agaccctggt gagaagagcc actgggggga ggggttgcac cagctacgcg aggctttgaa   1200

gattttagct gagagggttt taatcttgga aacaatgatt gggctctatg aaccagagct   1260

ggggtctggg gcgggccctg ccggcacagg cacccccagc ctccttcggg gcaagagggg   1320

cggacatgca accaactacc ggatcgtggc cccccaggagc cgggacgaga gaggctgagg   1380

gtggtggcgg cccctgaggc agaccaggcc aggcttcccc tcctacctgg actcggccag   1440

ctgcctccag ggaccgcccg tccatattta ttaatgtcct cagggtccct tctgccatct   1500

aggccttagg ggtaagcagg tctcagtcct ggcaccatgc acatgtctga ggctgagcaa   1560

gggctgagag gagaggcttg ggcctcagtt tccctctgtg aagtgggggg aggcaggcct   1620

tcaaggaggg atagaggtac aaggcttcgt ctcatctgct gtctgagcat ccaggcccaa   1680

aggcactgag ggagtcagga gctggggctc ggcacatgca gagatgacag ggcagggggc   1740

agtcttcctc cccctccccg accaaacctc ggggagccct cctgtgcccc tccctccttg   1800

ttgtccagtg ctgggctccc caccccgagg tcaggctgcc caatcctctg actggatcac   1860

cgggggcttc ttgcctcagt tcttccctct gagcccccag gccctcccgc atctcaggtt   1920

ggggatgggg acatggagag gaaggggccg cctactcctg caaatgcttg tgacagatgc   1980
```

```
caggaggtag atgtgtgctg gccaataaag gcccctacct gattccccgc a          2031


<210> SEQ ID NO 72
<211> LENGTH: 769
<212> TYPE: DNA
<213> ORGANISM: Homo sapiens

<400> SEQUENCE: 72

cgccctccgg ccgcggagct ggaaaccggg ctccgcgcgt ccggggcggc tggcggcgcg     60

ggcaggcagg cggggaggac aggctggggg cggcgaccgc gaggggccgc gcgcggaggg    120

cgcctggtgc agcatgggcg gcccgcgggc ttgggcgctg ctctgcctcg ggctcctgct    180

cccgggaggc ggcgctgcgt ggagcatcgg ggcagctccg ttctccggac gcaggaactg    240

gtgctcctat gtggtgaccc gcaccatctc atgccatgtg cagaatggca cctaccttca    300

gcgagtgctg cagaactgcc cctggcccat gagctgtccg gggagcagct acagaactgt    360

ggtgagaccc acatacaagg tgatgtacaa gatagtgacc gcccgtgagt ggaggtgctg    420

ccctgggcac tcaggagtga gctgcgagga agttgcagct tcctctgcct ccttggagcc    480

catgtggtcg ggcagtacca tgcggcggat ggcgcttcgg cccacagcct tctcaggttg    540

tctcaactgc agcaaagtgt cagagctgac agagcggctg aaggtgctgg aggccaagat    600

gaccatgctg actgtcatag agcagccagt acctccaaca ccagctaccc ctgaggaccc    660

tgccccgctc tggggtcccc ctcctgccca gggcagcccc ggagatggag gcctccaggg    720

agacccattg ctgtccaaca ccttcactga gaccaacaac cactggccc                769


<210> SEQ ID NO 73
<211> LENGTH: 641
<212> TYPE: DNA
<213> ORGANISM: Homo sapiens

<400> SEQUENCE: 73

gctggaaacc gggctccgcg cgtccggggc ggctggcggc gcgggcaggc aggcggggag     60

gacaggctgg gggcggcgac cgcgaggggc cgcgcgcgga gggcgcctgg tgcagcatgg    120

gcggcccgcg ggcttgggcg ctgctctgcc tcgggctcct gctcccggga ggcggcgctg    180

cgtggagcat cggggcagct ccgttctccg gacgcaggaa ctggtgctcc tatgtggtga    240

cccgcaccat ctcatgccat gtgcagaatg gcacctacct tcagcgagtg ctgcagaact    300

gcccctggcc catgagctgt ccggggagca gctacagaac tgtggtgaga cccacataca    360

aggtgatgta caagatagtg accgcccgtg agtggaggtg ctgccctggg cactcaggag    420

tgagctgcga ggaaggttgt ctcaactgca gcaaagtgtc agagctgaca gagcggctga    480

aggtgctgga ggccaagatg accatgctga ctgtcataga gcagccagta cctccaacac    540

cagctacccc tgaggaccct gccccgctct ggggtccccc tcctgcccag ggcagccccg    600

gagatggagg cctccaggac caagtcggtg cttgggggct t                        641


<210> SEQ ID NO 74
<211> LENGTH: 482
<212> TYPE: DNA
<213> ORGANISM: Homo sapiens

<400> SEQUENCE: 74

cggcgcgggc aggcaggcgg ggaggacagg ctgggggcgg cgaccgcgag ggggccgcgcg    60

cggagggcgc ctggtgcagc atgggcggcc cgcgggcttg ggcgctgctc tgcctcgggc    120
```

```
tcctgctccc gggaggcggc gctgcgtgga gcatcggggc agctccgttc tccggacgca    180

gatgaccatg ctgactgtca tagagcagcc agtacctcca acaccagcta cccctgagga    240

ccctgccccg ctctggggtc cccctcctgc ccagggcagc cccggagatg gaggcctcca    300

ggaccaagtc ggtgcttggg ggcttcccgg gcccaccggc cccaagggag atgccggcag    360

tcggggccca atggggatga gaggcccacc aggtccacag ggccccccag ggagccctgg    420

ccgggctgga gctgtgggca cccctggaga gaggggacct cctgggccac cagggcctcc    480

tg                                                                   482
```

<210> SEQ ID NO 75
<211> LENGTH: 2066
<212> TYPE: DNA
<213> ORGANISM: Homo sapiens

<400> SEQUENCE: 75

```
cgggcaggca ggcggggagg acaggctggg ggcggcgacc gcgaggggcc gcgcgcggag     60

ggcgcctggt gcagcatggg cggcccgcgg gcttgggcgc tgctctgcct cgggctcctg    120

ctcccgggag gcggcgctgc gtggagcatc ggggcagctc cgttctccgg acgcaggaac    180

tggtgctcct atgtggtgac ccgcaccatc tcatgccatg tgcagaatgg cacctacctt    240

cagcgagtgc tgcagaactg cccctggccc atgagctgtc cggggagcag ctacagaact    300

gtggtgagac ccacatacaa ggtgatgtac aagatagtga ccgcccgtga gtggaggtgc    360

tgccctgggc actcaggagt gagctgcgag gaagttgcag cttcctctgc ctccttggag    420

cccatgtggt cgggcagtac catgcggcgg atggcgcttc ggcccacagc cttctcaggt    480

tgtctcaact gcagcaaagt gtcagagctg acagagcggc tgaaggtgct ggaggccaag    540

atgaccatgc tgactgtcat agagcagcca gtacctccaa caccagctac ccctgaggac    600

cctgccccgc tctggggtcc ccctcctgcc cagggcagcc ccggagatgg aggcctccag    660

gaccaagtcg gtgcttgggg gcttcccggg cccaccggcc ccaagggaga tgccggcagt    720

cggggcccaa tggggatgag aggcccacca ggtccacagg gccccccagg gagccctggc    780

cgggctggag ctgtgggcac ccctggagag aggggacctc ctgggccacc agggcctcct    840

ggcccccctg ggcccccagc ccctgttggg ccaccccatg cccggatctc ccagcatgga    900

gacccattgc tgtccaacac cttcactgag accaacaacc actggcccca gggacccact    960

gggcctccag gccctccagg gcccatgggt ccccctgggc ctcctggccc cacaggtgtc   1020

cctgggagtc ctggtcacat aggacccccca ggccccactg gacccaaagg aatctctggc   1080

cacccaggag agaagggcga gagaggactg cgtggggagc ctggccccca aggctctgct   1140

gggcagcggg gggaacctgg ccctaaggga gaccctggtg agaagagcca ctgggctcct   1200

agcttacaga gcttcctgca gcagcaggct cagctggagc tcctggccag acgggtcacc   1260

ctcctggaag ccatcatctg gccagaacca gagctggggt ctggggcggg ccctgccggc   1320

acaggcaccc ccagcctcct tcggggcaag aggggcggac atgcaaccaa ctaccggatc   1380

gtggccccca ggagccggga cgagagaggc tgagggtggt ggcggcccct gaggcagacc   1440

aggccaggct tcccctccta cctggactcg gccagctgcc tccagggacc gcccgtccat   1500

atttattaat gtcctcaggg tcccttctgc catctaggcc ttaggggtaa gcaggtctca   1560

gtcctggcac catgcacatg tctgaggctg agcaagggct gagaggagag gcttgggcct   1620

cagtttccct ctgtgaagtg gggggaggca ggccttcaag gagggataga ggtacaaggc   1680

ttcgtctcat ctgctgtctg agcatccagg cccaaaggca ctgagggagt caggagctgg   1740
```

```
ggctcggcac atgcagagat gacagggcag ggggcagtct tcctccccct ccccgaccaa   1800
acctcgggga gccctcctgt gcccctccct ccttgttgtc cagtgctggg ctccccaccc   1860
cgaggtcagg ctgcccaatc ctctgactgg atcaccgggg gcttcttgcc tcagttcttc   1920
cctctgagcc cccaggccct cccgcatctc aggttgggga tggggacatg gagaggaagg   1980
ggccgcctac tcctgcaaat gcttgtgaca gatgccagga ggtagatgtg tgctggccaa   2040
taaaggcccc tacctgattc cccgca                                        2066
```

<210> SEQ ID NO 76
<211> LENGTH: 2060
<212> TYPE: DNA
<213> ORGANISM: Homo sapiens

<400> SEQUENCE: 76

```
cgggcaggca ggcggggagg acaggctggg ggcggcgacc gcgaggggcc gcgcgcggag     60
ggcgcctggt gcagcatggg cggcccgcgg gcttgggcgc tgctctgcct cgggctcctg    120
ctcccgggag gcggcgctgc gtggagcatc ggggcagctc cgttctccgg acgcaggaac    180
tggtgctcct atgtggtgac ccgcaccatc tcatgccatg tgcagaatgg cacctacctt    240
cagcgagtgc tgcagaactg cccctggccc atgagctgtc cggggagcag ctacagaact    300
gtggtgagac ccacatacaa ggtgatgtac aagatagtga ccgcccgtga gtggaggtgc    360
tgccctgggc actcaggagt gagctgcgag gaagttgcag cttcctctgc ctccttggag    420
cccatgtggt cgggcagtac catgcggcgg atggcgcttc ggcccacagc cttctcaggt    480
tgtctcaact gcagcaaagt gtcagagctg acagagcggc tgaaggtgct ggaggccaag    540
atgaccatgc tgactgtcat agagcagcca gtacctccaa caccagctac ccctgaggac    600
cctgccccgc tctggggtcc ccctcctgcc cagggcagcc ccggagatgg aggcctccag    660
gaccaagtcg gtgcttgggg gcttcccggg cccaccggcc ccaagggaga tgccggcagt    720
cggggcccaa tggggatgag aggcccacca ggtccacagg gccccccagg gagccctggc    780
cgggctggag ctgtgggcac ccctggagag aggggacctc ctgggccacc agggcctcct    840
ggcccccctg ggcccccagc ccctgttggg ccaccccatg cccggatctc ccagcatgga    900
gacccattgc tgtccaacac cttcactgag accaacaacc actggcccca gggacccact    960
gggcctccag gccctccagg gcccatgggt ccccctgggc ctcctggccc cacaggtgtc   1020
cctgggagtc ctggtcacat aggaccccca ggccccactg gacccaaagg aatctctggc   1080
cacccaggag agaagggcga gagaggactg cgtggggagc ctggccccca aggctctgct   1140
gggcagcggg gggaacctgg ccctaaggga gaccctggtg agaagagcca ctggggggag   1200
gggttgcacc agctacgcga ggctttgaag attttagctg agagggtttt aatcttggaa   1260
acaatgattg ggctctatga accagagctg gggtctgggg cgggccctgc cggcacaggc   1320
acccccagcc tccttcgggg caagaggggc ggacatgcaa ccaactaccg gatcgtggcc   1380
cccaggagcc gggacgagag aggctgaggg tggtggcggc ccctgaggca gaccaggcca   1440
ggcttcccct cctacctgga ctcggccagc tgcctccagg gaccgcccgt ccatatttat   1500
taatgtcctc agggtccctt ctgccatcta ggccttaggg gtaagcaggt ctcagtcctg   1560
gcaccatgca catgtctgag gctgagcaag ggctgagagg agaggcttgg gcctcagttt   1620
ccctctgtga agtgggggga ggcaggcctt caaggaggga tagaggtaca aggcttcgtc   1680
tcatctgctg tctgagcatc caggcccaaa ggcactgagg gagtcaggag ctggggctcg   1740
```

```
gcacatgcag agatgacagg gcagggggca gtcttcctcc ccctccccga ccaaacctcg   1800

gggagccctc ctgtgcccct ccctccttgt tgtccagtgc tgggctcccc accccgaggt   1860

caggctgccc aatcctctga ctggatcacc gggggcttct tgcctcagtt cttccctctg   1920

agcccccagg ccctcccgca tctcaggttg gggatgggga catggagagg aaggggccgc   1980

ctactcctgc aaatgcttgt gacagatgcc aggaggtaga tgtgtgctgg ccaataaagg   2040

cccctacctg attccccgca                                               2060
```

<210> SEQ ID NO 77
<211> LENGTH: 2054
<212> TYPE: DNA
<213> ORGANISM: Homo sapiens

<400> SEQUENCE: 77

```
cgggcaggca ggcggggagg acaggctggg ggcggcgacc gcgaggggcc gcgcgcggag     60

ggcgcctggt gcagcatggg cggcccgcgg gcttgggcgc tgctctgcct cgggctcctg    120

ctcccgggag gcggcgctgc gtggagcatc ggggcagctc cgttctccgg acgcaggaac    180

tggtgctcct atgtggtgac ccgcaccatc tcatgccatg tgcagaatgg cacctacctt    240

cagcgagtgc tgcagaactg cccctggccc atgagctgtc cggggagcag ctacagaact    300

gtggtgagac ccacatacaa ggtgatgtac aagatagtga ccgcccgtga gtggaggtgc    360

tgccctgggc actcaggagt gagctgcgag gaagcttcct ctgcctcctt ggagcccatg    420

tggtcgggca gtaccatgcg gcggatggcg cttcggccca cagccttctc aggttgtctc    480

aactgcagca aagtgtcaga gctgacagag cggctgaagg tgctggaggc caagatgacc    540

atgctgactg tcatagagca gccagtacct ccaacaccag ctacccctga ggaccctgcc    600

ccgctctggg gtcccccctcc tgcccagggc agccccggag atggaggcct ccaggaccaa    660

gtcggtgctt gggggcttcc cggcccacc ggccccaagg gagatgccgg cagtcggggc    720

ccaatgggga tgagaggccc accaggtcca cagggccccc cagggagccc tggccgggct    780

ggagctgtgg gcacccctgg agagagggga cctcctgggc caccagggcc tcctggcccc    840

cctgggcccc cagcccctgt tgggccaccc catgcccgga tctcccagca tggagaccca    900

ttgctgtcca acaccttcac tgagaccaac aaccactggc cccagggacc cactgggcct    960

ccaggccctc cagggcccat gggtcccccct gggcctcctg gccccacagg tgtccctggg   1020

agtcctggtc acataggacc cccaggcccc actggaccca aaggaatctc tggccaccca   1080

ggagagaagg gcgagagagg actgcgtggg gagcctggcc cccaaggctc tgctgggcag   1140

cggggggaac ctggccctaa gggagaccct ggtgagaaga gccactgggg ggaggggttg   1200

caccagctac gcgaggcttt gaagatttta gctgagaggg ttttaatctt ggaaacaatg   1260

attgggctct atgaaccaga gctggggtct ggggcgggcc ctgccggcac aggcaccccc   1320

agcctccttc ggggcaagag gggcggacat gcaaccaact accggatcgt ggcccccagg   1380

agccgggacg agagaggctg agggtggtgg cggcccctga ggcagaccag gccaggcttc   1440

ccctcctacc tggactcggc cagctgcctc cagggaccgc ccgtccatat ttattaatgt   1500

cctcagggtc ccttctgcca tctaggcctt aggggtaagc aggtctcagt cctggcacca   1560

tgcacatgtc tgaggctgag caagggctga gaggagaggc ttgggcctca gtttccctct   1620

gtgaagtggg gggaggcagg ccttcaagga gggatagagg tacaaggctt cgtctcatct   1680

gctgtctgag catccaggcc caaaggcact gagggagtca ggagctgggg ctcggcacat   1740

gcagagatga cagggcaggg ggcagtcttc ctcccctcc ccgaccaaac ctcggggagc   1800
```

```
cctcctgtgc ccctccctcc ttgttgtcca gtgctgggct ccccaccccg aggtcaggct   1860

gcccaatcct ctgactggat caccgggggc ttcttgcctc agttcttccc tctgagcccc   1920

caggccctcc cgcatctcag gttggggatg ggacatggga gaggaagggg ccgcctactc   1980

ctgcaaatgc ttgtgacaga tgccaggagg tagatgtgtg ctggccaata aaggccccta   2040

cctgattccc cgca                                                     2054
```

<210> SEQ ID NO 78
<211> LENGTH: 2048
<212> TYPE: DNA
<213> ORGANISM: Homo sapiens

<400> SEQUENCE: 78

```
cgggcaggca ggcggggagg acaggctggg ggcggcgacc gcgagggggcc gcgcgcggag    60

ggcgcctggt gcagcatggg cggcccgcgg gcttgggcgc tgctctgcct cgggctcctg   120

ctcccgggag gcggcgctgc gtggagcatc ggggcagctc cgttctccgg acgcaggaac   180

tggtgctcct atgtggtgac ccgcaccatc tcatgccatg tgcagaatgg cacctacctt   240

cagcgagtgc tgcagaactg cccctggccc atgagctgtc cggggagcag aactgtggtg   300

agacccacat acaaggtgat gtacaagata gtgaccgccc gtgagtggag gtgctgccct   360

gggcactcag gagtgagctg cgaggaagct tcctctgcct ccttggagcc catgtggtcg   420

ggcagtacca tgcggcggat ggcgcttcgg cccacagcct tctcaggttg tctcaactgc   480

agcaaagtgt cagagctgac agagcggctg aaggtgctgg aggccaagat gaccatgctg   540

actgtcatag agcagccagt acctccaaca ccagctaccc ctgaggaccc tgccccgctc   600

tggggtcccc ctcctgccca gggcagcccc ggagatggag gcctccagga ccaagtcggt   660

gcttgggggc ttcccgggcc caccggcccc aagggagatg ccggcagtcg ggcccaatg   720

gggatgagag gcccaccagg tccacagggc cccccaggga gccctggccg ggctggagct   780

gtgggcaccc ctggagagag gggacctcct gggccaccag ggcctcctgg cccccctggg   840

cccccagccc ctgttgggcc accccatgcc cggatctccc agcatggaga cccattgctg   900

tccaacacct tcactgagac caacaaccac tggccccagg gacccactgg gcctccaggc   960

cctccagggc ccatgggtcc ccctgggcct cctggcccca caggtgtccc tgggagtcct  1020

ggtcacatag gacccccagg ccccactgga cccaaaggaa tctctggcca cccaggagag  1080

aagggcgaga gaggactgcg tggggagcct ggcccccaag gctctgctgg gcagcggggg  1140

gaacctggcc ctaagggaga ccctggtgag aagagccact gggggggaggg gttgcaccag  1200

ctacgcgagg ctttgaagat tttagctgag agggttttaa tcttggaaac aatgattggg  1260

ctctatgaac cagagctggg gtctggggcg ggccctgccg gcacaggcac ccccagcctc  1320

cttcggggca agaggggcgg acatgcaacc aactaccgga tcgtggcccc caggagccgg  1380

gacgagagag gctgagggtg gtggcggccc ctgaggcaga ccaggccagg cttcccctcc  1440

tacctggact cggccagctg cctccaggga ccgcccgtcc atatttatta atgtcctcag  1500

ggtcccttct gccatctagg ccttaggggt aagcaggtct cagtcctggc accatgcaca  1560

tgtctgaggc tgagcaaggg ctgagaggag aggcttgggc ctcagtttcc ctctgtgaag  1620

tggggggagg caggccttca aggagggata gaggtacaag gcttcgtctc atctgctgtc  1680

tgagcatcca ggcccaaagg cactgaggga gtcaggagct ggggctcggc acatgcagag  1740

atgacagggc agggggcagt cttcctcccc ctccccgacc aaacctcggg gagccctcct  1800
```

```
gtgcccctcc ctccttgttg tccagtgctg ggctccccac cccgaggtca ggctgcccaa   1860

tcctctgact ggatcaccgg gggcttcttg cctcagttct tccctctgag cccccaggcc   1920

ctcccgcatc tcaggttggg gatggggaca tggagaggaa ggggccgcct actcctgcaa   1980

atgcttgtga cagatgccag gaggtagatg tgtgctggcc aataaaggcc cctacctgat   2040

tccccgca                                                             2048
```

<210> SEQ ID NO 79
<211> LENGTH: 1997
<212> TYPE: DNA
<213> ORGANISM: Homo sapiens

<400> SEQUENCE: 79

```
cgggcaggca ggcggggagg acaggctggg ggcggcgacc gcgaggggcc gcgcgcggag     60

ggcgcctggt gcagcatggg cggcccgcgg gcttgggcgc tgctctgcct cgggctcctg    120

ctcccgggag gcggcgctgc gtggagcatc ggggcagctc cgttctccgg acgcaggaac    180

tggtgctcct atgtggtgac ccgcaccatc tcatgccatg tgcagaatgg cacctacctt    240

cagcgagtgc tgcagaactg cccctggccc atgagctgtc cggggagcag ctacagaact    300

gtggtgagac ccacatacaa ggtgatgtac aagatagtga ccgcccgtga gtggaggtgc    360

tgccctgggc actcaggagt gagctgcgag gaagttgcag cttcctctgc ctccttggag    420

cccatgtggt cgggcagtac catgcggcgg atggcgcttc ggcccacagc cttctcaggt    480

tgtctcaact gcagcaaagt gtcagagctg acagagcggc tgaaggtgct ggaggccaag    540

atgaccatgc tgactgtcat agagcagcca gtacctccaa caccagctac ccctgaggac    600

cctgccccgc tctggggtcc ccctcctgcc cagggcagcc ccggagatgg aggcctccag    660

gaccaagtcg gtgcttgggg gcttcccggg cccaccggcc ccaagggaga tgccggcagt    720

cggggcccaa tggggatgag aggcccacca ggtccacagg gcccccccagg gagccctggc    780

cgggctggag ctgtgggcac ccctggagag aggggacctc ctgggccacc agggcctcct    840

ggcccccctg ggcccccagc ccctgttggg ccaccccatg cccggatctc ccagcatgga    900

gacccattgc tgtccaacac cttcactgag accaacaacc actggcccca gggacccact    960

gggcctccag gccctccagg gcccatgggt ccccctgggc ctcctggccc cacaggtgtc   1020

cctgggagtc ctggtcacat aggactgcgt ggggagcctg gcccccaagg ctctgctggg   1080

cagcgggggg aacctggccc taagggagac cctggtgaga agagccactg gggggagggg   1140

ttgcaccagc tacgcgaggc tttgaagatt ttagctgaga gggttttaat cttggaaaca   1200

atgattgggc tctatgaacc agagctgggg tctggggcgg gccctgccgg cacaggcacc   1260

cccagcctcc ttcggggcaa gaggggcgga catgcaacca actaccggat cgtggccccc   1320

aggagccggg acgagagagg ctgagggtgg tggcggcccc tgaggcagac caggccaggc   1380

ttcccctcct acctggactc ggccagctgc ctccagggac cgcccgtcca tatttattaa   1440

tgtcctcagg gtcccttctg ccatctaggc cttaggggta agcaggtctc agtcctggca   1500

ccatgcacat gtctgaggct gagcaagggc tgagaggaga ggcttgggcc tcagtttccc   1560

tctgtgaagt ggggggaggc aggccttcaa ggagggatag aggtacaagg cttcgtctca   1620

tctgctgtct gagcatccag gcccaaaggc actgagggag tcaggagctg gggctcggca   1680

catgcagaga tgacagggca gggggcagtc ttcctccccc tccccgacca aacctcgggg   1740

agccctcctg tgcccctccc tccttgttgt ccagtgctgg gctccccacc ccgaggtcag   1800

gctgcccaat cctctgactg gatcaccggg ggcttcttgc ctcagttctt ccctctgagc   1860
```

```
ccccaggccc tcccgcatct caggttgggg atggggacat ggagaggaag gggccgccta   1920

ctcctgcaaa tgcttgtgac agatgccagg aggtagatgt gtgctggcca ataaaggccc   1980

ctacctgatt ccccgca                                                  1997
```

<210> SEQ ID NO 80
<211> LENGTH: 1823
<212> TYPE: DNA
<213> ORGANISM: Homo sapiens

<400> SEQUENCE: 80

```
cgggcaggca ggcggggagg acaggctggg ggcggcgacc gcgaggggcc gcgcgcggag     60

ggcgcctggt gcagcatggg cggcccgcgg gcttgggcgc tgctctgcct cgggctcctg    120

ctcccgggag gcggcgctgc gtggagcatc ggggcagctc cgttctccgg acgcaggaac    180

tggtgctcct atgtggtgac ccgcaccatc tcatgccatg tgcagaatgg cacctacctt    240

cagcgagtgc tgcagaactg cccctggccc atgagctgtc cggggagcag ctacagaact    300

gtggtgagac ccacatacaa ggtgatgtac aagatagtga ccgcccgtga gtggaggtgc    360

tgccctgggc actcaggagt gagctgcgag gaagttgcag cttcctctgc ctccttggag    420

cccatgtggt cgggcagtac catgcggcgg atggcgcttc ggcccacagc cttctcaggt    480

tgtctcaact gcagcaaagt gtcagagctg acagagcggc tgaaggtgct ggaggccaag    540

atgaccatgc tgactgtcat agagcagcca gtacctccaa caccagctac ccctgaggac    600

cctgccccgc tctggggtcc ccctcctgcc cagggcagcc ccggagatgg aggcctccag    660

ggagacccat tgctgtccaa caccttcact gagaccaaca accactggcc ccagggaccc    720

actgggcctc caggccctcc agggcccatg ggtccccctg ggcctcctgg ccccacaggt    780

gtccctggga gtcctggtca cataggaccc ccaggcccca ctggacccaa aggaatctct    840

ggccacccag gagagaaggg cgagagagga ctgcgtgggg agcctggccc ccaaggctct    900

gctgggcagc ggggggaacc tggccctaag ggagaccctg gtgagaagag ccactggggg    960

gaggggttgc accagctacg cgaggctttg aagattttag ctgagagggt tttaatcttg   1020

gaaacaatga ttgggctcta tgaaccagag ctggggtctg ggcgggcccc tgccggcaca   1080

ggcaccccca gcctccttcg gggcaagagg ggcggacatg caaccaacta ccggatcgtg   1140

gcccccagga gccgggacga gagaggctga gggtggtggc ggcccctgag gcagaccagg   1200

ccaggcttcc cctcctacct ggactcggcc agctgcctcc agggaccgcc cgtccatatt   1260

tattaatgtc ctcagggtcc cttctgccat ctaggcctta ggggtaagca ggtctcagtc   1320

ctggcaccat gcacatgtct gaggctgagc aagggctgag aggagaggct tgggcctcag   1380

tttccctctg tgaagtgggg ggaggcaggc cttcaaggag ggatagaggt acaaggcttc   1440

gtctcatctg ctgtctgagc atccaggccc aaaggcactg agggagtcag gagctggggc   1500

tcggcacatg cagagatgac agggcagggg gcagtcttcc tccccctccc cgaccaaacc   1560

tcggggagcc ctcctgtgcc cctccctcct tgttgtccag tgctgggctc cccaccccga   1620

ggtcaggctg cccaatcctc tgactggatc accgggggct tcttgcctca gttcttccct   1680

ctgagccccc aggccctccc gcatctcagg ttggggatgg ggacatggag aggaaggggc   1740

cgcctactcc tgcaaatgct tgtgacagat gccaggaggt agatgtgtgc tggccaataa   1800

aggcccctac ctgattcccc gca                                           1823
```

<210> SEQ ID NO 81

<211> LENGTH: 1976
<212> TYPE: DNA
<213> ORGANISM: Homo sapiens

<400> SEQUENCE: 81

```
cgggcaggca ggcggggagg acaggctggg ggcggcgacc gcgaggggcc gcgcgcggag      60
ggcgcctggt gcagcatggg cggcccgcgg gcttgggcgc tgctctgcct cgggctcctg     120
ctcccgggag gcggcgctgc gtggagcatc ggggcagctc cgttctccgg acgcaggaac     180
tggtgctcct atgtggtgac ccgcaccatc tcatgccatg tgcagaatgg cacctacctt     240
cagcgagtgc tgcagaactg cccctggccc atgagctgtc cggggagcag ctacagaact     300
gtggtgagac ccacatacaa ggtgatgtac aagatagtga ccgcccgtga gtggaggtgc     360
tgccctgggc actcaggagt gagctgcgag gaaggttgtc tcaactgcag caaagtgtca     420
gagctgacag agcggctgaa ggtgctggag gccaagatga ccatgctgac tgtcatagag     480
cagccagtac ctccaacacc agctacccct gaggaccctg ccccgctctg ggtcccccct     540
cctgcccagg gcagccccgg agatggaggc ctccaggacc aagtcggtgc ttgggggctt     600
cccgggccca ccggccccaa gggagatgcc ggcagtcggg gcccaatggg gatgagaggc     660
ccaccaggtc cacagggccc cccagggagc cctggccggg ctggagctgt gggcacccct     720
ggagagaggg gacctcctgg gccaccaggg cctcctggcc cccctgggcc cccagcccct     780
gttgggccac cccatgcccg gatctcccag catggagacc cattgctgtc caacaccttc     840
actgagacca acaaccactg gccccaggga cccactgggc ctccaggccc tccagggccc     900
atgggtcccc ctgggcctcc tggccccaca ggtgtccctg ggagtcctgg tcacatagga     960
cccccaggcc ccactggacc caaaggaatc tctggccacc caggagagaa gggcgagaga    1020
ggactgcgtg gggagcctgg cccccaaggc tctgctgggc agcgggggga acctggccct    1080
aagggagacc ctggtgagaa gagccactgg ggggaggggt tgcaccagct acgcgaggct    1140
ttgaagattt tagctgagag ggttttaatc ttggaaacaa tgattgggct ctatgaacca    1200
gagctggggt ctggggcggg ccctgccggc acaggcaccc ccagcctcct tcggggcaag    1260
aggggcggac atgcaaccaa ctaccggatc gtggccccca ggagccggga cgagagaggc    1320
tgagggtggt ggcggcccct gaggcagacc aggccaggct tcccctccta cctggactcg    1380
gccagctgcc tccagggacc gcccgtccat atttattaat gtcctcaggg tcccttctgc    1440
catctaggcc ttaggggtaa gcaggtctca gtcctggcac catgcacatg tctgaggctg    1500
agcaagggct gagaggagag gcttgggcct cagtttccct ctgtgaagtg gggggaggca    1560
ggccttcaag gagggataga ggtacaaggc ttcgtctcat ctgctgtctg agcatccagg    1620
cccaaaggca ctgagggagt caggagctgg ggctcggcac atgcagagat gacagggcag    1680
ggggcagtct tcctccccct ccccgaccaa acctcgggga gccctcctgt gcccctccct    1740
ccttgttgtc cagtgctggg ctccccaccc cgaggtcagg ctgcccaatc ctctgactgg    1800
atcaccgggg gcttcttgcc tcagttcttc cctctgagcc cccaggccct cccgcatctc    1860
aggttgggga tggggacatg gagaggaagg ggccgcctac tcctgcaaat gcttgtgaca    1920
gatgccagga ggtagatgtg tgctggccaa taaaggcccc tacctgattc cccgca        1976
```

<210> SEQ ID NO 82
<211> LENGTH: 2111
<212> TYPE: DNA
<213> ORGANISM: Homo sapiens

<400> SEQUENCE: 82

```
cgggcaggca ggcggggagg acaggctggg ggcggcgacc gcgaggggcc gcgcgcggag      60
ggcgcctggt gcagcatggg cggcccgcgg gcttgggcgc tgctctgcct cgggctcctg     120
ctcccgggag gcggcgctgc gtggagcatc ggggcagctc cgttctccgg acgcaggaac     180
tggtgctcct atgtggtgac ccgcaccatc tcatgccatg tgcagaatgg cacctacctt     240
cagcgagtgc tgcagaactg cccctggccc atgagctgtc cggggagcag ctacagaact     300
gtggtgagac ccacatacaa ggtgatgtac aagatagtga ccgcccgtga gtggaggtgc     360
tgccctgggc actcaggagt gagctgcgag gaagttgcag cttcctctgc ctccttggag     420
cccatgtggt cgggcagtac catgcggcgg atggcgcttc ggcccacagc cttctcaggt     480
tgtctcaact gcagcaaagt gtcagagctg acagagcggc tgaaggtgct ggaggccaag     540
atgaccatgc tgactgtcat agagcagcca gtacctccaa caccagctac ccctgaggac     600
cctgccccgc tctggggtcc ccctcctgcc cagggcagcc ccggagatgg aggcctccag     660
gggctgccag gagccataga gagtgtgagg gtcccgctgc ttccccgaaa tgaccaagtc     720
ggtgcttggg ggcttcccgg gcccaccggc cccaagggag atgccggcag tcggggccca     780
atggggatga gaggcccacc aggtccacag ggcccccccag ggagccctgg ccgggctgga     840
gctgtgggca cccctggaga gaggggacct cctgggccac cagggcctcc tggccccccct     900
gggcccccag cccctgttgg gccaccccat gcccggatct cccagcatgg agacccattg     960
ctgtccaaca ccttcactga gaccaacaac cactggcccc agggacccac tgggcctcca    1020
ggccctccag ggcccatggg tccccctggg cctcctggcc ccacaggtgt ccctgggagt    1080
cctggtcaca taggaccccc aggccccact ggacccaaag gaatctctgg ccacccagga    1140
gagaagggcg agagaggact gcgtggggag cctggccccc aaggctctgc tgggcagcgg    1200
ggggaacctg gccctaaggg agaccctggt gagaagagcc actgggggga ggggttgcac    1260
cagctacgcg aggctttgaa gattttagct gagagggttt taatcttgga aacaatgatt    1320
gggctctatg aaccagagct ggggtctggg gcgggccctg ccggcacagg cacccccagc    1380
ctccttcggg gcaagagggg cggacatgca accaactacc ggatcgtggc ccccaggagc    1440
cgggacgaga gaggctgagg gtggtggcgg cccctgaggc agaccaggcc aggcttcccc    1500
tcctacctgg actcggccag ctgcctccag ggaccgcccg tccatattta ttaatgtcct    1560
cagggtccct tctgccatct aggccttagg ggtaagcagg tctcagtcct ggcaccatgc    1620
acatgtctga ggctgagcaa gggctgagag gagaggcttg ggcctcagtt tccctctgtg    1680
aagtgggggg aggcaggcct tcaaggaggg atagaggtac aaggcttcgt ctcatctgct    1740
gtctgagcat ccaggcccaa aggcactgag ggagtcagga gctggggctc ggcacatgca    1800
gagatgacag ggcagggggc agtcttcctc cccctccccg accaaacctc ggggagccct    1860
cctgtgcccc tccctccttg ttgtccagtg ctgggctccc caccccgagg tcaggctgcc    1920
caatcctctg actggatcac cgggggcttc ttgcctcagt tcttccctct gagcccccag    1980
gccctcccgc atctcaggtt ggggatgggg acatggagag gaagggggccg cctactcctg    2040
caaatgcttg tgacagatgc caggaggtag atgtgtgctg gccaataaag gcccctacct    2100
gattccccgc a                                                         2111
```

<210> SEQ ID NO 83
<211> LENGTH: 707
<212> TYPE: DNA
<213> ORGANISM: Homo sapiens

<400> SEQUENCE: 83
agatgaccat gctgactgtc atagagcagc cagtacctcc aacaccagct acccctgagg 60
accctgcccc gctctggggt ccccctcctg cccagggcag ccccggagat ggaggcctcc 120
aggggctgcc aggagccata gagagtgtga gggtcccgct gcttccccga aatgaccaag 180
tcggtgcttg gggcttccc gggcccaccg gccccaaggg agatgccggc agtcggggcc 240
caatggggat gagaggccca ccaggtccac agggccccc agggagccct ggccgggctg 300
gagctgtggg cacccctgga gagaggggac ctcctgggcc accagggcct cctggccccc 360
ctgggccccc agcccctgtt gggccacccc atgcccggat ctcccagcat ggagacccat 420
tgctgtccaa caccttcact gagaccaaca accactggcc ccagggaccc actgggcctc 480
caggccctcc agggcccatg ggtcccctg ggcctcctgg ccccacaggt gtccctggga 540
gtcctggtca cataggaccc ccaggcccca ctggacccaa aggaatctct ggccacccag 600
gagagaaggg cgagagagga ctgcgtgggg agcctggccc ccaaggctct gctgggcagc 660
ggggggaacc tggccctaag ggagaccctg gtgagaagag ccactgg 707

<210> SEQ ID NO 84
<211> LENGTH: 2034
<212> TYPE: DNA
<213> ORGANISM: Homo sapiens

<400> SEQUENCE: 84
ggtgagtgcc cgcaatgctg ccccacagct cctctggcca tcccctccac caggtgggcc 60
cttccctgct cctgacatgg ccaggatgac ctgggccctt tcatctactt gcctcttcac 120
tcagcacccc accacggagt gccctgccca cgcctgggct ccatgaagtc ctctcttatg 180
ttcactgacc cacattccct gggcacctac acttatcagg ctctgagctg ggcactgggt 240
ggggtcagac atgtccctgc ccttctggag cttccatgct gctgggagca gggctgggca 300
gaggagaagc agcaatgctt gccccatgtg accagggttt ctatgagggg ttttgggggt 360
ttgggagccc caaggaagga agactcagcc tggacgaggt ggagaactag gtgctgtgct 420 catcccctg ttagactacc aggcagccta ggcctgtgga ctccggggcc ctctctcatg 480
cccactgctc caggctgcct tgtcctgtcg ctcaaggcca ccctgggcct ccttgcctcc 540
tgtataccca caaatccgtg tgattccatt gcaggtccac agggcccccc agggagccct 600
ggccgggctg gagctgtggg cacccctgga gagaggggac ctcctgggcc accagggcct 660
cctggccccc ctgggccccc agcccctgtt gggccacccc atgcccggat ctcccagcat 720
ggtgagtccc cctgggatcc cagcaggtgg aggtgggggt ggagtagcca tcagcacagt 780
gcccgctacc atctgccacg tgccttctgt gtgccagccc tgctcacgat aggccacatg 840
tgacccagtc ctccagcagg cgccgttgtc ctcctgtggt tacaggtgag gaacactgag 900
gaccagagag ggaaggtggc ttgccagggt cccacagcct gggcgtaggg gaacggcttc 960
aaacccaggc tgcctccaga acctgtgctt agagccaccg ggcatcaggc cctcccaagc 1020
cttggaactg gctggaatcc agttctcgga acactgggac gcaaaagacc cggcggcagg 1080
aagtgagtcc tgaactccca aggccacagg cccggcccct cctccaggcc ctgacgtgcg 1140
tccttggctt cttccctttg gcagcccagc ctgacctgcc catgggctgc caggggtcag 1200
agtgtggagc gccaggtttc agcctcttct ccactgtgtt tttggtgcac aacccagcac 1260
accattcatt cattctgcca tcccagcatt cattccatct cactatccat acgatgggga 1320
caatgacagt gccagcctcc cagagctgcg taacatccat gtacagaagc ctggcacaca 1380

```
gtaggtggtg gataaatggt atcttttatt gtcattccca tttgacaggt gacagtacag   1440

gctctgaaaa gtagaaagtg ttgctggatg tcaccagctg gattgcagtg gggttagaac   1500

ccacatctcc ctgcctcctg gtcttgcggg accaacactc tccacactcc tcaccctgga   1560

gcaggtgccc aggtggtacc agccatgctg caggctgccc catagggcag tccaagctgt   1620

cttggcagag gtggcaggtg aagactaacc accccactct acccagctct actcactcat   1680

catctttgct cacccaggag acccattgct gtccaacacc ttcactgaga ccaacaacca   1740

ctggccccag ggacccactg ggcctccagg ccctccaggg cccatgggtc cccctgggcc   1800

tcctggcccc acaggtgtcc ctgggagtcc tggtcacata gtgagtagtt ctccttgtac   1860

tctcacccat gtgtctgtcc atctttccat ctatgcatac atccatacat ctgtccatca   1920

tccacccttg tatccatcta tccatccatc cattcatcct tccattcatt cattcaacaa   1980

gtatttattg agcacttaat atgcaaacta ccttccataa atcttattca atcc         2034
```

<210> SEQ ID NO 85
<211> LENGTH: 409
<212> TYPE: PRT
<213> ORGANISM: Homo sapiens

<400> SEQUENCE: 85

```
Met Glu Glu Ser Trp Glu Ala Ala Pro Gly Gly Gln Ala Gly Ala Glu
1               5                   10                  15

Leu Pro Met Glu Pro Val Gly Ser Leu Val Pro Thr Leu Glu Gln Pro
            20                  25                  30

Gln Val Pro Ala Lys Val Arg Gln Pro Glu Gly Pro Glu Ser Ser Pro
        35                  40                  45

Ser Pro Ala Gly Ala Val Glu Lys Ala Ala Gly Ala Gly Leu Glu Pro
    50                  55                  60

Ser Ser Lys Lys Lys Pro Pro Ser Pro Arg Pro Gly Ser Pro Arg Val
65                  70                  75                  80

Pro Pro Leu Ser Leu Gly Tyr Gly Val Cys Pro Glu Pro Pro Ser Pro
                85                  90                  95

Gly Pro Ala Leu Val Lys Leu Pro Arg Asn Gly Glu Ala Pro Gly Ala
            100                 105                 110

Glu Pro Ala Pro Ser Ala Trp Ala Pro Met Glu Leu Gln Val Asp Val
        115                 120                 125

Arg Val Lys Pro Val Gly Ala Ala Gly Gly Ser Ser Thr Pro Ser Pro
    130                 135                 140

Arg Pro Ser Thr Arg Phe Leu Lys Val Pro Val Pro Glu Ser Pro Ala
145                 150                 155                 160

Phe Ser Arg His Ala Asp Pro Ala His Gln Leu Leu Leu Arg Ala Pro
                165                 170                 175

Ser Gln Gly Gly Thr Trp Gly Arg Arg Ser Pro Leu Ala Ala Ala Arg
            180                 185                 190

Thr Glu Ser Gly Cys Asp Ala Glu Gly Arg Ala Ser Pro Ala Glu Gly
        195                 200                 205

Ser Ala Gly Ser Pro Gly Ser Pro Thr Cys Cys Arg Cys Lys Glu Leu
    210                 215                 220

Gly Leu Glu Lys Glu Asp Ala Ala Leu Leu Pro Arg Ala Gly Leu Asp
225                 230                 235                 240

Gly Asp Glu Lys Leu Pro Arg Ala Val Thr Leu Thr Gly Leu Pro Met
                245                 250                 255
```

```
Tyr Val Lys Ser Leu Tyr Trp Ala Leu Ala Phe Met Ala Val Leu Leu
            260                 265                 270

Ala Val Ser Gly Val Val Ile Val Val Leu Ala Ser Arg Ala Gly Ala
        275                 280                 285

Arg Cys Gln Gln Cys Pro Pro Gly Trp Val Leu Ser Glu Glu His Cys
    290                 295                 300

Tyr Tyr Phe Ser Ala Glu Ala Gln Ala Trp Glu Ala Ser Gln Ala Phe
305                 310                 315                 320

Cys Ser Ala Tyr His Ala Thr Leu Pro Leu Leu Ser His Thr Gln Asp
                325                 330                 335

Phe Leu Gly Arg Tyr Pro Val Ser Arg His Ser Trp Val Gly Ala Trp
            340                 345                 350

Arg Gly Pro Gln Gly Trp His Trp Ile Asp Glu Ala Pro Leu Pro Pro
        355                 360                 365

Gln Leu Leu Pro Glu Asp Gly Glu Asp Asn Leu Asp Ile Asn Cys Gly
    370                 375                 380

Ala Leu Glu Glu Gly Thr Leu Val Ala Ala Asn Cys Ser Thr Pro Arg
385                 390                 395                 400

Pro Trp Val Cys Ala Lys Gly Thr Gln
                405


<210> SEQ ID NO 86
<211> LENGTH: 314
<212> TYPE: PRT
<213> ORGANISM: Homo sapiens

<400> SEQUENCE: 86

Met Glu Glu Ser Trp Glu Ala Ala Pro Gly Gly Gln Ala Gly Ala Glu
1               5                   10                  15

Leu Pro Met Glu Pro Val Gly Ser Leu Val Pro Thr Leu Glu Gln Pro
            20                  25                  30

Gln Val Pro Ala Lys Val Arg Gln Pro Glu Gly Pro Glu Ser Ser Pro
        35                  40                  45

Ser Pro Ala Gly Ala Val Glu Lys Ala Ala Gly Ala Gly Leu Glu Pro
    50                  55                  60

Ser Ser Lys Lys Lys Pro Pro Ser Pro Arg Pro Gly Ser Pro Arg Val
65                  70                  75                  80

Pro Pro Leu Ser Leu Gly Tyr Gly Val Cys Pro Glu Pro Pro Ser Pro
                85                  90                  95

Gly Pro Ala Leu Val Lys Leu Pro Arg Asn Gly Glu Ala Pro Gly Ala
            100                 105                 110

Glu Pro Ala Pro Ser Ala Trp Ala Pro Met Glu Leu Gln Val Asp Val
        115                 120                 125

Arg Val Lys Pro Val Gly Ala Ala Gly Gly Ser Ser Thr Pro Ser Pro
    130                 135                 140

Arg Pro Ser Thr Arg Phe Leu Lys Val Pro Val Pro Glu Ser Pro Ala
145                 150                 155                 160

Phe Ser Arg His Ala Asp Pro Ala His Gln Leu Leu Leu Arg Ala Pro
                165                 170                 175

Ser Gln Gly Gly Thr Trp Gly Arg Arg Ser Pro Leu Ala Ala Ala Arg
            180                 185                 190

Thr Glu Ser Gly Cys Asp Ala Glu Gly Arg Ala Ser Pro Ala Glu Gly
        195                 200                 205

Ser Ala Gly Ser Pro Gly Ser Pro Thr Cys Cys Arg Cys Lys Glu Leu
    210                 215                 220
```

```
Gly Leu Glu Lys Glu Asp Ala Ala Leu Leu Pro Arg Ala Gly Leu Asp
225                 230                 235                 240

Gly Asp Glu Lys Leu Pro Arg Ala Val Thr Leu Thr Asp Ser Leu Arg
                245                 250                 255

Thr Ala Arg Thr Ile Trp Ile Ser Thr Val Gly Pro Trp Arg Lys Ala
            260                 265                 270

Arg Trp Trp Leu Gln Thr Ala Ala Leu Gln Asp Pro Gly Ser Val Pro
        275                 280                 285

Arg Gly Pro Ser Asp Leu Gly Ser Ala Trp Ser Ser Ala Cys Gln Ala
    290                 295                 300

Asp Ala Ala Pro Pro Thr Gly Glu Ala Ser
305                 310


<210> SEQ ID NO 87
<211> LENGTH: 1544
<212> TYPE: DNA
<213> ORGANISM: Homo sapiens

<400> SEQUENCE: 87

gagagcgaag ctcctctgca ctgggcccag gtgcgctcct cagcgtctcc gggtggcggg      60

gcgcgcggga tggaggagtc ttgggaggct gcgcccggag gccaagccgg ggcagagctc     120

ccaatggagc ccgtgggaag cctggtcccc acgctggagc agccgcaggt gcccgcgaag     180

gtgcgacaac ctgaaggtcc cgaaagcagc ccaagtccgg ccggggccgt ggagaaggcg     240

gcgggcgcag gcctggagcc ctcgagcaag aaaaagccgc cttcgcctcg ccccgggtcc     300

ccgcgcgtgc cgccgctcag cctgggctac ggggtctgcc ccgagccgcc gtcaccgggc     360

cctgccttgg tcaagctgcc ccggaatggc gaggcgcccg gggctgagcc tgcgcccagc     420

gcctgggcgc ccatggagct gcaggtagat gtgcgcgtga agcccgtggg cgcggccggt     480

ggcagcagca cgccatcgcc caggccctcc acgcgcttcc tcaaggtgcc ggtgcccgag     540

tcccctgcct tctcccgcca cgcggacccg gcgcaccagc tcctgctgcg cgcaccatcc     600

cagggcggca cgtggggccg ccgctcgccg ctggctgcag cccggacgga gagcggctgc     660

gacgcagagg gccgggccag ccccgcggaa ggaagcgccg gctccccggg ctcccccacg     720

tgctgccgct gcaaggagct ggggctggag aaggaggatg cggcgctgtt gccccgcgcg     780

gggttggacg gcgacgagaa gctgccccgg gccgtaacgc ttacggggct acccatgtac     840

gtgaagtccc tgtactgggc cctggcgttc atggctgtgc tcctggcagt ctctggggtt     900

gtcattgtgg tcctggcctc aagagcagga gccagatgcc agcagtgccc cccaggctgg     960

gtgttgtccg aggagcactg ttactacttc tctgcagaag cgcaggcctg ggaagccagc    1020

caggctttct gctcagccta ccacgctacc ctcccccctgc taagccacac ccaggacttc    1080

ctgggcagat acccagtctc caggcactcc tgggtggggg cctggcgagg cccccagggc    1140

tggcactgga tcgacgaggc cccactcccg ccccagctac tccctgagga cggcgaggac    1200

aatctggata tcaactgtgg ggccctggag gaaggcacgc tggtggctgc aaactgcagc    1260

actccaagac cctgggtctg tgccaagggg acccagtgat ctgggctctg cctggtcctc    1320

agcctgccag gcagatgcag cacccccctac aggggaggcc agttgagagc ttggcagcc    1380

tcttcctgga cccagttatc caggtcttca tgctctgctc aagggggcca catgagcgag    1440

cctaggagct ggacttcaac ccaggaagat gcatccgagg gaaaggagat tttctatggc    1500

ctcaggcctg agtgccaata ttagtctcca gcttctgtgg atga                     1544
```

<210> SEQ ID NO 88
<211> LENGTH: 1192
<212> TYPE: DNA
<213> ORGANISM: Homo sapiens

<400> SEQUENCE: 88

```
gagagcgaag ctcctctgca ctgggcccag gtgcgctcct cagcgtctcc gggtggcggg     60
gcgcgcggga tggaggagtc ttgggaggct gcgcccggag gccaagccgg ggcagagctc    120
ccaatggagc ccgtgggaag cctggtcccc acgctggagc agccgcaggt gcccgcgaag    180
gtgcgacaac ctgaaggtcc cgaaagcagc ccaagtccgg ccggggccgt ggagaaggcg    240
gcgggcgcag gcctggagcc ctcgagcaag aaaaagccgc cttcgcctcg ccccgggtcc    300
ccgcgcgtgc cgccgctcag cctgggctac ggggtctgcc ccgagccgcc gtcaccgggc    360
cctgccttgg tcaagctgcc ccggaatggc gaggcgcccg gggctgagcc tgcgcccagc    420
gcctgggcgc ccatggagct gcaggtagat gtgcgcgtga agcccgtggg cgcggccggt    480
ggcagcagca cgccatcgcc caggccctcc acgcgcttcc tcaaggtgcc ggtgcccgag    540
tcccctgcct tctcccgcca cgcggacccg gcgcaccagc tcctgctgcg cgcaccatcc    600
cagggcggca cgtggggccg ccgctcgccg ctggctgcag cccggacgga gagcggctgc    660
gacgcagagg gccgggccag ccccgcggaa ggaagcgccg gctccccggg ctcccccacg    720
tgctgccgct gcaaggagct ggggctggag aaggaggatg cggcgctgtt gccccgcgcg    780
gggttggacg gcgacgagaa gctgccccgg gccgtaacgc ttacggactc cctgaggacg    840
gcgaggacaa tctggatatc aactgtgggg ccctggagga aggcacgctg gtggctgcaa    900
actgcagcac tccaagaccc tgggtctgtg ccaaggggac ccagtgatct gggctctgcc    960
tggtcctcag cctgccaggc agatgcagca ccccctacag gggaggccag ttgagagctt   1020
gggcagcctc ttcctggacc cagttatcca ggtcttcatg ctctgctcaa gggggccaca   1080
tgagcgagcc taggagctgg acttcaaccc aggaagatgc atccgaggga aaggagattt   1140
tctatggcct caggcctgag tgccaatatt agtctccagc ttctgtggat ga           1192
```

<210> SEQ ID NO 89
<211> LENGTH: 518
<212> TYPE: PRT
<213> ORGANISM: Homo sapiens

<400> SEQUENCE: 89

```
Met Leu Ala Ala Ala Ser Lys Tyr Arg His Gly Asn Met Val Phe Phe
1               5                   10                  15

Asp Val Leu Gly Leu Phe Val Ile Ala Tyr Pro Ser Arg Ile Gly Ser
            20                  25                  30

Ile Ile Asn Tyr Met Val Val Met Gly Val Val Leu Tyr Leu Gly Lys
        35                  40                  45

Lys Phe Leu Gln Pro Lys His Lys Thr Gly Asn Tyr Lys Lys Asp Phe
    50                  55                  60

Leu Cys Gly Leu Gly Ile Thr Leu Ile Ser Trp Phe Thr Ser Leu Val
65                  70                  75                  80

Thr Val Leu Ile Ile Ala Val Phe Ile Ser Leu Ile Gly Gln Ser Leu
                85                  90                  95

Ser Trp Tyr Asn His Phe Tyr Val Ser Val Cys Leu Tyr Gly Thr Ala
            100                 105                 110

Thr Val Ala Lys Ile Ile Leu Ile His Thr Leu Ala Lys Arg Phe Tyr
        115                 120                 125
```

```
Tyr Met Asn Ala Ser Ala Gln Tyr Leu Gly Glu Val Phe Phe Asp Ile
    130                 135                 140

Ser Leu Phe Val His Cys Cys Phe Leu Val Thr Leu Thr Tyr Gln Gly
145                 150                 155                 160

Leu Cys Ser Ala Phe Ile Ser Ala Val Trp Val Ala Phe Pro Leu Leu
                165                 170                 175

Thr Lys Leu Cys Val His Lys Asp Phe Lys Gln His Gly Ala Gln Gly
            180                 185                 190

Lys Phe Ile Ala Phe Tyr Leu Leu Gly Met Phe Ile Pro Tyr Leu Tyr
        195                 200                 205

Ala Leu Tyr Leu Ile Trp Ala Val Phe Glu Met Phe Thr Pro Ile Leu
    210                 215                 220

Gly Arg Ser Gly Ser Glu Ile Pro Pro Asp Val Val Leu Ala Ser Ile
225                 230                 235                 240

Leu Ala Gly Cys Thr Met Ile Leu Ser Ser Tyr Phe Ile Asn Phe Ile
                245                 250                 255

Tyr Leu Ala Lys Ser Thr Lys Lys Thr Met Leu Thr Leu Thr Leu Val
            260                 265                 270

Cys Ala Ile Thr Phe Leu Leu Val Cys Ser Gly Thr Phe Phe Pro Tyr
        275                 280                 285

Ser Ser Asn Pro Ala Asn Pro Lys Pro Lys Arg Val Phe Leu Gln His
    290                 295                 300

Met Thr Arg Thr Phe His Asp Leu Glu Gly Asn Ala Val Lys Arg Asp
305                 310                 315                 320

Ser Gly Ile Trp Ile Asn Gly Phe Asp Tyr Thr Gly Ile Ser His Ile
                325                 330                 335

Thr Pro His Ile Pro Glu Ile Asn Asp Ser Ile Arg Ala His Cys Glu
            340                 345                 350

Glu Asn Ala Pro Leu Cys Gly Phe Pro Trp Tyr Leu Pro Val His Phe
        355                 360                 365

Leu Ile Arg Lys Asn Trp Tyr Leu Pro Ala Pro Glu Val Ser Pro Arg
    370                 375                 380

Asn Pro Pro His Phe Arg Leu Ile Ser Lys Glu Gln Thr Pro Trp Asp
385                 390                 395                 400

Ser Ile Lys Leu Thr Phe Glu Ala Thr Gly Pro Ser His Met Ser Phe
                405                 410                 415

Tyr Val Arg Ala His Lys Gly Ser Thr Leu Ser Gln Trp Ser Leu Gly
            420                 425                 430

Asn Gly Thr Pro Val Thr Ser Lys Gly Gly Asp Tyr Phe Val Phe Tyr
        435                 440                 445

Ser His Gly Leu Gln Ala Ser Ala Trp Gln Phe Trp Ile Glu Val Gln
    450                 455                 460

Val Ser Glu Glu His Pro Glu Gly Met Val Thr Val Ala Ile Ala Ala
465                 470                 475                 480

His Tyr Leu Ser Gly Glu Asp Lys Arg Ser Pro Gln Leu Asp Ala Leu
                485                 490                 495

Lys Glu Lys Phe Pro Asp Trp Thr Phe Pro Ser Ala Trp Val Cys Thr
            500                 505                 510

Tyr Asp Leu Phe Val Phe
        515
```

<210> SEQ ID NO 90
<211> LENGTH: 904

<212> TYPE: PRT
<213> ORGANISM: Homo sapiens

<400> SEQUENCE: 90

```
Met Glu Trp Gly Ser Glu Ser Ala Ala Val Arg Arg His Arg Val Gly
1               5                   10                  15

Val Glu Arg Arg Glu Gly Ala Ala Ala Ala Pro Pro Pro Glu Arg Glu
            20                  25                  30

Ala Arg Ala Gln Glu Pro Leu Val Asp Gly Cys Ser Gly Gly Gly Arg
        35                  40                  45

Thr Arg Lys Arg Ser Pro Gly Gly Ser Gly Gly Ala Ser Arg Gly Ala
    50                  55                  60

Gly Thr Gly Leu Ser Glu Val Arg Ala Ala Leu Gly Leu Ala Leu Tyr
65                  70                  75                  80

Leu Ile Ala Leu Arg Thr Leu Val Gln Leu Ser Leu Gln Gln Leu Val
                85                  90                  95

Leu Arg Gly Ala Ala Gly His Arg Gly Glu Phe Asp Ala Leu Gln Ala
            100                 105                 110

Arg Asp Tyr Leu Glu His Ile Thr Ser Ile Gly Pro Arg Thr Thr Gly
        115                 120                 125

Ser Pro Glu Asn Glu Ile Leu Thr Val His Tyr Leu Leu Glu Gln Ile
    130                 135                 140

Lys Leu Ile Glu Val Gln Ser Asn Ser Leu His Lys Ile Ser Val Asp
145                 150                 155                 160

Val Gln Arg Pro Thr Gly Ser Phe Ser Ile Asp Phe Leu Gly Gly Phe
                165                 170                 175

Thr Ser Tyr Tyr Asp Asn Ile Thr Asn Val Val Val Lys Leu Glu Pro
            180                 185                 190

Arg Asp Gly Ala Gln His Ala Val Leu Ala Asn Cys His Phe Asp Ser
        195                 200                 205

Val Ala Asn Ser Pro Gly Ala Ser Asp Asp Ala Val Ser Cys Ser Val
    210                 215                 220

Met Leu Glu Val Leu Arg Val Leu Ser Thr Ser Ser Glu Ala Leu His
225                 230                 235                 240

His Ala Val Ile Phe Leu Phe Asn Gly Ala Glu Glu Asn Val Leu Gln
                245                 250                 255

Ala Ser His Gly Phe Ile Thr Gln His Pro Trp Ala Ser Leu Ile Arg
            260                 265                 270

Ala Phe Ile Asn Leu Glu Ala Ala Gly Val Gly Gly Lys Glu Leu Val
        275                 280                 285

Phe Gln Thr Gly Pro Glu Asn Pro Trp Leu Val Gln Ala Tyr Val Ser
    290                 295                 300

Ala Ala Lys His Pro Phe Ala Ser Val Val Ala Gln Glu Val Phe Gln
305                 310                 315                 320

Ser Gly Ile Ile Pro Ser Asp Thr Asp Phe Arg Ile Tyr Arg Asp Phe
                325                 330                 335

Gly Asn Ile Pro Gly Ile Asp Leu Ala Phe Ile Glu Asn Gly Tyr Ile
            340                 345                 350

Tyr His Thr Lys Tyr Asp Thr Ala Asp Arg Ile Leu Thr Asp Ser Ile
        355                 360                 365

Gln Arg Ala Gly Asp Asn Ile Leu Ala Val Leu Lys His Leu Ala Thr
    370                 375                 380

Ser Asp Met Leu Ala Ala Ala Ser Lys Tyr Arg His Gly Asn Met Val
385                 390                 395                 400
```

```
Phe Phe Asp Val Leu Gly Leu Phe Val Ile Ala Tyr Pro Ser Arg Ile
                405                 410                 415

Gly Ser Ile Ile Asn Tyr Met Val Val Met Gly Val Val Leu Tyr Leu
            420                 425                 430

Gly Lys Lys Phe Leu Gln Pro Lys His Lys Thr Gly Asn Tyr Lys Lys
        435                 440                 445

Asp Phe Leu Cys Gly Leu Gly Ile Thr Leu Ile Ser Trp Phe Thr Ser
    450                 455                 460

Leu Val Thr Val Leu Ile Ile Ala Val Phe Ile Ser Leu Ile Gly Gln
465                 470                 475                 480

Ser Leu Ser Trp Tyr Asn His Phe Tyr Val Ser Val Cys Leu Tyr Gly
                485                 490                 495

Thr Ala Thr Val Ala Lys Ile Ile Leu Ile His Thr Leu Ala Lys Arg
            500                 505                 510

Phe Tyr Tyr Met Asn Ala Ser Ala Gln Tyr Leu Gly Glu Val Phe Phe
        515                 520                 525

Asp Ile Ser Leu Phe Val His Cys Cys Phe Leu Val Thr Leu Thr Tyr
    530                 535                 540

Gln Gly Leu Cys Ser Ala Phe Ile Ser Ala Val Trp Val Ala Phe Pro
545                 550                 555                 560

Leu Leu Thr Lys Leu Cys Val His Lys Asp Phe Lys Gln His Gly Ala
                565                 570                 575

Gln Gly Lys Phe Ile Ala Phe Tyr Leu Leu Gly Met Phe Ile Pro Tyr
            580                 585                 590

Leu Tyr Ala Leu Tyr Leu Ile Trp Ala Val Phe Glu Met Phe Thr Pro
        595                 600                 605

Ile Leu Gly Arg Ser Gly Ser Glu Ile Pro Pro Asp Val Val Leu Ala
    610                 615                 620

Ser Ile Leu Ala Gly Cys Thr Met Ile Leu Ser Ser Tyr Phe Ile Asn
625                 630                 635                 640

Phe Ile Tyr Leu Ala Lys Ser Thr Lys Lys Thr Met Leu Thr Leu Thr
                645                 650                 655

Leu Val Cys Ala Ile Thr Phe Leu Leu Val Cys Ser Gly Thr Phe Phe
            660                 665                 670

Pro Tyr Ser Ser Asn Pro Ala Asn Pro Lys Pro Lys Arg Val Phe Leu
        675                 680                 685

Gln His Met Thr Arg Thr Phe His Asp Leu Glu Gly Asn Ala Val Lys
    690                 695                 700

Arg Asp Ser Gly Ile Trp Ile Asn Gly Phe Asp Tyr Thr Gly Ile Ser
705                 710                 715                 720

His Ile Thr Pro His Ile Pro Glu Ile Asn Asp Ser Ile Arg Ala His
                725                 730                 735

Cys Glu Glu Asn Ala Pro Leu Cys Gly Phe Pro Trp Tyr Leu Pro Val
            740                 745                 750

His Phe Leu Ile Arg Lys Asn Trp Tyr Leu Pro Ala Pro Glu Val Ser
        755                 760                 765

Pro Arg Asn Pro Pro His Phe Arg Leu Ile Ser Lys Glu Gln Thr Pro
    770                 775                 780

Trp Asp Ser Ile Lys Leu Thr Phe Glu Ala Thr Gly Pro Ser His Met
785                 790                 795                 800

Ser Phe Tyr Val Arg Ala His Lys Gly Ser Thr Leu Ser Gln Trp Ser
                805                 810                 815
```

```
Leu Gly Asn Gly Thr Pro Val Thr Ser Lys Gly Gly Asp Tyr Phe Val
            820                 825                 830

Phe Tyr Ser His Gly Leu Gln Ala Ser Ala Trp Gln Phe Trp Ile Glu
        835                 840                 845

Val Gln Val Ser Glu Glu His Pro Glu Gly Met Val Thr Val Ala Ile
    850                 855                 860

Ala Ala His Tyr Leu Ser Gly Glu Asp Lys Arg Ser Pro Gln Leu Asp
865                 870                 875                 880

Ala Leu Lys Glu Lys Phe Pro Asp Trp Thr Phe Pro Ser Ala Trp Val
                885                 890                 895

Cys Thr Tyr Asp Leu Phe Val Phe
            900


<210> SEQ ID NO 91
<211> LENGTH: 419
<212> TYPE: PRT
<213> ORGANISM: Homo sapiens

<400> SEQUENCE: 91

Met Val Val Met Gly Val Val Leu Tyr Leu Gly Lys Lys Phe Leu Gln
1               5                   10                  15

Pro Lys His Lys Thr Gly Asn Tyr Lys Lys Asp Phe Leu Cys Gly Leu
            20                  25                  30

Gly Ile Thr Leu Ile Ser Trp Phe Thr Ser Leu Val Thr Val Leu Ile
        35                  40                  45

Ile Ala Val Phe Ile Ser Leu Ile Gly Gln Ser Leu Ser Trp Tyr Asn
    50                  55                  60

His Phe Tyr Val Ser Val Cys Leu Tyr Gly Thr Ala Thr Val Ala Lys
65                  70                  75                  80

Ile Ile Leu Ile His Thr Leu Ala Lys Arg Phe Tyr Tyr Met Asn Ala
                85                  90                  95

Ser Ala Gln Tyr Leu Gly Glu Val Phe Phe Asp Ile Ser Leu Phe Val
            100                 105                 110

His Cys Cys Phe Leu Val Thr Leu Thr Tyr Gln Gly Leu Cys Ser Ala
        115                 120                 125

Phe Ile Ser Ala Val Trp Val Ala Phe Pro Leu Leu Thr Lys Leu Cys
    130                 135                 140

Val His Lys Asp Phe Lys Gln His Gly Ala Gln Gly Lys Phe Ile Ala
145                 150                 155                 160

Phe Tyr Leu Leu Gly Met Phe Ile Pro Tyr Leu Tyr Ala Leu Tyr Leu
                165                 170                 175

Ile Trp Ala Val Phe Glu Met Phe Thr Pro Ile Leu Gly Arg Ser Gly
            180                 185                 190

Ser Glu Ile Pro Pro Asp Val Val Leu Ala Ser Ile Leu Ala Gly Cys
        195                 200                 205

Thr Met Ile Leu Ser Ser Tyr Phe Ile Asn Phe Ile Tyr Leu Ala Lys
    210                 215                 220

Ser Thr Lys Lys Thr Met Leu Thr Leu Thr Leu Val Cys Ala Ile Thr
225                 230                 235                 240

Phe Leu Leu Val Cys Ser Gly Thr Phe Phe Pro Tyr Ser Ser Asn Pro
                245                 250                 255

Ala Asn Pro Lys Pro Lys Arg Val Phe Leu Gln His Met Thr Arg Thr
            260                 265                 270

Phe His Asp Leu Glu Gly Asn Ala Val Lys Arg Asp Ser Gly Ile Trp
        275                 280                 285
```

```
Ile Asn Gly Phe Asp Tyr Thr Gly Ile Ser His Ile Thr Pro His Ile
    290                 295                 300

Pro Glu Ile Asn Asp Ser Ile Arg Ala His Cys Glu Glu Asn Ala Pro
305                 310                 315                 320

Leu Cys Gly Phe Pro Trp Tyr Leu Pro Val His Phe Leu Ile Arg Lys
                325                 330                 335

Asn Trp Tyr Leu Pro Ala Pro Glu Val Ser Pro Arg Asn Pro Pro His
            340                 345                 350

Phe Arg Leu Ile Ser Lys Glu Gln Thr Pro Trp Asp Ser Ile Lys Leu
        355                 360                 365

Thr Phe Glu Ala Thr Ala Cys Leu Pro Ile Leu Gln Ile Leu Asp Leu
    370                 375                 380

Pro Ala Ser Thr Ile Met Thr Lys Pro Tyr Val Leu Leu Cys Ser Ser
385                 390                 395                 400

Pro Gln Arg Val Asn Thr Phe Ser Val Val Ser Trp Gln Trp His Pro
                405                 410                 415

Ser His Lys


<210> SEQ ID NO 92
<211> LENGTH: 4974
<212> TYPE: DNA
<213> ORGANISM: Homo sapiens

<400> SEQUENCE: 92

ggcgcgggga ccgggctgtc tgaggtgcgc gccgcgctgg ggctcgcgct ctacctgatc     60

gcgctgcgga cgctggtgca gctctcgctg cagcagctcg tgctacgcgg ggccgctgga    120

caccgcgggg agttcgacgc gctccaagcc agggattatc ttgaacacat aacctccatt    180

ggccccagga ctacaggaag tccagaaaat gaaattctga ccgtgcacta ccttttggaa    240

cagattaaac tgattgaagt gcaaagcaac agccttcata agatttcagt agatgtacaa    300

cggcccacag gctcttttag cattgatttc ttgggaggtt ttacaagcta ttatgacaac    360

atcaccaatg ttgtggtaaa gctggaaccc agagatggag cccagcatgc tgtcttggct    420

aattgtcatt ttgactcagt agcaaactca ccaggccagt catggtttca ttactcagca    480

cccctgggct agcttgattc gtgcattcat taacctagag gcagcaggtg taggagggaa    540

agaacttgta ttccaaacag gtcctgaaaa tccttggttg gttcaagctt atgtttcagc    600

agctaaacac cctttttgctt ctgtggtggc tcaggaggtt tttcagagtg gaatcattcc    660

ttcagatact gactttcgta tctacaggga ttttgggaac attccaggaa tagacttagc    720

ttttattgag aatggataca tttatcacac caagtatgac acagcggaca gaattctaac    780

agattccatt cagagagcag gtgacaacat tttagcagtt cttaagcatc tagctacatc    840

tgatatgctg gctgctgctt ctaagtatcg acatggaaac atggtcttct ttgatgtgct    900

gggcctgttt gtcattgcct acccctctcg tattggctca atcataaact acatggtggt    960

aatgggtgtt gttttgtacc tgggcaaaaa atttttgcag cccaaacata agactggtaa   1020

ctacaagaag gacttcttgt gtggacttgg catcactttg atcagctggt tcactagcct   1080

tgttaccgtt ctcattatag cagtgttcat ctctcttatt ggacagtctc tctcatggta   1140

taaccacttc tatgtctccg tttgtctgta tggaactgca actgtagcca aaataatact   1200

tatacatact cttgcgaaaa gattttatta catgaatgcc agtgcccagt atctgggaga   1260

agtatttttt gacatttcgc tgtttgtcca ttgctgtttt cttgttaccc tcacttacca   1320
```

-continued

```
aggactttgc tcggcgttta ttagtgctgt ctgggtagca ttcccattgc tcacaaagct   1380
ctgtgtgcat aaggacttca agcagcatgg tgcccaagga aaatttattg ctttttacct   1440
tttggggatg tttattcctt atctttatgc attgtacctc atctgggcag tatttgagat   1500
gtttacccct atcctcggga gaagtggttc tgaaatccca cctgatgttg tgctggcatc   1560
cattttggct ggctgtacaa tgattctctc gtcctatttt attaacttca tctaccttgc   1620
caagagcaca aaaaaaacca tgctaacttt aactttggta tgtgcaatta cattcctcct   1680
tgtttgcagt ggaacatttt ttccatatag ctccaatcct gctaatccga agccaaagag   1740
agtgtttctt cagcatatga ctagaacatt ccatgacttg gaaggaaatg cagttaaacg   1800
ggactctgga atatggatca atgggtttga ttatactgga atttctcaca taacccctca   1860
cattcctgag atcaatgata gtatccgagc tcactgtgag gagaatgcac ctctttgtgg   1920
ttttccttgg tatcttccag tgcactttct gatcaggaaa aactggtatc ttcctgcccc   1980
agaagtttct ccaagaaatc ctcctcattt ccgactcata tccaaagaac agacaccttg   2040
ggattctata aaattgactt ttgaagcaac aggaccaagc catatgtcct tctatgttcg   2100
agcccacaaa gggtcaacac tttctcagtg gtctcttggc aatggcaccc cagtcacaag   2160
taaaggagga gactactttg tcttttactc ccatggactc caggcctctg catggcagtt   2220
ctggatagaa gtgcaggttt cagaagaaca tcctgaagga atggtcaccg tggccattgc   2280
tgcccactat ctgtctgggg aagacaagag atcccctcaa ctggatgctc tgaaggaaaa   2340
gttcccagat tggacatttc cctctgcctg ggtgtgcacc tacgatctct ttgtatttta   2400
atcttgtgga tgagctctaa gtacatgccc agtggatact ccatgtgaca tggtttctcc   2460
ctatgttacg tggatgtttg taacgtaagt caatgaattt taatgatcat atgttcaaag   2520
agctttctgg gttaacgctt ttcagggcca agcactataa gggtttagct gtggcgcagt   2580
gatgcatggc ctgttgacac ttgaaaatgc cagtcttttg gcacttcagc acatgtgggt   2640
actgccacta cacacacgtc attttatatg accttaagga caaagccaac aatccacttc   2700
aatagctgcc cctttaggat caagaaagat gtacactgtc agagcattgt taatgagaca   2760
aaagttgttt ccaatttaag ccccaaaacc atttgttgta ttagtggatg gtgggtaaaa   2820
tatcattcac tgaggtaatg attccccttg agaatataac tctgtgtagg tcactggaaa   2880
gtgattgcca tagggctggg agagaagcat tgcactcttg aggctgtagc ctgtgtcaag   2940
ctgtttcttc aggcagcctc tcaaatgtgc tttgtctctc tgtgctgagg cctggaccct   3000
gtgctgagct ggtgactcac tgtcctgaca agtggacaca cagatgcact gctgtgctgc   3060
tttcctgagg tggttttcta tgcctgtttt cctctgaaac atgtctgtta cccctctcca   3120
tcttaccaag ttgaaaaggg gaatatttgg ccacataccc ctctggtttt cgtaggttct   3180
tttggttcag aatattgttt gtgccagtac atgaccttaa cttccttcct cagagcactg   3240
agctgccatc tgggctattc tggggtagaa ggaaggctgg gagtggtggg aattttataa   3300
atatttattc tcttttcttt gtttcatagg agtcttgtgt tatacaaggt tagtccttca   3360
tggtataatc ttactgatgc actgggccta tctttttgtt ttccagccag ttgaatagat   3420
tagtttttct cagtaactta ctatccagca gactggcttt cctgagactt gaggttgtgg   3480
cttatactgg aatgagacca ctgtacgtgt aggtggttca gatcctgcgt aatggcagca   3540
tgaggactta aaaggtggtt ttcattttga agatggctat gtagcttgta aggtgtatca   3600
cagcagtacc tctcatggct tttggttcc agcagtgagg gcattggtga gatcaatggt   3660
aaactgtgca agctttcttt ttatcattag gaaatgtgaa acgttggaca aattttgagt   3720
```

```
tttaacaagg acaaaaagtt gaaagaaaag gcacagttaa caaaaaaggg tggctagatt   3780

tatcttgggt gatggaggaa atgagagagg aatgctcttg aaaggtggtc tgtggatctg   3840

tctgaataga aagagcacag taagtatgca ttgccggaga aaacgtcctt gaagctgctt   3900

gtctcatgtg tatgatgtgc tttttaaatc atgcccctcg ttgcctgcct aatctgtgac   3960

tccctaaaaa ctaactgggc ccatgtagat ggggctgcaa ccagagctga ataacatgtt   4020

aggctcacac atgcatcagc actgcacact ggaatcattg ctcttcctgg actttgtaga   4080

aatcagtctc aagtgcttca agagtctggc tcctgctact tttatctgtc aggtagcaca   4140

taaggtttgc agggtttata ttttgtatag aatcacagtt gtggagaaaa agtaataatt   4200

tctcaatgaa ttttaaaaat gggcctattt tctatccccg tggttcatct gatataatta   4260

gtgttccctg tgaattcccc ccctctatgg gaaggatgcc tttactcttt atcagtaata   4320

aattatgact gttttcatat tgccttaggg ttatttccct gtgtaaacca ttgtcttttg   4380

ttttggtttt ctttagcatt atgaagcttt ggtattgtac aaggtcagta gtaagatgct   4440

cactagtctc agggcttgtg taatattctg ggaggtcatt taaatgccag aaatggtcaa   4500

gcaattatac acagtattta tgactctgtt aagcataccg tttgtctgtc acattagtag   4560

attctgagat taaaaaaaat ttttaaagag tgatcattta aataatttct aaaagggtct   4620

tttcaagctc taacaaagtc actaacaaat gcattatttt ctacagaatt agatgttagt   4680

agtacagtac tgcatattca gggaaaaagt gtgaggaatt gatttcaaaa tagttcgttc   4740

ttgtgtttga cctaagaatg attgtcgcat gaagtgtttg tttttacagt ttagcatata   4800

taaacaaaca tgataggatt ccttaagatg ttaccaccca gggggccaca agccagcctg   4860

ctgtctcagg aagctgtaga aggagtgttt gtcaatttct tgtcactggt ttgctgactt   4920

actgaggatt aattgttgcc ttacaatgtt actgaaataa actgtttaat atac         4974
```

<210> SEQ ID NO 93
<211> LENGTH: 5338
<212> TYPE: DNA
<213> ORGANISM: Homo sapiens

<400> SEQUENCE: 93

```
ggccggggct gtcgcgggtt ggggcggttg ggctggcagc tgaggctcgt ggccatggag     60

tggggttctg agtcggctgc tgtgaggcgg caccgcgtcg gagtagagcg tcgagaggga    120

gcggcggccg cgccaccgcc ggagagggag gcccgagcgc aggagcctct ggtggatggg    180

tgcagcggcg gcgggaggac gcggaagagg agccccgggg gtagcggcgg cgcgagcagg    240

ggcgcgggga ccgggctgtc tgaggtgcgc gccgcgctgg ggctcgcgct ctacctgatc    300

gcgctgcgga cgctggtgca gctctcgctg cagcagctcg tgctacgcgg ggccgctgga    360

caccgcgggg agttcgacgc gctccaagcc agggattatc ttgaacacat aacctccatt    420

ggccccagga ctacaggaag tccagaaaat gaaattctga ccgtgcacta ccttttggaa    480

cagattaaac tgattgaagt gcaaagcaac agccttcata agatttcagt agatgtacaa    540

cggcccacag gctcttttag cattgatttc ttgggaggtt ttacaagcta ttatgacaac    600

atcaccaatg ttgtggtaaa gctggaaccc agagatggag cccagcatgc tgtcttggct    660

aattgtcatt ttgactcagt agcaaactca ccaggtgcca gtgatgatgc agttagctgc    720

tcagtgatgc tggaagtcct tcgcgtcttg tcaacatctt cagaagcctt gcatcatgct    780

gtcatatttc tctttaatgg tgctgaggaa aatgtcttgc aagccagtca tggtttcatt    840
```

```
actcagcacc cctgggctag cttgattcgt gcattcatta acctagaggc agcaggtgta    900
ggagggaaag aacttgtatt ccaaacaggt cctgaaaatc cttggttggt tcaagcttat    960
gtttcagcag ctaaacaccc ttttgcttct gtggtggctc aggaggtttt tcagagtgga   1020
atcattcctt cagatactga ctttcgtatc tacagggatt ttgggaacat tccaggaata   1080
gacttagctt ttattgagaa tggatacatt tatcacacca agtatgacac agcggacaga   1140
attctaacag attccattca gagagcaggt gacaacattt tagcagttct taagcatcta   1200
gctacatctg atatgctggc tgctgcttct aagtatcgac atggaaacat ggtcttcttt   1260
gatgtgctgg gcctgtttgt cattgcctac ccctctcgta ttggctcaat cataaactac   1320
atggtggtaa tgggtgttgt tttgtacctg ggcaaaaaat tttgcagcc caaacataag    1380
actggtaact acaagaagga cttcttgtgt ggacttggca tcactttgat cagctggttc   1440
actagccttg ttaccgttct cattatagca gtgttcatct ctcttattgg acagtctctc   1500
tcatggtata accacttcta tgtctccgtt tgtctgtatg gaactgcaac tgtagccaaa   1560
ataatactta tacatactct tgcgaaaaga ttttattaca tgaatgccag tgcccagtat   1620
ctgggagaag tatttttga catttcgctg tttgtccatt gctgttttct tgttaccctc    1680
acttaccaag gactttgctc ggcgtttatt agtgctgtct gggtagcatt cccattgctc   1740
acaaagctct gtgtgcataa ggacttcaag cagcatggtg cccaaggaaa atttattgct   1800
ttttaccttt tggggatgtt tattccttat ctttatgcat tgtacctcat ctgggcagta   1860
tttgagatgt ttacccctat cctcgggaga agtggttctg aaatcccacc tgatgttgtg   1920
ctggcatcca ttttggctgg ctgtacaatg attctctcgt cctattttat taacttcatc   1980
taccttgcca agagcacaaa aaaaaccatg ctaactttaa ctttggtatg tgcaattaca   2040
ttcctccttg tttgcagtgg aacattttt ccatatagct ccaatcctgc taatccgaag    2100
ccaaagagag tgtttcttca gcatatgact agaacattcc atgacttgga aggaaatgca   2160
gttaaacggg actctggaat atggatcaat gggtttgatt atactggaat ttctcacata   2220
acccctcaca ttcctgagat caatgatagt atccgagctc actgtgagga gaatgcacct   2280
ctttgtggtt ttccttggta tcttccagtg cactttctga tcaggaaaaa ctggtatctt   2340
cctgccccag aagtttctcc aagaaatcct cctcatttcc gactcatatc caaagaacag   2400
acaccttggg attctataaa attgactttt gaagcaacag gaccaagcca tatgtccttc   2460
tatgttcgag cccacaaagg gtcaacactt tctcagtggt ctcttggcaa tggcacccca   2520
gtcacaagta aaggaggaga ctactttgtc ttttactccc atggactcca ggcctctgca   2580
tggcagttct ggatagaagt gcaggtttca gaagaacatc ctgaaggaat ggtcaccgtg   2640
gccattgctg cccactatct gtctggggaa gacaagagat cccctcaact ggatgctctg   2700
aaggaaaagt tcccagattg gacatttccc tctgcctggg tgtgcaccta cgatctcttt   2760
gtattttaat cttgtggatg agctctaagt acatgcccag tggatactcc atgtgacatg   2820
gtttctccct atgttacgtg gatgtttgta acgtaagtca atgaatttta atgatcatat   2880
gttcaaagag ctttctgggt taacgctttt cagggccaag cactataagg gtttagctgt   2940
ggcgcagtga tgcatggcct gttgacactt gaaaatgcca gtcttttggc acttcagcac   3000
atgtgggtac tgccactaca cacacgtcat tttatatgac cttaaggaca aagccaacaa   3060
tccacttcaa tagctgcccc tttaggatca agaaagatgt acactgtcag agcattgtta   3120
atgagacaaa agttgtttcc aatttaagcc ccaaaaccat ttgttgtatt agtggatggt   3180
gggtaaaata tcattcactg aggtaatgat tccccttgag aatataactc tgtgtaggtc   3240
```

actggaaagt gattgccata gggctgggag agaagcattg cactcttgag gctgtagcct 3300
gtgtcaagct gtttcttcag gcagcctctc aaatgtgctt tgtctctctg tgctgaggcc 3360
tggaccctgt gctgagctgg tgactcactg tcctgacaag tggacacaca gatgcactgc 3420
tgtgctgctt tcctgaggtg gttttctatg cctgttttcc tctgaaacat gtctgttacc 3480
cctctccatc ttaccaagtt gaaaagggga atatttggcc acatacccct ctggttttcg 3540
taggttcttt tggttcagaa tattgtttgt gccagtacat gaccttaact tccttcctca 3600
gagcactgag ctgccatctg ggctattctg gggtagaagg aaggctggga gtggtgggaa 3660
ttttataaat atttattctc ttttctttgt ttcataggag tcttgtgtta tacaaggtta 3720
gtccttcatg gtataatctt actgatgcac tgggcctatc tttttgtttt ccagccagtt 3780
gaatagatta gtttttctca gtaacttact atccagcaga ctggctttcc tgagacttga 3840
ggttgtggct tatactggaa tgagaccact gtacgtgtag gtggttcaga tcctgcgtaa 3900
tggcagcatg aggacttaaa aggtggtttt cattttgaag atggctatgt agcttgtaag 3960
gtgtatcaca gcagtacctc tcatggcttt ttggttccag cagtgagggc attggtgaga 4020
tcaatggtaa actgtgcaag ctttcttttt atcattagga aatgtgaaac gttggacaaa 4080
ttttgagttt taacaaggac aaaaagttga aagaaaaggc acagttaaca aaaaagggtg 4140
gctagattta tcttgggtga tggaggaaat gagagaggaa tgctcttgaa aggtggtctg 4200
tggatctgtc tgaatagaaa gagcacagta agtatgcatt gccggagaaa acgtccttga 4260
agctgcttgt ctcatgtgta tgatgtgctt tttaaatcat gcccctcgtt gcctgcctaa 4320
tctgtgactc cctaaaaact aactgggccc atgtagatgg ggctgcaacc agagctgaat 4380
aacatgttag gctcacacat gcatcagcac tgcacactgg aatcattgct cttcctggac 4440
tttgtagaaa tcagtctcaa gtgcttcaag agtctggctc ctgctacttt tatctgtcag 4500
gtagcacata aggtttgcag ggtttatatt ttgtatagaa tcacagttgt ggagaaaaag 4560
taataatttc tcaatgaatt ttaaaaatgg gcctattttc tatccccgtg gttcatctga 4620
tataattagt gttccctgtg aattcccccc ctctatggga aggatgcctt tactctttat 4680
cagtaataaa ttatgactgt tttcatattg ccttagggtt atttccctgt gtaaaccatt 4740
gtcttttgtt ttggttttct ttagcattat gaagctttgg tattgtacaa ggtcagtagt 4800
aagatgctca ctagtctcag ggcttgtgta atattctggg aggtcattta aatgccagaa 4860
atggtcaagc aattatacac agtatttatg actctgttaa gcataccgtt tgtctgtcac 4920
attagtagat tctgagatta aaaaaaattt ttaaagagtg atcatttaaa taatttctaa 4980
aagggtcttt tcaagctcta acaaagtcac taacaaatgc attattttct acagaattag 5040
atgttagtag tacagtactg catattcagg gaaaaagtgt gaggaattga tttcaaaata 5100
gttcgttctt gtgtttgacc taagaatgat tgtcgcatga agtgtttgtt tttacagttt 5160
agcatatata aacaaacatg ataggattcc ttaagatgtt accacccagg gggccacaag 5220
ccagcctgct gtctcaggaa gctgtagaag gagtgtttgt caatttcttg tcactggttt 5280
gctgacttac tgaggattaa ttgttgcctt acaatgttac tgaaataaac tgtttaat 5338

<210> SEQ ID NO 94
<211> LENGTH: 5387
<212> TYPE: DNA
<213> ORGANISM: Homo sapiens

<400> SEQUENCE: 94

```
ggccggggct gtcgcgggtt ggggcggttg ggctggcagc tgaggctcgt ggccatggag     60
tggggttctg agtcggctgc tgtgaggcgg caccgcgtcg gagtagagcg tcgagaggga    120
gcggcggccg cgccaccgcc ggagagggag gcccgagcgc aggagcctct ggtggatggg    180
tgcagcggcg gcgggaggac gcggaagagg agccccgggg gtagcggcgg cgcgagcagg    240
ggcgcgggga ccgggctgtc tgaggtgcgc gccgcgctgg ggctcgcgct ctacctgatc    300
gcgctgcgga cgctggtgca gctctcgctg cagcagctcg tgctacgcgg ggccgctgga    360
caccgcgggg agttcgacgc gctccaagcc agggattatc ttgaacacat aacctccatt    420
ggccccagga ctacaggaag tccagaaaat gaaattctga ccgtgcacta ccttttggaa    480
cagattaaac tgattgaagt gcaaagcaac agccttcata agatttcagt agatgtacaa    540
cggcccacag gctcttttag cattgatttc ttgggaggtt ttacaagcta ttatgacaac    600
atcaccaatg ttgtggtaaa gctggaaccc agagatggag cccagcatgc tgtcttggct    660
aattgtcatt ttgactcagt agcaaactca ccaggtgcca gtgatgatgc agttagctgc    720
tcagtgatgc tggaagtcct tcgcgtcttg tcaacatctt cagaagcctt gcatcatgct    780
gtcatatttc tctttaatgg tgctgaggaa aatgtcttgc aagccagtca tggtttcatt    840
actcagcacc cctgggctag cttgattcgt gcattcatta acctagaggc agcaggtgta    900
ggagggaaag aacttgtatt ccaaacaggt cctgaaaatc cttggttggt tcaagcttat    960
gtttcagcag ctaaacaccc ttttgcttct gtggtggctc aggaggtttt tcagagtgga   1020
atcattcctt cagatactga ctttcgtatc tacagggatt ttgggaacat tccaggaata   1080
gacttagctt ttattgagaa tggatacatt tatcacacca agtatgacac agcggacaga   1140
attctaacag attccattca gagagcaggt gacaacattt tagcagttct taagcatcta   1200
gctacatctg atatgctggc tgctgcttct aagtatcgac atggaaacat ggtcttcttt   1260
gatgtgctgg gcctgtttgt cattgcctac ccctctcgta ttggctcaat cataaactac   1320
atggtggtaa tgggtgttgt tttgtacctg ggcaaaaaat tttgcagcc caaacataag   1380
actggtaact acaagaagga cttcttgtgt ggacttggca tcactttgat cagctggttc   1440
actagccttg ttaccgttct cattatagca gtgttcatct ctcttattgg acagtctctc   1500
tcatggtata accacttcta tgtctccgtt tgtctgtatg gaactgcaac tgtagccaaa   1560
ataatactta tacatactct tgcgaaaaga ttttattaca tgaatgccag tgcccagtat   1620
ctgggagaag tatttttga catttcgctg tttgtccatt gctgttttct tgttaccctc   1680
acttaccaag gactttgctc ggcgtttatt agtgctgtct gggtagcatt cccattgctc   1740
acaaagctct gtgtgcataa ggacttcaag cagcatggtg cccaaggaaa atttattgct   1800
ttttaccttt tggggatgtt tattccttat ctttatgcat tgtacctcat ctgggcagta   1860
tttgagatgt ttacccctat cctcgggaga agtggttctg aaatcccacc tgatgttgtg   1920
ctggcatcca ttttggctgg ctgtacaatg attctctcgt cctattttat taacttcatc   1980
taccttgcca agagcacaaa aaaaaccatg ctaactttaa ctttggtatg tgcaattaca   2040
ttcctccttg tttgcagtgg aacatttttt ccatatagct ccaatcctgc taatccgaag   2100
ccaaagagag tgtttcttca gcatatgact agaacattcc atgacttgga aggaaatgca   2160
gttaaacggg actctggaat atggatcaat gggtttgatt atactggaat ttctcacata   2220
acccctcaca ttcctgagat caatgatagt atccgagctc actgtgagga gaatgcacct   2280
ctttgtggtt ttccttggta tcttccagtg cactttctga tcaggaaaaa ctggtatctt   2340
cctgccccag aagtttctcc aagaaatcct cctcatttcc gactcatatc caaagaacag   2400
```

```
acaccttggg attctataaa attgactttt gaagcaacag cctgcctgcc tatccttcag   2460
attttggact tgccagcctc aacaatcatg accaagccat atgtccttct atgttcgagc   2520
ccacaaaggg tcaacacttt ctcagtggtc tcttggcaat ggcaccccag tcacaagtaa   2580
aggaggagac tactttgtct tttactccca tggactccag gcctctgcat ggcagttctg   2640
gatagaagtg caggtttcag aagaacatcc tgaaggaatg gtcaccgtgg ccattgctgc   2700
ccactatctg tctggggaag acaagagatc ccctcaactg gatgctctga aggaaaagtt   2760
cccagattgg acatttccct ctgcctgggt gtgcacctac gatctctttg tattttaatc   2820
ttgtggatga gctctaagta catgcccagt ggatactcca tgtgacatgg tttctcccta   2880
tgttacgtgg atgtttgtaa cgtaagtcaa tgaattttaa tgatcatatg ttcaaagagc   2940
tttctgggtt aacgcttttc agggccaagc actataaggg tttagctgtg gcgcagtgat   3000
gcatggcctg ttgacacttg aaaatgccag tcttttggca cttcagcaca tgtgggtact   3060
gccactacac acacgtcatt ttatatgacc ttaaggacaa agccaacaat ccacttcaat   3120
agctgcccct ttaggatcaa gaaagatgta cactgtcaga gcattgttaa tgagacaaaa   3180
gttgtttcca atttaagccc caaaaccatt tgttgtatta gtggatggtg ggtaaaatat   3240
cattcactga ggtaatgatt ccccttgaga atataactct gtgtaggtca ctggaaagtg   3300
attgccatag ggctgggaga gaagcattgc actcttgagg ctgtagcctg tgtcaagctg   3360
tttcttcagg cagcctctca aatgtgcttt gtctctctgt gctgaggcct ggaccctgtg   3420
ctgagctggt gactcactgt cctgacaagt ggacacacag atgcactgct gtgctgcttt   3480
cctgaggtgg ttttctatgc ctgttttcct ctgaaacatg tctgttaccc ctctccatct   3540
taccaagttg aaaaggggaa tatttggcca catacccctc tggttttcgt aggttctttt   3600
ggttcagaat attgtttgtg ccagtacatg accttaactt ccttcctcag agcactgagc   3660
tgccatctgg gctattctgg ggtagaagga aggctgggag tggtgggaat tttataaata   3720
tttattctct tttctttgtt tcataggagt cttgtgttat acaaggttag tccttcatgg   3780
tataatctta ctgatgcact gggcctatct ttttgttttc cagccagttg aatagattag   3840
tttttctcag taacttacta tccagcagac tggctttcct gagacttgag gttgtggctt   3900
atactggaat gagaccactg tacgtgtagg tggttcagat cctgcgtaat ggcagcatga   3960
ggacttaaaa ggtggttttc attttgaaga tggctatgta gcttgtaagg tgtatcacag   4020
cagtacctct catggctttt tggttccagc agtgagggca ttggtgagat caatggtaaa   4080
ctgtgcaagc tttcttttta tcattaggaa atgtgaaacg ttggacaaat tttgagtttt   4140
aacaaggaca aaaagttgaa agaaaaggca cagttaacaa aaaagggtgg ctagatttat   4200
cttgggtgat ggaggaaatg agagaggaat gctcttgaaa ggtggtctgt ggatctgtct   4260
gaatagaaag agcacagtaa gtatgcattg ccggagaaaa cgtccttgaa gctgcttgtc   4320
tcatgtgtat gatgtgcttt ttaaatcatg cccctcgttg cctgcctaat ctgtgactcc   4380
ctaaaaacta actgggccca tgtagatggg gctgcaacca gagctgaata acatgttagg   4440
ctcacacatg catcagcact gcacactgga atcattgctc ttcctggact ttgtagaaat   4500
cagtctcaag tgcttcaaga gtctggctcc tgctactttt atctgtcagg tagcacataa   4560
ggtttgcagg gtttatattt tgtatagaat cacagttgtg gagaaaaagt aataatttct   4620
caatgaattt taaaaatggg cctattttct atccccgtgg ttcatctgat ataattagtg   4680
ttccctgtga attccccccc tctatgggaa ggatgccttt actctttatc agtaataaat   4740
```

```
tatgactgtt ttcatattgc cttagggtta tttccctgtg taaaccattg tcttttgttt   4800

tggttttctt tagcattatg aagctttggt attgtacaag gtcagtagta agatgctcac   4860

tagtctcagg gcttgtgtaa tattctggga ggtcatttaa atgccagaaa tggtcaagca   4920

attatacaca gtatttatga ctctgttaag cataccgttt gtctgtcaca ttagtagatt   4980

ctgagattaa aaaaaatttt taaagagtga tcatttaaat aatttctaaa agggtctttt   5040

caagctctaa caaagtcact aacaaatgca ttattttcta cagaattaga tgttagtagt   5100

acagtactgc atattcaggg aaaaagtgtg aggaattgat ttcaaaatag ttcgttcttg   5160

tgtttgacct aagaatgatt gtcgcatgaa gtgtttgttt ttacagttta gcatatataa   5220

acaaacatga taggattcct taagatgtta ccacccaggg ggccacaagc cagcctgctg   5280

tctcaggaag ctgtagaagg agtgtttgtc aatttcttgt cactggtttg ctgacttact   5340

gaggattaat tgttgcctta caatgttact gaaataaact gtttaat                 5387
```

<210> SEQ ID NO 95
<211> LENGTH: 202
<212> TYPE: PRT
<213> ORGANISM: Homo sapiens

<400> SEQUENCE: 95

```
Met Glu Arg Gly Ala Gly Ala Lys Leu Leu Pro Leu Leu Leu Leu Leu
1               5                   10                  15

Arg Ala Thr Gly Phe Thr Cys Ala Gln Thr Asp Gly Arg Asn Gly Tyr
            20                  25                  30

Thr Ala Val Ile Glu Val Thr Ser Gly Gly Pro Trp Gly Asp Trp Ala
        35                  40                  45

Trp Pro Glu Met Cys Pro Asp Gly Phe Phe Ala Ser Gly Phe Ser Leu
    50                  55                  60

Lys Val Glu Pro Pro Gln Gly Ile Pro Gly Asp Asp Thr Ala Leu Asn
65                  70                  75                  80

Gly Ile Arg Leu His Cys Ala Arg Gly Asn Val Leu Gly Asn Thr His
                85                  90                  95

Val Val Glu Ser Gln Ser Gly Ser Trp Gly Glu Trp Ser Glu Pro Leu
            100                 105                 110

Trp Cys Arg Gly Gly Ala Tyr Leu Val Ala Phe Ser Leu Arg Val Glu
        115                 120                 125

Ala Pro Thr Thr Leu Gly Asp Asn Thr Ala Ala Asn Asn Val Arg Phe
    130                 135                 140

Arg Cys Ser Asp Gly Glu Glu Leu Gln Gly Pro Gly Leu Ser Trp Gly
145                 150                 155                 160

Asp Phe Gly Asp Trp Ser Asp His Cys Pro Lys Gly Ala Cys Gly Leu
                165                 170                 175

Gln Thr Lys Ile Gln Gly Pro Arg Gly Leu Gly Asp Asp Thr Ala Leu
            180                 185                 190

Asn Asp Ala Arg Leu Phe Cys Cys Arg Ser
        195                 200
```

<210> SEQ ID NO 96
<211> LENGTH: 70
<212> TYPE: PRT
<213> ORGANISM: Homo sapiens

<400> SEQUENCE: 96

```
Met Glu Arg Gly Ala Gly Ala Lys Leu Leu Pro Leu Leu Leu Leu Leu
1               5                   10                  15
```

```
Arg Ala Thr Gly Phe Thr Cys Ala Gln Thr Asp Gly Arg Asn Gly Tyr
            20                  25                  30

Thr Ala Val Ile Glu Val Thr Ser Gly Gly Pro Trp Gly Asp Trp Ala
        35                  40                  45

Trp Pro Glu Met Cys Pro Asp Gly Phe Phe Ala Ser Gly Phe Ser Leu
    50                  55                  60

Lys Leu Gly Arg Met Glu
65                  70


<210> SEQ ID NO 97
<211> LENGTH: 102
<212> TYPE: PRT
<213> ORGANISM: Homo sapiens

<400> SEQUENCE: 97

Met Glu Arg Gly Ala Gly Ala Lys Leu Leu Pro Leu Leu Leu Leu Leu
1               5                   10                  15

Arg Ala Thr Gly Phe Thr Cys Ala Gln Thr Asp Gly Arg Asn Gly Tyr
            20                  25                  30

Thr Ala Val Ile Glu Val Thr Ser Gly Gly Pro Trp Gly Asp Trp Ala
        35                  40                  45

Trp Pro Glu Met Cys Pro Asp Gly Phe Phe Ala Ser Gly Phe Ser Leu
    50                  55                  60

Lys Val Glu Pro Pro Gln Gly Ile Pro Gly Asp Asp Thr Ala Leu Asn
65                  70                  75                  80

Gly Ile Arg Leu His Cys Ala Arg Gly Asn Val Leu Gly Asn Thr His
                85                  90                  95

Val Leu Gly Arg Met Glu
            100


<210> SEQ ID NO 98
<211> LENGTH: 114
<212> TYPE: PRT
<213> ORGANISM: Homo sapiens

<400> SEQUENCE: 98

Met Glu Arg Gly Ala Gly Ala Lys Leu Leu Pro Leu Leu Leu Leu Leu
1               5                   10                  15

Arg Ala Thr Gly Phe Thr Cys Ala Gln Thr Asp Gly Arg Asn Gly Tyr
            20                  25                  30

Thr Ala Val Ile Glu Val Thr Ser Gly Gly Pro Trp Gly Asp Trp Ala
        35                  40                  45

Trp Pro Glu Met Cys Pro Asp Gly Phe Phe Ala Ser Gly Phe Ser Leu
    50                  55                  60

Lys Val Glu Pro Pro Gln Gly Ile Pro Gly Asp Asp Thr Ala Leu Asn
65                  70                  75                  80

Gly Ile Arg Leu His Cys Ala Arg Gly Asn Val Leu Gly Asn Thr His
                85                  90                  95

Val Val Glu Ser Gln Ser Gly Arg Trp Gly Ala Gly Val Glu Asp Pro
            100                 105                 110

Leu Gly


<210> SEQ ID NO 99
<211> LENGTH: 769
<212> TYPE: DNA
<213> ORGANISM: Homo sapiens
```

<400> SEQUENCE: 99

```
ggaggccctt ccgcaatcgg agccctcaca gaggccaaac tgatataaat ctgcttagga     60
ggcctgattc acagacgcta caggatggag cggggcgcag gagccaagct gctgccgctg    120
ctgctgcttc tgcgggcgac tggtttcaca tgtgcacaga cagatggccg gaacggctac    180
acggcggtca tcgaagtgac cagcgggggt ccctggggcg actgggcctg gcctgagatg    240
tgtcccgatg gattcttcgc cagcgggttc tcgctcaagg tggagcctcc ccaaggcatt    300
cctggcgacg acactgcact gaatgggatc aggctgcact gcgcgcgcgg gaacgtccta    360
ggcaatacgc acgtggtaga gtcccagtct ggaagctggg gcgaatggag tgagccgctg    420
tggtgtcgcg gcggcgccta cctagtggct ttctcgcttc gcgtggaggc acccacgacc    480
ctcggtgaca acacagcagc gaacaacgtg cgcttccgct gttcagacgg cgaggaactg    540
caggggcctg ggctgagctg ggagactttt ggagactgga gtgaccattg ccccaagggc    600
gcgtgcggcc tgcagaccaa gatccaggga cctagaggcc tcggcgatga cactgcgctg    660
aacgacgcgc gcttattctg ctgccgcagt tgaacggcgc cgccgccgcc gctctctccc    720
gggccaggag gctagtccca cctcttgcta ttaaagcttc tctgagttg                769
```

<210> SEQ ID NO 100
<211> LENGTH: 653
<212> TYPE: DNA
<213> ORGANISM: Homo sapiens

<400> SEQUENCE: 100

```
ggaggccctt ccgcaatcgg agccctcaca gaggccaaac tgatataaat ctgcttagga     60
ggcctgattc acagacgcta caggatggag cggggcgcag gagccaagct gctgccgctg    120
ctgctgcttc tgcgggcgac tggtttcaca tgtgcacaga cagatggccg gaacggctac    180
acggcggtca tcgaagtgac cagcgggggt ccctggggcg actgggcctg gcctgagatg    240
tgtcccgatg gattcttcgc cagcgggttc tcgctcaagc tggggcgaat ggagtgagcc    300
gctgtggtgt cgcggcggcg cctacctagt ggctttctcg cttcgcgtgg aggcacccac    360
gaccctcggt gacaacacag cagcgaacaa cgtgcgcttc cgctgttcag acggcgagga    420
actgcagggg cctgggctga gctggggaga ctttggagac tggagtgacc attgccccaa    480
gggcgcgtgc ggcctgcaga ccaagatcca gggacctaga ggcctcggcg atgacactgc    540
gctgaacgac gcgcgcttat tctgctgccg cagttgaacg gcgccgccgc cgccgctctc    600
tcccgggcca ggaggctagt cccacctctt gctattaaag cttctctgag ttg           653
```

<210> SEQ ID NO 101
<211> LENGTH: 747
<212> TYPE: DNA
<213> ORGANISM: Homo sapiens

<400> SEQUENCE: 101

```
aggcccttcc gcaatcggag ccctcacaga ggccaaactg atataaatct gcttaggagg     60
cctgattcac agacgctaca ggatggagcg gggcgcagga gccaagctgc tgccgctgct    120
gctgcttctg cgggcgactg gtttcacatg tgcacagaca gatggccgga acggctacac    180
ggcggtcatc gaagtgacca gcgggggtcc ctggggcgac tgggcctggc ctgagatgtg    240
tcccgatgga ttcttcgcca gcgggttctc gctcaaggtg gagcctcccc aaggcattcc    300
tggcgacgac actgcactga atgggatcag gctgcactgc gcgcgcggga acgtcctagg    360
caatacgcac gtgctggggc gaatggagtg agccgctgtg gtgtcgcggc ggcgcctacc    420
```

tagtggcttt ctcgcttcgc gtggaggcac ccacgaccct cggtgacaac acagcagcga 480
acaacgtgcg cttccgctgt tcagacggcg aggaactgca ggggcctggg ctgagctggg 540
gagactttgg agactggagt gaccattgcc ccaagggcgc gtgcggcctg cagaccaaga 600
tccagggacc tagaggcctc ggcgatgaca ctgcgctgaa cgacgcgcgc ttattctgct 660
gccgcagttg aacggcgccg ccgccgccgc tctctcccgg gccaggaggc tagtcccacc 720
tcttgctatt aaagcttctc tgagttg 747

<210> SEQ ID NO 102
<211> LENGTH: 803
<212> TYPE: DNA
<213> ORGANISM: Homo sapiens

<400> SEQUENCE: 102
aggcccttcc gcaatcggag ccctcacaga ggccaaactg atataaatct gcttaggagg 60
cctgattcac agacgctaca ggatggagcg gggcgcagga gccaagctgc tgccgctgct 120
gctgcttctg cgggcgactg gtttcacatg tgcacagaca gatggccgga acggctacac 180
ggcggtcatc gaagtgacca gcgggggtcc ctggggcgac tgggcctggc ctgagatgtg 240
tcccgatgga ttcttcgcca gcgggttctc gctcaaggtg gagcctcccc aaggcattcc 300
tggcgacgac actgcactga atgggatcag gctgcactgc gcgcgcggga acgtcctagg 360
caatacgcac gtggtagagt cccagtctgg aaggtggggc gcaggggtcg aggatccctt 420
ggggtgatgc tggggcgaat ggagtgagcc gctgtggtgt cgcggcggcg cctacctagt 480
ggctttctcg cttcgcgtgg aggcacccac gaccctcggt gacaacacag cagcgaacaa 540
cgtgcgcttc cgctgttcag acggcgagga actgcagggg cctgggctga gctggggaga 600
ctttggagac tggagtgacc attgccccaa gggcgcgtgc ggcctgcaga ccaagatcca 660
gggacctaga ggcctcggcg atgacactgc gctgaacgac gcgcgcttat tctgctgccg 720
cagttgaacg gcgccgccgc cgccgctctc tcccgggcca ggaggctagt cccacctctt 780
gctattaaag cttctctgag ttg 803

<210> SEQ ID NO 103
<211> LENGTH: 21
<212> TYPE: DNA
<213> ORGANISM: Homo sapiens

<400> SEQUENCE: 103
cgaggacaat ctggatatca a 21

<210> SEQ ID NO 104
<211> LENGTH: 21
<212> TYPE: DNA
<213> ORGANISM: Homo sapiens

<400> SEQUENCE: 104
ctggagccct cgagcaagaa a 21

<210> SEQ ID NO 105
<211> LENGTH: 21
<212> TYPE: DNA
<213> ORGANISM: Homo sapiens

<400> SEQUENCE: 105
cccgtggttc atctgatata a 21

```
<210> SEQ ID NO 106
<211> LENGTH: 21
<212> TYPE: DNA
<213> ORGANISM: Homo sapiens

<400> SEQUENCE: 106

aaggactttg ctcggcgttt a                                               21


<210> SEQ ID NO 107
<211> LENGTH: 21
<212> TYPE: DNA
<213> ORGANISM: Homo sapiens

<400> SEQUENCE: 107

tacgtggatg tttgtaacgt a                                               21


<210> SEQ ID NO 108
<211> LENGTH: 21
<212> TYPE: DNA
<213> ORGANISM: Homo sapiens

<400> SEQUENCE: 108

ctcgtattgg ctcaatcata a                                               21
```